(12) United States Patent
Alessi et al.

(10) Patent No.: US 10,583,080 B2
(45) Date of Patent: *Mar. 10, 2020

(54) THERAPEUTIC METHODS FOR THE TREATMENT OF DIABETES AND RELATED CONDITIONS FOR PATIENTS WITH HIGH BASELINE HBA1C

(71) Applicant: Intarcia Therapeutics, Inc., Boston, MA (US)

(72) Inventors: Thomas R. Alessi, Hayward, CA (US); Michelle Baron, Boston, MA (US)

(73) Assignee: INTARCIA THERAPEUTICS, INC., Boston, MA (US)

(*) Notice: Subject to any disclaimer, the term of this patent is extended or adjusted under 35 U.S.C. 154(b) by 66 days.

This patent is subject to a terminal disclaimer.

(21) Appl. No.: 15/868,708

(22) Filed: Jan. 11, 2018

(65) Prior Publication Data

US 2018/0256491 A1     Sep. 13, 2018

Related U.S. Application Data

(63) Continuation of application No. 14/871,420, filed on Sep. 30, 2015, now Pat. No. 9,889,085.

(60) Provisional application No. 62/212,539, filed on Aug. 31, 2015, provisional application No. 62/171,876, filed on Jun. 5, 2015, provisional application No. 62/139,520, filed on Mar. 27, 2015, provisional application No. 62/057,892, filed on Sep. 30, 2014.

(51) Int. Cl.
| | | |
|---|---|---|
| *A61K 38/26* | (2006.01) | |
| *A61K 9/00* | (2006.01) | |
| *A61K 38/17* | (2006.01) | |
| *A61K 45/06* | (2006.01) | |
| *G01N 33/72* | (2006.01) | |

(52) U.S. Cl.
CPC ........ *A61K 9/0004* (2013.01); *A61K 38/1709* (2013.01); *A61K 38/26* (2013.01); *A61K 45/06* (2013.01); *G01N 33/721* (2013.01); *G01N 2333/805* (2013.01); *G01N 2800/042* (2013.01); *G01N 2800/52* (2013.01)

(58) Field of Classification Search
CPC .............................. A61K 9/0004; A61K 38/26
See application file for complete search history.

(56) References Cited

U.S. PATENT DOCUMENTS

| | | |
|---|---|---|
| 2,110,208 A | 3/1938 | Eggert |
| 2,168,437 A | 8/1939 | Buercklin |
| 2,531,724 A | 11/1950 | Cevasco |
| D179,537 S | 1/1957 | Floyd et al. |
| 3,025,991 A | 3/1962 | Gillon |
| 3,122,162 A | 2/1964 | Sands |
| 3,523,906 A | 8/1970 | Vrancken et al. |
| 3,625,214 A | 12/1971 | Higuchi |
| 3,632,768 A | 1/1972 | Bergy et al. |
| 3,691,090 A | 9/1972 | Kitajima et al. |
| D226,915 S | 5/1973 | Huggins |
| 3,732,865 A | 5/1973 | Higuchi et al. |
| 3,737,337 A | 6/1973 | Schnoring et al. |
| 3,773,919 A | 11/1973 | Boswell et al. |
| 3,797,492 A | 3/1974 | Place |
| 3,869,549 A | 3/1975 | Geller |
| 3,891,570 A | 6/1975 | Fukushima et al. |
| D236,035 S | 7/1975 | Ciencewicki |
| 3,960,757 A | 6/1976 | Morishita et al. |
| 3,987,790 A | 10/1976 | Eckenhoff et al. |
| 3,995,631 A | 12/1976 | Higuchi et al. |
| 3,995,632 A | 12/1976 | Nakano et al. |
| 4,008,719 A | 2/1977 | Theeuwes et al. |
| 4,034,756 A | 7/1977 | Higuchi et al. |
| 4,078,060 A | 3/1978 | Benson et al. |
| 4,111,201 A | 9/1978 | Theeuwes |

(Continued)

FOREIGN PATENT DOCUMENTS

| | | |
|---|---|---|
| EP | 0052510 A2 | 5/1982 |
| EP | 0079405 | 5/1983 |

(Continued)

OTHER PUBLICATIONS

Georgios, et al., "Pharmacokinetics and Tolerability of Exenatide Delivered by 7-Day Continuous Subcutaneous Infusion in Healthy Volunteers", Advances in Therapy, Health Communications, Metuchen, NJ, US, vol. 32, No. 7, Jul. 10, 2015, pp. 650-661.

(Continued)

*Primary Examiner* — Gyan Chandra

(74) *Attorney, Agent, or Firm* — Brian C. Trinque; Lathrop GPM LLP

(57) ABSTRACT

The present invention is directed to treatments for a disease or condition, in a subject in need thereof, that provide alternatives to treatment by injection that give, relative to treatment by injection, improved treatment outcomes, 100% treatment compliance, reduced side effects, and rapid establishment and/or termination of substantial steady-state drug delivery. The method includes providing continuous delivery of a drug from an implanted osmotic delivery device, wherein substantial steady-state delivery of the drug at therapeutic concentrations is achieved within about 7 days after implantation of the osmotic delivery device in the subject and the substantial steady-state delivery of the drug from the osmotic delivery device is continuous over a period of at least about 3 months. In one embodiment, the present invention is directed to treatment of type 2 diabetes mellitus using insulinotrophic peptides. In embodiments, a subject has a baseline HbA1c % of greater than 6.5% or 10.0%.

27 Claims, 36 Drawing Sheets

Specification includes a Sequence Listing.

(56) References Cited

U.S. PATENT DOCUMENTS

| | | |
|---|---|---|
| 4,111,202 A | 9/1978 | Theeuwes |
| 4,111,203 A | 9/1978 | Theeuwes |
| 4,203,439 A | 5/1980 | Theeuwes |
| 4,211,771 A | 7/1980 | Witkowski et al. |
| 4,221,862 A | 9/1980 | Naito et al. |
| 4,243,030 A | 1/1981 | Lynch et al. |
| D258,837 S | 4/1981 | Spranger et al. |
| D259,458 S | 6/1981 | Fuller et al. |
| 4,305,927 A | 12/1981 | Theeuwes et al. |
| 4,310,516 A | 1/1982 | Chang et al. |
| 4,340,054 A | 7/1982 | Michaels |
| 4,350,271 A | 9/1982 | Eckenhoff |
| 4,373,527 A | 2/1983 | Fischell |
| 4,376,118 A | 3/1983 | Daher |
| 4,384,975 A | 5/1983 | Fong |
| 4,389,330 A | 6/1983 | Tice et al. |
| 4,439,196 A | 3/1984 | Higuchi |
| 4,444,498 A | 4/1984 | Heinemann |
| 4,455,143 A | 6/1984 | Theeuwes et al. |
| 4,455,145 A | 6/1984 | Theeuwes |
| 4,530,840 A | 7/1985 | Tice et al. |
| 4,552,561 A | 11/1985 | Eckenhoff et al. |
| 4,588,614 A | 5/1986 | Lauchenauer |
| 4,594,108 A | 6/1986 | Greminger, Jr. et al. |
| 4,609,374 A | 9/1986 | Ayer |
| 4,639,244 A | 1/1987 | Rizk et al. |
| 4,655,462 A | 4/1987 | Balsells |
| 4,673,405 A | 6/1987 | Guittard et al. |
| 4,675,184 A | 6/1987 | Hasegawa et al. |
| 4,695,623 A | 9/1987 | Stabinsky |
| 4,727,138 A | 2/1988 | Goeddel et al. |
| 4,734,284 A | 3/1988 | Terada et al. |
| 4,737,437 A | 4/1988 | Gutsell, Jr. et al. |
| 4,743,449 A | 5/1988 | Yoshida et al. |
| 4,753,651 A | 6/1988 | Eckenhoff |
| 4,762,791 A | 8/1988 | Goeddel et al. |
| 4,765,989 A | 8/1988 | Wong et al. |
| 4,783,337 A | 11/1988 | Wong et al. |
| 4,818,517 A | 4/1989 | Kwee et al. |
| 4,820,638 A | 4/1989 | Swetly et al. |
| 4,826,144 A | 5/1989 | Balsells |
| 4,830,344 A | 5/1989 | Balsells |
| 4,840,896 A | 6/1989 | Reddy et al. |
| 4,845,196 A | 7/1989 | Cowling |
| 4,847,079 A | 7/1989 | Kwan |
| 4,851,228 A | 7/1989 | Zentner et al. |
| 4,865,845 A | 9/1989 | Eckenhoff et al. |
| 4,873,080 A | 10/1989 | Brickl et al. |
| 4,874,388 A | 10/1989 | Wong et al. |
| 4,876,781 A | 10/1989 | Balsells |
| 4,885,166 A | 12/1989 | Meyer et al. |
| 4,886,668 A | 12/1989 | Haslam et al. |
| 4,892,778 A | 1/1990 | Theeuwes et al. |
| 4,893,795 A | 1/1990 | Balsells |
| 4,897,471 A | 1/1990 | Stabinsky |
| 4,907,788 A | 3/1990 | Balsells |
| 4,915,366 A | 4/1990 | Balsells |
| 4,915,949 A | 4/1990 | Wong et al. |
| 4,915,954 A | 4/1990 | Ayer et al. |
| 4,917,887 A | 4/1990 | Hauptmann et al. |
| 4,917,895 A | 4/1990 | Lee et al. |
| 4,923,805 A | 5/1990 | Reddy et al. |
| 4,927,687 A | 5/1990 | Nuwayser |
| 4,929,554 A | 5/1990 | Goeddel et al. |
| 4,931,285 A | 6/1990 | Edgren et al. |
| 4,934,666 A | 6/1990 | Balsells |
| 4,940,465 A | 7/1990 | Theeuwes et al. |
| 4,940,588 A | 7/1990 | Sparks et al. |
| 4,952,402 A | 8/1990 | Sparks et al. |
| 4,957,119 A | 9/1990 | de Nijs |
| 4,961,253 A | 10/1990 | Balsells |
| 4,964,204 A | 10/1990 | Balsells |
| 4,969,884 A | 11/1990 | Yum |
| 4,974,821 A | 12/1990 | Balsells |
| 4,976,966 A | 12/1990 | Theeuwes et al. |
| 5,004,689 A | 4/1991 | Fiers et al. |
| 5,006,346 A | 4/1991 | Theeuwes et al. |
| 5,019,382 A | 5/1991 | Cummins, Jr. |
| 5,019,400 A | 5/1991 | Gombotz et al. |
| 5,023,088 A | 6/1991 | Wong et al. |
| 5,024,842 A | 6/1991 | Edgren et al. |
| 5,030,216 A | 7/1991 | Theeuwes et al. |
| 5,034,229 A | 7/1991 | Magruder et al. |
| 5,057,318 A | 10/1991 | Magruder et al. |
| 5,059,423 A | 10/1991 | Magruder et al. |
| 5,066,436 A | 11/1991 | Komen et al. |
| 5,071,642 A | 12/1991 | Lahr et al. |
| 5,072,070 A | 12/1991 | Balsells |
| 5,079,388 A | 1/1992 | Balsells |
| 5,091,188 A | 2/1992 | Haynes |
| 5,108,078 A | 4/1992 | Balsells |
| 5,110,596 A | 5/1992 | Magruder et al. |
| 5,112,614 A | 5/1992 | Magruder et al. |
| 5,113,938 A | 5/1992 | Clayton |
| 5,117,066 A | 5/1992 | Balsells |
| D326,718 S | 6/1992 | Maxwell |
| 5,118,666 A | 6/1992 | Habener |
| 5,120,306 A | 6/1992 | Gosselin |
| 5,120,712 A | 6/1992 | Habener |
| 5,120,832 A | 6/1992 | Goeddel et al. |
| 5,122,128 A | 6/1992 | Cardinal et al. |
| 5,122,377 A | 6/1992 | Miller |
| 5,126,142 A | 6/1992 | Ayer et al. |
| 5,126,147 A | 6/1992 | Silvestri et al. |
| 5,134,244 A | 7/1992 | Balsells |
| 5,137,727 A | 8/1992 | Eckenhoff |
| D329,278 S | 9/1992 | Gallup |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Margruder et al. |
| 5,190,765 A | 3/1993 | Jao et al. |
| 5,203,849 A | 4/1993 | Balsells |
| 5,204,108 A | 4/1993 | Illum |
| 5,207,752 A | 5/1993 | Sorensen et al. |
| 5,209,746 A | 5/1993 | Balaban et al. |
| 5,213,809 A | 5/1993 | Wright et al. |
| 5,213,810 A | 5/1993 | Steber |
| 5,219,572 A | 6/1993 | Sivaramakrishnan |
| 5,221,278 A | 6/1993 | Linkwitz et al. |
| 5,223,265 A | 6/1993 | Wong |
| 5,225,205 A | 7/1993 | Orsolini |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| D342,855 S | 1/1994 | Butler, II |
| 5,278,151 A | 1/1994 | Korb et al. |
| 5,279,608 A | 1/1994 | Cherif Cheikh |
| 5,284,655 A | 2/1994 | Bogdansky et al. |
| 5,288,501 A | 2/1994 | Nürnberg et al. |
| 5,288,502 A | 2/1994 | Mcginity et al. |
| 5,290,271 A | 3/1994 | Jernberg |
| 5,300,079 A | 4/1994 | Niezink et al. |
| 5,300,302 A | 4/1994 | Tachon et al. |
| 5,308,348 A | 5/1994 | Balaban et al. |
| 5,312,335 A | 5/1994 | McKinnon et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magruder et al. |
| 5,324,280 A | 6/1994 | Wong et al. |
| 5,336,057 A | 8/1994 | Fukuda et al. |
| 5,336,505 A | 8/1994 | Ng et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |

(56) References Cited

U.S. PATENT DOCUMENTS

| | | |
|---|---|---|
| 5,385,738 A | 1/1995 | Yamahira et al. |
| 5,385,887 A | 1/1995 | Yim et al. |
| 5,407,609 A | 4/1995 | Tice et al. |
| D358,644 S | 5/1995 | Park |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,428,024 A | 6/1995 | Chu et al. |
| 5,429,602 A | 7/1995 | Hauser |
| 5,439,688 A | 8/1995 | Orsolini et al. |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,478,564 A | 12/1995 | Wantier et al. |
| 5,486,365 A | 1/1996 | Takado et al. |
| 5,498,255 A | 3/1996 | Wong et al. |
| 5,511,355 A | 4/1996 | Dingler |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,541,172 A | 7/1996 | Labrie et al. |
| 5,542,682 A | 8/1996 | Goldstein et al. |
| 5,543,156 A | 8/1996 | Roorda et al. |
| 5,545,618 A | 8/1996 | Buckley et al. |
| 5,556,642 A | 9/1996 | Kobayashi et al. |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,589,167 A | 12/1996 | Cleland et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,630,796 A | 5/1997 | Bellhouse et al. |
| 5,633,011 A | 5/1997 | Dong et al. |
| 5,635,213 A | 6/1997 | Nystrom et al. |
| 5,639,477 A | 6/1997 | Maruyama et al. |
| 5,639,640 A | 6/1997 | Reddy et al. |
| 5,645,850 A | 7/1997 | Bezwada et al. |
| 5,648,088 A | 7/1997 | Bezwada et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,660,847 A | 8/1997 | Magruder et al. |
| 5,660,858 A | 8/1997 | Parikh et al. |
| 5,660,861 A | 8/1997 | Jao et al. |
| 5,667,808 A | 9/1997 | Johnson et al. |
| 5,668,170 A | 9/1997 | Gyory |
| 5,672,549 A | 9/1997 | Minami et al. |
| 5,676,942 A | 10/1997 | Testa et al. |
| 5,686,097 A | 11/1997 | Taskovich et al. |
| 5,688,801 A | 11/1997 | Mesens et al. |
| 5,690,925 A | 11/1997 | Gray et al. |
| 5,690,952 A | 11/1997 | Magruder et al. |
| 5,697,113 A | 12/1997 | Shatz et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,707,644 A | 1/1998 | Illum |
| 5,711,967 A | 1/1998 | Juch |
| 5,713,847 A | 2/1998 | Howard, III et al. |
| 5,718,922 A | 2/1998 | Herrero-Vanrell |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Hahn et al. |
| 5,767,251 A | 6/1998 | Reddy et al. |
| 5,770,231 A | 6/1998 | Mesens et al. |
| 5,782,396 A | 7/1998 | Mastri et al. |
| 5,792,477 A | 8/1998 | Rickey et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| D399,821 S | 10/1998 | Tyneski et al. |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,851,451 A | 12/1998 | Takechi et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Margruder et al. |
| 5,871,778 A | 2/1999 | Kino et al. |
| 5,874,388 A | 2/1999 | Hsu |
| 5,876,746 A | 3/1999 | Jona et al. |
| 5,882,676 A | 3/1999 | Lee et al. |
| D408,917 S | 4/1999 | Hacker |
| 5,904,935 A | 5/1999 | Eckenhoff et al. |
| 5,906,816 A | 5/1999 | Soos et al. |
| 5,906,830 A | 5/1999 | Farinas et al. |
| 5,908,621 A | 6/1999 | Glue et al. |
| 5,916,598 A | 6/1999 | Rickey et al. |
| 5,922,253 A | 7/1999 | Herbert et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,942,253 A | 8/1999 | Gombotz et al. |
| 5,945,126 A | 8/1999 | Thanoo et al. |
| 5,948,430 A | 9/1999 | Zerbe et al. |
| 5,958,909 A | 9/1999 | Habener |
| D415,073 S | 10/1999 | Meehan et al. |
| 5,962,023 A | 10/1999 | Jamiolkowski et al. |
| 5,965,168 A | 10/1999 | Mesens et al. |
| 5,972,370 A | 10/1999 | Eckenhoff et al. |
| 5,972,373 A | 10/1999 | Yajima et al. |
| 5,976,109 A | 11/1999 | Heruth |
| 5,980,945 A | 11/1999 | Ruiz |
| 5,981,719 A | 11/1999 | Woiszwillo et al. |
| 5,984,890 A | 11/1999 | Gast et al. |
| 5,985,305 A | 11/1999 | Peery et al. |
| 5,989,463 A | 11/1999 | Tracy et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,023,802 A | 2/2000 | King |
| 6,029,361 A | 2/2000 | Newman |
| 6,056,718 A | 5/2000 | Funderburk et al. |
| 6,060,450 A | 5/2000 | Soos et al. |
| 6,069,133 A | 5/2000 | Carlo et al. |
| 6,074,660 A | 6/2000 | Jamiolkowski et al. |
| 6,074,673 A | 6/2000 | Guillen |
| 6,100,346 A | 8/2000 | Jamiolkowski et al. |

(56) References Cited

U.S. PATENT DOCUMENTS

| | | |
|---|---|---|
| 6,110,503 A | 8/2000 | Rickey et al. |
| 6,113,938 A | 9/2000 | Chen et al. |
| 6,113,947 A | 9/2000 | Cleland et al. |
| 6,120,787 A | 9/2000 | Gustafsson et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,190,700 B1 | 2/2001 | Okada et al. |
| 6,190,702 B1 | 2/2001 | Takada et al. |
| 6,191,102 B1 | 2/2001 | DiMarchi et al. |
| 6,204,022 B1 | 3/2001 | Johnson et al. |
| 6,217,893 B1 | 4/2001 | Pellet et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,349 B1 | 6/2001 | Yiv et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| D445,975 S | 7/2001 | Stratford |
| 6,258,377 B1 | 7/2001 | New et al. |
| 6,261,584 B1 | 7/2001 | Peery et al. |
| 6,268,343 B1 | 7/2001 | Knudsen et al. |
| 6,270,700 B1 | 8/2001 | Ignatious |
| 6,270,787 B1 | 8/2001 | Ayer |
| 6,277,413 B1 | 8/2001 | Sankaram |
| 6,283,949 B1 | 9/2001 | Roorda |
| 6,284,264 B1 | 9/2001 | Zerbe et al. |
| 6,284,725 B1 | 9/2001 | Coolidge et al. |
| 6,284,727 B1 | 9/2001 | Kim et al. |
| 6,287,295 B1 | 9/2001 | Chen et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,387 B1 | 10/2002 | Scott et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,495,164 B1 | 12/2002 | Ramstack et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamilolkowski et al. |
| 6,524,305 B1 | 2/2003 | Peterson et al. |
| 6,528,093 B1 | 3/2003 | Kamei et al. |
| 6,528,486 B1 | 3/2003 | Larsen et al. |
| D472,896 S | 4/2003 | Peiker |
| 6,541,021 B1 | 4/2003 | Johnson et al. |
| 6,544,252 B1 | 4/2003 | Theeuwes et al. |
| 6,547,250 B1 | 4/2003 | Noble |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,667,061 B2 | 12/2003 | Ramstack et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiwicz et al. |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B2 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |
| 6,899,887 B2 | 5/2005 | Ayer |
| 6,899,898 B2 | 5/2005 | Albayrak |
| 6,902,744 B1 | 6/2005 | Kolterman et al. |
| 6,903,186 B1 | 6/2005 | Dong |
| 6,913,767 B1 | 7/2005 | Cleland et al. |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,163,697 B2 | 1/2007 | Hanes et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| D555,589 S | 11/2007 | Hussaini et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |

(56) References Cited

U.S. PATENT DOCUMENTS

| | | |
|---|---|---|
| 7,589,169 B2 | 9/2009 | Bolotin |
| 7,612,176 B2 | 11/2009 | Wright et al. |
| 7,635,463 B2 | 12/2009 | Bolotin et al. |
| D608,447 S | 1/2010 | Meyer et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 | 3/2010 | Alessi et al. |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,790,140 B2 | 9/2010 | Bolotin |
| 7,825,091 B2 | 11/2010 | Bloom et al. |
| 7,829,109 B2 | 11/2010 | Chen et al. |
| 7,833,543 B2 | 11/2010 | Gibson et al. |
| 7,879,028 B2 | 2/2011 | Alessi et al. |
| 7,879,794 B2 | 2/2011 | Weyer et al. |
| 7,919,109 B2 | 4/2011 | Berry et al. |
| 7,928,065 B2 | 4/2011 | Young et al. |
| D638,478 S | 5/2011 | Block |
| 7,959,938 B2 | 6/2011 | Rohloff et al. |
| 7,964,183 B2 | 6/2011 | Eliaz et al. |
| 8,039,432 B2 | 10/2011 | Bridon et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,202,836 B2 | 6/2012 | Moore et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,231,859 B2 | 7/2012 | Bolotin et al. |
| 8,257,682 B2 | 9/2012 | Bolotin et al. |
| 8,257,691 B2 | 9/2012 | Eliaz et al. |
| 8,262,667 B1 | 9/2012 | Silver et al. |
| 8,263,545 B2 | 9/2012 | Levy et al. |
| 8,263,736 B2 | 9/2012 | Berry |
| 8,268,341 B2 | 9/2012 | Berry |
| 8,273,365 B2 | 9/2012 | Lautenbach et al. |
| 8,273,713 B2 | 9/2012 | Pittner et al. |
| D669,589 S | 10/2012 | Delaey |
| 8,277,776 B2 | 10/2012 | Bolotin et al. |
| 8,278,267 B2 | 10/2012 | Weyer et al. |
| 8,288,338 B2 | 10/2012 | Young et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| D678,889 S | 3/2013 | Chiu |
| 8,398,967 B2 | 3/2013 | Eliaz et al. |
| 8,440,226 B2 | 5/2013 | Rohloff et al. |
| 8,460,694 B2 | 6/2013 | Rohloff et al. |
| 8,470,353 B2 | 6/2013 | Lautenbach et al. |
| 8,801,700 B2 | 8/2014 | Alessi et al. |
| 8,815,802 B2 | 8/2014 | Kalthoff et al. |
| 8,858,621 B2 | 10/2014 | Oba et al. |
| 8,865,202 B2 | 10/2014 | Zerbe et al. |
| 8,888,745 B2 | 11/2014 | Van Der Graaf et al. |
| 8,926,595 B2 | 1/2015 | Alessi et al. |
| 8,940,316 B2 | 1/2015 | Alessi et al. |
| 8,992,961 B2 | 3/2015 | Berry et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 9,241,722 B2 | 1/2016 | Yu |
| D750,764 S | 3/2016 | DeSocio |
| 9,332,995 B2 | 5/2016 | Russo |
| 9,526,763 B2 | 12/2016 | Rohloff et al. |
| 9,539,200 B2 | 1/2017 | Lautenbach |
| 9,572,889 B2 | 2/2017 | Alessi et al. |
| D789,539 S | 6/2017 | Kleiner et al. |
| D789,540 S | 6/2017 | Gyorgy |
| 9,682,127 B2 | 6/2017 | Alessi et al. |
| RE46,577 E | 10/2017 | Collins et al. |
| 9,889,085 B1 | 2/2018 | Alessi et al. |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0031790 A1 | 10/2001 | Beisswenger |
| 2001/0036472 A1 | 11/2001 | Wong et al. |
| 2001/0040326 A1 | 11/2001 | Balczun |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jaworowicz et al. |
| 2002/0048600 A1 | 4/2002 | Bhatt et al. |
| 2002/0098180 A1 | 7/2002 | Lei |
| 2002/0136848 A1 | 9/2002 | Yoshii et al. |
| 2002/0137666 A1 | 9/2002 | Beeley et al. |
| 2002/0141985 A1 | 10/2002 | Pittner et al. |
| 2002/0197185 A1 | 12/2002 | Jamiolkowski et al. |
| 2002/0197235 A1 | 12/2002 | Moran |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0097121 A1 | 5/2003 | Jolly et al. |
| 2003/0104063 A1 | 6/2003 | Babcock et al. |
| 2003/0108608 A1 | 6/2003 | Laridon et al. |
| 2003/0108609 A1 | 6/2003 | Berry et al. |
| 2003/0113380 A1 | 6/2003 | Ramstack et al. |
| 2003/0114837 A1 | 6/2003 | Peterson et al. |
| 2003/0118660 A1 | 6/2003 | Rickey et al. |
| 2003/0138403 A1 | 7/2003 | Drustrup |
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith et al. |
| 2004/0001889 A1 | 1/2004 | Chen et al. |
| 2004/0002442 A1 | 1/2004 | Pan et al. |
| 2004/0022859 A1 | 2/2004 | Chen et al. |
| 2004/0024068 A1 | 2/2004 | Levy et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 7/2004 | Struijker-Boudier |
| 2004/0151753 A1 | 8/2004 | Chen et al. |
| 2004/0157951 A1 | 8/2004 | Wolf |
| 2004/0198654 A1 | 10/2004 | Glaesner et al. |
| 2004/0209801 A1 | 10/2004 | Brand et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0010942 A1 | 1/2005 | Kim et al. |
| 2005/0070883 A1 | 3/2005 | Brown et al. |

(56) References Cited

U.S. PATENT DOCUMENTS

| | | |
|---|---|---|
| 2005/0070927 A1 | 3/2005 | Feinberg |
| 2005/0079200 A1 | 4/2005 | Rathenow et al. |
| 2005/0079202 A1 | 4/2005 | Chen et al. |
| 2005/0095284 A1 | 5/2005 | Trautman |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0131389 A1 | 6/2005 | Peterson et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0216087 A1 | 9/2005 | Zucherman, Jr. et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0073182 A1 | 4/2006 | Wong et al. |
| 2006/0084604 A1 | 4/2006 | Kitaura et al. |
| 2006/0084922 A1 | 4/2006 | Botha |
| 2006/0094652 A1 | 5/2006 | Levy et al. |
| 2006/0094693 A1 | 5/2006 | Aziz et al. |
| 2006/0106399 A1 | 5/2006 | Taras et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0224145 A1 | 10/2006 | Gills |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1 | 6/2007 | Kent et al. |
| 2007/0166352 A1 | 7/2007 | Wright et al. |
| 2007/0207958 A1 | 9/2007 | Bridon et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0065090 A1 | 3/2008 | Scribner et al. |
| 2008/0091176 A1 | 4/2008 | Alessi et al. |
| 2008/0110515 A1 | 5/2008 | Angelosanto et al. |
| 2008/0112994 A1 | 5/2008 | Junnarkar et al. |
| 2008/0200383 A1 | 8/2008 | Jennings et al. |
| 2008/0207512 A1 | 8/2008 | Roth et al. |
| 2008/0208194 A1 | 8/2008 | Bickenbach |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0234392 A1 | 9/2009 | Dziedzic |
| 2009/0247463 A1 | 10/2009 | Wright et al. |
| 2009/0254143 A1 | 10/2009 | Tweden et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2010/0298840 A1 | 11/2010 | Schwartz |
| 2011/0076317 A1 | 3/2011 | Alessi et al. |
| 2011/0091527 A1 | 4/2011 | Moonen et al. |
| 2011/0104111 A1 | 5/2011 | Rohloff et al. |
| 2011/0152181 A1 | 6/2011 | Alsina-Fernandez et al. |
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2013/0030417 A1 | 1/2013 | Alessi |
| 2013/0034210 A1 | 2/2013 | Rohloff et al. |
| 2013/0052237 A1 | 2/2013 | Eliaz et al. |
| 2014/0058425 A1 | 2/2014 | Porat |
| 2014/0121741 A1 | 5/2014 | Bennett et al. |
| 2014/0257272 A1 | 9/2014 | Clark, III et al. |
| 2014/0378900 A1 | 12/2014 | Alessi et al. |
| 2015/0111818 A1 | 1/2015 | Alessi et al. |
| 2015/0057227 A1 | 2/2015 | Leung |
| 2015/0133791 A1 | 5/2015 | Sato et al. |
| 2015/0231062 A1 | 8/2015 | Lautenbach et al. |
| 2015/0231256 A1 | 8/2015 | Berry et al. |
| 2015/0297509 A1 | 10/2015 | Schwarz |
| 2016/0022582 A1 | 1/2016 | Alessi et al. |
| 2016/0030337 A1 | 2/2016 | Kuzma et al. |
| 2016/0354115 A1 | 12/2016 | Smith et al. |
| 2016/0354305 A1 | 12/2016 | Alessi et al. |
| 2017/0056476 A1 | 3/2017 | Rohloff et al. |
| 2017/0079906 A1 | 3/2017 | Alessi et al. |
| 2017/0119854 A1 | 5/2017 | Alessi et al. |
| 2017/0119855 A1 | 5/2017 | Berry et al. |
| 2017/0181964 A1 | 6/2017 | Lautenbach et al. |
| 2017/0252409 A1 | 9/2017 | Leung |
| 2017/0273706 A1 | 9/2017 | Mirza et al. |
| 2017/0319470 A1 | 11/2017 | Eliaz et al. |
| 2017/0319662 A1 | 11/2017 | Berry et al. |
| 2017/0348392 A1 | 12/2017 | Rohloff et al. |
| 2017/0368145 A1 | 12/2017 | Alessi et al. |
| 2018/0009871 A1 | 1/2018 | Blackwell et al. |
| 2018/0185451 A1 | 7/2018 | Young et al. |

FOREIGN PATENT DOCUMENTS

| | | |
|---|---|---|
| EP | 0254394 | 1/1988 |
| EP | 0295411 | 12/1988 |
| EP | 0302582 A1 | 2/1989 |
| EP | 0368339 | 5/1990 |
| EP | 0373867 | 6/1990 |
| EP | 0431942 | 6/1991 |
| EP | 0486959 A1 | 5/1992 |
| EP | 0521586 A1 | 1/1993 |
| EP | 0596161 | 5/1994 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1300129 A2 | 4/2003 |
| EP | 1300173 A2 | 4/2003 |
| EP | 1600187 | 1/2009 |
| EP | 2133073 A1 | 12/2009 |
| EP | 2020990 | 9/2010 |

(56) References Cited

FOREIGN PATENT DOCUMENTS

| | | |
|---|---|---|
| FR | 640907 | 7/1928 |
| GB | 1049104 | 11/1966 |
| GB | 1518683 | 7/1978 |
| GB | 2501400 | 10/2013 |
| JP | H02124814 A | 5/1990 |
| JP | H07196479 A | 8/1995 |
| JP | 9241153 | 9/1997 |
| JP | 11-100353 | 4/1999 |
| JP | 2006/213727 A | 8/2006 |
| NL | 9100160 A | 8/1992 |
| NZ | 592113 | 8/2012 |
| TW | 200634060 | 10/2006 |
| WO | WO-1989/003678 A1 | 5/1989 |
| WO | WO-1990/013285 A1 | 11/1990 |
| WO | WO-1990/013361 A1 | 11/1990 |
| WO | WO-1990/013780 A1 | 11/1990 |
| WO | WO 91/07160 | 5/1991 |
| WO | WO-1992/019241 A1 | 11/1992 |
| WO | WO-93/06819 | 4/1993 |
| WO | WO 93/06821 | 4/1993 |
| WO | WO 93/008832 | 5/1993 |
| WO | WO 93/09763 | 5/1993 |
| WO | WO 93/23083 | 11/1993 |
| WO | WO 94/09743 | 5/1994 |
| WO | WO-1994010982 A1 | 5/1994 |
| WO | WO-94/21262 | 9/1994 |
| WO | WO 95/01167 | 1/1995 |
| WO | WO 95/09006 | 4/1995 |
| WO | WO 95/09007 | 4/1995 |
| WO | WO-1995/013799 A1 | 5/1995 |
| WO | WO 95/34285 | 12/1995 |
| WO | WO-96/001134 | 1/1996 |
| WO | WO 96/003116 | 2/1996 |
| WO | WO-1996/036317 A1 | 11/1996 |
| WO | WO-96/39142 | 12/1996 |
| WO | WO-96/40049 | 12/1996 |
| WO | WO 96/40139 | 12/1996 |
| WO | WO 96/40355 | 12/1996 |
| WO | WO-1996/040049 A1 | 12/1996 |
| WO | WO 97/15289 | 5/1997 |
| WO | WO 97/15296 | 5/1997 |
| WO | WO 97/28181 | 8/1997 |
| WO | WO-1997/031943 A1 | 9/1997 |
| WO | WO-1997/044039 A1 | 11/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO-1997/041837 A3 | 2/1998 |
| WO | WO-1998/007412 A1 | 2/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO-98/027962 | 7/1998 |
| WO | WO-98/27963 | 7/1998 |
| WO | WO 98/030231 | 7/1998 |
| WO | WO 98/32463 | 7/1998 |
| WO | WO-1998/030231 A1 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/004768 | 2/1999 |
| WO | WO-1999/012549 A2 | 3/1999 |
| WO | WO 99/16419 | 4/1999 |
| WO | WO 99/025728 | 5/1999 |
| WO | WO 99/29306 | 6/1999 |
| WO | WO-99/033446 | 7/1999 |
| WO | WO 99/33449 | 7/1999 |
| WO | WO 99/39700 | 8/1999 |
| WO | WO 99/040788 | 8/1999 |
| WO | WO 99/044659 | 9/1999 |
| WO | WO 99/062501 | 12/1999 |
| WO | WO 99/064061 | 12/1999 |
| WO | WO 00/013663 | 3/2000 |
| WO | WO 00/029206 | 5/2000 |
| WO | WO 00/038652 | 7/2000 |
| WO | WO 00/039280 | 7/2000 |
| WO | WO 00/040273 | 7/2000 |
| WO | WO 00/041548 | 7/2000 |
| WO | WO-00/045790 | 8/2000 |
| WO | WO 00/054745 | 9/2000 |
| WO | WO-2000/059476 A1 | 10/2000 |
| WO | WO 00/066138 | 11/2000 |
| WO | WO 00/067728 | 11/2000 |
| WO | WO-2000/066087 A2 | 11/2000 |
| WO | WO-2001/019345 A1 | 3/2001 |
| WO | WO-2001/028525 A2 | 4/2001 |
| WO | WO 01/043528 | 6/2001 |
| WO | WO 01/051041 | 7/2001 |
| WO | WO 01/78683 | 10/2001 |
| WO | WO 02/028366 | 4/2002 |
| WO | WO-02/036072 | 5/2002 |
| WO | WO 02/043800 | 6/2002 |
| WO | WO 02/045752 | 6/2002 |
| WO | WO 02/47716 | 6/2002 |
| WO | WO 02/067895 | 9/2002 |
| WO | WO 02/069983 | 9/2002 |
| WO | WO 02/76344 | 10/2002 |
| WO | WO-02/085428 | 10/2002 |
| WO | WO 03/000230 | 1/2003 |
| WO | WO-03/007981 | 1/2003 |
| WO | WO 03/011892 | 2/2003 |
| WO | WO-03/024357 | 3/2003 |
| WO | WO 03/024503 | 3/2003 |
| WO | WO-2003/020245 A1 | 3/2003 |
| WO | WO 03/030923 | 4/2003 |
| WO | WO 03/041684 | 5/2003 |
| WO | WO-03/041757 | 5/2003 |
| WO | WO-03/053400 | 7/2003 |
| WO | WO-2003/066585 A2 | 8/2003 |
| WO | WO 03/072113 | 9/2003 |
| WO | WO 03/072133 | 9/2003 |
| WO | WO 04/002565 | 1/2004 |
| WO | WO-2004/034975 A2 | 4/2004 |
| WO | WO-2004/035754 A2 | 4/2004 |
| WO | WO-2004/035762 A2 | 4/2004 |
| WO | WO-2004/036186 A2 | 4/2004 |
| WO | WO 04/052336 | 6/2004 |
| WO | WO 04/056338 | 7/2004 |
| WO | WO-04/089335 | 10/2004 |
| WO | WO-2004/103342 A2 | 12/2004 |
| WO | WO-05/048930 | 6/2005 |
| WO | WO-05/048952 | 6/2005 |
| WO | WO 05/102293 | 11/2005 |
| WO | WO-2005/102293 A1 | 11/2005 |
| WO | WO-2005/110425 | 11/2005 |
| WO | WO-06/017772 | 2/2006 |
| WO | WO 06/023526 | 3/2006 |
| WO | WO-06/081279 | 8/2006 |
| WO | WO-06/083761 | 8/2006 |
| WO | WO 06/084139 | 8/2006 |
| WO | WO 06/086727 | 8/2006 |
| WO | WO-06/101815 | 9/2006 |
| WO | WO-06/111169 | 10/2006 |
| WO | WO-2006/131730 | 12/2006 |
| WO | WO 07/024700 | 3/2007 |
| WO | WO 07/056681 | 5/2007 |
| WO | WO-07/075534 | 7/2007 |
| WO | WO-07/084460 | 7/2007 |
| WO | WO 07/133778 | 11/2007 |
| WO | WO 07/140416 | 12/2007 |
| WO | WO-08/021133 | 2/2008 |
| WO | WO-2008/041245 A2 | 4/2008 |
| WO | WO-08/061355 | 5/2008 |
| WO | WO-2008/086086 A2 | 7/2008 |
| WO | WO-08/133908 | 11/2008 |
| WO | WO 08/134425 | 11/2008 |

(56) References Cited

FOREIGN PATENT DOCUMENTS

| WO | WO 09/109927 | 9/2009 |
|---|---|---|
| WO | WO-2009/143285 A2 | 11/2009 |
| WO | WO-2013/004983 A1 | 1/2013 |

OTHER PUBLICATIONS

Yu et al., "Glucagon-like peptide 1 based therapy for type 2 diabetes", World Journal of Pediatrics vol. 4, No. 1, Feb. 1, 2008, pp. 8-13.
Taylor et al., "Day-long subcutaneous infusion of exenatide lowers glycemia in patients with type 2 diabetes", Horm Metab Res 37: 627-632 (2005).
Gao et al., "Target-Mediated Pharmacokinetic and Pharmacodynamic Model of Exendin-4 in Rats, Monkeys. and Humans," Drug Metabolism and Disposition, vol. 40, No. 5, pp. 990-997 (2012).
Adolf, "Human interferon omega—a review," Mult. Sclr. 1:S44-47 (1995).
Costantino et al., "Protein Spray Freeze Drying. 2. Effect of Formulation Variables on particle Size and Stability," J. Pharm. Sci. 91:388-395 (2002).
Henry et al., "Comparing ITCA 650, continuous subcutaneous delivery of exenatide via DUROS® device, vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).
Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).
Ishiwata et al., "Clinical effects of the recombinant feline interferon-omega on experimental parvovirus infection in beagle dogs," J. Vet. Med. Sci. 60(8):911-917 (1998).
Johnson et al., "How interferons fight disease," Sci. Am. 270(5):68-75 (May 1994).
Lublin et al., "Defining the clinical course of multiple sclerosis: results of an international survey," Neurology. 46:907-911 (1996).
Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).
Nielsen, "Incretin mimetics and DPP-IV inhibitors for the treatment of type 2 diabetes," Drug Discovery Today 10(10):703-710 (May 15, 2005).
Palmeri et al., "5-Fluorouracil and recombinant α-interferon-2a in the treatment of advanced colorectal carcinoma: a dose optimization study," J. Chemotherapy 2(5):327-330 (Oct. 1990).
Patti et al., "Natural interferon-b treatment of relapsing-remitting and secondary-progressive multiple sclerosis patients: two-year study," Acta. Neurol. Scand. 100:283-289 (1999).
Paty et al., "Interferon beta-1 b is effective in relapsing-remitting multiple sclerosis," Neurology 43:662-667 (1993).
PCT International Search Report for PCT/US2009/006, 4 pages (dated Aug. 12, 2009).
"Intarcia Therapeutics Announces Final Results from a Phase 2 Study of Injectable Omega Interferon plus Ribavirin for the Treatment of Hepatitis C Genotype-1," NLV Partners Press Coverage Portfolio News (Apr. 12, 2007) (Press Release).
Quianzon et al., "Lixisenatide-Once-daily Glucagon-like Peptide-1 Diabetes," US Endocrinology 7(2):104-109 (2011).
Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).
Roberts et al., "The Evolution of the Type I Interferons1," J. Interferon Cytokine Res. 18(10):805-816 (Oct. 1998).
Rohloff et al., "DUROS Technology Delivers Peptides and Proteins at Consistent Rate Continuously for 3 to 12 Months," J. Diabetes Sci. & Tech., 2(3):461-467 (May 1, 2008).
"Sequence Listings for International Patent Application Publication No. W02009109927, WIPO Patentscope", http://patentscope.wipo.int/search/docservicepdf_pct/id00000008776887, 1 page (last visited Nov. 14, 2012).
Shire et al., "Challenges in the Development of High Protein Concentration Formulations," J. Pharm. Sci. 93:1390-1402 (2004).
Smith, "Peripheral Neuro-hormones as a Strategy to Treat Obesity," oral presentation at the 2007 Cardiometabolic Health Congress in Boston, MA, pp. 1-35 (Sep. 26-29, 2007).
Written Opinion for International Patent Application No. PCT/US2009/005629 (corresponding to U.S. Appl. No. 12/587,946), 5 pages (dated Apr. 15, 2011).
Zhang et al., "Efficacy observations of different dosages of interferon to treat 150 Hepatitis B carriers," Current Physician 2(12):45-46 (1997).
Pratley et al., "Targeting Incretins in Type 2 Diabetes: Role of GLP-1 Receptor Agonists and DPP-4 Inhibitors," Rev. Diabet. Stud., 5(2):73-94 (2008).
Gonzalez, et al., "Hemoglobin Alc: A Reliable and Accurate Test for Diabetes Care? A Prospective Study in Mexico," Salud Publica Mex 55:462-468 (2013).
Ahn et al., "A New Approach to Search for the Bioactive Confirmation of Glucagon: Positional Cyclization Scanning" Journal of Medicinal Chemistry, vol. 44, No. 19, (2001): 3109-3116.
Glumetza Brochure 2009, 13 Pages.
Erowid,"Introduction to the Federal Controlled Substance Analog Act" 2001.
Li et al. ("Glucagon-Like Peptide-I Receptor Agonists Versus Insulin Glargine for Type 2 Diabetes Mellitus: A Systematic Review and Meta-Analysis of Randomized Controlled Trials" in Current Therapeutic Research, vol. 71, No. 4, Aug. 2010.
"Abstracts 2007," Diabetologia Clinical & Experimental Diabetes & Metabolism, Springer, Berlin, Germany, vol. 50 S243 (Aug. 21, 2007) (paragraph [0586]) (XP002538652).
Jetschmann et al., "Open-label rising-dose study of omega interferon in IFN-naive patients with chronic hepatitis C," Gastroenterology 122:A278-A347 (Apr. 1, 2002) (Abstract M1454).
Bray, "Gut Signals and Energy Balance: Ghrelin, Peptide YY, Leptin, and Amylin," (Dec. 19, 2007) (slides and transcript for presentation at Medscape CME).
"Implantable infusion pumps: technology poised for takeoff," BBI Newsletter 17(12):209-211 (Dec. 1994).
Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).
Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).
Adolf et al., "Antigenic structure of human interferon ω1 (Interferon αll1): comparison with other human interferons," J. Gen. Virol. 68(6):1669-1676 (Jun. 1987).
Adolf et al., "Purification and characterization of natural human interferon ω1," J. Bio. Chem. 265(16):9290-9295 (Jun. 1990).
Adolf et al., "Human interferon ω1: isolation of the gene, expression in Chinese hamster ovary cells and characterization of the recombinant protein," Biochim. Biophys. Acta 108(9):167-174 (Jun. 1991).
Andrx Pharmaceuticals, LLC, ANDA for Concerta® Extended-Release Tablets, 6 pages (correspondence dated Sep. 6, 2005).
ASTM International, Annual Book of ASTM Standards, 8.02:208-211, 584-587 (1984).
Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).
Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).

(56) References Cited

OTHER PUBLICATIONS

Aulitzky, "Successful Treatment of Metastatic Renal Cell Carcinoma With a Biologically Active Dose of Recombinant Interferon-Gama," Journal of Clinical Oncology 7(12):1875-1884 (1989).
Hauck, "Engineer's Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill,F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al., "Hamster preproglucagon contains the sequence of glucagon and two related peptides," Nature 302:716-718 (1983).
Bell et al, "Impact of moisture on thermally induced denaturation and decomposition of lyophilized bovine somatotropin," Drug Delivery Research & Dev. Biopolymers, (35):201-209 (1995).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boué et al., "Antiviral and antiluteolytic activity of recombinant bovine IFN-ω1 obtained from Pichia pastoris," J. Interferon & Cytokine Res. 20:677-683 (2000).
Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
Chang et al., "Biodegradable polyester implants and suspension injection for sustained release of a cognitive enhancer," Pharm. Tech. 20(1):80-84 (1996).
Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).

Das et al., "Reviewing Antisense Oligonucleotide Therapy: Part 2, Delivery Issues," BioPharm, 2(11):44-51 (1999).
Dash et al., "Therapeutic applications of implantable drug delivery systems," Journal of Pharmacological and Toxicological Methods, 40(1):1-12 (1998).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Deacon et al., "GLP-1-(9-36) amide reduces blood glucose in anesthetized pigs by a mechanism that does not involve insulin secretion," Am. J. Physiol. Endocrinol. Metab., 282:E873-E879 (2002).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-osmotic actuation of implantable insulin micropumps," J. Biomed. Materials Res. 17:931-943 (1983).
Efendic et al., "Overview of incretin hormones," Horm. Metab. Res., 36(11-12):742-746 (2004).
Eissele et al., "Rat gastric somatostatin and gastrin release: interactions of exendin-4 and truncated glucagon-like peptide-1 (GLP-1) amide," Life Sci., 55(8):629-634 (1994).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eng et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Eng et al., "Purification and structure of exendin-3, a new pancreatic secretagogue isolated from Heloderma horridum venom," J. Biol. Chem., 265(33):20259-20262 (1990).
Eppstein et al., "Biological activity of liposome-encapsulated murine interferon γ is mediated by a cell membrane receptor," PNAS USA 82:3688-3692 (1985).
Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±ρ ribavirin therapy in patients with chronic hepatitis C," Prog. Abstr. 50th Annu. Mtg. Postgrad. Courses Am. Assn. Study Liver Dis., Dallas, TX (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al., "Combination of interferon (IFN) induction therapy and ribavirin in chronic hepatitis C," Prog. Abstr. Dig. Dis. Week 2000, San Diego, CA (May 21-24, 2000) (Abstract 977).
Fontaine et al., "Recovery from chronic hepatitis C in long-term responders to ribarivin plus interferon α ," Lancet 356(9223):41 (Jul. 2000).
Franchetti et al., "Furanfurin and Thiophenfurin: Two Novel Tiazofurin Analogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (DDAIP)," Int'l J. Pharmaceutics 234(12):121-128 (2002).

(56) References Cited

OTHER PUBLICATIONS

Luft et al., "Electro-osmotic valve for the controlled administration of drugs," Med. & Biological Engineering & Computing 45-50 (Jan. 1978) (non-English with English abstract).
Gan to Kagaku Ryoho, "Phase II study of recombinant leukocyte A interferon (Ro22-8181) in malignant brain tumors," Cancer & Chemotherapy 12(4):913-920 (Apr. 1985) (non-English with English abstract).
Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Ghiglione et al., "How glucagon-like is glucagon-like peptide-1?" Diabetologia 27:599-600 (1984).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX(Nov. 5-9, 1999)(Abstract 571).
Goke et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-α plus N-acetyl cysteine for chronic hepatitis C: a placebo controlled double-blind multicentre study," J. Med. Virol. 61(4):439-442 (Aug. 2000).
Gutniak et al., "Antidiabetogenic effect of glucagon-like peptide-1 (7-36)amide in normal subjects and patients with diabetes mellitus," N. Engl. J. Med., 326(20):1316-1322 (1992).
Hageman, "The Role of Moisture in Protein Stability," Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Heinrich et al., "Pre-proglucagon messenger ribonucleic acid: nucleotide and encoded amino acid sequences of the rat pancreatic complementary deoxyribonucleic acid," Endocrinol., 115:2176-2181 (1984).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).
Hisatomi et al., "Toxicity of polyoxyethylene hydrogenated castor oil 60 (HCO-60) in experimental animals," J. Toxicol. Sci., 18(3):1-9 (1993).
Hodoshima et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec. 1997).

Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).
IFNB Multiple Sclerosis Study Group, "Interferonβ-1b is effective in relapsing-remitting multiple sclerosis," Neurology 43(4):655-667 (Apr. 1993).
Intermune® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0-8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon 13-1b therapy in patients with MS," Neurology 54(1):193-199 (Jan. 2000).
Kronenberger et al., "Influence of interferon-αon CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).
Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).
Lee, "Therapy of hepatitis C: interferon alfa-2A trials," Hepatology 26: 89S-95S (Sep. 1997) (XP000981288).

(56) References Cited

OTHER PUBLICATIONS

Lopez et al., "Mammalian pancreatic preproglucagon contains three glucagon-related peptides," Proc. Natl. Acad. Sci. USA, 80(18):5485-5489 (1983).
Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lund et al., "Pancreatic preproglucagon cDNA contains two glucagon-related coding sequences arranged in tandem," Proc. Natl. Acad. Sci. USA, 79(2):345-349 (1982).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).
Marincola et al., "Combination therapy with interferon alfa-2a and interleukin-2 for the treatment of metastatic cancer," J. Clinical Oncol. 13(5):1110-1122 (1995) (XP009078965).
Massey, "Interaction of vitamin E with saturated phospholipid bilayers," Biochem. & Biophys. Res. Comms. 106(3):842-847 (1982).
McHutchison et al., "Interferon α-2b alone or in combination with ribavirin as initial treatment for chronic hepatitis C," N. Engl. J. Med. 339(21):1485-1492 (Nov. 1998).
McHutchison et al., "Open-label phase 1B study of hepatitis C viral dynamics with omega interferon treatment," Hepatology 34(4):A333 (Oct. 1, 2001) (XP004716177) (Abstract Only).
Meier et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).
Milella et al., "Neutralizing antibodies to recombinant α-interferon and response to therapy in chronic hepatitis C virus infection," Liver 13(3):146-150 (Jun. 1993).
Mohler, "Primer on electrodeposited coatings," Materials Engineering 5:38-45 (1972).
Mojsov, "Structural requirements for biological activity of glucagon-like peptide-I," Int. J. Peptide Protein Research, 40:333-343 (1992).
Morgan, "Structure and Moisture Permeability of Film-Forming Poloyers," Ind. Eng. Chem. 45(10):2296-2306 (1953).
Motzer et al., "Phase I trial of 40-kd branched pegylated interferon alfa-2a for patients with advanced renal cell carcinoma," J. Clinical Oncol. 19(5):1312-1319 (2001).
Nauck et al., "Normalization of fasting glycaemia by intravenous GLP-1 ([7-36 amide] or [7-37]) in type 2 diabetic patients," Diabet. Med., 15(11):937-945(1998).
Neumann et al., "Hepatitis C Viral Dynamics In Vivo and the Antiviral Efficacy of Interferon-alpha Therapy," Science 282:103-107 (Dec. 1998).
Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).
Norden et al., "Physicochemical characterization of a drug-containing phospholipid-stabilized o / w emulsion for intravenous administration," Eur. J. Pharm. Sci. 13(4):393-401 (2001).
Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).
Ortiz et al., "A differential scanning calorimetry study of the interaction of a-tocopherol with mixtures of phospholipids," Biochim et Biophys Acta 898(2):214-222 (1987).
Panitch, "Interferons in multiple sclerosis," Drugs 44(6):946-962 (Dec. 1992).
Patzelt et al., "Identification and processing of proglucagon in pancreatic islets," Nature, 282:260-266 (1979).
Peterson et al., "Zucker Diabetic Fatty Rat as a Model for Non-insulin-dependent Diabetes Mellitus," ILAR Journal, 32(3):16-19 (1990).
Peterson et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).
Plauth et al, "Open-label phase II study of omega interferon in previously untreated HCV infected patients," Hepatology 34(4):A331 (Oct. 1, 2001) (XP004716169) (Abstract Only).
Plauth et al, "Open-label study of omega interferon in previously untreated HCV-infected patients," J. Hepatology 36(Supp. 1):125 (Apr. 2002) (XP002511882) (Abstract Only).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J. Biol. Chem., 273(16):9778-9784 (1998).
Poynard et al., "Is an 'a la carte' combined interferon α 2b plus ribavirin possible for the first line treatment in patients with chronic hepatitis C," Hepatology 31(1):211-218 (Jan. 2000).
Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).
"Intarcia Presents Positive ITCA 650 Phase 2 Study Results for Type 2 Diabetes at EASD,"Intarcia Therapeutics, Inc. (Sep. 22, 2010) (Press Release).
Quesada et al., "Interferons in Hematological Malignancies", eds. Baron et al., U. Tex. 487-495 (1987).
Quintanar-Guerrero et al., "Applications of the ion-pair concept to hydrophilic substances with special emphasis on peptides," Pharm. Res. 14(2):119-127 (1997).
Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).
Roche Pharmaceuticals, Roferon®-A (Interferon alfa-2a, recombinant), 22 pages (2003).
Roff et al., "Handbook of Common Polymers", Cleveland Rubber Co. 72 pages (1971).
Rogers et al., "Permeability Valves," Ind. & Eng. Chem. 49(11):1933-1936 (Nov. 17, 1957).
Roman et al., "Cholestasis in the rat by means of intravenous administration of cyclosporine vehicle, Cremophor EL," Transplantation 48(4):554-558 (1989).
Roth et al., "High Dose Etretinate and Interferon-alpha—A Phase I Study in Squamous Cell Carcinomas and Transitional Cell Carcinomas," Acta Oncol. 38(5):613-617 (1999).
Roth et al., "Combination therapy with amylin and peptide YY[3-36] in obese rodents: anorexigenic synergy and weight loss additivity," Endocrinol. 148(12):6054-61 (Dec. 2007).
Schepp et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).
Schering Corp., Intron® A for Injection, 6 pages (2001).
Schering Corp., PEG-Intron™ (Peginterferon alfa-2b) Powder for Injection, 29 pages (2003).

(56) References Cited

OTHER PUBLICATIONS

Schmalfub et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).
Shiffman et al., "A decline in HCV-RNA level during interferon or interferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS: MSCRG trial of interferon β1a," Neurology 55(2):185-192 (Jul. 2000).
Sparks et al., "Lipoprotein alterations in 10- and 20-week-old Zucker diabetic fatty rats: hyperinsulinemic versus insulinopenic hyperglycemia," Metabolism, 47(11):1315-1324 (1998).
Sulkowski et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).
Sulkowski et al., "Peginterferon-α-2a (40kD) and ribavirin in patients with chronic hepatitis C: a phase II open label study," Biodrugs 16(2):105-109 (2002).
Talpaz et al., "Phase I study of polyethylene glycol formulation of interferon alpha-2B (Schering 54031) in Philadelphia chromosome-positive chronic myelogenous leukemia," Blood 98(6):1708-1713 (2001).
Talsania et al., "Peripheral exendin-4 and peptide YY(3-36) synergistically reduce food intake through different mechanisms in mice," Endocrinology 146(9):3748-56 ( Sep. 2005).
Tanaka et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).
Tong et al., "Prediction of response during interferon α 2b therapy in chronic hepatitis C patients using viral and biochemical characteristics: a comparison," Hepatology 26(6):1640-01645 (Dec. 1997).
Touza Rey et al., "The clinical response to interferon-γ in a patient with chronic granulomatous disease and brain abscesses due to Aspergillus fumigatus," Ann. Med. Int. 17(2):86-87 (Feb. 2000).
Trudeau et al., "A phase I study of recombinant human interferon alpha-2b combined with 5-fluorouracil and cisplatin in patients with advanced cancer," Cancer Chemother. Pharmacol. 35(6):496-500 (1995).
Tseng et al., "Glucose-dependent insulinotropic peptide: structure of the precursor and tissue-specific expression in rat," PNAS USA, 90(5):1992-1996 (1993).
Tsung et al., "Preparation and Stabilization of Heparin/Gelatin Complex Coacervate Microcapsules," J. Pharm. Sci. 86(5):603-7 (May 1997).
Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).
Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).
Vrabec, "Tympanic membrane perforations in the diabetic rat: a model of impaired wound healing," Otolaryngol. Head Neck Surg., 118(3 Pt. 1):304-308 (1998).

Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).
Wang et al., "Ripple phases induced by α-tocopherol in saturated diacylphosphatidylcholines," Archives of Biochem. & Biophys. 377(2):304-314 (2000).
Wang et al., "The distribution of α-tocopherol in mixed aqueous dispersions of phosphatidylcholine and phosphattidylethanolamine," Biochimica et Biophysica Acta—Biomembranes 1509(1-2):361-372 (2000).
Wang et al, "Parenteral formulations of proteins and peptides: stability and stabilizers," J. Parenter. Sci. Technol. 42(2S):S4-S26 (1988).
Weinstock-Guttman et al., "What is new in the treatment of multiple sclerosis?" Drugs 59(3):401-410 (Mar. 2000).
Weissmann et al., "The interferon genes," Prog. Nucleic Acid Res. Mol. Biol. 33:251-300 (1986).
Wright et al., "Preliminary experience with α-2b-interferon therapy of viral hepatitis in liver allograft recipients," Transplantation 53(1):121-123 (Jan. 1992).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes, 48(5):1026-1034 (1999).
Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).
Yu et al., "Preparation, characterization, and in vivo evaluation of an oil suspension of a bovine growth hormone releasing factor analog," J. Pharm. Sci. 85(4):396-401 (1996).
Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).
Zein, "Interferons in the management of viral hepatitis," Cytokines Cell Mol. Ther. 4(4):229-241 (Dec. 1998).
Zeuzem et al., "Peginterferon Alfa-2a in Patients with Chronic Hepatitis C," New Engl. J. Med. 343(23):1666-1672 (2000).
Zeuzem et al., "Hepatitis C virus dynamics in vivo: effect of ribavirin and interferon α on viral turnover," Hepatology 28(1):245-252 (Jul. 1998).
Zhang et al., "Report on Large Dosage Interferon to Treat 30 Cases of Viral Encephalitis," J. Clinical Pediatrics 14(2):83-84 (1996).
Zhang et al, "A new strategy for enhancing the stability of lyophilized protein: the effect of the reconstitution medium on keratinocyte growth factor," Pharm. Res. 12(10):1447-1452 (1995).
Zheng et al. "Therapeutic Effect of Interferon Varied Dose in Treating Virus Encephalitis," Beijing Med. J. 13(2):80-81 (1998).
Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).
Sanofi-Aventis U.S. LLC, Prescribing Information for ADLYXIN® (Lixisenatide) Injection, for Subcutaneous Use, rev. Jul. 2016, 31 pages.
Amylin Pharmaceuticals, Inc., Prescribing Information for BYETTA® (Exenatide) Injection, rev. Oct. 2009, 34 pages.
Astrazeneca Pharmaceuticals LP, Prescribing Information for BYDUREON® (Exenatide Extended-Release for Injectable Suspension), rev. Mar. 2015, 60 pages.
Novo Nordisk A/S, Prescribing Information for Victoza® (Liraglutide [rDNA Origin] Injection), Solution for Subcutaneous Use, v. 1, Jan. 2010, 23 pages.
Glaxosmithkline LLC, Prescribing Information for TANZEUM® (Albiglutide) for Injection, for Subcutaneous Use, rev. Jun. 2014, 55 pages.
Eli Lilly & Company, Prescribing Information for TRULICITY® (Dulaglutide) Injection, for Subcutaneous Use, rev. Mar. 2015, 19 pages.

(56) References Cited

OTHER PUBLICATIONS

Akers, et al., "Formulation Design and Development of Parenteral Suspensions," Journal of Parenteral Science & Technology, 41(3): 88-96 (1987).
Alonso, et al., "Determinants of Release Rate of Tetanus Vaccine from Polyester Microspheres," Pharmaceutical Research, 10(7):945-953 (1993).
Beck, et al., "Poly(dl-lactide-co-glycolide)/norethisterone microcapsules: An injectable biodegradable contraceptive," Biology of Reproduction, 28(1): 186-195 (1983).
Bodmeier and McGinity, "Solvent selection in the preparation of poly(dl-lactide) microspheres prepared by the solvent evaporation method," International Journal of Pharmaceutics, 43(1-2): 179-186 (Apr. 1988).
Cha and Pitt, "A one-week subdermal delivery system for I-methadone based on biodegradable microcapsules," Journal of Controlled Release, 7: 69-78 (1988).
Cha and Pitt, "The acceleration of degradation-controlled drug delivery from polyester microspheres," Journal of Controlled Release, 8: 259-265 (1989).
Cohen, et al., "Controlled delivery systems for proteins based on poly(lactic/glycolic acid) microspheres," Pharmaceutical Research, 8(6): 713-720 (1991).
Conti, et al., "Use of polylactic acid for the preparation of microparticulate drug delivery systems," Journal of Microencapsulation, 9(2): 153-166 (1992).
Hodgman, et al., Eds., Handbook of Chemistry and Physics, 35th Edition, 1024-1025 (1953).
Jalil and Nixon, "Biodegradable poly(lactic acid) and poly(lactide-co-glycolide) microcapsules: Problems associated with preparative techniques and release properties," Journal of Microencapsulation, 7(3): 297-325 (Jul.-Sep. 1990).
Lee and Timasheff, "The stabilization of proteins by sucrose," J. Biological Chem., 256(14): 7193-7201 (Jul. 1981).
Li, et al., "Prediction of solvent removal profile and effect on properties for peptide-loaded PLGA microspheres prepared by solvent extraction/evaporation method," Journal of Controlled Release, 37: 199-214 (1995).
Maa and Hsu, "Liquid-liquid emulsification by static mixers for use in microencapsulation," Journal of Microencapsulation, 13(4): 419-433 (Jul.-Aug. 1996).
Maulding, et al., "Biodegradable microcapsules: Acceleration of polymeric excipient hydrolytic rate by incorporation of a basic medicament," Journal of Controlled Release, 3: 103-117 (1986).
Mehta, et al.,"Peptide containing microspheres from low molecular weight and hydrophilic poly(d,l-lactide-co-glycolide)," Journal of Controlled Release, 41: 249-257 (1996).
Sah, et al., "A novel method of preparing PLGA microcapsules utilizing methylethyl ketone," Pharmaceutical Research, 13(3): 360-367 (1996).
Sato, et al., "Porous biodegradable microspheres for controlled drug delivery. I. Assessment of processing conditions and solvent removal techniques," Pharmaceutical Research, 5(1): 21-30 (1988).
Szayna, et al., "Exendin-4 decelerates food intake, weight gain, and fat deposition in Zucker rats," Endocrinology, 141(6): 1936-1941 (2000).
Thomasin, et al., "A contribution to overcoming the problem of residual solvents in biodegradable microspheres prepared by coacervation," Eur. J. Pharm. Biopharm., 42(1): 16-24 (1996).
Van Santbrink and Fauser, "Urinary follicle-stimulating hormone for normogonadotropic colomiphene-resistant anovulatory infertility: Prospective, randomized comparison between low dose step-up and step-down dose regimens," J. Clin. Endocrin. Metab., 82(11): 3597-3602 (1997).
Tracy et al., "Factors affecting the degradation rate of poly(lactide-co-glycolide) microspheresin vivo and in vitro." Biomaterials. 20(11:): 1057-1062 (1999).
Ertl et al., "Poly (DL-lactide-co-glycolide) microspheres as carriers for peptide vaccines," Vaccine 14(9):879-885.(1996).
Thompson et al., "Biodegradable microspheres as a delivery system for rismorelin porcine, a porcine-growth-hormone-releasing hormone," Journal of Controlled Release 43(1):9-22 (1997).
Registry of 1,2,3-Propanetriol (CAS No. 56-81-5) (Compound registered with CAS Nov. 16, 1984).

FIG. 20

Double Blind Placebo Controlled

| | ITCA 650 20 / 60 mcg | |
|---|---|---|
| | PBO Adjusted | Overall |
| Nausea | 22% | 31% |
| | 2.7% | 12.4% |
| | 22% | 24% |
| | 2.6% | 3.3% |
| | 2.6% | 3.3% |
| | 0% | 0% |

Open label Exenatide

| | Exenatide (N=461) | Liraglutide (N=450) |
|---|---|---|
| Patients with one or more adverse event* | 283 (61%) | 307 (68%) |
| Adverse events occurring in ≥2% of patients* | | |
| Nausea | 43 (9%) | 93 (21%) |
| Diarrhoea | 28 (6%) | 59 (13%) |
| Headache | 27 (6%) | 38 (8%) |
| Vomiting | 17 (4%) | 48 (11%) |
| Discontinuations because of adverse events | | |
| Nausea | 1 (<1%) | 9 (2%) |
| Vomiting | 1 (<1%) | 4 (<1%) |
| Diarrhoea | 1 (<1%) | 3 (<1%) |

FIG. 23

THERAPEUTIC METHODS FOR THE TREATMENT OF DIABETES AND RELATED CONDITIONS FOR PATIENTS WITH HIGH BASELINE HBA1C

CROSS-REFERENCE TO RELATED APPLICATIONS

This application is a continuation of U.S. patent application Ser. No. 14/871,420 filed Sep. 30, 2015 which claims priority to and the benefit of U.S. Provisional Patent Application Ser. Nos. 62/212,539, filed Aug. 31, 2015, 62/171,876, filed Jun. 5, 2015, 62/139,520, filed Mar. 27, 2015, and 62/057,892, filed Sep. 30, 2014. The entire contents of each above-mentioned application are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jan. 11, 2018, is named ITCA-042C01US_ST25.txt and is 1,563 bytes in size.

TECHNICAL FIELD

The present invention relates to organic chemistry, formulation chemistry, and peptide chemistry applied to pharmaceutical research and development. Aspects of the present invention include, but are not limited to, methods of treatment for a disease or condition in a subject in need of such treatment. In one embodiment, the disease is type 2 diabetes mellitus. In other embodiments, the present invention relates to therapeutic methods for lowering plasma glucose and HbA1c levels in diabetic subjects, including subjects having high baseline HbA1c levels, by continuous subcutaneous delivery of an anti-diabetic medication such as an exenatide from an implanted drug delivery device (subdermal) over an administration period. Improvements with respect to weight loss, the incidence and severity of side effects, quality of life measures, and patient tolerance to dose escalation during treatment are also provided. In some embodiments, a subject has a baseline HbA1c % of greater than 6.5% or greater than 10.0%.

BACKGROUND OF THE INVENTION

Type 2 diabetes mellitus is a metabolic disorder characterized by hyperglycemia (high blood sugar) resulting from insulin deficiency (the inability of the body to produce sufficient insulin) or insulin resistance (the inability of the body to use insulin properly). Chronic hyperglycemia is likely to worsen type 2 diabetes mellitus, as excessive glucose in the blood can damage the pancreas (and thus impair insulin release, a condition which can become permanent) and contribute to insulin deficiency. Long-term complications of type 2 diabetes mellitus include heart disease, stroke, diabetic retinopathy, kidney failure, and poor blood circulation to the limbs, which may require amputation.

Long term hyperglycemia is monitored by periodic measurement of a subject's hemoglobin A1c (HbA1c) levels. HbA1c levels reflect a subject's average blood glucose levels over the previous two to three months. Studies have shown that the incidences of clinical complications from type 2 diabetes are significantly associated with a subject's degree of hyperglycemia, as indicated by HbA1c levels. In the UK Prospective Diabetes Study (UKPDS), incidence rates for any end point related to diabetes (e.g., fatal or non-fatal myocardial infarction, amputation or death from peripheral vascular disease, and fatal or non-fatal microvascular disease) was three-fold greater for subjects in the highest HbA1c level category, e.g., greater than or equal to 10%, when compared to subjects with HbA1c of less than 6%. Furthermore, the UKPDS study showed that there are many benefits from reducing a high HbA1c level; as examples, reducing HbA1c levels by 1% results in a 14% decrease in risk of fatal or non-fatal myocardial infarction, a 12% decrease in risk of fatal or non-fatal stroke, a 21% decrease in risk of diabetes-related death, a 43% decrease in risk of amputation, and a 37% decrease in risk of small blood vessel disease (e.g., retinal blood vessel disease causing vision loss). Methods for reducing HbA1c levels in subjects with type 2 diabetes, particularly those with high (e.g., >10%) HbA1c levels, is warranted.

A variety of drug dosage forms and methods of drug administration have been developed for delivery of drugs to mammals, in particular, for delivery of drugs to humans (see, e.g., the Merck Manual of Diagnosis and Therapy, 18th edition, Published by Merck Sharp & Dohme Corp., Whitehouse Station, N.J.). Such dosage forms include, for example, use of the following routes of administration: oral; injection (e.g., intravenously, intramuscularly, intrathecally, subdermally, and subcutaneously); implantation (e.g., subcutaneous); and across a skin or mucosal barrier (e.g., sublingual, rectal, vaginal, ocular, nasal, inhalation into the lungs, topical, and transdermal). Each route of administration has specific purposes, advantages, and disadvantages.

The oral route of administration is the most common and generally considered to be the most convenient. Oral administration, however, poses some limitations because drugs administered by this route can be subject to inter- and/or intra-subject variability and result in variable 24 hour plasma drug exposure. Other routes of administration may be required when the oral route cannot be used.

When drugs are prepared for administration by injection (e.g., subcutaneous, intramuscular, intravenous, and intrathecal administration), the drug can be formulated in a variety of ways including formulations that prolong drug absorption from the injection site for hours, days, or longer. Such formulations are typically used for subcutaneous injection. Injectable products formulated for prolonged delivery typically are not administered as often as injectable drug products having more rapid absorption. Subcutaneous administration is used for many protein or peptide drugs because such drugs are typically broken down by the digestive system to inactive forms if taken orally. Subcutaneous administration of a drug typically requires frequent self-injection, for example, one or more times daily or once-weekly injections.

When a large volume of a drug product is required, intramuscular administration is generally the preferred route of administration. Typically, intramuscular administration of drugs is by injection into the muscle of the upper arm, thigh, or buttock. The rate of drug absorption into the bloodstream in large part depends on the blood supply to the muscle, that is, the more blood supply the faster the drug is absorbed.

Intravenous drug administration requires that a needle be inserted directly into a vein. A drug may be given in a single dose or continuously infused. For infusion, a drug solution is either delivered using gravity (e.g., from a collapsible plastic bag) or using an infusion pump through a tube inserted in a vein, usually in the forearm. An intravenous injection can be more difficult to administer than a subcutaneous or intramuscular injection, for example, because inserting a needle or catheter into a vein may be difficult, drugs typically must be mixed within a relatively short time before beginning administration, there is an increased chance of infection (e.g., abscessed infections of injection sites caused by lack of hygiene and/or a lack of correct aseptic technique), and over time there is scarring damage to the peripheral veins.

When drugs are administered by intravenous injection it is often desirable for health care practitioners to closely monitor subjects for signs that the drug is working and that the drug is not causing undesired side effects. Typically, the effect of intravenously administered drugs tends to last for a shorter periods of time than drugs administered by subcutaneous injection or intramuscular injection. Therefore, some drugs must be administered by continuous infusion to provide appropriate therapeutic effect. Because of the difficulties associated with intravenous drug administration it is most typically used in hospital or skilled care settings; it is rarely used for long-term self-administered treatment.

A number of complications negatively impact compliance with injection treatment regimens, including, but not limited to, the following. For a subject that is needle phobic, this is particularly troublesome when a drug must be self-injected over extended periods of time. Compliance can also be complicated by the inconvenience of administration of a drug by injection, for example, when subjects are in public or busy with daily activities. Also, frequent self-administration of a drug reminds subjects of their disease state and carries a stigma associated with the disease and/or treatment. Additionally, there is a risk of depot of drug at injection site, such as when the drug does not sufficiently or rapidly diffuse or distributed into adjoining tissues. Such depot can lead to undesirable immune reactions, e.g., immune complex formation, inflammation, and high antibody titer, and/or can lead to local swelling, redness, and pain.

The implantable osmotic delivery devices of the present invention, and use of these osmotic delivery devices in methods for the treatment of diseases or conditions in subjects in need of treatment, uniquely address unmet needs of previously described drug dosage forms and methods of treatment. For example, the present invention provides treatment of subjects at a target drug dose that is continuously administered over time with the ability to rapidly establish and sustain over time substantial steady-state drug delivery while also providing the ability to rapidly terminate administration of the drug. Heretofore, drug administration via injection has not typically been able to provide rapid establishment and long-term maintenance (e.g., three months or more) of steady-state drug delivery and, even if that were possible, treatment using drugs administered by injection (e.g., drugs formulated for prolonged delivery) has not been able to be rapidly terminated. The present invention also provides for enhanced tolerization of subjects to drug dose escalation relative to dose escalation performed by administration of drug by injection.

The clinical challenges encountered with long-term pharmacological treatment of type 2 diabetes include hypoglycemia, weight gain, and side effects and aversion to self-injection, which often contribute to poor adherence and persistence with therapy. Poor adherence and persistence with antidiabetic therapy are common; a systematic review of the literature reported that adherence rates to oral drugs ranged from 36% to 93% and for insulin was approximately 60%, and a recent report found discontinuation rates >80% with Glucagon-like peptide-1 receptor agonists (GLP-1 RAs; a class of drug for treating type 2 diabetes) at 12 months. An evaluation of persistence with injectable antidiabetic agents, including insulin and an exenatide, found that only 28.7% of patients persisted with therapy to 1 year. Much of this non-adherence may be because of the inconvenience and discomfort associated with injectable antidiabetic drugs. The consequences of poor adherence include inadequate glycemic control, increased morbidity and mortality, impacts on the benefit/risk ratio of a drug and overall tolerability, and markedly increased healthcare costs. Many interventions have been studied and recommended to increase medication adherence, but most require extensive and continuous use of costly healthcare resources, and the beneficial effects on adherence are temporary. These concerns about poor compliance and adherence are abrogated by the use of an osmotic delivery device and formulations useful in the present invention.

SUMMARY OF THE INVENTION

The present invention generally relates to improved methods of treating diseases or conditions in subjects in need of treatment, wherein the methods of the invention provide rapid establishment and/or rapid termination of substantial steady-state drug delivery. Further, the present invention relates to methods of escalating drug dose that provide improved tolerization of subjects to increased drug dose levels relative to dose escalation by standard drug injection methods. Preferred subjects for the methods of the present invention are humans.

The present invention relates to methods of treating type 2 diabetes mellitus. The subject is in need of treatment for type 2 diabetes. The subject has a baseline hemoglobin A1c (HbA1c) % of greater than 6.5%. The subject may have a baseline HbA1c % of greater than 10.0%. The subject may not have previously received a drug for treating type 2 diabetes mellitus. The subject may have a baseline HbA1c % of less than or equal to 12%.

The methods comprise providing continuous delivery of an insulinotrophic peptide from an osmotic delivery device to the subject, wherein substantial steady-state delivery of the insulinotrophic peptide at a therapeutic concentration is achieved within a time period up to about 7 days after implantation of the osmotic delivery device in the subject, e.g., subcutaneously and/or subdermally. Thus, steady-state delivery of the insulinotrophic peptide occurs at any time point after implantation and up to about 7 days after implantation; non-limiting examples include 1 hour after implantation, 18 hours after implantation, 2 and a half days after implantation, and five days after implantation. In some embodiments of the invention, the substantial steady-state delivery of the insulinotrophic peptide at therapeutic concentrations is achieved after implantation of the osmotic delivery device in the subject within a time period selected from the group consisting of about 6 days, about 5 days, about 4 days, about 3 days, about 2 days, and about 1 day. The substantial steady-state delivery of the insulinotrophic peptide from the osmotic delivery device is typically continuous over an administration period of at least about 1 month, e.g., at least about 1 month, at least about 2 months, and at least about 3 months.

The substantial steady-state delivery of the insulinotrophic peptide from the osmotic delivery device is continuous over an administration period of, for example, at least about 1 month to about two years, at least about 2 months to about two years, at least about 3 months to about two years, at least about 4 months to about two years, at least about 5 months to about two years, at least about 6 months to about two years, at least about 8 months to about two years, or at least about 9 months to about two years, about 1 year, at least one year to about two years, at least about 14 months to about two years, at least about 16 months to about two years, at least 18 months to about two years, at least about 20 months to about two years, at least about 22 months to about two years, and about two years.

The substantial steady-state delivery of the insulinotrophic peptide from the osmotic delivery device is continuous over an administration period selected from the group consisting of at least about 12 months to about 18 months, at least about 13 months to about 18 months, at least about 14 months to about 18 months, at least about 15 months to about 18 months, at least about 16 months to about 18 months, at least about 17 months to about 18 months, and about 18 months.

The substantial steady-state delivery of the insulinotrophic peptide from the osmotic delivery device is continuous over an administration period selected from the group consisting of at least about 1 month to about a year, at least about 2 months to about a year, about 3 months, at least about 3 months to about a year, at least about 4 months to about a year, at least about 5 months to about a year, about 6 months, at least about 6 months to about a year, at least about 8 months to about a year, about 9 months, at least about 9 months to about a year, at least about 10 months to about a year, at least about 11 months to about a year, and about a year.

The continuous delivery can, for example, be zero-order, controlled continuous delivery.

The methods can further comprise providing a significant decrease in the subject's fasting plasma glucose concentration after implantation of the osmotic delivery device in the subject, relative to the subject's fasting plasma glucose concentration before implantation of the osmotic delivery device. The decrease is typically obtained within, for example, about 7 days, about 6 days, about 5 days, about 4 days, about 3 days, about 2 days, and about 1 day. Normally, a significant decrease in fasting plasma glucose is maintained over the administration period. Thus, a subject's fasting plasma glucose concentration will initially decrease within any time point after implantation and up to about 7 days after implantation.

The methods can further comprise providing a significant decrease in the subject's HbA1c % after implantation of the osmotic delivery device in the subject, relative to the subject's HbA1c % before implantation of the osmotic delivery device. The decrease is typically achieved within about six weeks after implantation of the osmotic delivery device (e.g., within about five weeks after implantation of the osmotic delivery device, within about four weeks after implantation of the osmotic delivery device, within about three weeks after implantation of the osmotic delivery device, within about two weeks after implantation of the osmotic delivery device, or within about one week after implantation of the osmotic delivery device). The significant decrease in the subject's HbA1c % is maintained over the administration period.

The methods can further provide a decrease in a subject's HbA1c % over the administration period of at least about 0.5%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, or at least about 6.0% from baseline over the administration period or a reduction in the amount of HbA1c in the subject's serum of at least about 35 percent, at least about 40 percent, at least about 45 percent, at least about 50 percent, or at least about 55 percent at the end of an administration period relative to the beginning of the administration period.

Also, in any of the methods provided herein, termination of the continuous delivery of the insulinotrophic peptide (e.g., an exenatide) produces a serum concentration of the insulinotrophic peptide that is substantially undetectable in a blood sample from the subject within about 6 half-lives, about 5 half-lives, about 4 half-lives, or about 3 half-lives of the insulinotrophic peptide after termination of continuous delivery. Thus, the insulinotrophic peptide will be substantially undetectable in a subject's blood sample within any time point after termination of continuous delivery and up to about 6 half-lives after termination of continuous delivery. Termination of the continuous delivery produces a serum concentration of the insulinotrophic peptide (e.g., an exenatide) that is substantially undetectable in a blood sample from the subject after termination of continuous delivery within a number of hours selected from the group consisting of about 72 hours, about 48 hours, about 24, about 18 hours, about 14 hours, about 12 hours, about 10 hours, about 8 hours, about 6 hours, and about 4 hours. Thus, the insulinotrophic peptide will be substantially undetectable in a subject's blood sample within any time point after termination of continuous delivery and up to about 72 hours after termination of continuous delivery. In some embodiments, continuous delivery of the insulinotrophic peptide is terminated by removal of the osmotic delivery device from the subject. The serum concentration of the insulinotrophic peptide is, for example, detected by a radioimmunoassay (RIA), a chromatographic method, an electrochemiluminescent (ECL) assay, an enzyme linked immunosorbent assay (ELISA) or an immunoenzymatic sandwich assay (IEMA).

Osmotic delivery devices for use in the methods of the present invention can comprise the components described herein including, but not limited to, a reservoir, a semipermeable membrane, an osmotic engine, a piston, a suspension formulation, and a diffusion moderator. In some embodiments, the osmotic delivery device comprises: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable. The osmotic delivery device comprises a diffusion moderator inserted in the second open end of the reservoir, the diffusion moderator adjacent the suspension formulation. In some embodiments, the reservoir comprises titanium or a titanium alloy.

Suspension formulations used in the methods of the present invention typically comprise a particle formulation comprising a therapeutic agent (e.g., an insulinotrophic peptide, preferably, an exenatide) and a vehicle formulation. A vehicle formulation comprises a solvent (e.g., benzyl benzoate, lauryl lactate, and lauryl alcohol) and a polymer (e.g., polyvinylpyrrolidone: also herein referred to as PVP, polyvidone, and povidone). Preferably, the polymer is polyvinylpyrrolidone. The vehicle formulation may have a viscosity of between about 10,000 poise and about 20,000 poise at 37° C.

Examples of insulinotrophic peptides useful in the methods of the present invention include, but are not limited to, the exenatide having the amino acid sequence of SEQ ID NO: 1, native exendin-4, exenatide peptides, exenatide peptide analogs, exenatide peptide derivatives, glucagon-like peptide 1 (GLP-1), GLP-1 peptides, GLP-1 peptide analogs, or GLP-1 peptide derivatives. Examples of preferred insulinotrophic peptides include the exenatide having the amino acid sequence of the native exendin-4 (SEQ ID NO: 1), exenatide-LAR, lixisenatide, GLP-1(7-36), liraglutide, dulaglutide, albiglutide, and taspoglutide. Short-acting insulinotrophic peptides (2-5 hours) include the exenatide having the amino acid sequence of SEQ ID NO: 1 (e.g., BYETTA®) and lixisenatide and long-acting insulinotrophic peptides include liraglutide, dulaglutide, albiglutide, and exenatide-LAR.

An insulinotrophic peptide can be included in a particle formulation, in a suspension formulation, and/or in a single osmotic delivery device along with one or more (e.g., one, two, three, four, or more) other therapeutic agents; thus, an osmotic delivery device may provide substantial steady-state delivery of the insulinotrophic peptide and one or more other therapeutic agents. Non-limiting examples of the one or more other therapeutic agents include amylin, an amylin analogue (e.g., pramlintide), a ghrelin antagonist, a G protein coupled receptor 119 (GRP 119) agonist, and leptin. An osmotic delivery device may provide substantial steady-state delivery of two or more insulinotrophic peptides.

Particles of a particle formulation comprising an insulinotrophic peptide have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. When the insulinotrophic peptide is an exenatide, particles have diameters of between about 2 microns and about 50 microns.

In some methods, continuous delivery provides to the subject a μg/day dose (also referenced to herein as a mcg/day dose) of an insulinotrophic peptide (e.g., an exenatide) selected from the group consisting of about 10 μg/day, about 15 μg/day, about 20 μg/day, about 30 μg/day, about 40 μg/day, about 50 μg/day, about 60 μg/day, about 70 μg/day, and about 80 μg/day. The upper limit to the daily dose depends to the peptide/active agent and the total capacity of the device itself. A skilled artisan would be able to determine a suitable dose (with regards to safety and efficacy) for a specific insulinotrophic peptide. Thus, the daily dose may exceed 80 μg/day.

Preferably, the mcg/day dose of the insulinotrophic peptide is about 20 mcg/day. More preferably, the insulinotrophic peptide is an exenatide and the mcg/day dose is about 20 mcg/day.

Preferably, the mcg/day dose of the insulinotrophic peptide is about 40 mcg/day. More preferably, the insulinotrophic peptide is an exenatide and the mcg/day dose is about 40 mcg/day.

Preferably, the mcg/day dose of the insulinotrophic peptide is about 60 mcg/day. More preferably, the insulinotrophic peptide is an exenatide and the mcg/day dose is about 60 mcg/day.

Some methods further comprise a first continuous administration period of the insulinotrophic peptide at a first μg/day dose that is followed by a second continuous administration period providing a dose escalation of the insulinotrophic peptide to a second μg/day dose, wherein the second μg/day dose is greater than the first μg/day dose. The first μg/day dose is, for example, delivered by a first osmotic delivery device and the second μg/day dose is delivered by an, at least, second osmotic delivery device. Delivery of the insulinotrophic peptide from the first osmotic delivery device is continuous over the administration period of at least about 1 month, e.g., at least about 1 month, at least about 2 months, and at least about 3 months. Delivery of the insulinotrophic peptide from the at least second osmotic delivery device is continuous over the administration period of at least about 1 month, e.g., at least about 1 month, at least about 2 months, and at least about 3 months. In one embodiment, the second μg/day dose is at least two times greater than the first μg/day dose. The method can further comprise at least one more continuous administration period providing a dose escalation of the insulinotrophic peptide to a higher μg/day dose relative to the second μg/day dose. In some embodiments, the method further comprises at least one more continuous administration period, subsequent to the second continuous administration period, providing a dose at the same mcg/day dose as the second mcg/day dose. Dose escalation allows a subject to receive a therapeutic benefit while being gradually exposed to the insulinotrophic peptide. This tolerizes the subject to the insulinotrophic peptide and reduces the incidence of side effects. Later, once the subject has completed an initial tolerization period with a first, low daily dose, the dose is escalated to a maintenance dose.

Exemplary dose escalations for the insulinotrophic peptide (e.g., an exenatide) are as follows: about 10 μg/day followed by about 20 μg/day; about 10 μg/day followed by about 30 μg/day; about 10 μg/day followed by about 40 μg/day; about 10 μg/day followed by about 50 μg/day; about 10 μg/day followed by about 60 μg/day; about 10 μg/day followed by about 70 μg/day; about 10 μg/day followed by about 80 μg/day; about 15 μg/day followed by about 20 μg/day; about 15 μg/day followed by about 30 μg/day; about 15 μg/day followed by about 40 μg/day; about 15 μg/day followed by about 50 μg/day; about 15 μg/day followed by about 60 μg/day; about 15 μg/day followed by about 70 μg/day; about 15 μg/day followed by about 80 μg/day; about 20 μg/day followed by about 30 μg/day; about 20 μg/day followed by about 40 μg/day; about 20 μg/day followed by about 50 μg/day; about 20 μg/day followed by about 60 μg/day; about 20 μg/day followed by about 70 μg/day; about 20 μg/day followed by about 80 μg/day; about 40 μg/day followed by about 50 μg/day; about 40 μg/day followed by about 60 μg/day; about 40 μg/day followed by about 70 μg/day; about 40 μg/day followed by about 80 μg/day; about 50 μg/day followed by about 60 μg/day; about 50 μg/day followed by about 60 μg/day; about 50 μg/day followed by about 70 μg/day; about 50 μg/day followed by about 80 μg/day; about 60 μg/day followed by about 70 μg/day or about 60 μg/day followed by about 80 μg/day.

Preferably, the first mcg/day dose of the insulinotrophic peptide (e.g., an exenatide) followed by the second mcg/day dose for continuous delivery is about 20 mcg/day followed by about 40 mcg/day.

Preferably, the first mcg/day dose of the insulinotrophic peptide (e.g., an exenatide) followed by the second mcg/day dose for continuous delivery is about 20 mcg/day followed by about 60 mcg/day.

In some methods of the present invention, the subject has not previously received a drug for treating type 2 diabetes mellitus.

In any of the above-described methods, the insulinotrophic peptide may comprise GLP-1 or an incretin mimetic selected the group consisting of a GLP-1 peptide, a peptide analog of GLP-1, or a peptide derivative of GLP-1, an exenatide (which includes the exenatide having the amino acid sequence of SEQ ID NO: 1, native exendin-4, an exenatide peptide, a peptide analog of exenatide, and a peptide derivative of exenatide). In any of the above methods, the insulinotrophic peptide is selected from the group consisting of lixisenatide, liraglutide, albiglutide, and taspoglutide.

In any of the above-described methods, the subject may further be provided one or more other drugs for treating type 2 diabetes mellitus, e.g., insulin and/or oral anti-diabetic drugs including, without limitation, DPP4 inhibitors, SGLT2 inhibitors, metformin, sulfonylureas, and thiazolidinediones (TZDs).

Any of the above-described methods further promote weight loss in a subject in need thereof. Preferably, the subject has a baseline HbA1c % of greater than 6.5%. More preferably, the subject has a baseline HbA1c % of greater than 10.0%. The subject may have a baseline HbA1c % of less than or equal to 12%. Significant weight loss is achieved by about six weeks (e.g., about five weeks, about four weeks, about three weeks, about two weeks, and about one week) after initial implantation of the osmotic delivery device and up to 39 weeks after initial implantation.

The present invention relates to methods of treating type 2 diabetes mellitus comprising providing continuous delivery of an exenatide from an osmotic delivery device to the subject. The subject is in need of treatment for type 2 diabetes. The subject has a baseline hemoglobin A1c (HbA1c) % of greater than 6.5%. The subject may have a baseline HbA1c % of greater than 10.0%. The subject may not have previously received a drug for treating type 2 diabetes mellitus. The subject may have a baseline HbA1c % of less than or equal to 12%.

Substantial steady-state delivery of the exenatide at a therapeutic concentration is achieved within a time period up to about 7 days after implantation of the osmotic delivery device in the subject, e.g., subcutaneously and/or subdermally. Thus, steady-state delivery of the exenatide occurs at any time point after implantation and up to about 7 days after implantation; non-limiting examples include 1 hour after implantation, 18 hours after implantation, 2 and a half days after implantation, and five days after implantation. In some embodiments of the invention, the substantial steady-state delivery of the exenatide at therapeutic concentrations is achieved after implantation of the osmotic delivery device in the subject within a time period selected from the group consisting of about 6 days, about 5 days, about 4 days, about 3 days, about 2 days, and about 1 day. The substantial steady-state delivery of the exenatide from the osmotic delivery device is typically continuous over an administration period of at least about 1 month, e.g., at least about 1 month, at least about 2 months, and at least about 3 months.

The substantial steady-state delivery of the exenatide from the osmotic delivery device is continuous over an administration period of, for example, at least about 1 month to about two years, at least about 2 months to about two years, at least about 3 months to about two years, at least about 4 months to about two years, at least about 5 months to about two years, at least about 6 months to about two years, at least about 8 months to about two years, or at least about 9 months to about two years, about 1 year, at least one year to about two years, at least about 14 months to about two years, at least about 16 months to about two years, at least 18 months to about two years, at least about 20 months to about two years, at least about 22 months to about two years, and about two years.

The substantial steady-state delivery of the exenatide from the osmotic delivery device is continuous over an administration period selected from the group consisting of at least about 12 months to about 18 months, at least about 13 months to about 18 months, at least about 14 months to about 18 months, at least about 15 months to about 18 months, at least about 16 months to about 18 months, at least about 17 months to about 18 months, and about 18 months.

The substantial steady-state delivery of the exenatide from the osmotic delivery device is continuous over an administration period selected from the group consisting of at least about 1 month to about a year, at least about 2 months to about a year, about 3 months, at least about 3 months to about a year, at least about 4 months to about a year, at least about 5 months to about a year, about 6 months, at least about 6 months to about a year, at least about 8 months to about a year, about 9 months, at least about 9 months to about a year, at least about 10 months to about a year, at least about 11 months to about a year, and about a year.

The continuous delivery can, for example, be zero-order, controlled continuous delivery.

The methods can further comprise providing a significant decrease in the subject's fasting plasma glucose concentration after implantation of the osmotic delivery device in the subject, relative to the subject's fasting plasma glucose concentration before implantation of the osmotic delivery device. The decrease is typically obtained within, for example, about 7 days, about 6 days, about 5 days, about 4 days, about 3 days, about 2 days, and about 1 day. Normally, a significant decrease in fasting plasma glucose is maintained over the administration period. Thus, a subject's fasting plasma glucose concentration will initially decrease within any time point after implantation and up to about 7 days after implantation.

The methods can further comprise providing a significant decrease in the subject's HbA1c % after implantation of the osmotic delivery device in the subject, relative to the subject's HbA1c % before implantation of the osmotic delivery device. The decrease is typically achieved within about six weeks after implantation of the osmotic delivery device (e.g., within about five weeks after implantation of the osmotic delivery device, within about four weeks after implantation of the osmotic delivery device, within about three weeks after implantation of the osmotic delivery device, within about two weeks after implantation of the osmotic delivery device, or within about one week after implantation of the osmotic delivery device). The significant decrease in the subject's HbA1c % is maintained over the administration period.

The methods can further provide a decrease in a subject's HbA1c % over the administration period of at least about 0.5%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, or at least about 6.0% from baseline over the administration period or a reduction in the amount of HbA1c in the subject's serum of at least about 35 percent, at least about 40 percent, at least about 45 percent, at least about 50 percent, or at least about 55 percent at the end of an administration period relative to the beginning of the administration period.

Also, in any of the methods provided herein, termination of the continuous delivery of the exenatide produces a serum concentration of the exenatide that is substantially undetectable in a blood sample from the subject within about 6 half-lives, about 5 half-lives, about 4 half-lives, or about 3 half-lives of the exenatide after termination of continuous delivery. Thus, the exenatide will be substantially undetectable in a subject's blood sample within any time point after termination of continuous delivery and up to about 6 half-lives after termination of continuous delivery. Termination of the continuous delivery produces a serum concentration of the exenatide that is substantially undetectable in a blood sample from the subject after termination of continuous delivery within a number of hours selected from the group consisting of about 72 hours, about 48 hours, about 24, about 14 hours, about 12 hours, about 10 hours, about 8 hours, about 6 hours, and about 4 hours. Thus, the exenatide will be substantially undetectable in a subject's blood sample within any time point after termination of continuous delivery and up to about 72 hours after termination of continuous delivery. In some embodiments, continuous delivery of the exenatide is terminated by removal of the osmotic delivery device from the subject. The serum concentration of the exenatide is, for example, detected by a radioimmunoassay (RIA), a chromatographic method, an electrochemiluminescent (ECL) assay, an enzyme linked immunosorbent assay (ELISA) or an immunoenzymatic sandwich assay (IEMA).

Osmotic delivery devices used in the methods of the present invention can comprise the components described herein including, but not limited to, a reservoir, a semi-permeable membrane, an osmotic engine, a piston, a suspension formulation, and a diffusion moderator. In some embodiments, the osmotic delivery device comprises: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable. The osmotic delivery device comprises a diffusion moderator inserted in the second open end of the reservoir, the diffusion moderator adjacent the suspension formulation. In some embodiments, the reservoir comprises titanium or a titanium alloy.

Suspension formulations used in methods of the present invention typically comprise a particle formulation comprise an exenatide and a vehicle formulation.

A vehicle formulation comprises a solvent (e.g., benzyl benzoate, lauryl lactate, and lauryl alcohol) and a polymer (e.g., polyvinylpyrrolidone: also herein referred to as PVP, polyvidone, and povidone). Preferably, the polymer is polyvinylpyrrolidone. The vehicle formulation may have a viscosity of between about 10,000 poise and about 20,000 poise at 37° C.

Examples of exenatides useful in the methods of the present invention include, but are not limited to, exenatide peptides, exenatide peptide analogs, exenatide peptide derivatives, the exenatide having the amino acid sequence of the native exendin-4 (SEQ ID NO: 1), native exendin-4, exenatide-LAR, and lixisenatide. Short-acting exenatides (2-5 hours) include the exenatide having the amino acid sequence of SEQ ID NO: 1 (e.g., BYETTA) and lixisenatide and long-acting exenatides include liraglutide and exenatide-LAR.

An exenatide can be included in a particle formulation, in a suspension formulation, and/or in a single osmotic delivery device along with one or more (e.g., one, two, three, four, or more) other therapeutic agents; thus, an osmotic delivery device may provide substantial steady-state delivery of the exenatide and one or more other therapeutic agents. Non-limiting examples of the one or more other therapeutic agents include amylin, an amylin analogue (e.g., pramlintide), a ghrelin antagonist, a G protein coupled receptor 119 (GRP 119) agonist, and leptin. An osmotic delivery device may provide substantial steady-state delivery of two or more exenatides.

Particles of a particle formulation comprising an exenatide have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. Preferably, particles have diameters of between about 2 microns and about 50 microns.

In some methods, continuous delivery provides to the subject a µg/day dose of the exenatide selected from the group consisting of about 10 µg/day, about 15 µg/day, about 20 µg/day, about 30 µg/day, about 40 µg/day, about 50 µg/day, about 60 µg/day, about 70 µg/day, and about 80 µg/day. The upper limit to the daily dose depends to the peptide/active agent and the total capacity of the device itself. Thus, the daily dose may exceed 80 µg/day.

Preferably, the mcg/day dose of the exenatide is about 20 mcg/day.

Preferably, the mcg/day dose of the exenatide is about 40 mcg/day.

Preferably, the mcg/day dose of the exenatide is about 60 mcg/day.

Some methods further comprise a first continuous administration period of the exenatide at a first µg/day dose that is followed by a second continuous administration period providing a dose escalation of the exenatide to a second µg/day dose, wherein the second µg/day dose is greater than the first µg/day dose. The first µg/day dose is, for example, delivered by a first osmotic delivery device and the second µg/day dose is delivered by an, at least, second osmotic delivery device. Delivery of the exenatide from the first osmotic delivery device is continuous over the administration period of at least about 1 month, e.g., at least about 1 month, at least about 2 months, and at least about 3 months. Delivery of the exenatide from the at least second osmotic delivery device is continuous over the administration period of at least about 1 month, e.g., at least about 1 month, at least about 2 months, and at least about 3 months. In one embodiment, the second µg/day dose is at least two times greater than the first µg/day dose. The method can further comprise at least one more continuous administration period providing a dose escalation of the exenatide to a higher µg/day dose relative to the second µg/day dose. In some embodiments, the method further comprises at least one more continuous administration period, subsequent to the second continuous administration period, providing a dose at the same mcg/day dose as the second mcg/day dose. Dose escalation allows a subject to receive a therapeutic benefit while being gradually exposed to the exenatide. This tolerizes the subject to the exenatide and reduces the incidence of side effects. Later, once the subject has completed an initial tolerization period with a first, low daily dose, the dose is escalated to a maintenance dose.

Exemplary dose escalations for the exenatide are as follows: about 10 µg/day followed by about 20 µg/day; about 10 µg/day followed by about 30 µg/day; about 10 µg/day followed by about 40 µg/day; about 10 µg/day followed by about 50 µg/day; about 10 µg/day followed by about 60 µg/day; about 10 µg/day followed by about 70 µg/day; about 10 µg/day followed by about 80 µg/day; about 15 µg/day followed by about 20 µg/day; about 15 µg/day followed by about 30 µg/day; about 15 µg/day followed by about 40 µg/day; about 15 µg/day followed by about 50 µg/day; about 15 µg/day followed by about 60 µg/day; about 15 µg/day followed by about 70 µg/day; about 15 µg/day followed by about 80 µg/day; about 20 µg/day followed by about 30 µg/day; about 20 µg/day followed by about 40 µg/day; about 20 µg/day followed by about 50 µg/day; about 20 µg/day followed by about 60 µg/day; about 20 µg/day followed by about 70 µg/day; about 20 µg/day followed by about 80 µg/day; about 40 µg/day followed by about 50 µg/day; about 40 µg/day followed by about 60 µg/day; about 40 µg/day followed by about 70 µg/day; about 40 µg/day followed by about 80 µg/day; about 50 µg/day followed by about 60 µg/day; about 50 µg/day followed by about 70 µg/day; about 50 µg/day followed by about 80 µg/day; about 60 µg/day followed by about 70 µg/day or about 60 µg/day followed by about 80 µg/day.

Preferably, the first mcg/day dose of the exenatide followed by the second mcg/day dose for continuous delivery is about 20 mcg/day followed by about 40 mcg/day.

Preferably, the first mcg/day dose of the exenatide followed by the second mcg/day dose for continuous delivery is about 20 mcg/day followed by about 60 mcg/day.

In some methods of the present invention, the subject has not previously received a drug for treating type 2 diabetes mellitus.

In any of the above methods, the exenatide may be the exenatide having the sequence of SEQ ID NO: 1, natural exendin-4, an exenatide peptide, a peptide analog of exenatide, a peptide derivative of exenatide, lixisenatide, or exenatide-LAR.

In any of the above methods, the subject may further be provided one or more other drugs for treating type 2 diabetes mellitus, e.g., insulin and/or oral anti-diabetic drugs including, without limitation, DPP4 inhibitors, SGLT2 inhibitors, metformin, sulfonylureas, and thiazolidinediones (TZDs).

Any of the above-described methods further promote weight loss in a subject in need thereof. Preferably, the subject has a baseline HbA1c % of greater than 6.5%. More preferably, the subject has a baseline HbA1c % of greater than 10.0%. The subject may have a baseline HbA1c % of less than or equal to 12%. Significant weight loss is achieved by about six weeks (e.g., about five weeks, about four weeks, about three weeks, about two weeks, and about one week) after initial implantation of the osmotic delivery device and up to 39 weeks after initial implantation.

The present invention also relates to a method of treating a disease or condition in a subject in need of treatment. The method comprises providing continuous delivery of a drug from an osmotic delivery device.

In the above-described invention, an exenatide for use in a method of treating type 2 diabetes mellitus in a subject is provided.

In the above-described invention, provided is the use of an exenatide in the manufacture of a medicament for use in a method of treating type 2 diabetes mellitus in a subject.

In the above-described invention, the use of an exenatide in the manufacture of an osmotic delivery device, as described herein, for use in a method of treating type 2 diabetes mellitus in a subject is provided.

These and other embodiments of the present invention will readily occur to those of ordinary skill in the art in view of the disclosure herein.

Any of the above aspects and embodiments can be combined with any other aspect or embodiment as disclosed herein.

"ITCA 650 40 mcg/day" or "40 mcg/d" indicates that subjects were treated with ITCA 650 20 µg/day for 13 weeks followed by ITCA 650 40 µg/day for 26 weeks; "ITCA 650 60 mcg/day" or "60 mcg/d" indicates that subjects were treated with ITCA 650 20 µg/day for 13 weeks followed by ITCA 650 60 µg/day for 26 weeks.

Figure 7:
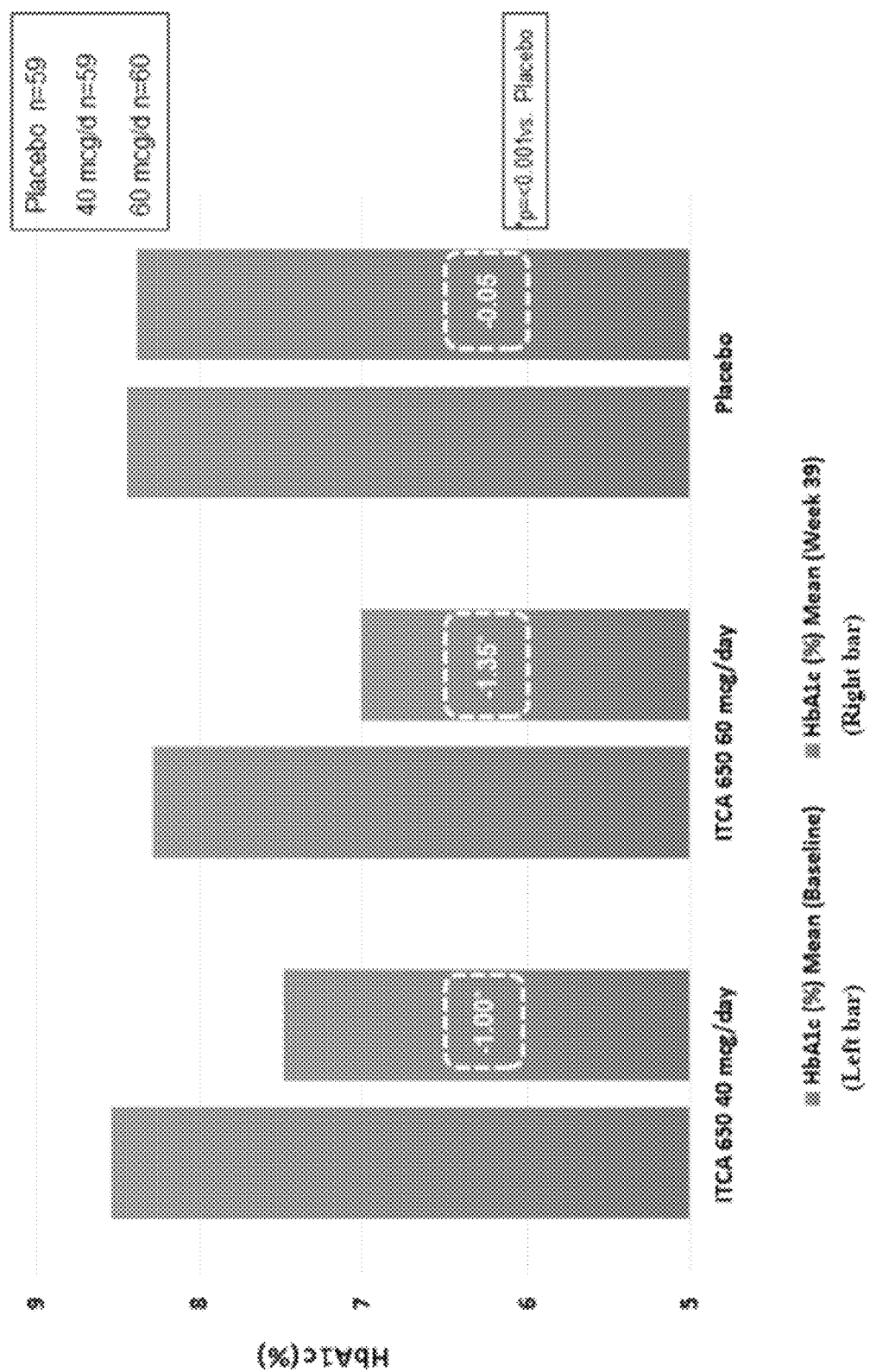

FIG. 7 is a graph showing decreases in HbA1c % relative to baseline at LOCF endpoint for subjects in the phase 3 clinical trial described in Example 1 for subjects with type 2 diabetes and a baseline HbA1c % of ≤10% in the mITT population who received background metformin monotherapy. Subjects in the "ITCA 650 40 mcg/day" or "40 mcg/d" group were treated with ITCA 650 20 µg/day for 13 weeks followed by ITCA 650 40 µg/day for 26 weeks; subjects in the "ITCA 650 60 mcg/day" or "60 mcg/d" group were treated with ITCA 650 20 µg/day for 13 weeks followed by ITCA 650 60 µg/day for 26 weeks. Baseline HbA1c percentages are represented by the left bars and HbA1c percentages at LOCF endpoint are represented by the right bars.

Figure 8:
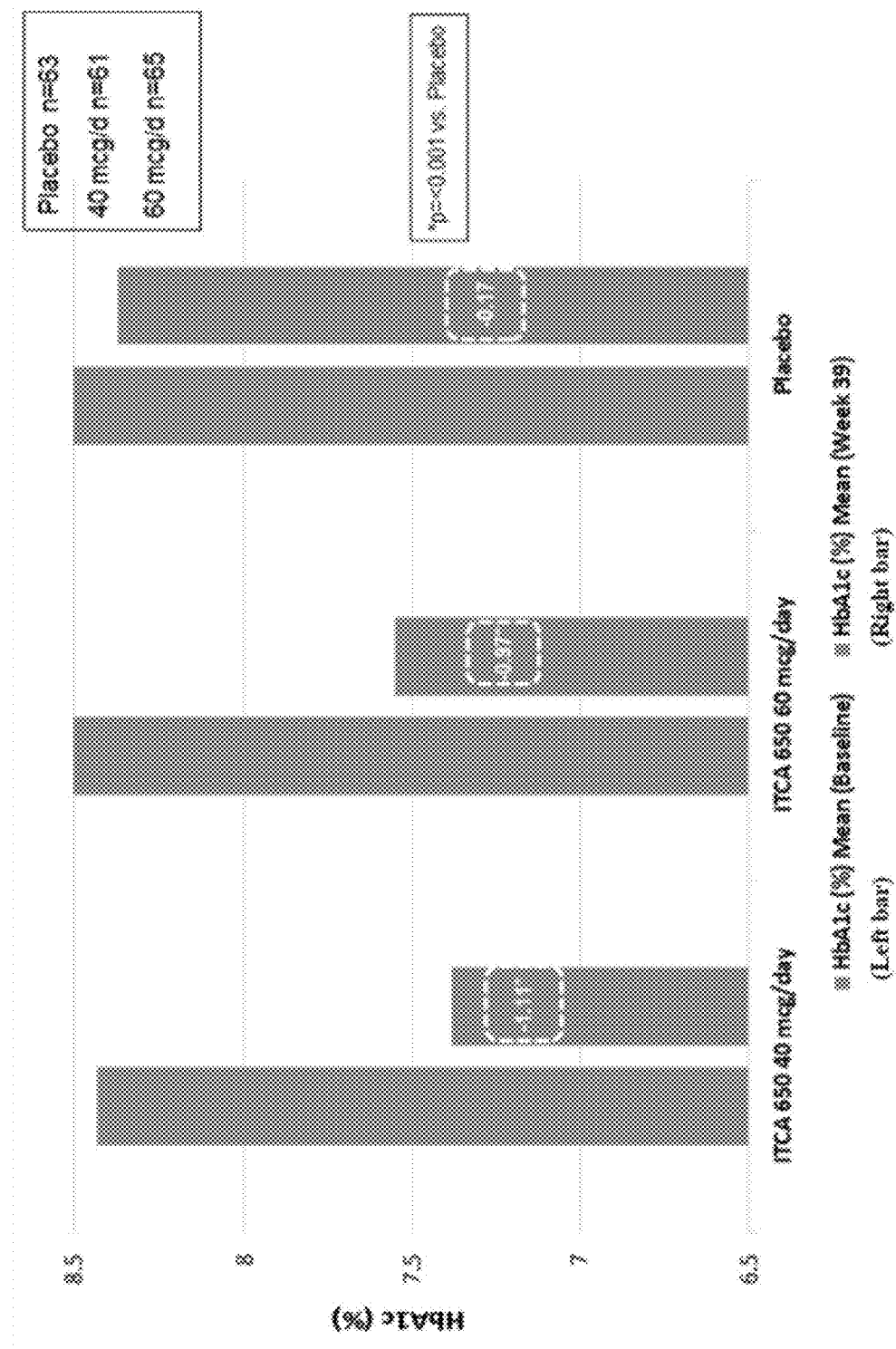

FIG. 8 is a graph showing decreases in HbA1c % relative to baseline at LOCF endpoint for subjects in the phase 3 clinical trial described in Example 1 for subjects with type 2 diabetes and a baseline HbA1c % of ≤10% in the mITT population who received background metformin and sulfonylurea combination therapy. Subjects in the "ITCA 650 40 mcg/day" or "40 mcg/d" group were treated with ITCA 650 20 µg/day for 13 weeks followed by ITCA 650 40 µg/day for 26 weeks; subjects in the "ITCA 650 60 mcg/day" or "60 mcg/d" group were treated with ITCA 650 20 µg/day for 13 weeks followed by ITCA 650 60 µg/day for 26 weeks. Baseline HbA1c percentages are represented by the left bars and HbA1c percentages at LOCF endpoint are represented by the right bars.

Figure 9:
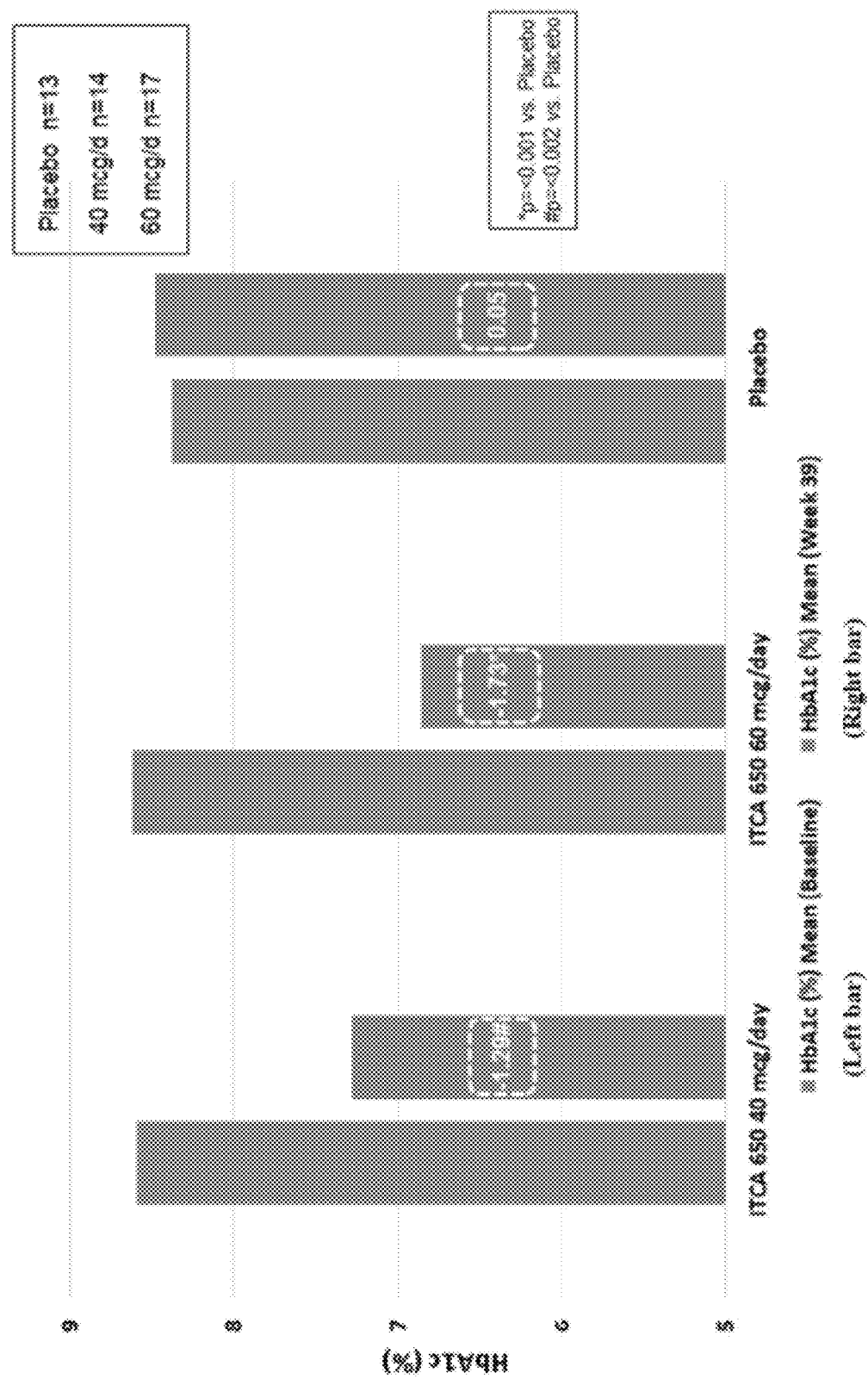

FIG. 9 is a graph showing changes from baseline HbA1c (%) at LOCF endpoint for subjects in the mITT population on diet and exercise therapy only (i.e., no concomitant oral antidiabetic treatment). Left bars show baseline values and right bars show values at LOCF endpoint. Subjects in the "ITCA 650 40 mcg/day" or "40 mcg/d" group were treated with ITCA 650 20 µg/day for 13 weeks followed by ITCA 650 40 µg/day for 26 weeks; subjects in the "ITCA 650 60 mcg/day" or "60 mcg/d" group were treated with ITCA 650 20 µg/day for 13 weeks followed by ITCA 650 60 µg/day for 26 weeks.

Figure 10:
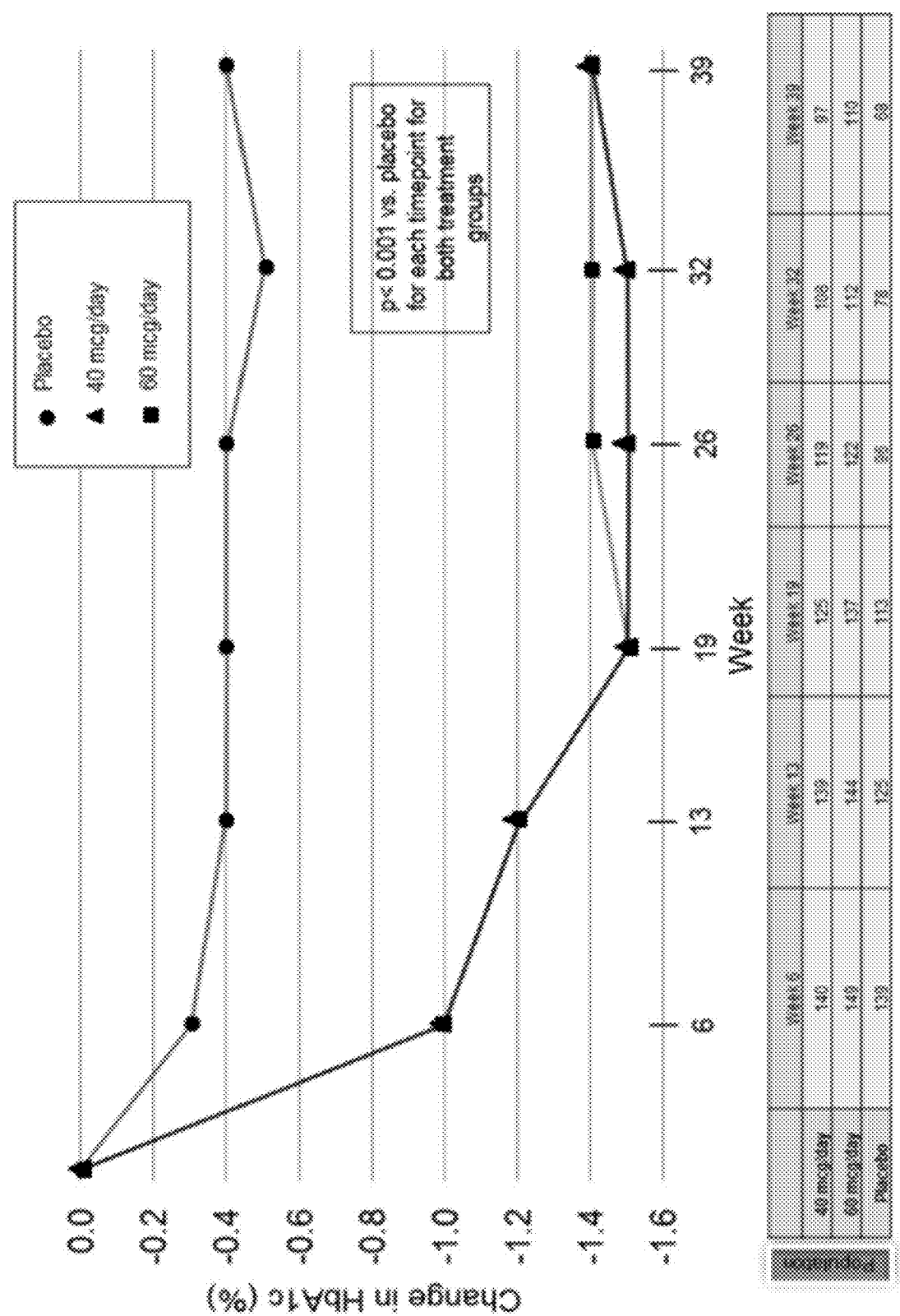

FIG. 10 is a graph showing decreases in HbA1c % relative to baseline at week 6, week 13, week 19, week 26, week 32, and week 39 for subjects in the phase 3 clinical trial described in Example 1 for subjects with type 2 diabetes and a baseline HbA1c % of ≥7.5% to ≤10%. Data identified with closed squares are from subjects treated with ITCA 650 20 µg/day for 13 weeks followed by ITCA 650 40 µg/day for 26 weeks ("40 mcg/day"), data identified with closed triangles are from subjects treated with ITCA 650 20 µg/day for 13 weeks followed by ITCA 650 60 µg/day for 26 weeks ("60 mcg/day"), and data identified with closed circles are from subjects treated with a placebo.

Figure 11:
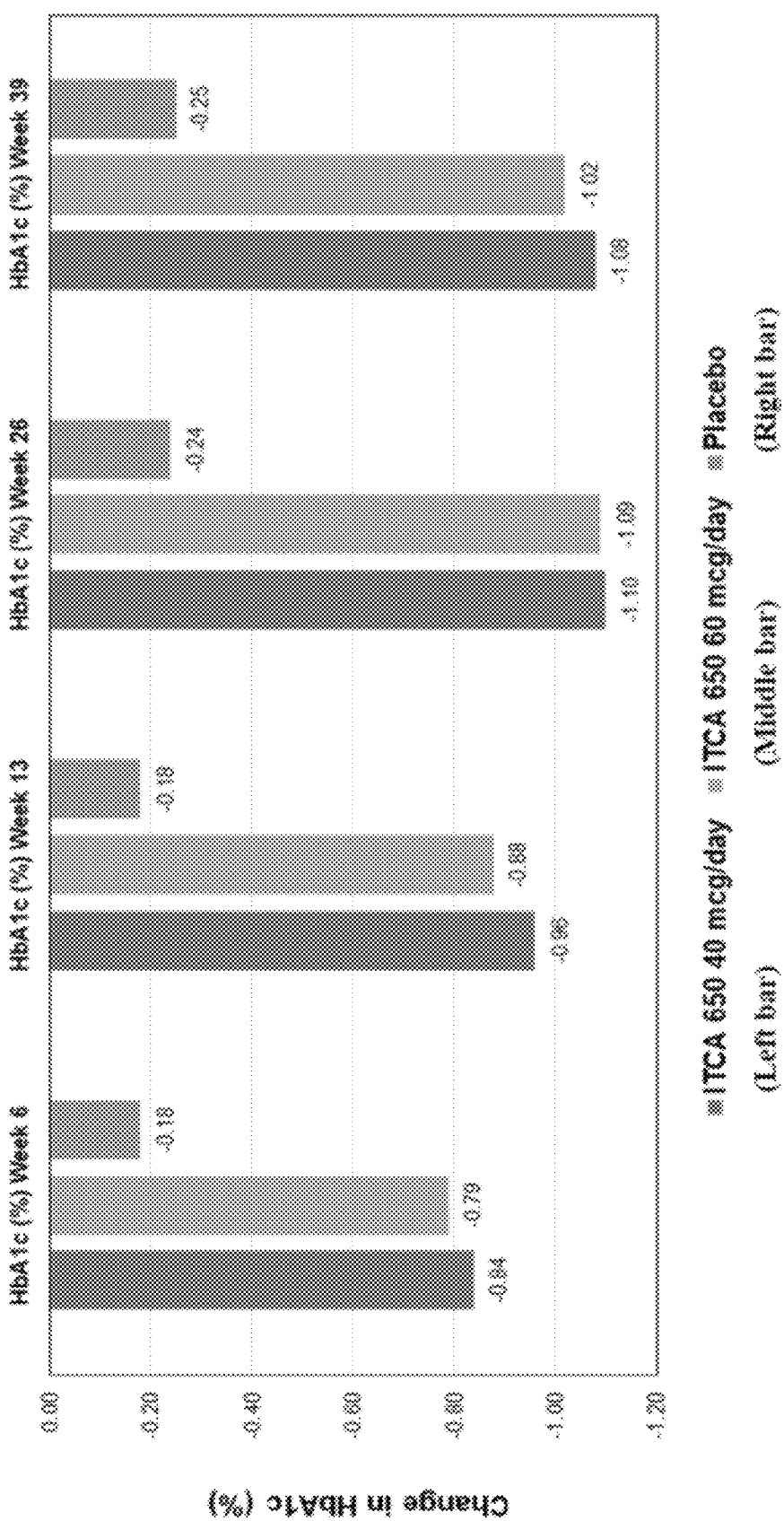

FIG. 11 is a graph showing decreases in HbA1c % relative to baseline at week 6, week 13, week 26, and week 39 for subjects in the phase 3 trial described in Example 1 for subjects with type 2 diabetes and with baseline Hb1A1c % of ≤8.5%. Left bars are data from subjects treated with ITCA 650 20 µg/day for 13 weeks followed by ITCA 650 40 µg/day for 26 weeks ("ITCA 650 40 mcg/day"), middle bars are data from subjects treated with ITCA 650 20 µg/day for 13 weeks followed by ITCA 650 60 µg/day for 26 weeks ("ITCA 650 60 mcg/day"), and right bars are data from subjects treated with a placebo.

Figure 12:
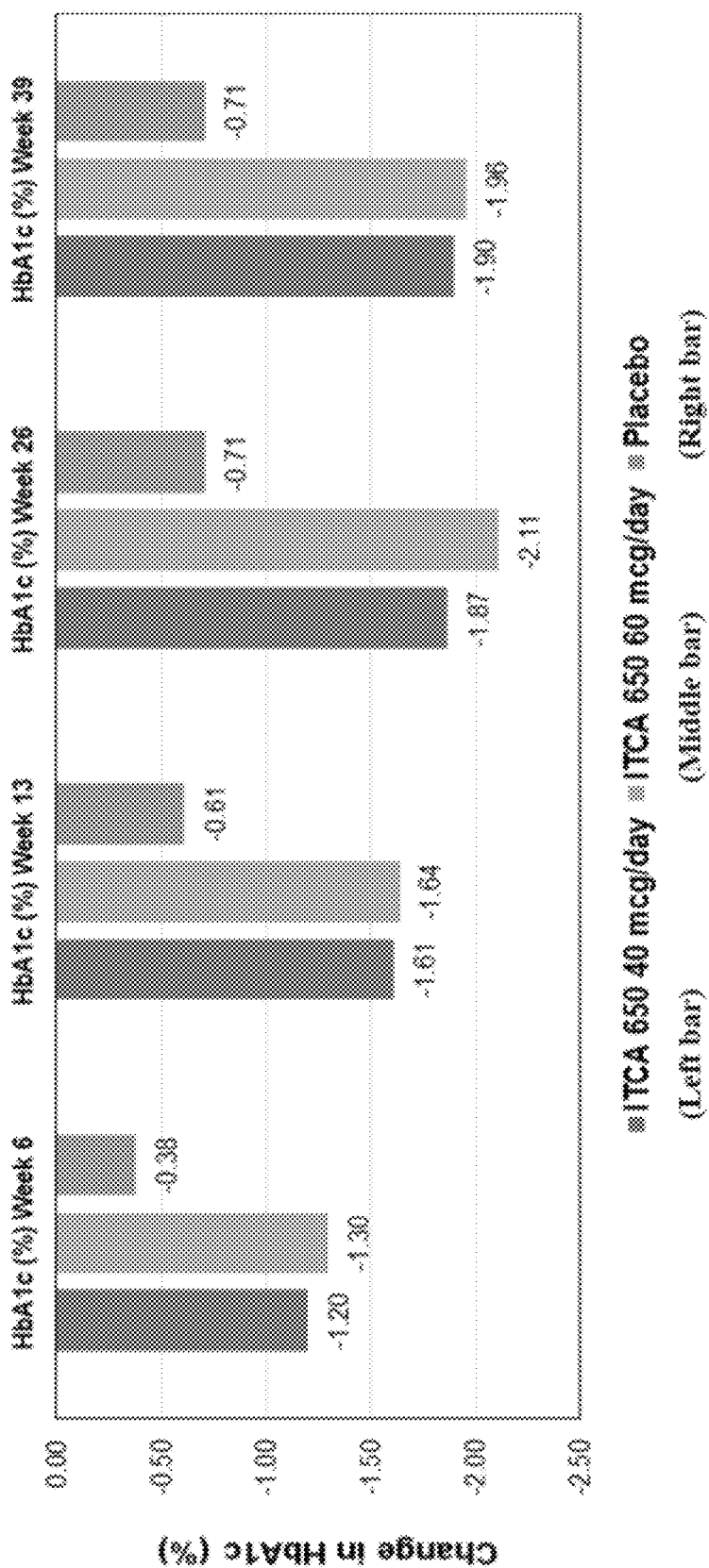

FIG. 12 is a graph showing decreases in HbA1c % relative to baseline at week 6, week 13, week 26, and week 39 for subjects in the phase 3 trial described in Example 1 for subjects with type 2 diabetes and with baseline Hb1A1c % of ≥8.5% (and ≤10%). Left bars are data from subjects treated with ITCA 650 20 µg/day for 13 weeks followed by ITCA 650 40 µg/day for 26 weeks ("ITCA 650 40 mcg/day"), middle bars are data from subjects treated with ITCA 650 20 µg/day for 13 weeks followed by ITCA 650 60 µg/day for 26 weeks ("ITCA 650 60 mcg/day"), and right bars are data from subjects treated with a placebo.

Figure 13:
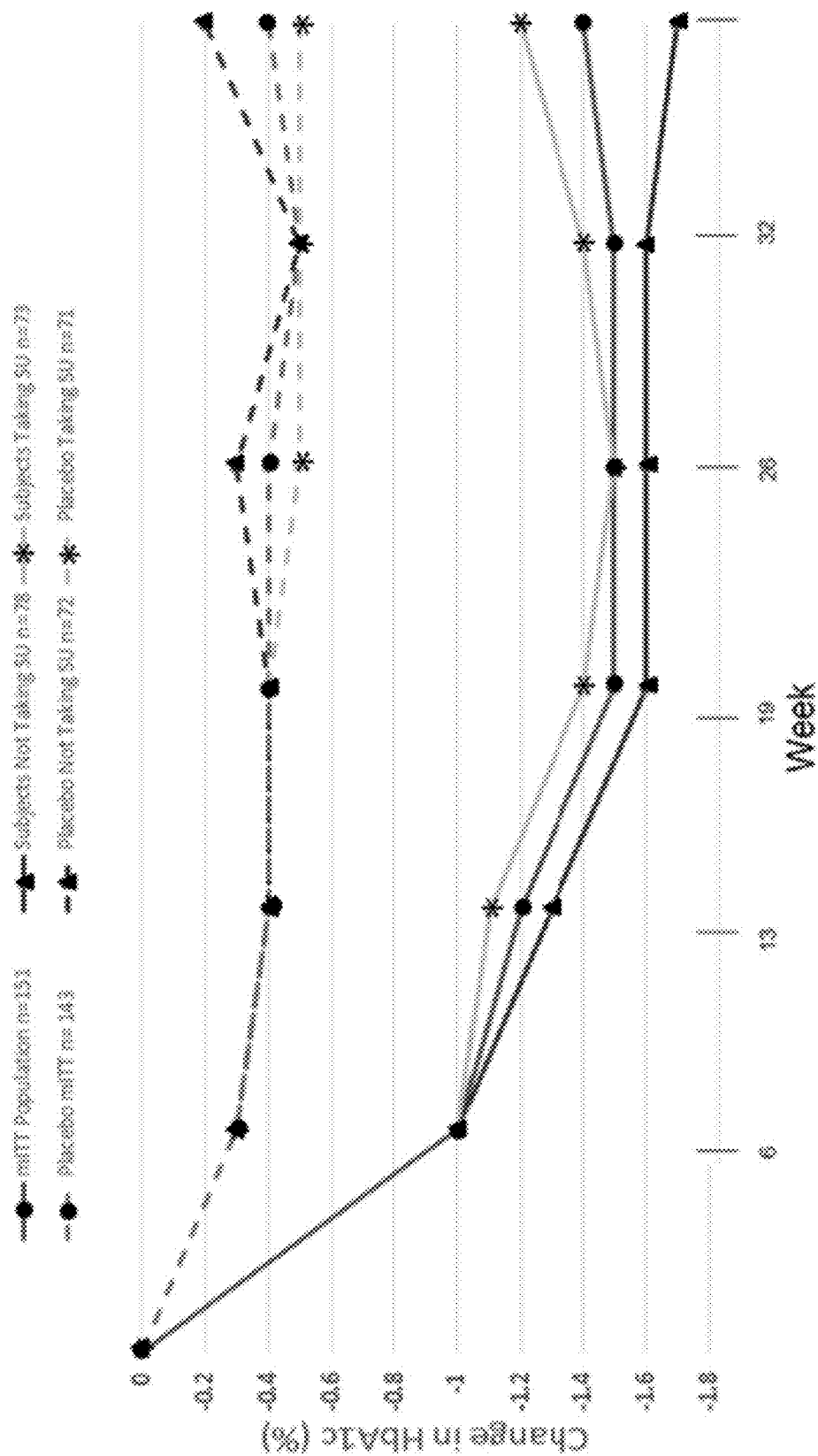

FIG. 13 is a graph showing changes in HbA1c % over time for subjects in the phase 3 trial described in Example 1 for subjects with type 2 diabetes and with baseline Hb1A1c % of >8.5% (and ≤10%) who were treated with ITCA 650 20 µg/day for 13 weeks followed by ITCA 650 60 µg/day for 26 weeks ("ITCA 650 20/60 µg/day"). Data is separated for subjects who were treated with sulfonylurea (SU) and subjects who were not treated with SU. Data shown in a solid line and identified with closed circles are from subjects treated with ITCA 650 20/60 µg/day and SU, data shown in a solid line and identified with closed squares are from subjects treated with ITCA 650 20/60 µg/day but not SU, and data shown in a solid line and identified with closed triangles is from all subjects from the ITCA 650 20/60 µg/day groups. Data shown in a dotted line and identified closed squares are from placebo subjects treated with SU and not with ITCA 650 20/60 µg/day, data shown in a dotted line and identified with closed circles are from placebo subjects not treated with either SU or ITCA 650 20/60 µg/day, and data shown in a dotted line and identified with closed triangle are from all placebo subjects.

Figure 14:
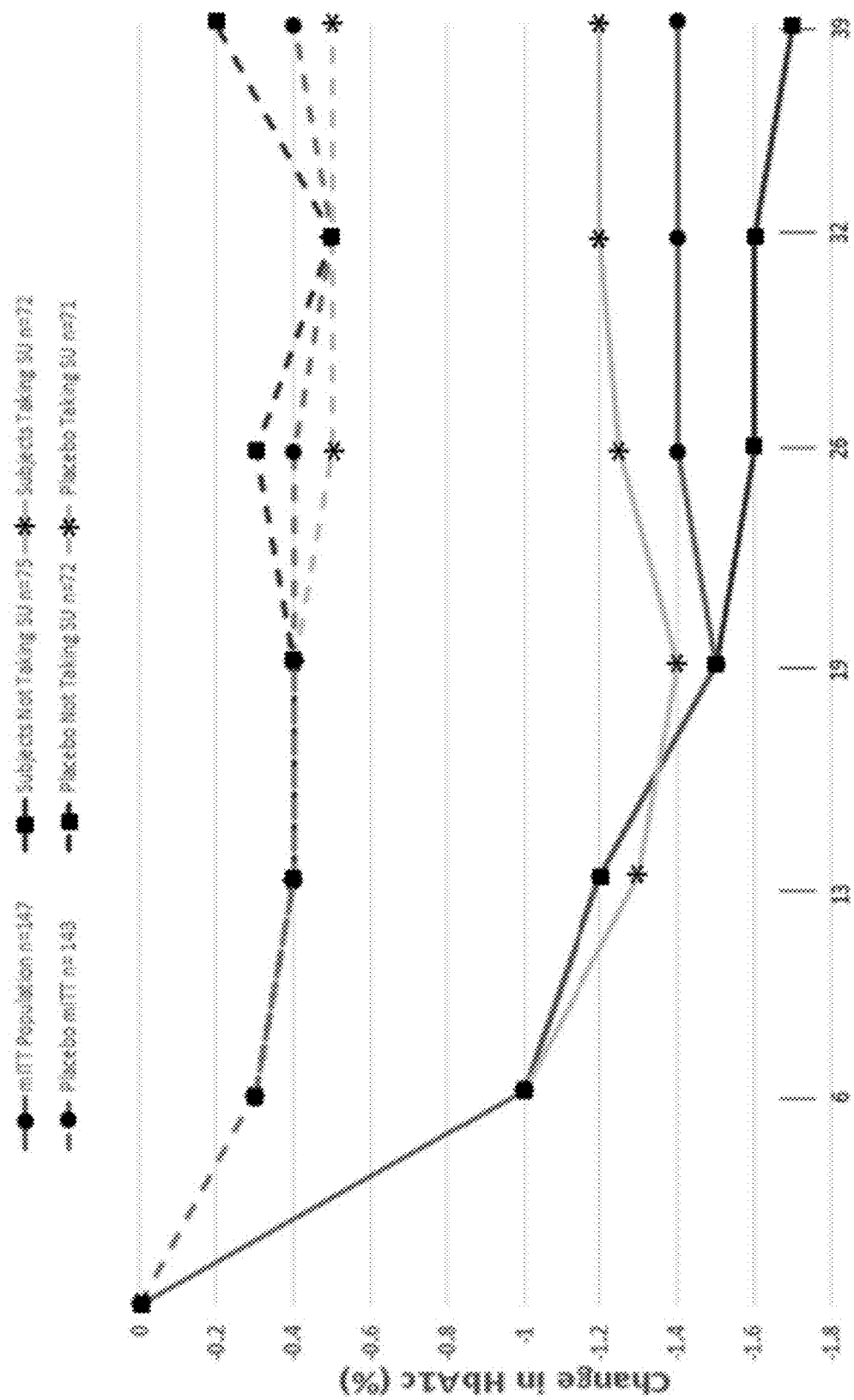

FIG. 14 is a graph showing changes in HbA1c % over time for subjects in the phase 3 trial described in Example 1 for subjects with type 2 diabetes and with baseline Hb1A1c % of >8.5% (and ≤10%) who were treated with ITCA 650 20 µg/day for 13 weeks followed by ITCA 650 40 µg/day for 26 weeks ("ITCA 650 20/40 µg/day"). Data is separated for subjects who were treated with sulfonylurea (SU) and subjects who were not treated with SU. Data shown in a solid line identified with closed circles are from subjects treated with ITCA 650 20/40 µg/day and SU, data shown in a solid line and identified with closed squares are from subjects treated with ITCA 650 20/40 µg/day but not SU, and data shown in a solid line and identified with closed triangles are from all subjects from the ITCA 650 20/40 µg/day groups. Data shown in a dotted line and identified with closed squares are from placebo subjects treated with SU and not with ITCA 650 20/40 µg/day, data shown in a dotted line and identified with closed circles are from placebo subjects not treated with either SU or ITCA 650 20/40 µg/day, and data shown in a dotted line and identified with closed triangles is from all placebo subjects.

Figure 15:
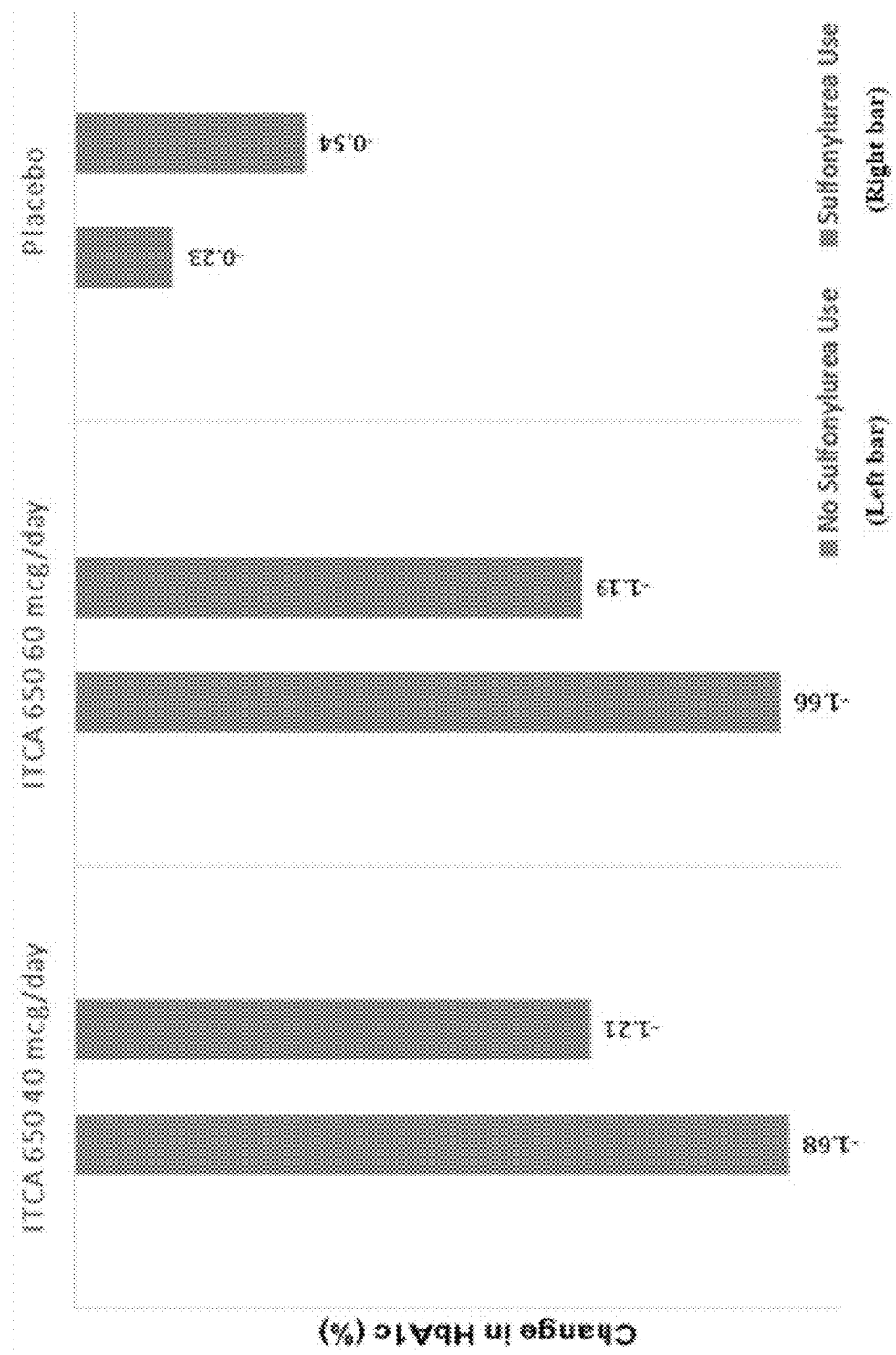

FIG. 15 includes a graph showing changes in HbA1c % at the $39^{th}$ week for subjects in the phase 3 trial described in Example 1 for subjects with type 2 diabetes and with baseline Hb1A1c % of >8.5% (and ≤10%) who were treated with ITCA 650 20 µg/day for 13 weeks followed by ITCA 650 40 µg/day for 26 weeks ("ITCA 650 40 mcg/day"), who were treated with ITCA 650 20 µg/day for 13 weeks followed by ITCA 650 60 µg/day for 26 weeks ("ITCA 650 60 mcg/day"), or received a placebo ITCA treatment. Data is separated for subjects who were treated with sulfonylurea (SU), shown in right bards, and subjects who were not treated with SU, shown in left bards.

Figure 16:
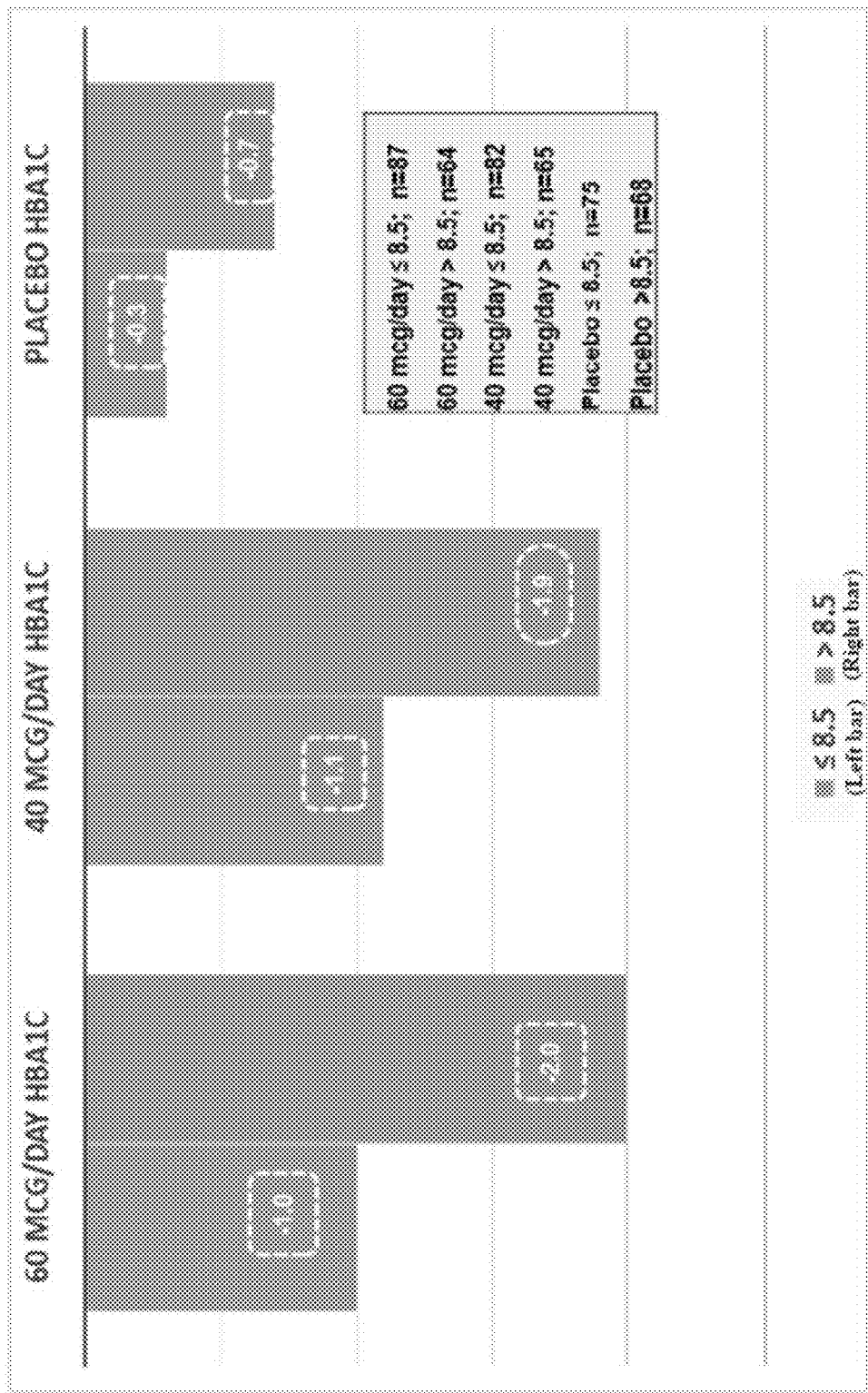

FIG. 16 is a graph showing changes in HbA1c % at week 39 from baseline for subjects in mITT population for subjects in the phase 3 trial described in Example 1 for subjects with type 2 diabetes. Subjects were treated with ITCA 650 20 µg/day for 13 weeks followed by ITCA 650 40 µg/day for 26 weeks ("40 MCG/DAY HBA1C") or were treated with ITCA 650 20 µg/day for 13 weeks followed by ITCA 650 60 µg/day for 26 weeks ("60 MCG/DAY HBA1C"). Data is separated for subjects (data in right bars) who had a baseline HbA1c % of greater than 8.5% (and less than or equal to 10.0%) and by subjects (data in left bars) who had a baseline HbA1c % of less than or equal to 8.5%.

Figure 17:
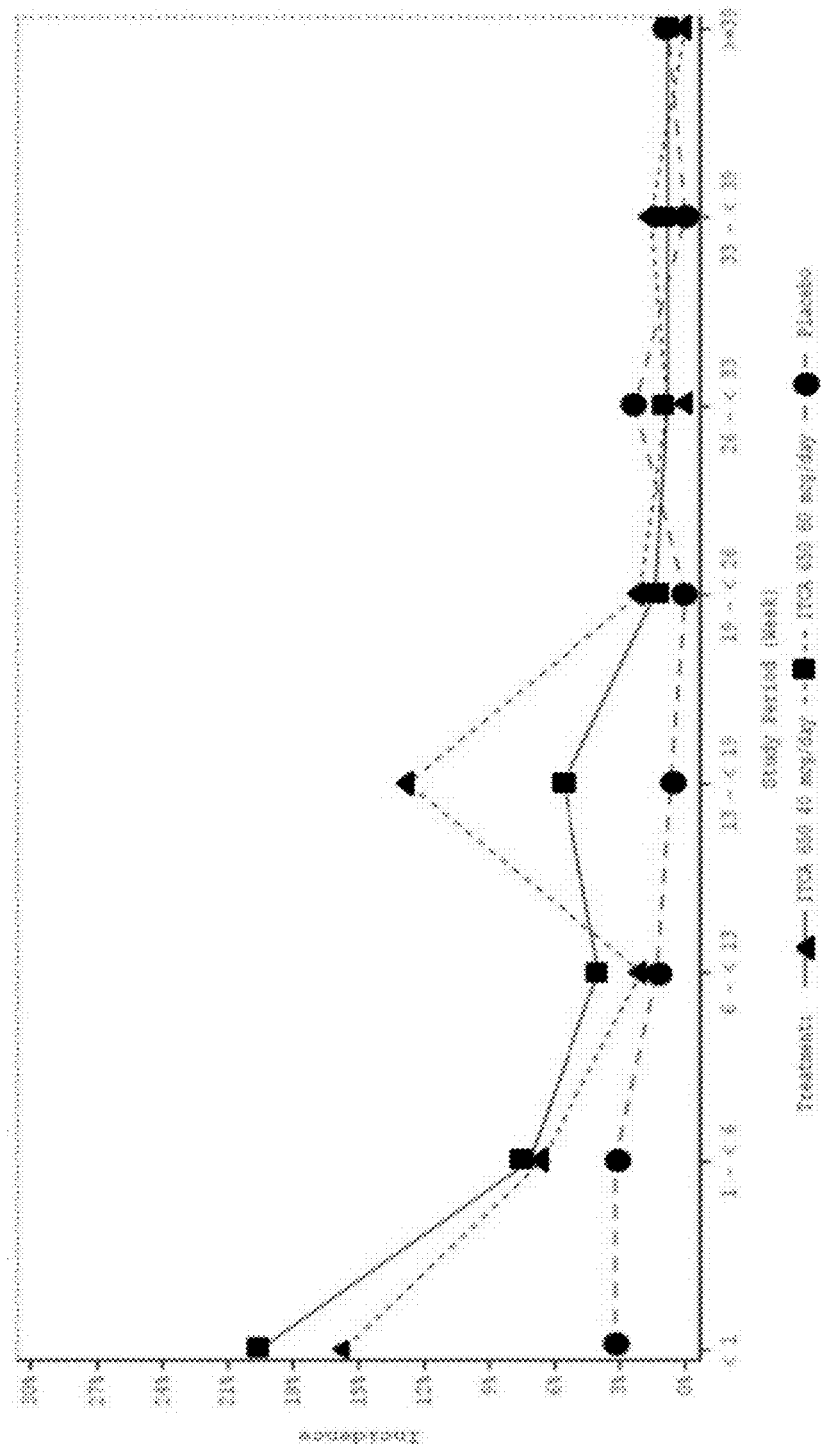

FIG. 17 is a graph showing the incidence of nausea by study period for subjects in the phase 3 clinical trial described in Example 1 for subjects with type 2 diabetes and with a baseline HbA1c % pursuant to the study protocol inclusion criterion. Data identified with closed circles are from subjects who were treated with ITCA 650 20 µg/day for 13 weeks followed by ITCA 650 40 µg/day for 26 weeks ("ITCA 650 40 mcg/day"), data identified with closed triangles are from subjects who were treated with ITCA 650 20 µg/day for 13 weeks followed by ITCA 650 60 µg/day for 26 weeks ("ITCA 650 60 mcg/day"), and data identified by closed circles are from subjects treated with a placebo.

Figure 18:
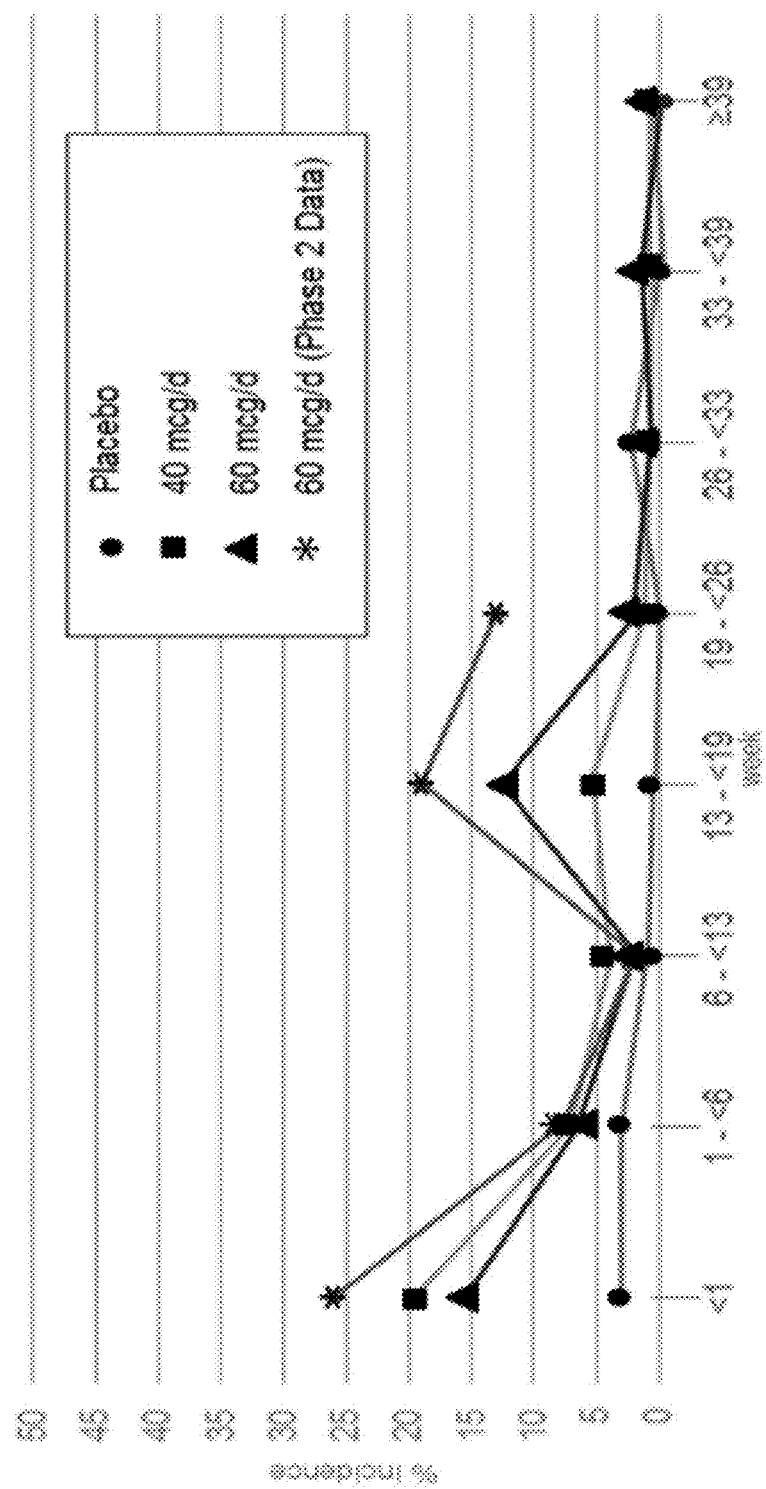

FIG. 18 is a graph showing the incidence of nausea for subjects in a phase 2 clinical trial (described in Henry et al 2014) and the phase 3 clinical trial described in Example 1 for subjects with type 2 diabetes and with a baseline HbA1c % pursuant to the study protocol inclusion criterion. Data identified with closed circles are from placebo subjects in the phase 3 trial, data identified with closed squares are from subjects in the phase 3 trial who were treated with ITCA 650 20 µg/day for 12 weeks and then treated with ITCA 650 40 µg/day for 26 weeks ("40 mcg/d"), data identified with closed triangles are from subjects in the phase 3 trial who were treated with ITCA 650 20 µg/day for 12 weeks and then treated with ITCA 650 60 µg/day for 26 weeks ("60 mcg/d"), and data identified with open circles are for subjects in the phase 2 trial who were treated with ITCA 650 20 µg/day for 12 weeks and then treated with ITCA 650 60 µg/day for 12 weeks ("60 mcg/d (Phase 2 Data)").

Figure 19:
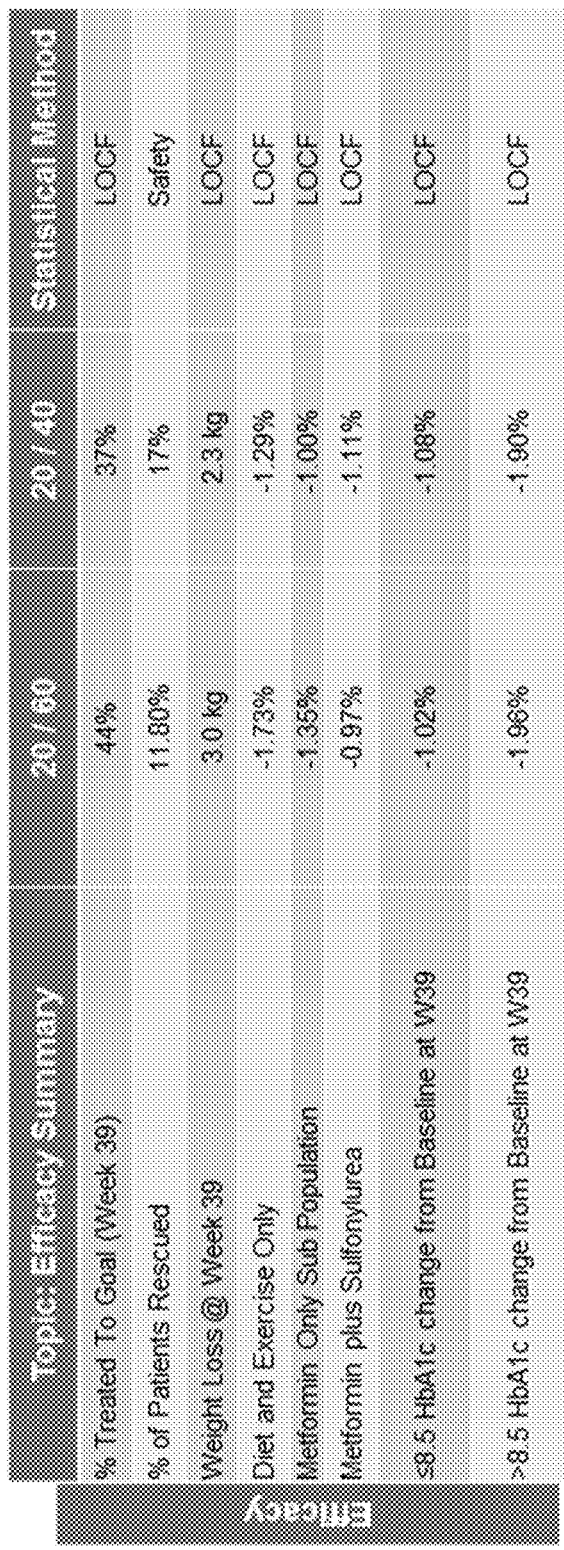

FIG. 19 is a table that compares certain endpoint data for subjects with type 2 diabetes treated with ITCA 650 60 µg/day ("20/60") or ITCA 650 40 µg/day ("20/40") in the phase 3 trial described in Example 1 and with a baseline HbA1c % pursuant to the study protocol inclusion criterion.

Figure 20:
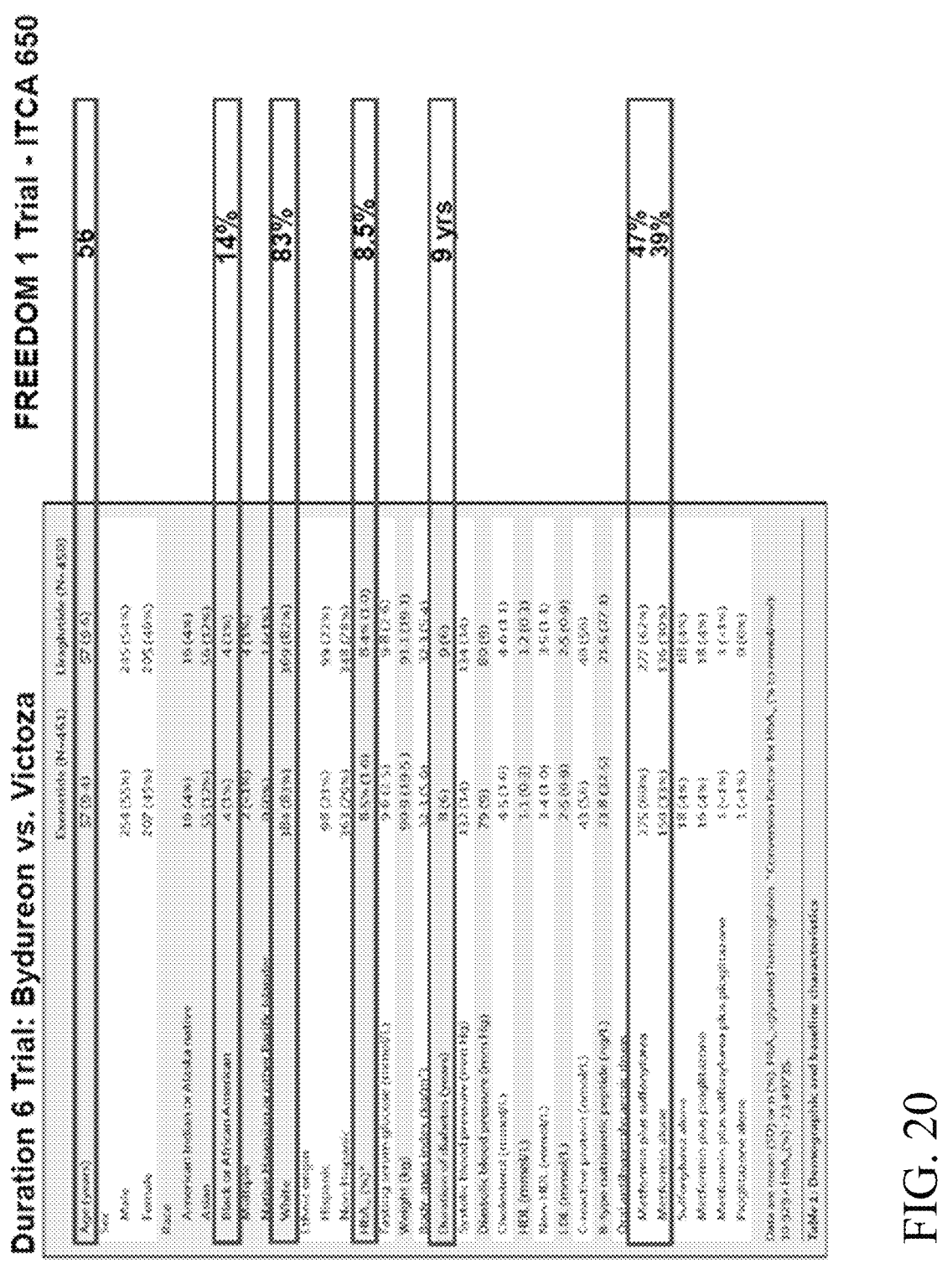

FIG. 20 is a table that compares subject profiles for those subjects participating in the phase 3 study described in Example 1 who have type 2 diabetes and a baseline HbA1c % of ≤10% and those subjects participating in the Duration 6 Trial.

Figure 21:
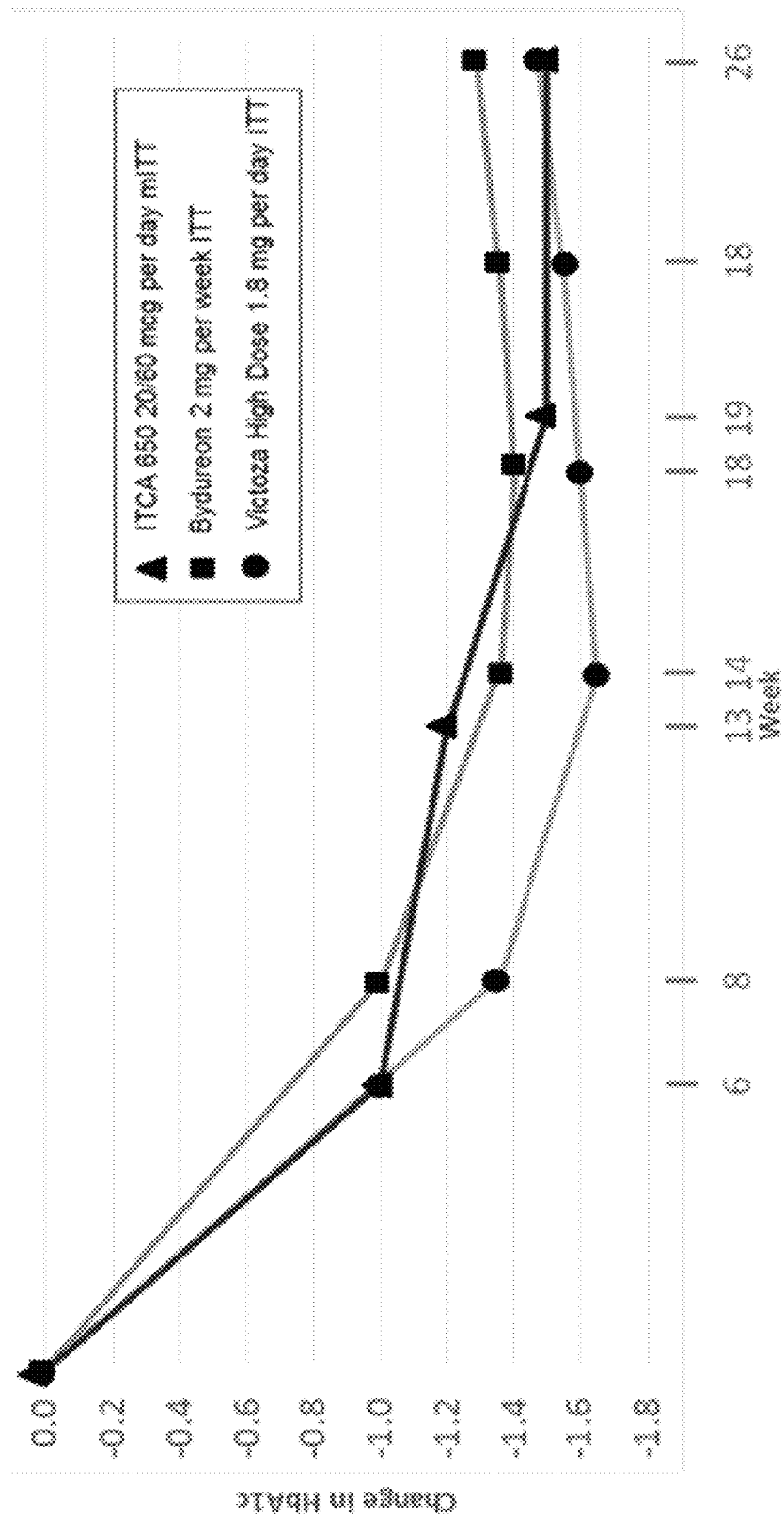

FIG. 21 is a graph showing progressive decreases in HbA1c % from baseline for subjects in the Duration 6 Trial and in the phase 3 clinical trial for subjects who have type 2 diabetes and a baseline HbA1c % of pursuant to the study protocol inclusion criterion as described in Example 1. Data identified with closed circles are for subjects who received once-daily injections of liraglutide (1.8 mg) and data identified with closed squares are for subjects who received once-weekly exenatide (2 mg) injections in a published study Duration-6 (Buse et al., *The Lancet*, Volume 381, Issue 9861, 12-18 January, pages 117-124). Data identified with closed triangles were obtained here for subjects in the phase 3 clinical trial described in Example 1 and who were treated with ITCA 650 20 µg/day for 13 weeks followed by ITCA 650 60 µg/day for 26 weeks ("ITCA 650 20/60 mcg per day mITT"); this data was not included in the Duration 6 Trial or in a separate comparison study between Duration 6 methods and methods described in Example 1.

Figure 22:
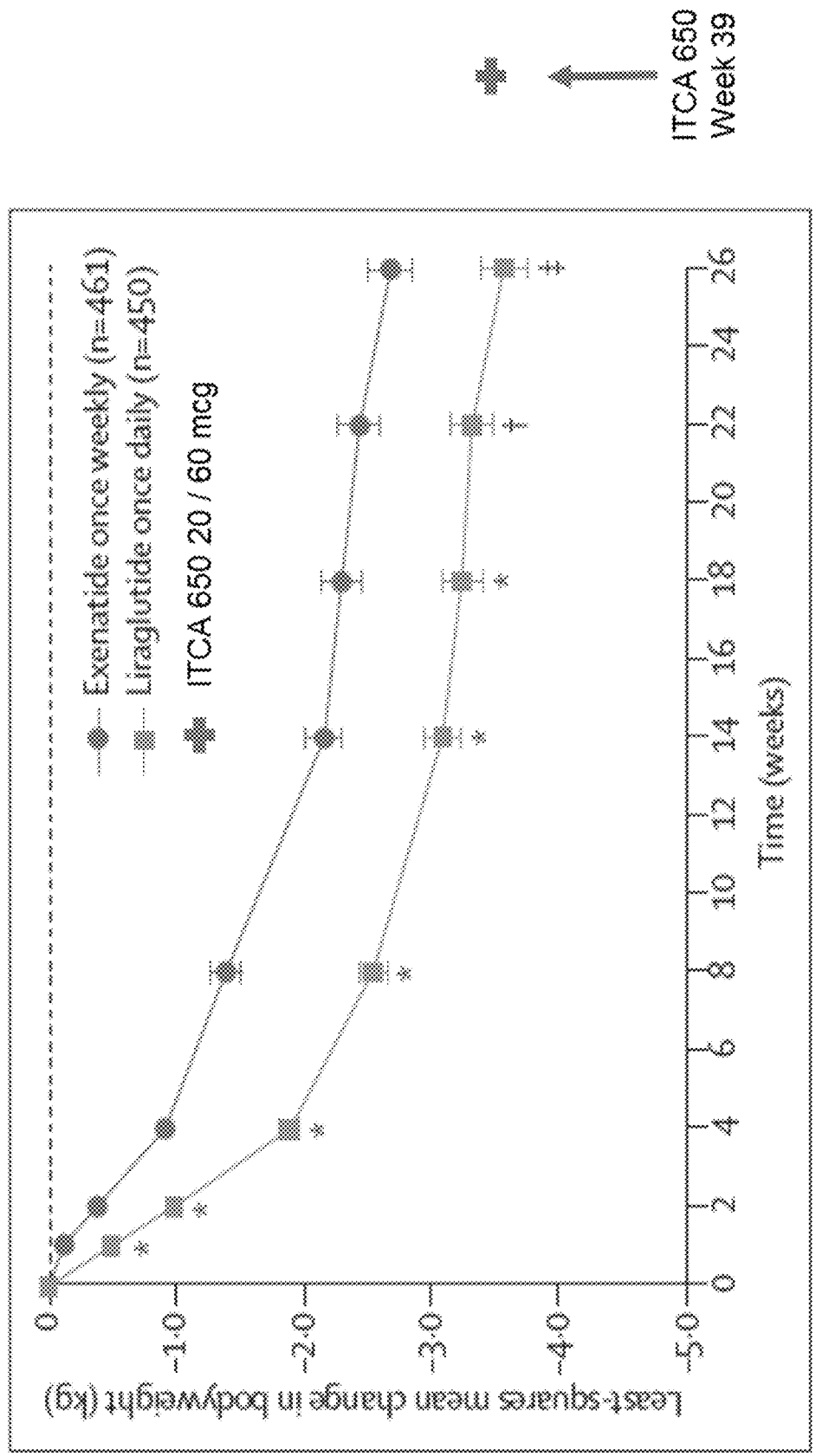

FIG. 22 is a graph showing progressive decreases in bodyweight from baseline for subjects in the Duration 6 Trial. Data identified with a closed square are for subjects who received once-daily injections of liraglutide (1.8 mg) and data identified closed circles are for subjects who received once-weekly exenatide (2 mg) injections. Data identified by a closed plus sign were obtained here for subjects in the phase 3 clinical trial described in Example 1 who were treated with ITCA 650 20 µg/day for 13 weeks followed by ITCA 650 60 µg/day for 26 weeks ("ITCA 650 20/60 mcg"); this data was not included in the Duration 6 Trial or in a separate comparison study between Duration 6 methods and methods described in Example 1. Data (closed plus sign) for the above-described phase 3 trial is only shown for week 39.

FIG. 23 is a table that compares rates of adverse events for subjects in the Duration 6 study and for subjects in the phase 3 clinical trial described in Example 1 ("ITCA 650 20/60 mcg").

Figure 24:
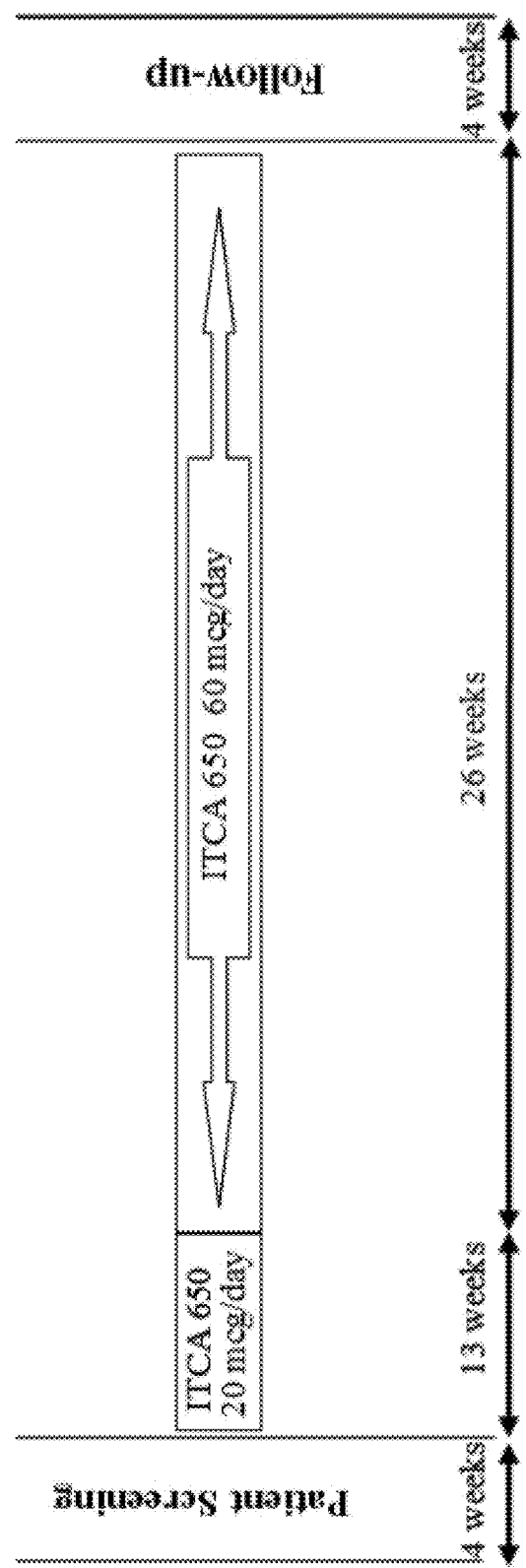

FIG. 24 presents an overview of a 39-week open-label initial phase of the randomized, phase 3 study for subjects with type 2 diabetes and with high baseline HbA1c as described in Example 2.

Figure 25:
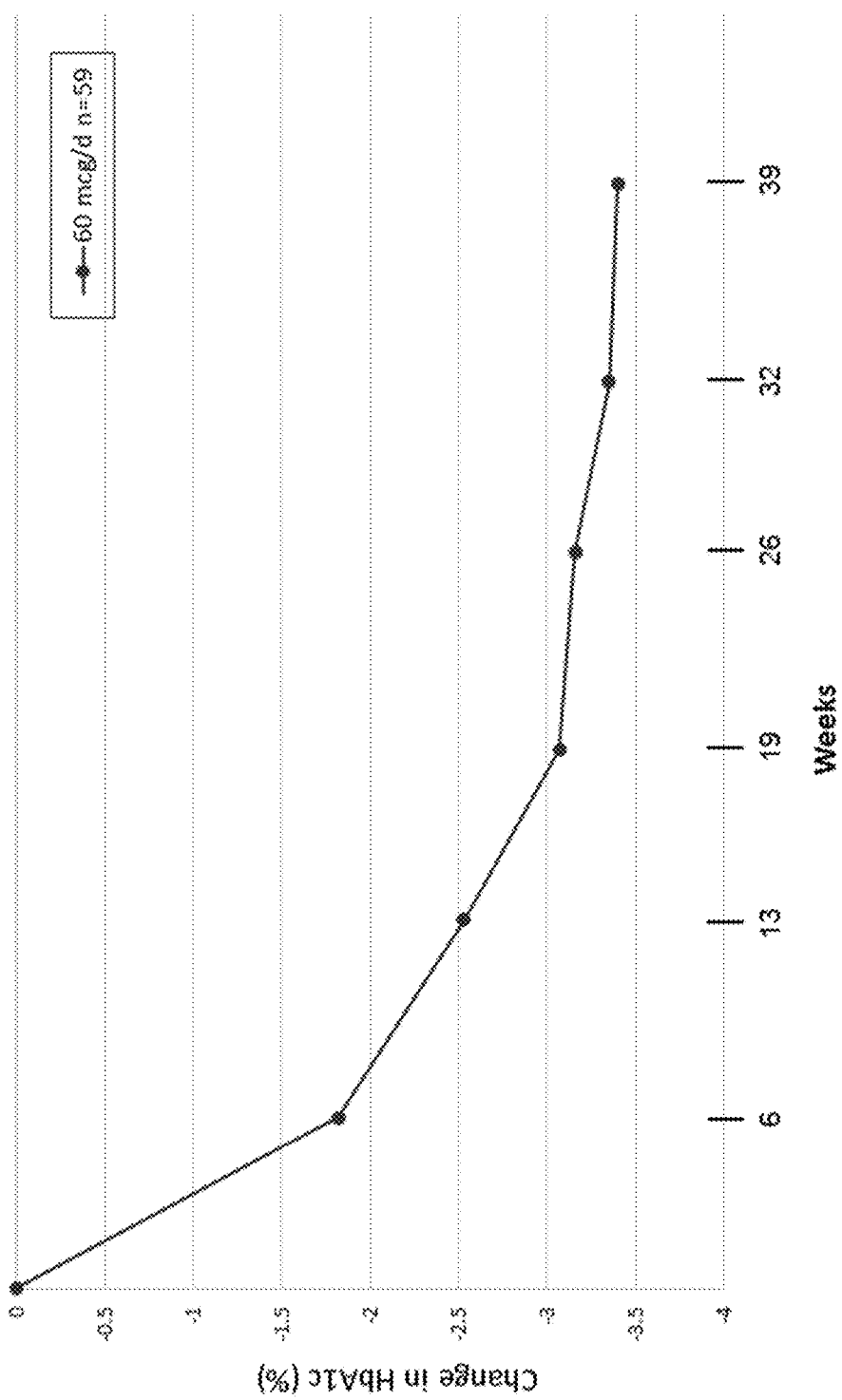

FIG. 25 is a graph showing the average change from baseline HbA1c % by visit for the mITT population with a high baseline HbA1c described in Example 2. Subjects were treated with ITCA 650 20 µg/day for the first 13 weeks followed by ITCA 650 60 µg/day for the following 26 weeks ("60 mcg/day").

Figure 26:
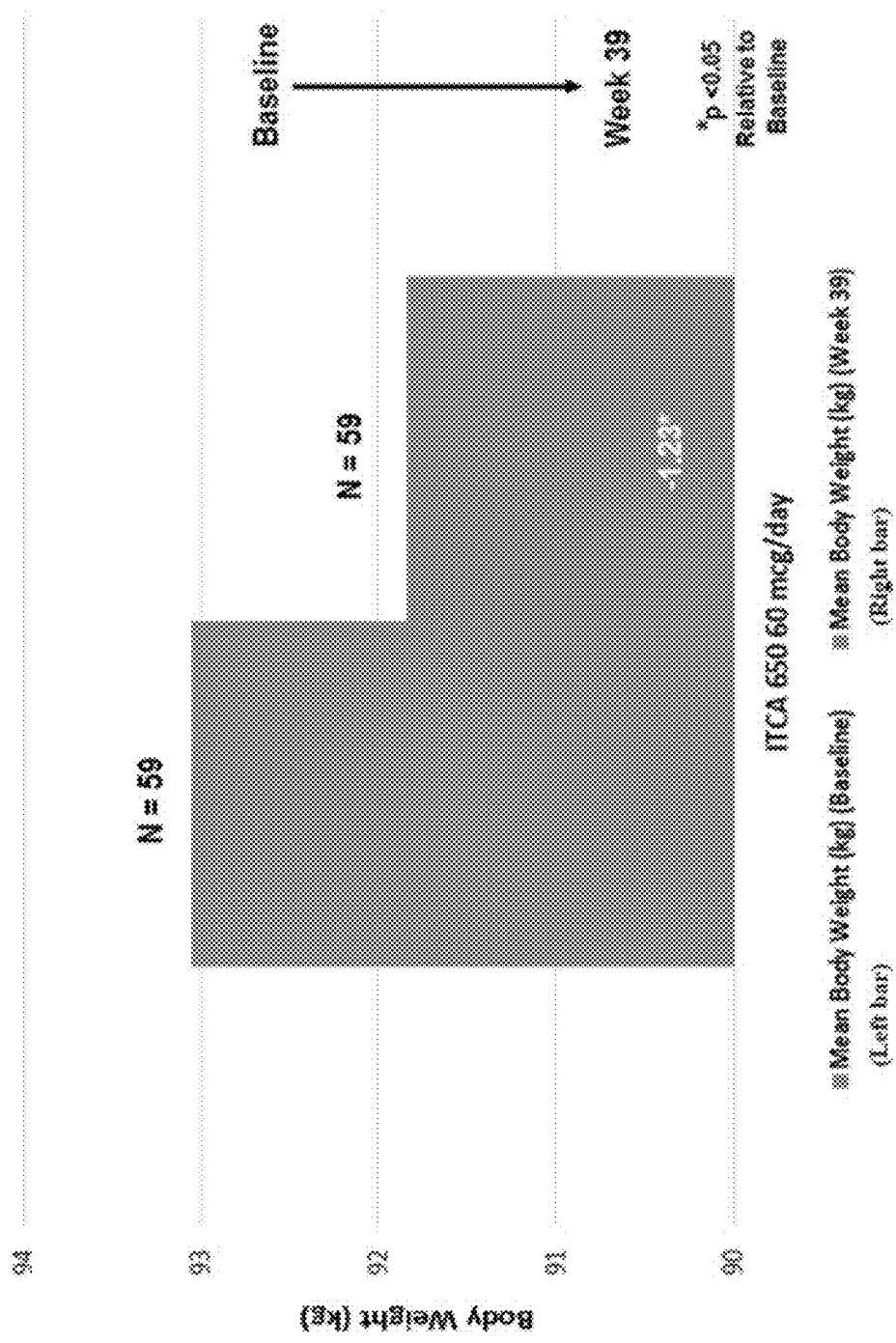

FIG. 26 is a graph showing decreases in body weight relative to baseline at Last Observation Carried Forward (LOCF) endpoint for subjects in the mITT population in the phase 3 clinical trial described in Example 2 for subjects with type 2 diabetes and a high baseline HbA1c % pursuant to the study protocol inclusion criterion. Subjects were treated with ITCA 650 20 µg/day for the first 13 weeks followed by ITCA 650 60 µg/day for 26 weeks ("ITCA 650 60 mcg/day"). The reduction in body weight from baseline to week 39 was statistically significant. Mean body weight baseline value is represented by the left bar and mean body weight value at LOCF endpoint is represented by the right bar.

Figure 27:
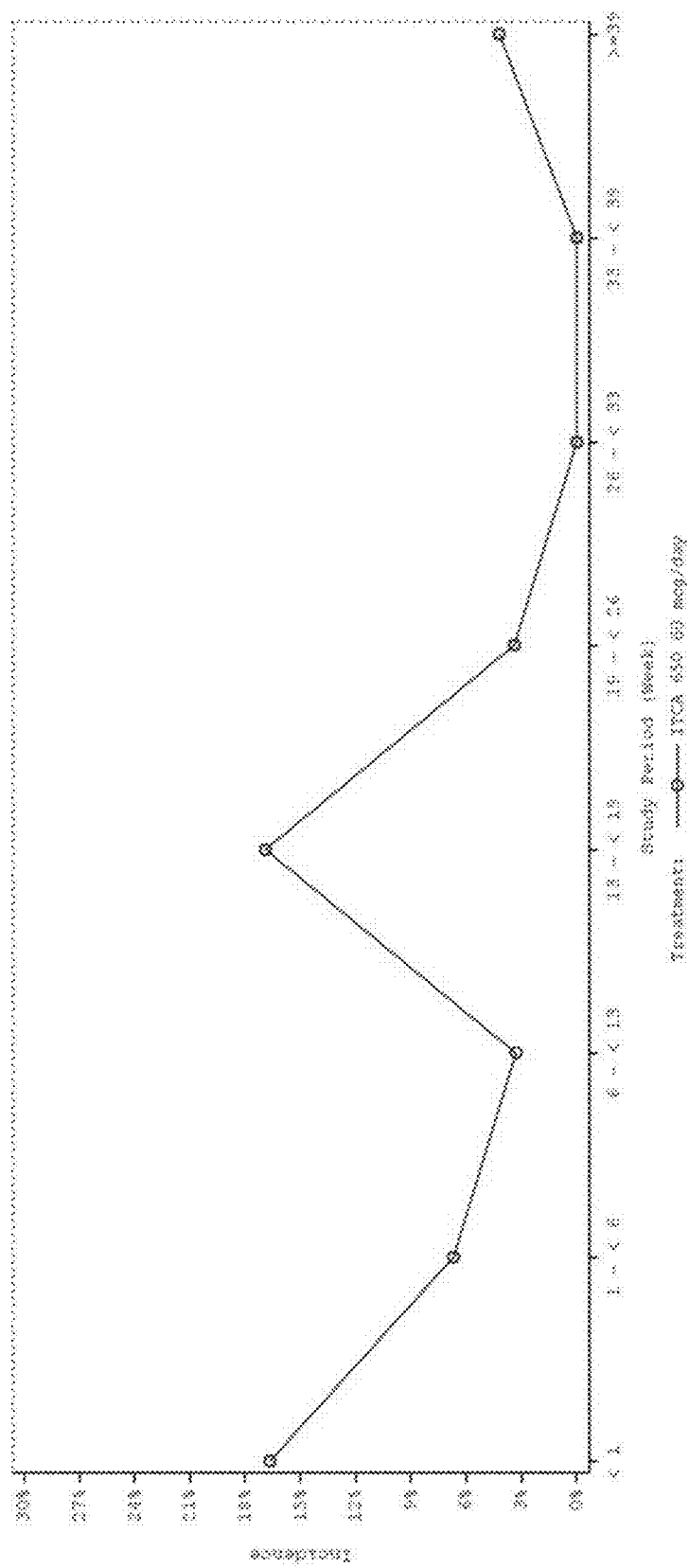

FIG. 27 is a graph showing the incidence of nausea by study period for subjects in the phase 3 clinical trial described in Example 2 for subjects with type 2 diabetes and with a high baseline HbA1c % pursuant to the study protocol inclusion criterion. Subjects were treated with ITCA 650 20 µg/day for 13 weeks followed by ITCA 650 60 µg/day for 26 weeks ("ITCA 650 60 mcg/day").

Figure 28:
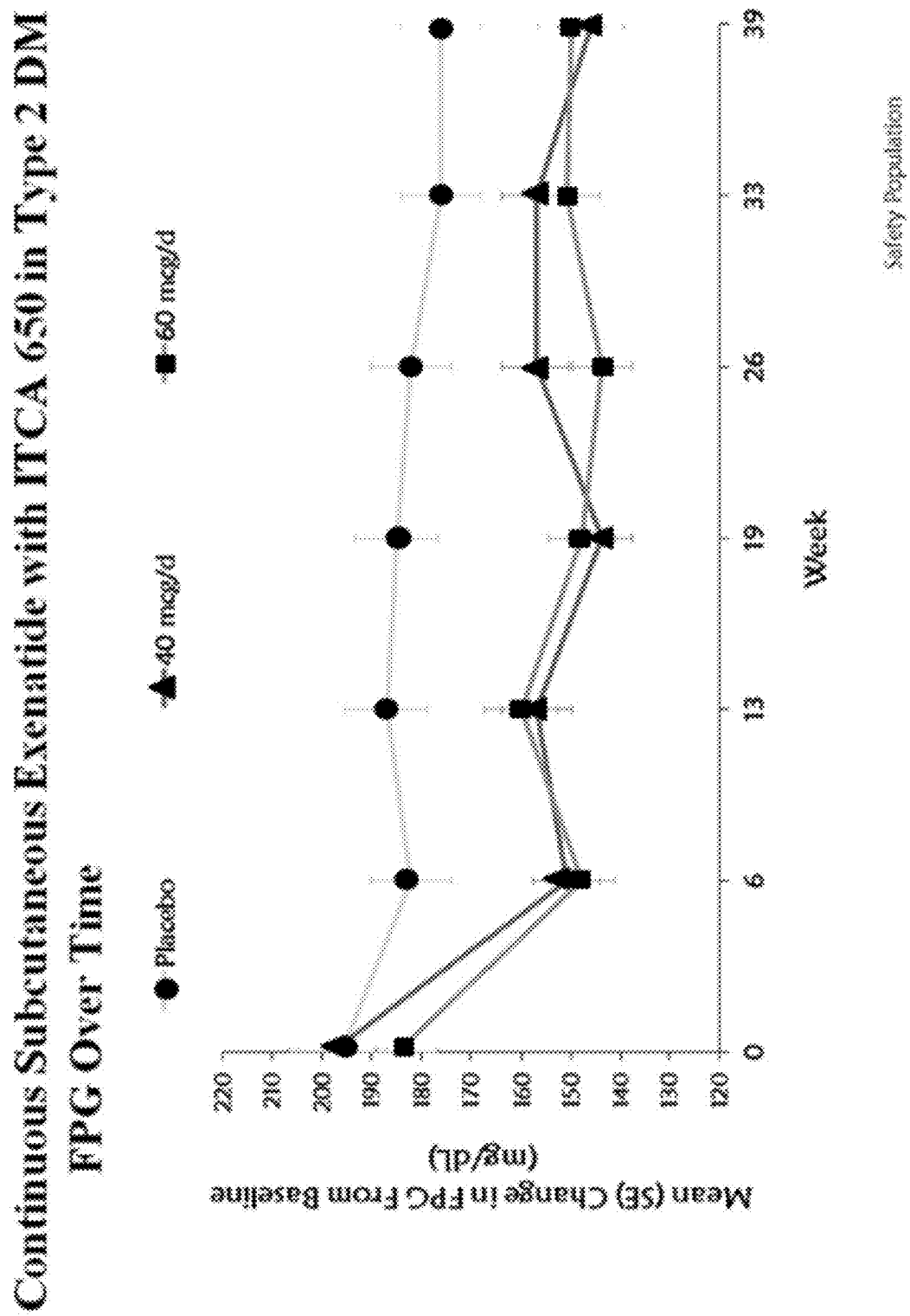

FIG. 28 is a graph showing changes in Fasting Plasma Glucose (FPG) over time for subjects in the phase 3 clinical trial described in Example 1 for subjects in the Safety Population with type 2 diabetes and with a baseline HbA1c % pursuant to the study protocol inclusion criterion. Data identified with closed circles are from placebo subjects, data identified with closed squares are from subjects treated with ITCA 650 20 µg/day for 13 weeks followed by ITCA 650 40 µg/day for 26 weeks, and data identified with closed triangles are from subjects treated with ITCA 650 20 µg/day for 13 weeks followed by ITCA 650 60 µg/day for 26 weeks.

Figure 29:
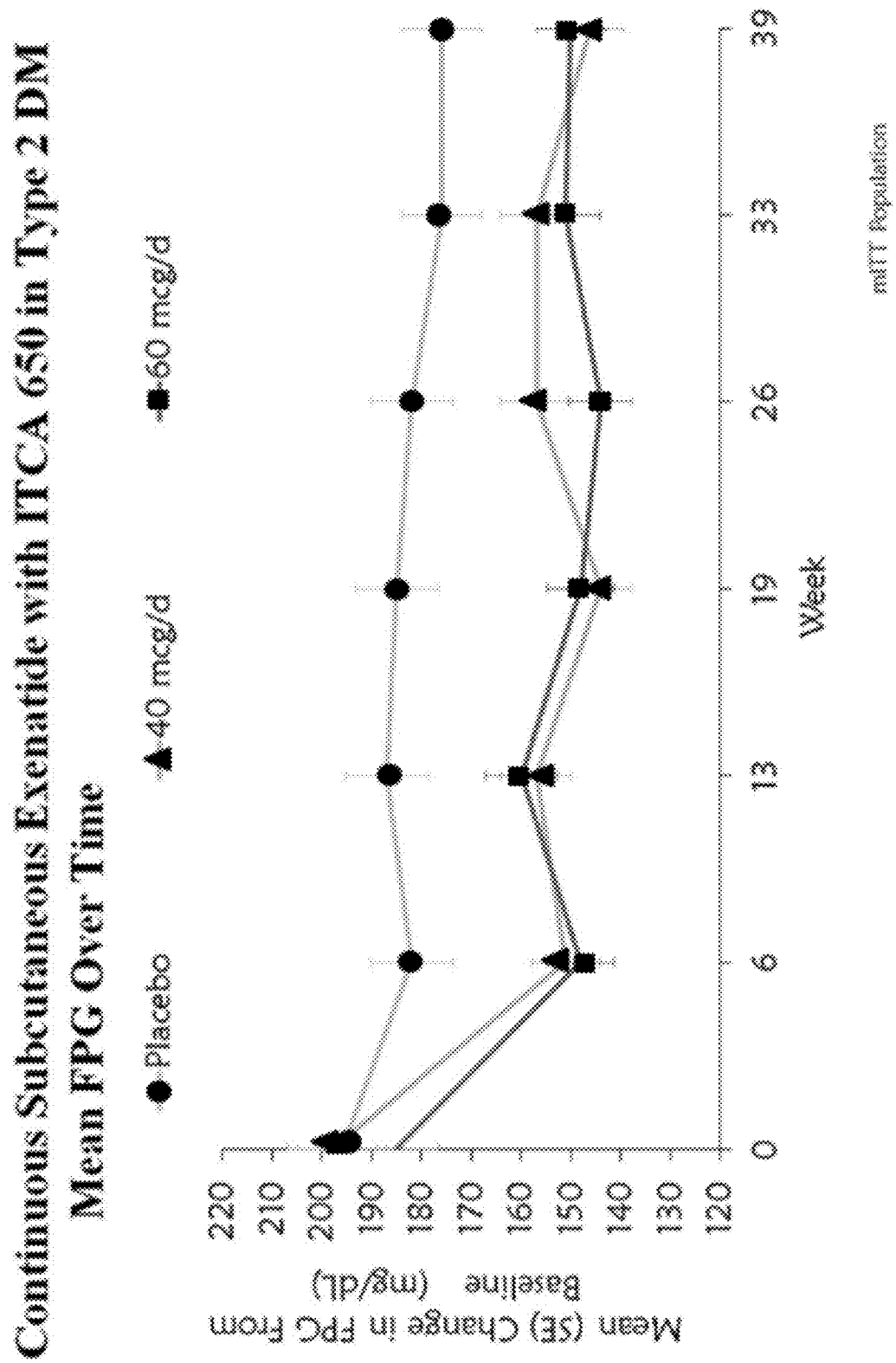

FIG. 29 is a graph showing changes in mean FPG over time for subjects in the phase 3 clinical trial described in Example 1 for subjects in the mITT Population with type 2 diabetes and with a baseline HbA1c % pursuant to the study protocol inclusion criterion. Data identified with closed circles are from placebo subjects, data identified with closed squares are from subjects treated with ITCA 650 20 μg/day for 13 weeks followed by ITCA 650 40 μg/day for 26 weeks, and data identified with closed triangles are from subjects treated with ITCA 650 20 μg/day for 13 weeks followed by ITCA 650 60 μg/day for 26 weeks.

Figure 30:
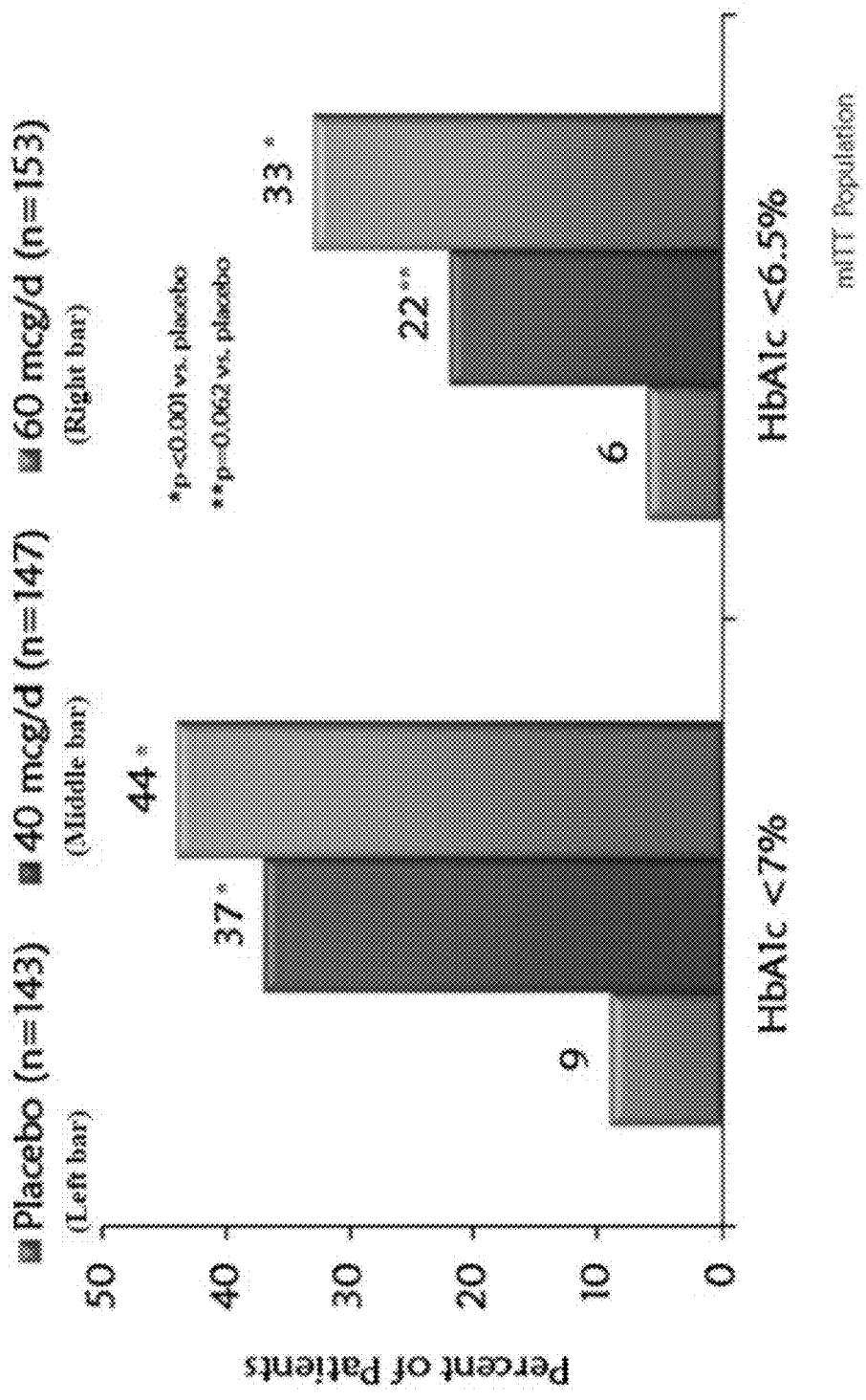

FIG. 30 is a graph showing percentages of patients reaching an HbA1c target of less than 7% or less than 6.5% at week 39 for subjects in the phase 3 clinical trial described in Example 1 for subjects in the mITT Population. Data in the left bars are from placebo subjects, data in the middle bars are from subjects treated with ITCA 650 20 μg/day for 13 weeks followed by ITCA 650 40 μg/day for 26 weeks, and data in the right bars are from subjects treated with ITCA 650 20 μg/day for 13 weeks followed by ITCA 650 60 μg/day for 26 weeks.

Figure 31:
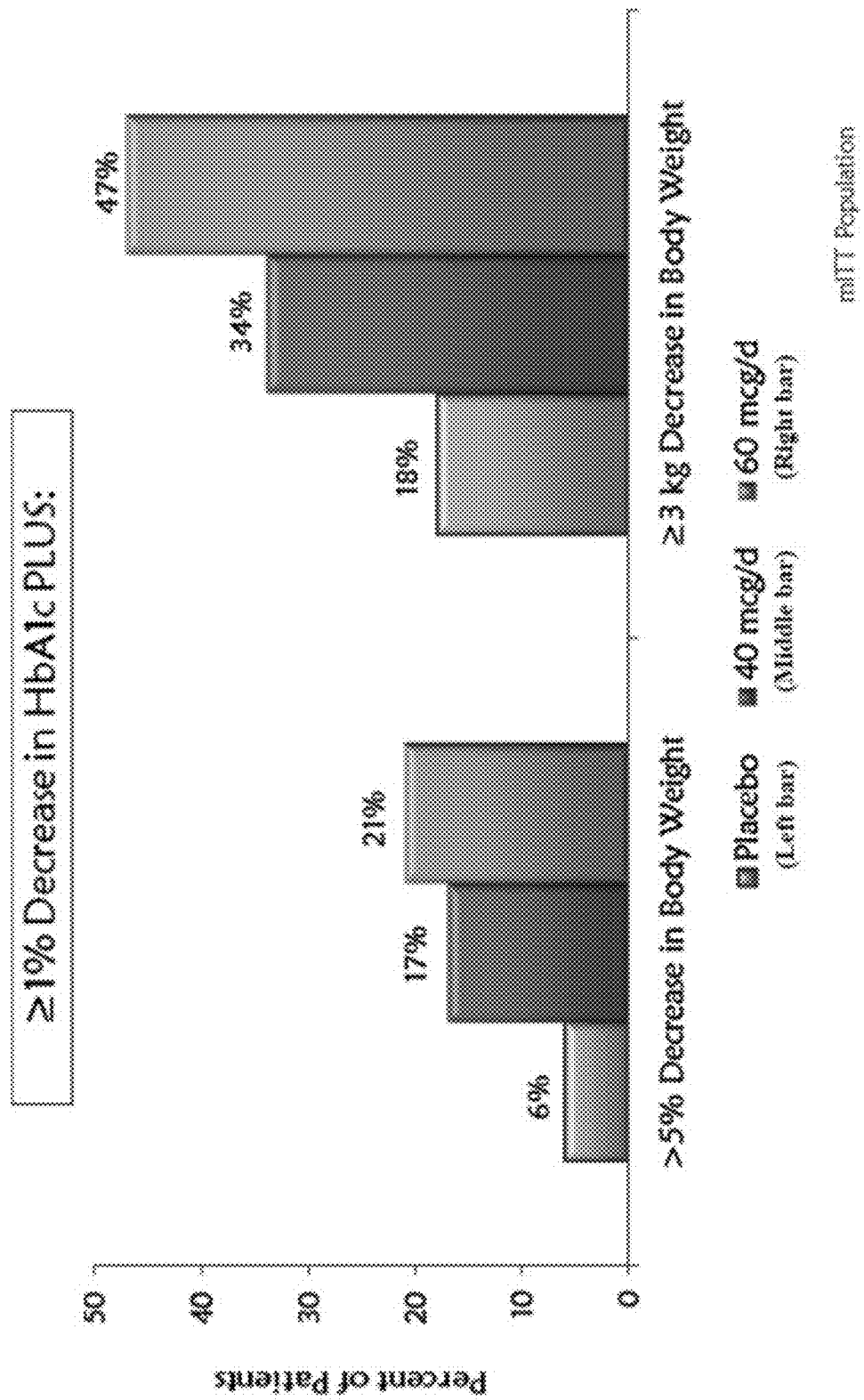

FIG. 31 is a graph showing percentages of patients who experienced a greater than 5% decrease in weight loss or who experienced a greater than or equal to 3 kilogram weight loss for subjects in the phase 3 clinical trial described in Example 1 for subjects in the mITT Population. Data is divided by Exenatide dose. Data in the left bars are from placebo subjects, data in the middle bars are from subjects treated with ITCA 650 20 μg/day for 13 weeks followed by ITCA 650 40 μg/day for 26 weeks, and data in the right bars are from subjects treated with ITCA 650 20 μg/day for 13 weeks followed by ITCA 650 60 μg/day for 26 weeks.

Figure 32:
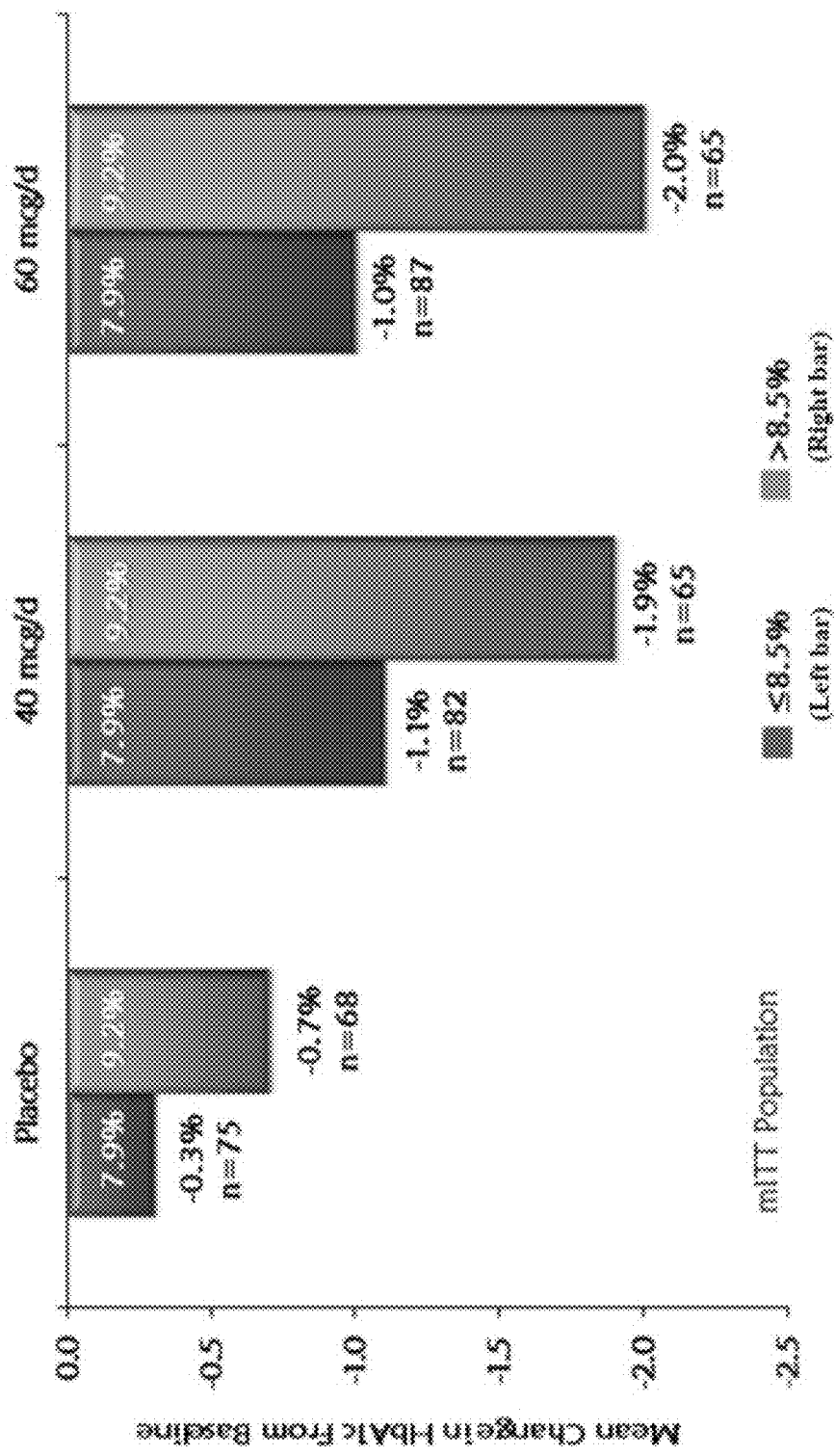

FIG. 32 is a graph showing mean changes in HbA1c % for subjects in the phase 3 clinical trial described in Example 1 for subjects in the mITT Population. Data is divided by Exenatide dose and for patients having a baseline HbA1c % of less than or equal to 8.5% (left bars) or greater than 8.5% and ≤10% (right bars).

Figure 33:
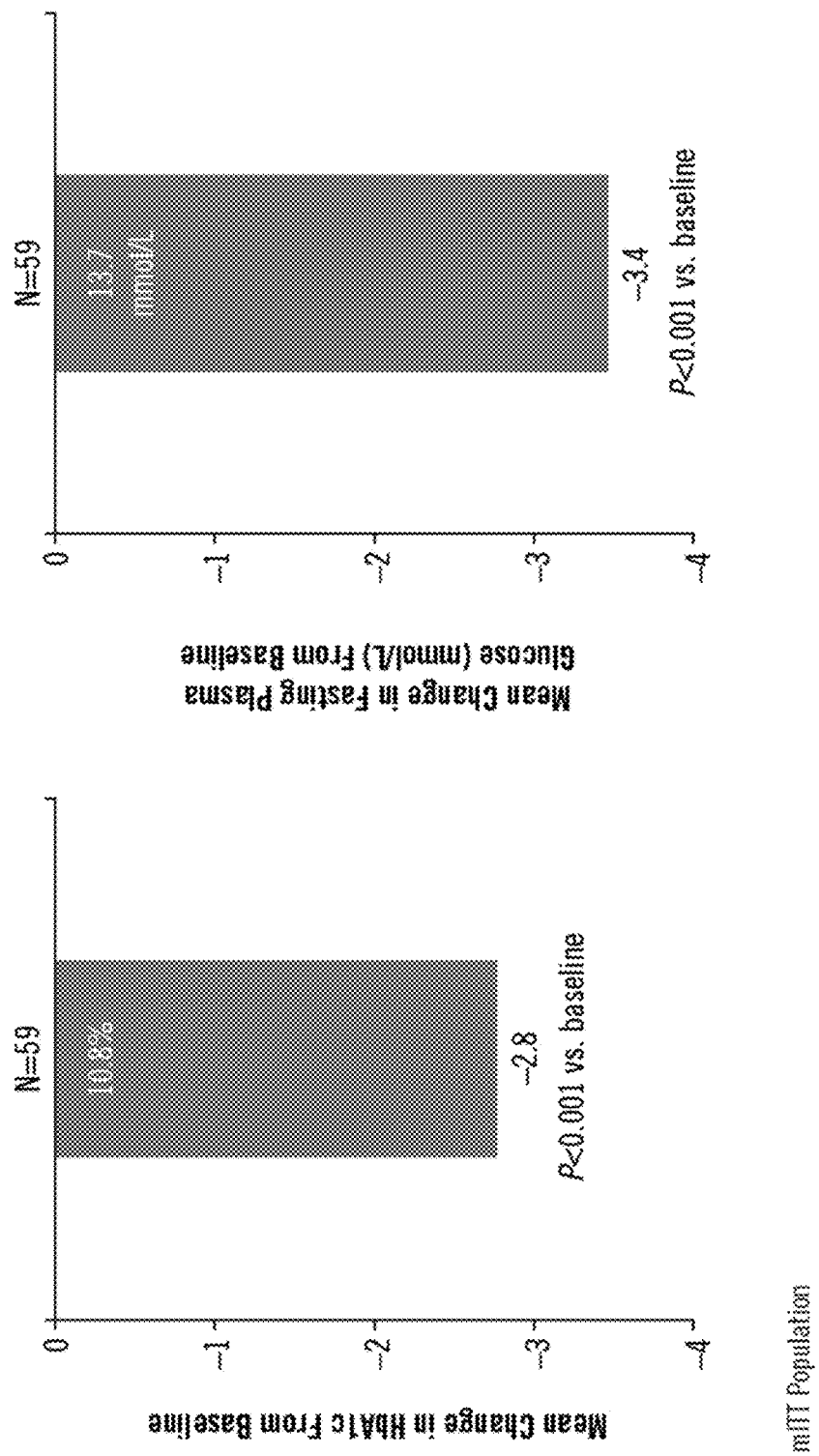

FIG. 33 is a graph showing mean changes in HbA1c % and Fasting Plasma Glucose (FPG) from baseline for subjects in the phase 3 clinical trial described in Example 1 for subjects in the mITT Population.

Figure 34:
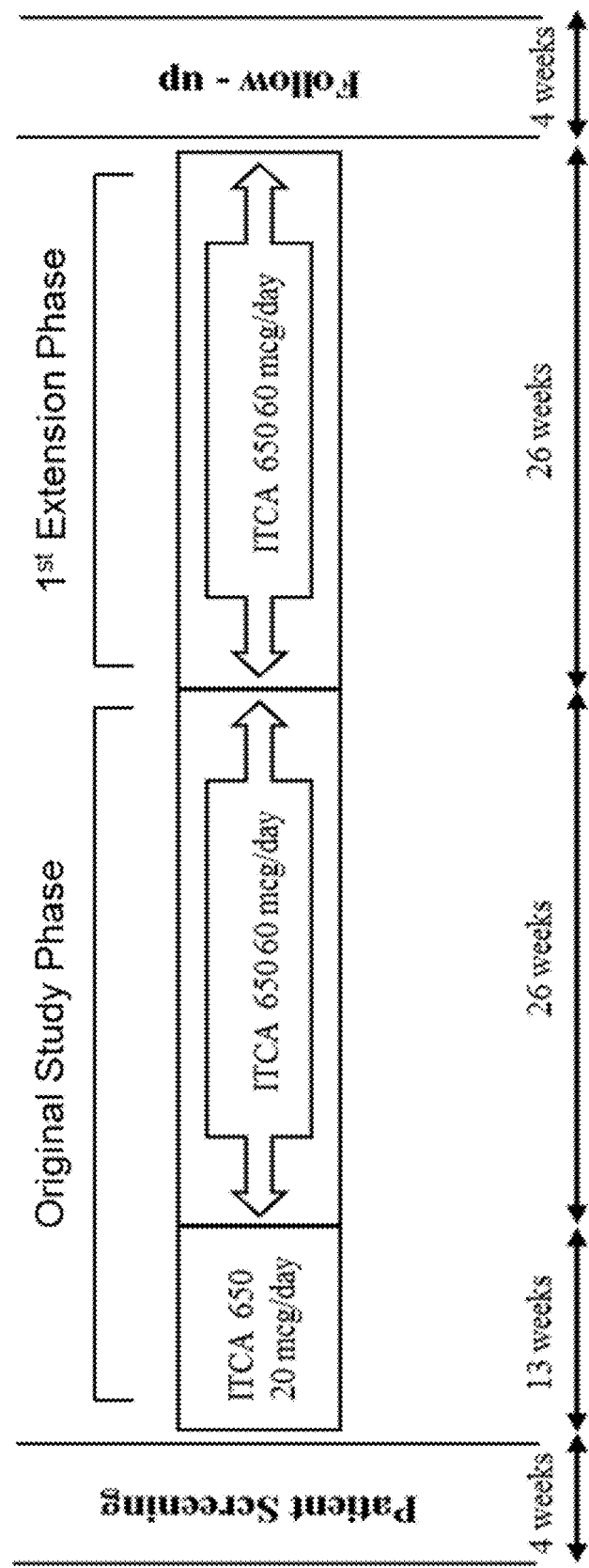

FIG. 34 presents an overview of the open-label initial phase with 39 weeks of treatment and the first 26-week extension phase ("first extension phase" or "extension phase 1") for subjects with type 2 diabetes and with high baseline HbA1c as described in Example 2.

Figure 35:
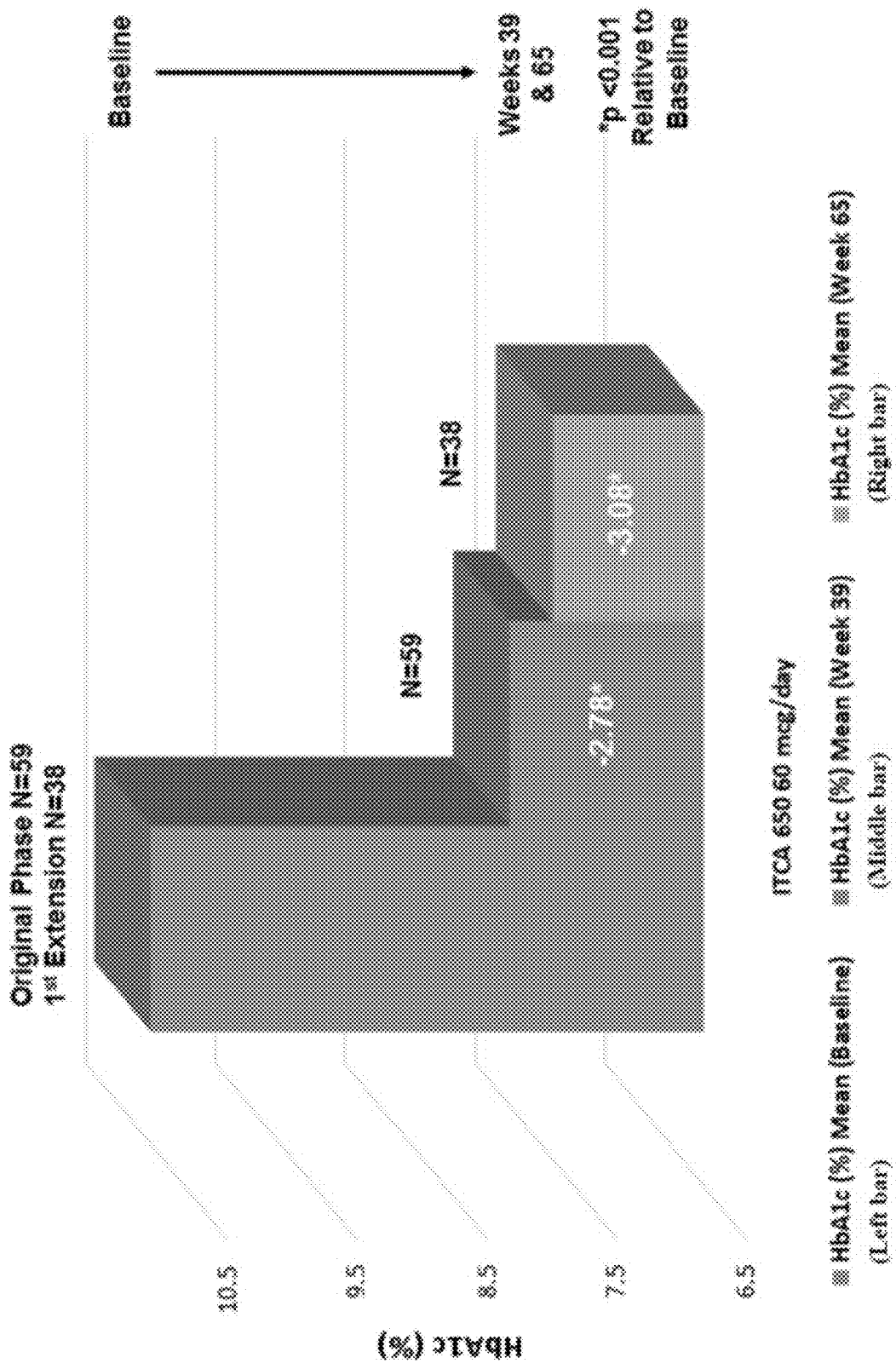

FIG. 35 is a graph showing the relative change from baseline in HbA1c (%) at LOCF endpoint for mITT populations in the original 39 week study phase of this phase 3 open-label trial and in the first extension phase of this phase 3 trial (up to 65 weeks), respectively. Average baseline HbA1c (%) value is represented by the left, average HbA1c (%) value at 39 weeks for subjects treated with ITCA 650 60 mcg/day are represented by the middle bar, and average HbA1c (%) value at 65 weeks for subjects treated with ITCA 650 60 mcg/day are represented by the right bar. "ITCA 650 60 mcg/day" indicates that subjects were treated with ITCA 650 20 μg/day for 13 weeks followed by ITCA 650 60 μg/day for up to 26 weeks (week 39) or for an additional 26 weeks (up to week 65).

Figure 36:
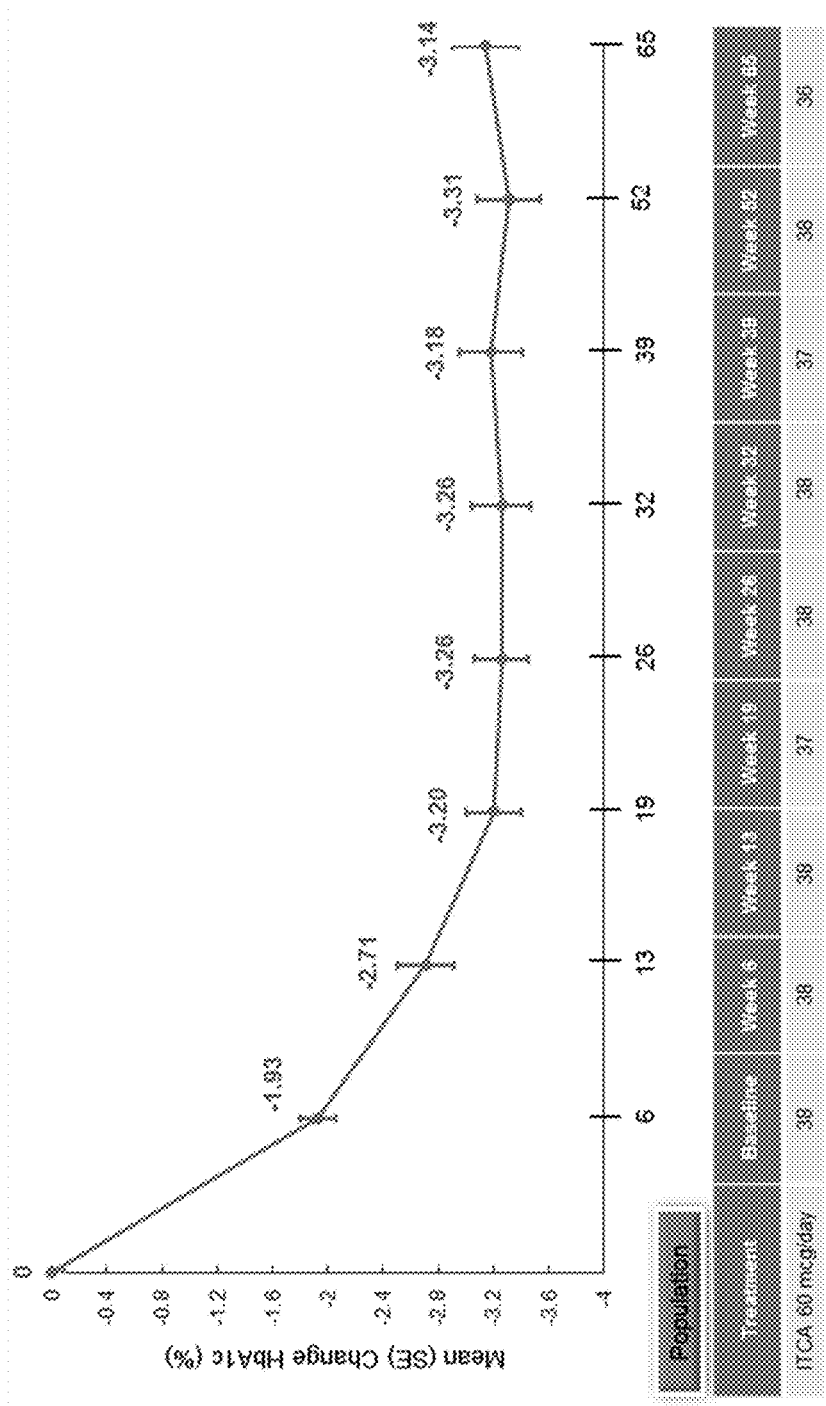

FIG. 36 is a graph showing the relative change from baseline in HbA1c (%) at LOCF endpoint by visit for mITT population who participated in the first extension phase of the phase 3 trial (up to 65 weeks). Average decreases for subjects relative to placebo were clinically and statistically significant at every study visit throughout the trial. Subjects were treated with ITCA 650 20 mcg/day for the first 13 weeks followed by ITCA 650 60 mcg/day for the following 52 weeks ("60 mcg/day").

DETAILED DESCRIPTION OF THE INVENTION

All patents, publications, and patent applications cited in this specification are herein incorporated by reference as if each individual patent, publication, or patent application was specifically and individually indicated to be incorporated by reference in its entirety for all purposes.

A subject in need thereof may have a baseline hemoglobin A1c (HbA1c) % of greater than greater than 6.5%. Preferably, the subject has a baseline HbA1c % of greater than 10.0%, e.g., at least about 10.01%, at least about 10.1%, at least about 10.5%, at least about 11.0%, at least about 11.5%, at least about 11.9%, and about 12.0% prior to administration of the pharmaceutical composition. A subject with an HbA1c % of greater than about 10% is referred to herein as a high baseline (HBL) subject. Methods and uses according to the present invention may comprise a step of selecting a subject, including a subject who is a high baseline subject, prior to treatment, or prior to continued treatment, with an insulinotrophic peptide (e.g., an exenatide). Methods and uses according to the present invention may comprise a step of determining, e.g., in vitro, the percentage HbA1c in a subject's blood, e.g., in a blood sample, and optionally selecting a subject determined to be a high baseline subject for treatment with an exenatide.

In some embodiments, the subject's serum HbA1c % is decreased by at least about 0.5%, at least about 1.0%, at least about 1.5%, or at least about 2.0% from baseline over the administration period. In other embodiments, the subject's HbA1c level is decreased by at least about 2.5%, at least about 3.0%, at least about 3.5%, at least about 4.0%, at least about 4.5%, at least about 5.0%, at least about 5.5%, or at least about 6.0% from baseline over the administration period. For example, when the subject's HbA1c % decreases from 11.4% to 7.4%, this is a 4% decrease.

In some embodiments, the amount of HbA1c in the subject's serum is at least about 35 percent less (i.e., reduced) at the end of an administration period relative to the beginning of the administration period. In certain other embodiments, the amount of HbA1 in the subject's serum is at least about 40 percent, at least about 45 percent, at least about 50 percent, or at least about 55 percent less at the end of an administration period relative to at the beginning of the administration period. For example, the subject's HbA1c % reduces from 11.4% to about 7.4%, which is a 35 percent reduction.

In some embodiments, the present invention is directed to methods of treating diabetes in patients having baseline HbA1c levels of greater than 6.5% or greater than 10%, by administering a therapeutically effective amount of a pharmaceutical exenatide composition from an implanted osmotic delivery device over an administration period. The administration may provide improved tolerization to escalation of a dose of the pharmaceutical exenatide composition during the administration period.

In some embodiments, the present invention is directed to methods of effecting weight loss and/or treating excess weight or obesity in a subject undergoing diabetes treatment by administering a therapeutically effective amount of an exenatide from an implanted osmotic delivery device over an administration period. In this embodiment, weight loss and/or treating excess weight or obesity is achieved within about six weeks after initial implantation of the osmotic delivery device and up to at least 39 weeks after initial implantation.

In some embodiments, the present invention is directed to methods of abating nausea in a subject undergoing diabetes treatment, e.g., a subject having a baseline HbA1c % of greater than 6.5% or greater than 10%, by administering a therapeutically effective amount of a pharmaceutical exenatide composition from an implanted osmotic delivery device over an administration period, wherein nausea abates in the patient within at least about 7 days of implantation of the osmotic delivery device and the abatement remains throughout the administration period. Abating nausea will increase the likelihood that a subject will continue (e.g., not withdraw from) a treatment comprising the implanted osmotic delivery device.

In some embodiments, the present invention is directed to methods for lowering plasma glucose levels (e.g., fasting plasma glucose levels; FPG) in a subject undergoing diabetes treatment, e.g., a subject having a baseline HbA1c % of greater than 6.5% or greater than 10%, by administering a therapeutically effective amount of an exenatide from an implanted osmotic delivery device over an administration period.

In some embodiments, the present invention is directed to methods of reducing incidence and severity of side effects from a type 2 diabetes treatment in a subject undergoing diabetes treatment, e.g., a subject having a baseline HbA1c % of greater than 6.5% or greater than 10%, by administering a therapeutically effective amount of an exenatide from an implanted osmotic delivery device over an administration period. Reducing incidence and severity of side effects increases the likelihood that a subject will continue (e.g., not withdraw from) a treatment comprising the implanted osmotic delivery device.

In some embodiments, the present invention is directed to methods of improving a Quality of Life (QOL) assessment/score in a subject undergoing diabetes treatment, e.g., a subject having a baseline HbA1c % of greater than 6.5% or greater than 10%, by administering a therapeutically effective amount of an exenatide from an implanted osmotic delivery device over an administration period. Improving the QOL assessment/score will increase the likelihood that a subject will continue (e.g., not withdraw from) a treatment comprising the implanted osmotic delivery device.

In some embodiments, the present invention is directed to methods of lowering low-density lipoprotein (LDL) levels in a subject undergoing diabetes treatment, e.g., a subject having a baseline HbA1c % of greater than 6.5% or greater than 10%, by administering a therapeutically effective amount of an exenatide from an implanted osmotic delivery device over an administration period In some embodiments, the present invention is directed to methods of reducing systolic blood pressure in a subject undergoing diabetes treatment, e.g., a subject having a baseline HbA1c % of greater than 6.5% or greater than 10% and undergoing diabetes treatment, by administering a therapeutically effective amount of an exenatide from an implanted osmotic delivery device over an administration period.

In some embodiments, the present invention is directed to methods of achieving rapid onset and consistent long-term plasma levels of an exenatide in a subject undergoing diabetes treatment, e.g., a subject having a baseline HbA1c % of greater than 6.5% or greater than 10% and undergoing diabetes treatment, by administering a therapeutically effective amount of an exenatide from an implanted osmotic delivery device over an administration period.

Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides or mixtures of peptides, reference to "a drug" includes one or more drugs, reference to "an osmotic delivery device" includes one or more osmotic delivery devices, and the like. Unless specifically stated or obvious from context, as used herein, the term "or" is understood to be inclusive and covers both "or" and "and."

Unless specifically stated or obvious from context, as used herein, the term "about" is understood as within a range of normal tolerance in the art, for example, within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. Exemplary polypeptides include the insulinotrophic peptides described herein, e.g., the exenatide having the amino acid sequence of SEQ ID NO: 1, exenatide peptides, exenatide peptide analogs, exenatide peptide derivatives), glucagon-like peptide 1 (GLP-1), GLP-1 peptides, GLP-1 peptide analogs, and GLP-1 peptide derivatives. The polypeptide may be an antibody or an antibody fragment. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 (1995)); single-chain antibody molecules; and multispecific antibodies formed from antibody fragments. In another embodiment of the present invention, the drug is a small molecule, for example, hormones such as androgens or estrogens. Examples of suitable drugs include, but are not limited to, the herein-described insulinotrophic peptides, Gastric inhibitory peptide (GIP), Glucagon, Glucagon-like peptide 2 (GLP-2), Oxyntomodulin, PYY (also known as peptide YY, peptide tyrosine tyrosine), PYY(3-36), amylin, an amylin analogue (e.g., pramlintide), a ghrelin antagonist, a G protein coupled receptor 119 (GRP 119) agonist, and leptin. The devices and methods of the present invention are well suited for the delivery of proteins, small molecules and combinations thereof.

Two or more (e.g., two, three, four, or more) "drugs," "therapeutic agents," or "beneficial agents" can be included in a particle formulation, in a suspension formulation, and/or in a single osmotic delivery device; thus, an osmotic delivery device may provide substantial steady-state delivery of the two or more "drugs," "therapeutic agents," or "beneficial agents." One of the two or more "therapeutic agents" may be an insulinotrophic peptide (e.g., an exenatide). Examples of such particle formulations, in a suspension formulations, and osmotic delivery devices are described, e.g., U.S. Pat. No. 8,343,140 and U.S. Patent Publication No. 2015-0111818, each of which is incorporated herein by reference in its entirety. The two or more "therapeutic agents" may be two or more different insulinotrophic polypeptides.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetic). Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, desamino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. In one embodiment, a peptide may be modified by addition of a small-molecule drug.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the peptide's amino terminus and increasing in the direction of its carboxy terminus.

The phrase "amino acid residue" as used herein refers to an amino acid that is incorporated into a peptide by an amide bond or an amide bond mimetic.

GLP-1 is produced by the L-cell located mainly in the ileum and colon, and to a lesser extent by L-cells in the duodenum and jejunum. GLP-1 is a regulatory peptide of a G-coupled protein receptor on β cell and via adenyl cyclase activity and production of cAMP stimulates the insulin response to the nutrients that are absorbed from the gut (Baggio 2007, Holst 2008). The effects of GLP-1R agonism are multiple. GLP-1 maintains glucose homeostasis by enhancing endogenous glucose dependent insulin secretion, rendering the β cells glucose competent and sensitive to GLP-1, suppressing glucagon release, restoring first and second phase insulin secretion, slowing gastric emptying, decreasing food intake, and increasing satiety (Holst 2008, Kjems 2003, Holst 2013, Seufret 2014). The risk of hypoglycemia is minimal given the mode of action of GLP-1. GLP-1 is an exemplary incretin; the incretins are a group of metabolic hormones that stimulate a decrease in blood glucose levels.

The term "insulinotrophic" as used herein typically refers to the ability of a compound, e.g., a peptide, to stimulate or affect the production and/or activity of insulin (e.g., an insulinotrophic hormone). Such compounds typically stimulate the secretion or biosynthesis of insulin in a subject. Thus, an "insulinotrophic peptide" is an amino acid-containing molecule capable of stimulating secretion or biosynthesis of insulin.

The term "insulinotrophic peptide" as used herein includes, but is not limited to, glucagon-like peptide 1 (GLP-1), as well as derivatives and analogues thereof, and exenatide having the amino acid sequence of SEQ ID NO; 1, as well as derivatives and analogues thereof.

The phrase "incretin mimetics" as used herein includes, but is not limited to GLP-1 peptide, peptide derivatives of GLP-1, and peptide analogs of GLP-1; and the exenatide having the amino acid sequence of SEQ ID NO: 1, exenatide peptide, peptide derivatives of exenatide, and peptide analogs of exenatide). Examples of preferred incretin mimetics include the exenatide having the amino acid sequence of exendin-4 (the naturally-occurring form of exenatide, and has the amino acid sequence of SEQ ID NO: 1), exenatide-LAR, lixisenatide, GLP-1 (7-36), liraglutide, dulaglutide, albiglutide, and taspoglutide. Incretin mimetics are also known in the literature as "insulinotrophic peptides." Incretin mimetics which target the GLP-1 receptor are also known in the literature as"GLP-1 receptor agonists."

The term "an exenatide" as used herein includes, but is not limited to the exenatide having the amino acid sequence of SEQ ID NO: 1, native exendin-4, exenatide peptides, exenatide peptide analogs, and exenatide peptide derivatives.

The term "vehicle" as used herein refers to a medium used to carry a compound, e.g., a drug or a particle containing a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid and gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a drug particle formulation, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where F/A=shear stress (force per unit area),
μ=proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometry performed under selected conditions (for example, a temperature of about 37° C.). Other methods for the determination of viscosity include measurement of a kinematic viscosity using viscometers, for example, a Cannon-Fenske viscometer, an Ubbelohde viscometer for the Cannon-Fenske opaque solution, or an Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, preferably less than or equal to about 7 wt %, more preferably less than or equal to about 5 wt %, and more preferably less than about 4 wt %. Also, a particle formulation of the present invention comprises less than about 10 wt %, e.g., preferably less than about 5 wt % residual moisture.

The term "subject" as used herein refers to any member of the subphylum Chordata, including, without limitation, humans and other primates, including non-human primates such as rhesus macaques and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age or gender. Thus, both adult and newborn individuals are intended to be covered. Preferably the subject is a human.

The term "osmotic delivery device" as used herein typically refers to a device used for delivery of a drug (e.g., an insulinotrophic peptide) to a subject, wherein the device comprises, for example, a reservoir (made, e.g., from a titanium alloy) having a lumen that contains a suspension formulation comprising a drug (e.g., an insulinotrophic peptide) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subdermally or subcutaneously (e.g., in the inside, outside, or back of the upper arm and in the abdominal area). An exemplary osmotic delivery device is the DUROS® delivery device. Examples of terms synonymous to "osmotic delivery device" include but are not limited to "osmotic drug delivery device," "osmotic drug delivery system," "osmotic device," "osmotic delivery device," "osmotic delivery system," "osmotic pump," "implantable drug delivery device," "drug delivery system," "drug delivery device," "implantable osmotic pump," "implantable drug delivery system," and "implantable delivery system." Other terms for "osmotic delivery device" are known in the art. The DUROS® device is an example of an osmotic delivery device. As used herein, "ITCA 650" is a DUROS® device comprising exenatide having the amino acid sequence of SEQ ID NO: 1.

The term "continuous delivery" as used herein typically refers to a substantially continuous release of drug from an osmotic delivery device and into tissues near the implantation site, e.g., subdermal and subcutaneous tissues. For example, the DUROS® delivery device releases drug essentially at a predetermined rate based on the principle of osmosis. Extracellular fluid enters the DUROS® device through the semi-permeable membrane directly into the osmotic engine that expands to drive the piston at a slow and consistent rate of travel. Movement of the piston forces the drug formulation to be released through the orifice of the diffusion moderator. Thus release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic delivery device is substantially zero-order delivery. Substantial zero-order delivery of a therapeutic agent (e.g., an insulinotrophic peptide, preferably an exenatide) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

The phrase "drug half-life" as used herein refers to how long it takes a drug to be eliminated from blood plasma by one half of its concentration. A drug's half-life is usually measured by monitoring how a drug degrades when it is administered via injection or intravenously. A drug is usually detected using, as examples, a radioimmunoassay (RIA), a chromatographic method, an electrochemiluminescent (ECL) assay, an enzyme linked immunosorbent assay (ELISA) or an immunoenzymatic sandwich assay (IEMA).

The terms "μg" and "mcg" are understood to mean "micrograms." Similarly, the terms "μl" is understood to mean "microliter."

The term "serum" is meant to mean any blood product from which a substance can be detected. Thus, "serum" includes at least whole blood, serum, and plasma. For example, "an amount of [a substance] in a subject's serum" would cover "an amount of [the substance] in a subject's plasma."

The term "LOCF" means "Last Observation Carried Forward." LOCF is an imputation method that can be used to analyze clinical trial data, when such data are longitudinal, to address dropouts. In the LOCF method, the last observed non-missing value is used to fill in missing values at later points. As used herein, LOCF includes the last post-randomization data obtained from a subject with at least one post-randomization HbA1c value when the subject stopped participating in the study.

The term "mITT" stands for "Modified Intention-to-Treat Population." Here, primary efficacy analyses and safety analyses will be performed on an mITT population that includes all subjects who were randomized and received at least one treatment with ITCA 650 or ITCA placebo, who had a valid baseline, and who had at least one post-baseline HbA$_{1c}$ value.

Baseline is defined as the last assessment on or before the day of the initial placement of an ITCA 650 osmotic delivery device (containing drug or placebo).

2.0.0 General Overview of the Invention

Before describing the present invention in detail, it is to be understood that this invention is not limited to particular types of drug delivery devices, particular sources of drugs, particular solvents, particular polymers, and the like, as use of such particulars may be selected in view of the teachings of the present specification. It is also to be understood that the terminology used herein is for the purpose of describing particular embodiments of the invention only, and is not intended to be limiting.

In some aspects, the present invention relates to a method of treating type 2 diabetes mellitus. The subject is in need of treatment for type 2 diabetes. In some embodiments, the subject in need thereof has a baseline HbA1c % of greater than 6.5%. In other embodiments, the subject in need thereof has a baseline HbA1c % of greater than 10.0%, i.e., a high baseline (HBL) subject. In some embodiments, the subject has a baseline HbA1c % of greater than 10% and less than or equal to 12.0%. The method comprises providing continuous delivery of an insulinotrophic peptide from an osmotic delivery device, wherein substantial steady-state delivery of the insulinotrophic peptide at a therapeutic concentration is achieved within a time period of with the first day of implantation up to about 7 days after implantation of the osmotic delivery device in the subject, e.g., subcutaneously and/or subdermally. Thus, steady-state delivery of the insulinotrophic peptide occurs at any time point after implantation and up to about 7 days after implantation; non-limiting examples include 2 hours after implantation, 36 hours after implantation, 3 and a half days after implantation, and six days after implantation. The substantial steady-state delivery of the insulinotrophic peptide from the osmotic delivery device is continuous over an administration period. Humans are preferred subjects for the practice of the present invention. The present invention includes particles comprising an insulinotrophic peptide (e.g., an exenatide), formulations comprising the insulinotrophic peptide, and formulations comprising particles comprising the insulinotrophic peptide, as well as an osmotic delivery device comprising the insulinotrophic peptide for use in the present methods of treating type 2 diabetes mellitus in a subject in need of treatment. The subject may not have previously received a drug for treating type 2 diabetes mellitus. In some embodiments, the subject is further provided one or more other drugs for treating type 2 diabetes mellitus, e.g., insulin and/or oral anti-diabetic drugs including, without limitation, DPP4 inhibitors, SGLT2 inhibitors, metformin, sulfonylureas, and thiazolidinediones (TZDs).

In some embodiments of the present invention, the administration period is, for example, at least about 1 month, at least about 1 month to about two years, at least about 2 months to about two years, at least about 3 months to about two years, at least about 3 months to about two years, at least about 4 months to about two years, at least about 5 months to about two years, at least about 6 months to about two years, at least about 8 months to about two years, or at least about 9 months to about two years, about 1 year, at least one year to about two years, at least about 12 months to about two years, at least about 14 months to about two years, at least about 16 months to about two years, at least 18 months to about two years, at least about 20 months to about two years, at least about 22 months to about two years, and about two years.

In some embodiments, the administration period is, for example, at least about 12 months to about 18 months, at least about 13 months to about 18 months, at least about 14 months to about 18 months, at least about 15 months to about 18 months, at least about 16 months to about 18 months, at least about 17 months to about 18 months, and about 18 months.

In some embodiments, the administration period is, for example, at least about 1 month to about a year, at least about 2 months to about a year, about 3 months, at least about 3 months to about a year, at least about 4 months to about a year, at least about 5 months to about a year, about 6 months, at least about 6 months to about a year, at least about 8 months to about a year, about 9 months, at least about 9 months to about a year, at least about 10 months to about a year, at least about 11 month to about a year, and about a year.

In some embodiments of the present invention, the substantial steady-state delivery of an insulinotrophic peptide (e.g., an exenatide) at therapeutic concentrations is achieved within about 7 days after implantation of the osmotic delivery device in the subject, within about 6 days after implantation of the osmotic delivery device in the subject, within about 5 days after implantation of the osmotic delivery device in the subject, within about 4 days after implantation of the osmotic delivery device in the subject, within about 3 days after implantation of the osmotic delivery device in the subject, within about 2 days after implantation of the osmotic delivery device in the subject, or within about 1 day after implantation of the osmotic delivery device in the subject. Steady-state delivery of the insulinotrophic peptide occurs at any time point after implantation and up to within about 7 days after implantation. In preferred embodiments of the present invention, the substantial steady-state delivery of the insulinotrophic peptide at therapeutic concentrations is achieved within about 2 days and more preferably within about 1 day after implantation of the osmotic delivery device in the subject.

Continuous delivery can, for example, be zero-order, controlled continuous delivery.

In further embodiments, the treatment methods of the present invention provide a significant decrease in the subject's fasting plasma glucose concentration after implantation of the osmotic delivery device in the subject (relative to the subject's fasting plasma glucose concentration before implantation of the osmotic delivery device) that is achieved within about 7 days after implantation of the osmotic delivery device in the subject, within about 6 days after implantation of the osmotic delivery device in the subject, within about 5 days after implantation of the osmotic delivery device in the subject, within about 4 days after implantation of the osmotic delivery device in the subject, within about 3 days after implantation of the osmotic delivery device in the subject, within about 2 days after implantation of the osmotic delivery device in the subject, or within about 1 day after implantation of the osmotic delivery device in the subject. Thus, a subject's fasting plasma glucose concentration will initially decrease within any time point after implantation and up to about 7 days after implantation. In preferred embodiments, the significant decrease in the subject's fasting plasma glucose concentration after implantation of the osmotic delivery device, relative to the subject's fasting plasma glucose concentration before implantation, is achieved within about 2 days or preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

The treatment methods can further comprise providing a significant decrease in the subject's HbA1c % after implantation of the osmotic delivery device in the subject, relative to the subject's HbA1c % before implantation of the osmotic delivery device. The decrease is typically achieved within about six weeks after implantation of the osmotic delivery device (e.g., within about five weeks after implantation of the osmotic delivery device, within about four weeks after implantation of the osmotic delivery device, within about three weeks after implantation of the osmotic delivery device, within about two weeks after implantation of the osmotic delivery device, or within about one week after implantation of the osmotic delivery device). The significant decrease in the subject's HbA1c % is maintained over the administration period.

The treatment methods can further provide a decrease in a subject's HbA1c % over the administration period of at least about 0.5%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, or at least about 6.0% from baseline over the administration period or a reduction in the amount of HbA1c in the subject's serum of at least about 35 percent, at least about 40 percent, at least about 45 percent, at least about 50 percent, or at least about 55 percent at the end of an administration period relative to the beginning of the administration period.

In yet further embodiments of the present invention, the treatment methods further comprise the capability to terminate the continuous delivery of the insulinotrophic peptide (e.g., an exenatide) such that the concentration of the insulinotrophic peptide is substantially undetectable in a blood sample from the subject within about 6 half-lives of the insulinotrophic peptide after termination of continuous delivery, within about 5 half-lives of the insulinotrophic peptide after termination of continuous delivery, within about 4 half-lives of the insulinotrophic peptide after termination of continuous delivery, or within about 3 half-lives of the insulinotrophic peptide after termination of continuous delivery. Thus, the insulinotrophic peptide will be substantially undetectable in a subject's blood sample within any time point after termination of continuous delivery and up to about 6 half-lives after termination of continuous delivery. Examples of insulinotrophic peptide half-lives are the exenatide having the amino acid sequence of SEQ ID NO: 1, approximately 2.5 hours, and GLP-1, approximately 2 minutes. The serum concentration of the insulinotrophic peptide is, for example, detected by a radioimmunoassay (RIA), a chromatographic method, an electrochemiluminescent (ECL) assay, an enzyme linked immunosorbent assay (ELISA) or an immunoenzymatic sandwich assay (IEMA). Termination of the continuous delivery can be accomplished, for example, by removal of the osmotic delivery device from the subject.

In some embodiments of the present invention, the method of treating type 2 diabetes mellitus further comprises terminating the continuous delivery such that the concentration of the insulinotrophic peptide (e.g., an exenatide) is substantially undetectable in a blood sample from the subject after termination of continuous delivery, for example, within about 72 hours, about 48 hours, about 24, about 14 hours, about 12 hours, about 10 hours, about 8 hours, about 6 hours, or about 4 hours. Thus, the insulinotrophic peptide will be substantially undetectable in a subject's blood sample within any time point after termination of continuous delivery and up to about 72 hours after termination of continuous delivery. In some embodiments, continuous delivery of the insulinotrophic peptide is terminated by removal of the osmotic delivery device from the subject. The insulinotrophic peptide may be detected in a serum sample from the subject, for example, by an RIA, a chromatographic method, an ECL assay, an ELISA, or an IEMA.

Osmotic delivery devices for use in the methods of the present invention can comprise the components described herein including, but not limited to, a reservoir, a semi-permeable membrane, an osmotic engine, a piston, a suspension formulation, and a diffusion moderator. In some embodiments, the osmotic delivery device comprises: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable. The osmotic delivery device comprises a diffusion moderator inserted in the second open end of the reservoir, the diffusion moderator adjacent the suspension formulation. In some embodiments, the reservoir comprises titanium or a titanium alloy.

Suspension formulations used in the methods of the present invention typically comprise a particle formulation comprising a therapeutic agent (e.g., an insulinotrophic peptide, preferably, an exenatide) and a vehicle formulation.

A vehicle formulation comprises a solvent (e.g., benzyl benzoate, lauryl lactate, and lauryl alcohol) and a polymer (e.g., polyvinylpyrrolidone: also herein referred to as PVP, polyvidone, and povidone). Preferably, the polymer is polyvinylpyrrolidone. The vehicle formulation may have a viscosity of between about 10,000 poise and about 20,000 poise at 37° C.

In preferred embodiments, the insulinotrophic peptide is GLP-1 or an incretin mimetic, e.g., an exenatide peptide, a peptide analog of exenatide, or a peptide derivative of exenatide; and a GLP-1 peptide (e.g., GLP-1(7-36) amide peptide), a peptide analog of GLP-1, or a peptide derivative of GLP-1. Specific examples of preferred insulinotrophic peptides useful in the practice of the present invention include the exenatide having the amino acid sequence of SEQ ID NO: 1 (e.g., native exendin-4), exenatide-LAR, lixisenatide, GLP-1(7-36), liraglutide, albiglutide, dulaglutide, and taspoglutide. The sequence of exendin-4 is H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 1).

Particles of a particle formulation comprising an insulinotrophic peptide have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. When the insulinotrophic peptide is an exenatide, particles have diameters of between about 2 microns and about 50 microns.

An insulinotrophic peptide can be included in a particle formulation, in a suspension formulation, and/or in a single osmotic delivery device along with one or more (e.g., one, two, three, four, or more) other therapeutic agents; thus, an osmotic delivery device may provide substantial steady-state delivery of the insulinotrophic peptide and one or more other therapeutic agents. Non-limiting examples of the one or more other therapeutic agents include amylin, an amylin analogue (e.g., pramlintide), a ghrelin antagonist, a G protein coupled receptor 119 (GRP 119) agonist, and leptin. An osmotic delivery device may provide substantial steady-state delivery of two or more different insulinotrophic peptides.

In some embodiments, the subject is further provided one or more other drugs for treating type 2 diabetes mellitus, e.g., insulin and/or oral anti-diabetic drugs including, without limitation, DPP4 inhibitors, SGLT2 inhibitors, metformin, sulfonylureas, and thiazolidinediones (TZDs).

In some embodiments of the present invention, continuous delivery can provide to the subject a μg/day dose of an insulinotrophic peptide, for example, a dose of about 10 μg/day, about 15 μg/day, about 20 μg/day, about 30 μg/day, about 40 μg/day, about 50 μg/day, about 60 μg/day, about 70 μg/day, and about 80 μg/day. The upper limit to the daily dose depends to the peptide/active agent and the total capacity of the device itself. A skilled artisan would be able to determine a suitable dose (with regards to safety and efficacy) for a specific insulinotrophic peptide. Thus, the daily dose may exceed 80 μg/day.

Preferably, the mcg/day dose of the insulinotrophic peptide is about 20 mcg/day. More preferably, the insulinotrophic peptide is an exenatide and the mcg/day dose is about 20 mcg/day.

Preferably, the mcg/day dose of the insulinotrophic peptide is about 40 mcg/day. More preferably, the insulinotrophic peptide is an exenatide and the mcg/day dose is about 40 mcg/day.

Preferably, the mcg/day dose of the insulinotrophic peptide is about 60 mcg/day. More preferably, the insulinotrophic peptide is an exenatide and the mcg/day dose is about 60 mcg/day.

In additional embodiments of the present invention, the method of treating type 2 diabetes mellitus further comprises a first continuous administration period of the insulinotrophic peptide (e.g., an exenatide) at a first μg/day dose that is followed by a second continuous administration period providing a dose escalation of the insulinotrophic peptide to a second μg/day dose, wherein the second μg/day dose is greater than the first μg/day dose. In some embodiments, the first μg/day dose is delivered by a first osmotic delivery device and the second μg/day dose is delivered by an at least second osmotic delivery device, and delivery of the insulinotrophic peptide from at least the first or the at least second osmotic delivery device is continuous over the administration period of at least about 1 month (e.g., at least about 1 month, at least about 2 months, and at least about 3 months). In one embodiment, the second μg/day dose is at least two times greater than the first μg/day dose. Further, the method can comprise at least one more continuous administration period providing a dose escalation of the insulinotrophic peptide to a higher μg/day dose relative to the second μg/day dose. Dose escalation can be accomplished, for example, by removal of the first osmotic delivery device and implantation of a second osmotic delivery device, or by implantation of a second or further osmotic delivery device where the total dose delivered by the first and second osmotic delivery devices results in the desired dose escalation. Dose escalation allows a subject to receive a therapeutic benefit while being gradually exposed to the insulinotrophic peptide. This tolerizes the subject to the insulinotrophic peptide and reduces the incidence of side effects. Later, once the subject has completed an initial tolerization period with a first, low daily dose, the dose is escalated to a (higher) maintenance dose. A skilled artisan would be able to determine suitable doses (with regards to safety and efficacy) for a first dose and subsequent doses.

Exemplary dose escalations for the insulinotrophic peptide (e.g., an exenatide) are as follows: about 10 μg/day followed by about 20 μg/day; about 10 μg/day followed by about 30 μg/day; about 10 μg/day followed by about 40 μg/day; about 10 μg/day followed by about 50 μg/day; about 10 μg/day followed by about 60 μg/day; about 10 μg/day followed by about 70 μg/day; about 10 μg/day followed by about 80 μg/day; about 15 μg/day followed by about 20 μg/day; about 15 μg/day followed by about 30 μg/day; about 15 μg/day followed by about 40 μg/day; about 15 μg/day followed by about 50 μg/day; about 15 μg/day followed by about 60 μg/day; about 15 μg/day followed by about 70 μg/day; about 15 μg/day followed by about 80 μg/day; about 20 μg/day followed by about 30 μg/day; about 20 μg/day followed by about 40 μg/day; about 20 μg/day followed by about 50 μg/day; about 20 μg/day followed by about 60 μg/day; about 20 μg/day followed by about 70 μg/day; about 20 μg/day followed by about 80 μg/day; about 40 μg/day followed by about 50 μg/day; about 40 μg/day followed by about 60 μg/day; about 40 μg/day followed by about 70 μg/day; about 40 μg/day followed by about 80 μg/day; about 50 μg/day followed by about 60 μg/day; about 50 μg/day followed by about 60 μg/day; about 50 μg/day followed by about 70 μg/day; about 50 μg/day followed by about 80 μg/day; about 60 μg/day followed by about 70 μg/day or about 60 μg/day followed by about 80 μg/day.

Preferably, the first mcg/day dose of the insulinotrophic peptide (e.g., an exenatide) followed by the second mcg/day dose for continuous delivery is about 20 mcg/day followed by about 40 mcg/day.

Preferably, the first mcg/day dose of the insulinotrophic peptide (e.g., an exenatide) followed by the second mcg/day dose for continuous delivery is about 20 mcg/day followed by about 60 mcg/day.

In some embodiments, the method further comprises at least one more continuous administration period, subsequent to a second administration period, providing a dose at the same mcg/day dose as the second mcg/day dose.

In some embodiments, the subject has not previously received a drug for treating type 2 diabetes mellitus.

In any of the above-described embodiments, the insulinotrophic peptide may comprise GLP-1 or an incretin mimetic selected the group consisting of a GLP-1 peptide, a peptide analog of GLP-1, or a peptide derivative of GLP-1, an exenatide (which includes the exenatide having the amino acid sequence of SEQ ID NO: 1, native exendin-4, an exenatide peptide, a peptide analog of exenatide, and a peptide derivative of exenatide). In any of the above methods, the insulinotrophic peptide is selected from the group consisting of lixisenatide, liraglutide, albiglutide, and taspoglutide.

In any of the above-described embodiments, the subject may further be provided one or more other drugs for treating type 2 diabetes mellitus, e.g., insulin and/or oral antidiabetic drugs including, without limitation, DPP4 inhibitors, SGLT2 inhibitors, metformin, sulfonylureas, and thiazolidinediones (TZDs).

Any of the above-described embodiments further promote weight loss in a subject in need thereof. Preferably, the subject has a baseline HbA1c % of greater than 6.5%. More preferably, the subject has a baseline HbA1c % of greater than 10.0%. The subject may have a baseline HbA1c % of less than or equal to 12%. Significant weight loss is achieved by about six weeks (e.g., about five weeks, about four weeks, about three weeks, about two weeks, and about one week) after initial implantation of the osmotic delivery device and up to 39 weeks after initial implantation.

The present invention also relates to a method of treating type 2 diabetes mellitus comprising providing continuous delivery of an exenatide from an osmotic delivery device. The subject is in need of treatment for type 2 diabetes. In some embodiments, the subject in need thereof has a baseline HbA1c % of greater than 6.5%. In other embodiments, the subject in need thereof has a baseline HbA1c % of greater than 10.0%, i.e., a high baseline (HBL) subject. In some embodiments, the subject has a baseline HbA1c % of greater than 10% and less than or equal to 12.0%.

Substantial steady-state delivery of the exenatide at a therapeutic concentration is achieved within a time period of with the first day of implantation up to about 7 days after implantation of the osmotic delivery device in the subject, e.g., subcutaneously and/or subdermally. Thus, steady-state delivery of the exenatide occurs at any time point after implantation and up to about 7 days after implantation; non-limiting examples include 2 hours after implantation, 36 hours after implantation, 3 and a half days after implantation, and six days after implantation. The substantial steady-state delivery of the exenatide from the osmotic delivery device is continuous over an administration period. Humans are preferred subjects for the practice of the present invention. The present invention includes particles comprising an exenatide, formulations comprising the exenatide, and formulations comprising particles comprising the exenatide, as well as an osmotic delivery device comprising the exenatide for use in the present methods of treating type 2 diabetes mellitus in a subject in need of treatment. The subject may not have previously received a drug for treating type 2 diabetes mellitus. In some embodiments, the subject is further provided one or more other drugs for treating type 2 diabetes mellitus, e.g., insulin and/or oral anti-diabetic drugs including, without limitation, DPP4 inhibitors, SGLT2 inhibitors, metformin, sulfonylureas, and thiazolidinediones (TZDs).

In some embodiments of the present invention, the administration period is, for example, at least about 1 month, at least about 1 month to about two years, at least about 2 months to about two years, at least about 3 months to about two years, at least about 3 months to about two years, at least about 4 months to about two years, at least about 5 months to about two years, at least about 6 months to about two years, at least about 8 months to about two years, or at least about 9 months to about two years, about 1 year, at least one year to about two years, at least about 14 months to about two years, at least about 16 months to about two years, at least 18 months to about two years, at least about 20 months to about two years, at least about 22 months to about two years, and about two years.

In some embodiments, the administration period is, for example, at least about 12 months to about 18 months, at least about 13 months to about 18 months, at least about 14 months to about 18 months, at least about 15 months to about 18 months, at least about 16 months to about 18 months, at least about 17 months to about 18 months, and about 18 months.

In some embodiments, the administration period is, for example, at least about 1 month to about a year, at least about 2 months to about a year, about 3 months, at least about 3 months to about a year, at least about 4 months to about a year, at least about 5 months to about a year, about 6 months, at least about 6 months to about a year, at least about 8 months to about a year, about 9 months, at least about 9 months to about a year, at least about 10 months to about a year, at least about 11 month to about a year, and about a year.

In some embodiments of the present invention, the substantial steady-state delivery of an exenatide at therapeutic concentrations is achieved within about 7 days after implantation of the osmotic delivery device in the subject, within about 6 days after implantation of the osmotic delivery device in the subject, within about 5 days after implantation of the osmotic delivery device in the subject, within about 4 days after implantation of the osmotic delivery device in the subject, within about 3 days after implantation of the osmotic delivery device in the subject, within about 2 days after implantation of the osmotic delivery device in the subject, or within about 1 day after implantation of the osmotic delivery device in the subject. Steady-state delivery of the exenatide occurs at any time point after implantation and up to about 7 days after implantation. In preferred embodiments of the present invention, the substantial steady-state delivery of the exenatide at therapeutic concentrations is achieved within about 2 days and more preferably within about 1 day after implantation of the osmotic delivery device in the subject.

Continuous delivery can, for example, be zero-order, controlled continuous delivery.

In further embodiments, the treatment methods of the present invention provide a significant decrease in the subject's fasting plasma glucose concentration after implantation of the osmotic delivery device in the subject (relative to the subject's fasting plasma glucose concentration before implantation of the osmotic delivery device) that is achieved within about 7 days after implantation of the osmotic delivery device in the subject, within about 6 days after implantation of the osmotic delivery device in the subject, within about 5 days after implantation of the osmotic delivery device in the subject, within about 4 days after implantation of the osmotic delivery device in the subject, within about 3 days after implantation of the osmotic delivery device in the subject, within about 2 days after implantation of the osmotic delivery device in the subject, or within about 1 day after implantation of the osmotic delivery device in the subject. Thus, a subject's fasting plasma glucose concentration will initially decrease within any time point after implantation and up to about 7 days after implantation. In preferred embodiments, the significant decrease in the subject's fasting plasma glucose concentration after implantation of the osmotic delivery device, relative to the subject's fasting plasma glucose concentration before implantation, is achieved within about 2 days or preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

The treatment methods can further comprise providing a significant decrease in the subject's HbA1c % after implantation of the osmotic delivery device in the subject, relative to the subject's HbA1c % before implantation of the osmotic delivery device. The decrease is typically achieved within about six weeks after implantation of the osmotic delivery device (e.g., within about five weeks after implantation of the osmotic delivery device, within about four weeks after implantation of the osmotic delivery device, within about three weeks after implantation of the osmotic delivery device, within about two weeks after implantation of the osmotic delivery device, or within about one week after implantation of the osmotic delivery device). The significant decrease in the subject's HbA1c % is maintained over the administration period.

The treatment methods can further provide a decrease in a subject's HbA1c % over the administration period of at least about 0.5%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, or at least about 6.0% from baseline over the administration period or a reduction in the amount of HbA1c in the subject's serum of at least about 35 percent, at least about 40 percent, at least about 45 percent, at least about 50 percent, or at least about 55 percent at the end of an administration period relative to the beginning of the administration period.

In yet further embodiments of the present invention, the treatment methods further comprise the capability to terminate the continuous delivery of the exenatide such that the concentration of the exenatide is substantially undetectable in a blood sample from the subject within about 6 half-lives of the exenatide after termination of continuous delivery, within about 5 half-lives of the exenatide after termination of continuous delivery, within about 4 half-lives of the exenatide after termination of continuous delivery, or within about 3 half-lives of the exenatide after termination of continuous delivery. Thus, the exenatide will be substantially undetectable in a subject's blood sample within any time point after termination of continuous delivery and up to about 6 half-lives after termination of continuous delivery. Examples of exenatide half-lives are the exenatide having the amino acid sequence of SEQ ID NO: 1, approximately 2.5 hours, and GLP-1, approximately 2 minutes. Termination of the continuous delivery can be accomplished, for example, by removal of the osmotic delivery device from the subject. The serum concentration of the exenatide is, for example, detected by a radioimmunoassay (RIA), a chromatographic method, an electrochemiluminescent (ECL) assay, an enzyme linked immunosorbent assay (ELISA) or an immunoenzymatic sandwich assay (IEMA).

In some embodiments of the present invention, the method of treating type 2 diabetes mellitus further comprises terminating the continuous delivery such that the concentration of the exenatide is substantially undetectable in a blood sample from the subject after termination of continuous delivery, for example, within about 72 hours, about 48 hours, about 24, about 14 hours, about 12 hours, about 10 hours, about 8 hours, about 6 hours, or about 4 hours. Thus, the exenatide will be substantially undetectable in a subject's blood sample within any time point after termination of continuous delivery and up to about 72 hours after termination of continuous delivery. In some embodiments, continuous delivery of the exenatide is terminated by removal of the osmotic delivery device from the subject. The exenatide may be detected in a serum sample from the subject, for example, by an RIA, a chromatographic method, an ECL assay, an ELISA, or an IEMA.

Osmotic delivery devices for use in the methods of the present invention can comprise the components described herein including, but not limited to, a reservoir, a semipermeable membrane, an osmotic engine, a piston, a suspension formulation, and a diffusion moderator. In some embodiments, the osmotic delivery device comprises: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable. The osmotic delivery device comprises a diffusion moderator inserted in the second open end of the reservoir, the diffusion moderator adjacent the suspension formulation. In some embodiments, the reservoir comprises titanium or a titanium alloy.

Suspension formulations used in the methods of the present invention typically comprise a particle formulation comprising an exenatide and a vehicle formulation.

A vehicle formulation comprises a solvent (e.g., benzyl benzoate, lauryl lactate, and lauryl alcohol) and a polymer (e.g., polyvinylpyrrolidone: also herein referred to as PVP, polyvidone, and povidone). Preferably, the polymer is polyvinylpyrrolidone. The vehicle formulation may have a viscosity of between about 10,000 poise and about 20,000 poise at 37° C.

Specific examples of preferred exenatides useful in the practice of the present invention include the exenatide having the amino acid sequence of SEQ ID NO: 1, native exendin-4, an exenatide peptide, a peptide analog of exenatide, a peptide derivative of exenatide, lixisenatide, or exenatide-LAR.

Particles of a particle formulation comprising an exenatide have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. Preferably, the particles have diameters of between about 2 microns and about 50 microns.

An exenatide can be included in a particle formulation, in a suspension formulation, and/or in a single osmotic delivery device along with one or more (e.g., one, two, three, four, or more) other therapeutic agents; thus, an osmotic delivery device may provide substantial steady-state delivery of the exenatide and one or more other therapeutic agents. Non-limiting examples of the one or more other therapeutic agents include amylin, an amylin analogue (e.g., pramlintide), a ghrelin antagonist, a G protein coupled receptor 119 (GRP 119) agonist, and leptin. An osmotic delivery device may provide substantial steady-state delivery of two or more different exenatides.

In some embodiments, the subject is further provided one or more other drugs for treating type 2 diabetes mellitus, e.g., insulin and/or oral anti-diabetic drugs including, without limitation, DPP4 inhibitors, SGLT2 inhibitors, metformin, sulfonylureas, and thiazolidinediones (TZDs).

In some embodiments of the present invention, continuous delivery can provide to the subject a µg/day dose of an exenatide, for example, a dose of about 10 µg/day, about 15 µg/day, about 20 µg/day, about 30 µg/day, about 40 µg/day, about 50 µg/day, about 60 µg/day, about 70 µg/day, and about 80 µg/day. The upper limit to the daily dose depends to the peptide/active agent and the total capacity of the device itself. Thus, the daily dose may exceed 80 µg/day.

Preferably, the mcg/day dose of the exenatide is about 20 mcg/day.

Preferably, the mcg/day dose of the exenatide is about 40 mcg/day.

Preferably, the mcg/day dose of the exenatide is about 60 mcg/day.

In additional embodiments of the present invention, the method of treating type 2 diabetes mellitus further comprises a first continuous administration period of the exenatide at a first µg/day dose that is followed by a second continuous administration period providing a dose escalation of the exenatide to a second µg/day dose, wherein the second µg/day dose is greater than the first µg/day dose. In some embodiments, the first µg/day dose is delivered by a first osmotic delivery device and the second µg/day dose is delivered by an at least second osmotic delivery device, and delivery of the exenatide from at least the first or the at least second osmotic delivery device is continuous over the administration period of at least about 1 month (e.g., at least about 1 month, at least about 2 months, and at least about 3 months). In one embodiment, the second µg/day dose is at least two times greater than the first µg/day dose. Further, the method can comprise at least one more continuous administration period providing a dose escalation of the exenatide to a higher µg/day dose relative to the second µg/day dose. Dose escalation can be accomplished, for example, by removal of the first osmotic delivery device and implantation of a second osmotic delivery device, or by implantation of a second or further osmotic delivery device where the total dose delivered by the first and second osmotic delivery devices results in the desired dose escalation. Dose escalation allows a subject to receive a therapeutic benefit while being gradually exposed to the exenatide. This tolerizes the subject to the exenatide and reduces the incidence of side effects. Later, once the subject has completed an initial tolerization period with a first, low daily dose, the dose is escalated to a (higher) maintenance dose.

Exemplary dose escalations for the exenatide are as follows: about 10 µg/day followed by about 20 µg/day; about 10 µg/day followed by about 30 µg/day; about 10 µg/day followed by about 40 µg/day; about 10 µg/day followed by about 50 µg/day; about 10 µg/day followed by about 60 µg/day; about 10 µg/day followed by about 70 µg/day; about 10 µg/day followed by about 80 µg/day; about 15 µg/day followed by about 20 µg/day; about 15 µg/day followed by about 30 µg/day; about 15 µg/day followed by about 40 µg/day; about 15 µg/day followed by about 50 µg/day; about 15 µg/day followed by about 60 µg/day; about 15 µg/day followed by about 70 µg/day; about 15 µg/day followed by about 80 µg/day; about 20 µg/day followed by about 30 µg/day; about 20 µg/day followed by about 40 µg/day; about 20 µg/day followed by about 50 µg/day; about 20 µg/day followed by about 60 µg/day; about 20 µg/day followed by about 70 µg/day; about 20 µg/day followed by about 80 µg/day; about 40 µg/day followed by about 50 µg/day; about 40 µg/day followed by about 60 µg/day; about 40 µg/day followed by about 70 µg/day; about 40 µg/day followed by about 80 µg/day; about 50 µg/day followed by about 60 µg/day; about 50 µg/day followed by about 60 µg/day; about 50 µg/day followed by about 70 µg/day; about 50 µg/day followed by about 80 µg/day; about 60 µg/day followed by about 70 µg/day or about 60 µg/day followed by about 80 µg/day.

Preferably, the first mcg/day dose of the exenatide followed by the second mcg/day dose for continuous delivery is about 20 mcg/day followed by about 40 mcg/day.

Preferably, the first mcg/day dose of the exenatide followed by the second mcg/day dose for continuous delivery is about 20 mcg/day followed by about 60 mcg/day.

In some embodiments, the method further comprises at least one more continuous administration period, subsequent to a second administration period, providing a dose at the same mcg/day dose as the second mcg/day dose.

In some embodiments, the subject has not previously received a drug for treating type 2 diabetes mellitus.

In any of the above-described embodiments, the exenatide may comprise the exenatide having the amino acid sequence of SEQ ID NO: 1, native exendin-4, an exenatide peptide, a peptide analog of exenatide, and a peptide derivative of exenatide. In any of the above methods, the exenatide is selected from the group consisting of lixisenatide, liraglutide, albiglutide, and taspoglutide.

In any of the above-described embodiments, the subject may further be provided one or more other drugs for treating type 2 diabetes mellitus, e.g., insulin and/or oral antidiabetic drugs including, without limitation, DPP4 inhibitors, SGLT2 inhibitors, metformin, sulfonylureas, and thiazolidinediones (TZDs).

Any of the above-described embodiments further promote weight loss in a subject in need thereof. Preferably, the subject has a baseline HbA1c % of greater than 6.5%. More preferably, the subject has a baseline HbA1c % of greater than 10.0%. The subject may have a baseline HbA1c % of less than or equal to 12%. Significant weight loss is achieved by about six weeks (e.g., about five weeks, about four weeks, about three weeks, about two weeks, and about one week) after initial implantation of the osmotic delivery device and up to 39 weeks after initial implantation.

The present invention also relates to a method of treating a disease or condition in a subject in need of treatment. The subject has a baseline hemoglobin A1c (HbA1c) % of greater than 6.5%. The subject may have a baseline HbA1c % of greater than 10.0%. The subject may have a baseline HbA1c % of less than or equal to 12%. The method comprises providing continuous delivery of a drug from an osmotic delivery device. Substantial steady-state delivery of the drug at a therapeutic concentration is achieved within a time period of with the first day of implantation up to about 7 days after implantation of the osmotic delivery device in the subject. Thus, steady-state delivery of the drug occurs at any time point after implantation and up to about 7 days after implantation; non-limiting examples include 2 hours after implantation, 36 hours after implantation, 3 and a half days after implantation, and six days after implantation. The substantial steady-state delivery of the drug from the osmotic delivery device is continuous over an administration period. Humans are preferred subjects for the practice of the present invention. The present invention includes particles comprising a drug, formulations comprising the drug, and formulations comprising particles comprising the drug, as well as an osmotic delivery device comprising the drug for use in the present methods of treating the disease or condition in a subject in need of treatment. The subject may not have previously received a drug for treating the disease or condition. In some embodiments, the subject is further provided one or more other drugs for treating the disease or condition.

In some embodiments of the present invention, the administration period is, for example, at least about 1 month, at least about 1 month to about two years, at least about 2 months to about two years, at least about 3 months to about two years, at least about 3 months to about two years, at least about 4 months to about two years, at least about 5 months to about two years, at least about 6 months to about two years, at least about 8 months to about two years, or at least about 9 months to about two years, about 1 year, at least one year to about two years, at least about 14 months to about two years, at least about 16 months to about two years, at least 18 months to about two years, at least about 20 months to about two years, at least about 22 months to about two years, and about two years.

In some embodiments, the administration period is, for example, at least about 12 months to about 18 months, at least about 13 months to about 18 months, at least about 14 months to about 18 months, at least about 15 months to about 18 months, at least about 16 months to about 18 months, at least about 17 months to about 18 months, and about 18 months.

In some embodiments, the administration period is, for example, at least about 1 month to about a year, at least about 2 months to about a year, about 3 months, at least about 3 months to about a year, at least about 4 months to about a year, at least about 5 months to about a year, about 6 months, at least about 6 months to about a year, at least about 8 months to about a year, about 9 months, at least about 9 months to about a year, at least about 10 months to about a year, at least about 11 months to about a year, and about a year.

In some embodiments of the present invention, the substantial steady-state delivery of a drug at therapeutic concentrations is achieved within about 7 days after implantation of the osmotic delivery device in the subject, within about 6 days after implantation of the osmotic delivery device in the subject, within about 5 days after implantation of the osmotic delivery device in the subject, within about 4 days after implantation of the osmotic delivery device in the subject, within about 3 days after implantation of the osmotic delivery device in the subject, within about 2 days after implantation of the osmotic delivery device in the subject, or within about 1 day after implantation of the osmotic delivery device in the subject. Steady-state delivery of the drug occurs at any time point after implantation and up to about 7 days after implantation. In preferred embodiments of the present invention, the substantial steady-state delivery of the drug at therapeutic concentrations is achieved within about 2 days and more preferably within about 1 day after implantation of the osmotic delivery device in the subject.

In yet further embodiments of the present invention, the treatment methods further comprise the capability to terminate the continuous delivery of the drug such that the concentration of the drug is substantially undetectable in a blood sample from the subject within about 6 half-lives of the drug after termination of continuous delivery, within about 5 half-lives of the drug after termination of continuous delivery, within about 4 half-lives of the drug after termination of continuous delivery, or within about 3 half-lives of the drug after termination of continuous delivery. Thus, the drug will be substantially undetectable in a subject's blood sample within any time point after termination of continuous delivery and up to about 6 half-lives after termination of continuous delivery. Some examples of drug half-lives are as follows: GIP, approximately 5 minutes; PYY, approximately 8 minutes; glucagon, approximately 6 minutes; oxyntomodulin, approximately 6 minutes; and GLP-2, approximately 6 minutes. The drug may be detected in a serum sample from the subject, for example, by an RIA, a chromatographic method, an ECL assay, an ELISA, or an IEMA. Termination of the continuous delivery can be accomplished, for example, by removal of the osmotic delivery device from the subject.

In some embodiments of the present invention, the method of treating a disease or condition further comprises terminating the continuous delivery such that the concentration of the drug is substantially undetectable in a blood sample from the subject after termination of continuous delivery, for example, within about 72 hours, about 48 hours, about 24, about 14 hours, about 12 hours, about 10 hours, about 8 hours, about 6 hours, or about 4 hours. Thus, the drug will be substantially undetectable in a subject's blood sample within any time point after termination of continuous delivery and up to about 72 hours after termination of continuous delivery. In some embodiments, continuous delivery of the drug is terminated by removal of the osmotic delivery device from the subject. In some embodiments, continuous delivery of the drug may be terminated by removal of the osmotic delivery device from the subject. The serum concentration of the drug is, for example, detected by a radioimmunoassay (RIA), a chromatographic method, an electrochemiluminescent (ECL) assay, an enzyme linked immunosorbent assay (ELISA) or an immunoenzymatic sandwich assay (IEMA).

Osmotic delivery devices for use in the methods of the present invention can comprise the components described herein including, but not limited to, a reservoir, a semi-permeable membrane, an osmotic engine, a piston, a suspension formulation, and a diffusion moderator. In some embodiments, the osmotic delivery device comprises: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable. The osmotic delivery device comprises a diffusion moderator inserted in the second open end of the reservoir, the diffusion moderator adjacent the suspension formulation. In some embodiments, the reservoir comprises titanium or a titanium alloy.

Suspension formulations used in the methods of the present invention typically comprise a particle formulation comprising a drug and a vehicle formulation.

Two or more (e.g., two, three, four, or more) "drugs," "therapeutic agents," or "beneficial agents" can be included in a particle formulation, in a suspension formulation, and/or in a single osmotic delivery device; thus, an osmotic delivery device may provide substantial steady-state delivery of the two or more "drugs," "therapeutic agents," or "beneficial agents." Examples of such particle formulations, in a suspension formulations, and osmotic delivery devices are described, e.g., U.S. Pat. No. 8,343,140 and U.S. Patent Publication No. 2015-0111818, each of which is incorporated herein by reference in its entirety.

A vehicle formulation comprises a solvent (e.g., benzyl benzoate, lauryl lactate, and lauryl alcohol) and a polymer (e.g., polyvinylpyrrolidone: also herein referred to as PVP, polyvidone, and povidone). Preferably, the polymer is polyvinylpyrrolidone. The vehicle formulation may have a viscosity of between about 10,000 poise and about 20,000 poise at 37° C.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. In some embodiments, the polypeptide is an insulinotrophic peptide described herein. In some embodiments, the polypeptide may be an antibody or an antibody fragment. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 (1995)); single-chain antibody molecules; and multispecific antibodies formed from antibody fragments. In another embodiment of the present invention, the drug is a small molecule, for example, hormones such as androgens or estrogens. Examples of preferred drugs include, but are not limited to, the herein-described insulinotrophic peptides and Gastric inhibitory peptide (GIP), Glucagon, Glucagon-like peptide 2 (GLP-2), Oxyntomodulin, PYY (also known as peptide YY, peptide tyrosine tyrosine), PYY(3-36), amylin, an amylin analogue (e.g., pramlintide), a ghrelin antagonist, a G protein coupled receptor 119 (GRP 119) agonist, and leptin. The devices and methods of the present invention are well suited for the delivery of proteins, small molecules and combinations thereof.

Particles of a particle formulation comprising a drug have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. Preferably, the particles have diameters of between about 2 microns and about 50 microns.

In some embodiments, the subject is further provided one or more other drugs for treating a disease or condition.

In some embodiments of the present invention, continuous delivery can provide to the subject a steady μg/day dose of a drug. The upper limit to the daily dose depends to the drug and the total capacity of the device itself.

In additional embodiments of the present invention, the method of treating a disease or condition further comprises a first continuous administration period of the drug at a first μg/day dose that is followed by a second continuous administration period providing a dose escalation of the drug to a second μg/day dose, wherein the second μg/day dose is greater than the first μg/day dose. In some embodiments, the first μg/day dose is delivered by a first osmotic delivery device and the second μg/day dose is delivered by an at least second osmotic delivery device, and delivery of the drug from at least the first or the at least second osmotic delivery device is continuous over the administration period of at least about 1 month (e.g., at least about 1 month, at least about 2 months, and at least about 3 months). In one embodiment, the second μg/day dose is at least two times greater than the first μg/day dose. Further, the method can comprise at least one more continuous administration period providing a dose escalation of the drug to a higher μg/day dose relative to the second μg/day dose. Dose escalation can be accomplished, for example, by removal of the first osmotic delivery device and implantation of a second osmotic delivery device, or by implantation of a second or further osmotic delivery device where the total dose delivered by the first and second osmotic delivery devices results in the desired dose escalation. Dose escalation allows a subject to receive a therapeutic benefit while being gradually exposed to the drug. This tolerizes the subject to the drug and reduces the incidence of side effects. Later, once the subject has completed an initial tolerization period with a first, low daily dose, the dose is escalated to a (higher) maintenance dose.

In some embodiments, the method further comprises at least one more continuous administration period, subsequent to a second administration period, providing a dose at the same mcg/day dose as the second mcg/day dose.

In some embodiments, the subject has not previously received a drug for treating a disease or condition.

In any of the above-described embodiments, the subject may further be provided one or more other drugs for treating a disease or condition.

Any of the above aspects and embodiments can be combined with any other aspect or embodiment as disclosed herein.

3.0.0 Formulations and Compositions

Drugs for use in the practice of the present invention are typically uniformly suspended, dissolved or dispersed in a suspension vehicle to form a suspension formulation.

3.1.0 Drug Particle Formulations

In one aspect, the present invention provides drug particle formulations for pharmaceutical use. The particle formulation typically comprises a drug and includes one or more stabilizing component. Examples of stabilizing components include, but are not limited to, carbohydrates, antioxidants, amino acids, buffers, inorganic compounds, and surfactants.

3.1.1 Exemplary Drugs

The drug particle formulations comprise a drug. The drug may be any physiologically or pharmacologically active substance, particularly those known to be delivered to the body of a human or an animal.

Suitable drugs include, but are not limited to: peptides, proteins, polypeptides or synthetic analogs of these species, as well as mixtures thereof.

In one embodiment, preferred drugs include macromolecules. Such macromolecules include, but are not limited to, pharmacologically active peptides, proteins, or polypeptides. Numerous peptides, proteins, or polypeptides that are useful in the practice of the present invention are described herein.

In one embodiment of the present invention, the drug is a polypeptide. In some embodiments, the polypeptide is an insulinotrophic peptide described herein. In some embodiments, the polypeptide may be an antibody or an antibody fragment. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 (1995)); single-chain antibody molecules; and multispecific antibodies formed from antibody fragments. In addition to the peptides, proteins, or polypeptides described, modifications of these peptides, proteins, or polypeptides are also known to one of skill in the art and can be used in the practice of the present invention following the guidance presented herein. Such modifications include, but are not limited to, amino acid analogs, amino acid mimetics, analog polypeptides, or derivative polypeptides. Further, the drugs disclosed herein may be formulated or administered singly or in combination (e.g., using mixtures of drugs or multiple devices; U.S. Patent Publication No. 2009/0202608).

Some embodiments of the present invention comprise use of peptide hormones, for example, glucagon and incretin mimetics (e.g., GLP-1 peptides and exenatide peptides), as well as peptide analogs and peptide derivatives thereof; PYY (also known as peptide YY, peptide tyrosine tyrosine), as well as peptide analogs and peptide derivatives thereof, for example, PYY(3-36); oxyntomodulin, as well as peptide analogs and peptide derivatives thereof); and gastric inhibitory peptide (GIP), as well as peptide analogs and peptide derivatives thereof.

Some embodiments of the present invention comprise use of amylin, an amylin analogue (e.g., pramlintide), a ghrelin antagonist, a G protein coupled receptor 119 (GRP 119) agonist, and leptin for treating type 2 diabetes and/or promoting weight loss.

GLP-1, including three forms of the peptide, GLP-1(1-37), GLP-1(7-37) and GLP-1(7-36) amide, as well as peptide analogs of GLP-1 have been shown to stimulate insulin secretion (i.e., is insulinotrophic), which induces glucose uptake by cells and results in decreases in serum glucose concentrations (see, e g., Mojsov, S., *Int. J. Peptide Protein Research*, 40:333-343 (1992)). The amino acid sequence of GLP-1 is EGTFTSDVSSYLEGQAAKEFIAWLVKGR (SEQ ID NO: 2).

Numerous GLP-1 peptide derivatives and peptide analogs demonstrating insulinotrophic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217), as well as in clinical trials (e.g., taspoglutide and albiglutide). One example of a GLP-1 peptide derivative useful in the practice of the present invention is VICTOZA® (Novo Nordisk A/S, Bagsvaerd D K) (liraglutide; U.S. Pat. Nos. 6,268,343, 6,458,924, and 7,235,627). Once-daily injectable VICTOZA® (liraglutide) is commercially available in the United States, Europe, and Japan. For ease of reference, herein, the family of GLP-1 peptides (other than GLP-1 itself), GLP-1 peptide derivatives and GLP-1 peptide analogs having insulinotrophic activity is referred to collectively as "GLP-1 receptor agonists."

The molecule exenatide has the amino acid sequence of exendin-4 (Kolterman et al., *J. Clin. Endocrinol. Metab.* 88(7):3082-9 (2003)) and is produced by chemical synthesis or recombinant expression. Twice-daily injectable exenatide is commercially available in the United States and Europe, and sold under the trade name of BYETTA® (Amylin Pharmaceuticals, Inc., San Diego, Calif.). Exendin-3 and exendin-4 are known in the art and were originally isolated from *Heloderma* spp. (Eng, J., et al., *J. Biol. Chem.*, 265: 20259-62 (1990); Eng., J., et al., *J. Biol. Chem.*, 267:7402-05 (1992)). Use of exendin-3 and exendin-4 for the treatment of type 2 diabetes mellitus and the prevention of hyperglycemia has been proposed (see, e.g., U.S. Pat. No. 5,424,286). Numerous exenatide peptide derivatives and peptide analogs (including, e.g., exendin-4 agonists) are known in the art (see, e.g., U.S. Pat. Nos. 5,424,286; 6,268,343; 6,329,336; 6,506,724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555). One example of an exenatide derivative useful in the practice of the present invention is lixisenatide (also known as ZP10, AVE0010) (see, e.g., U.S. Pat. No. 6,528,486), which is in clinical trials. For ease of reference, herein, the family of exenatide peptides (e.g., including exendin-3, exendin-4, and exendin-4-amide), exenatide peptide derivatives, and exenatide peptide analogs is referred to collectively as "exenatides."

Peptide YY (PYY) is a 36 amino acid residue peptide amide. PYY inhibits gut motility and blood flow (Laburthe, M., *Trends Endocrinol Metab.* 1(3):168-74 (1990), mediates intestinal secretion (Cox, H. M., et al., *Br J Pharmacol* 101(2):247-52 (1990); Playford, R. J., et al., *Lancet* 335 (8705):1555-7 (1990)), and stimulate net absorption (MacFayden, R. J., et al., *Neuropeptides* 7(3):219-27 (1986)). Two major in vivo variants, PYY(1-36) and PYY(3-36), have been identified (e.g., Eberlein, G. A., et al., *Peptides* 10(4), 797-803 (1989)). The sequence of PYY, as well as peptide analogs and peptide derivatives thereof, are known in the art (e.g., U.S. Pat. Nos. 5,574,010 and 5,552,520).

Oxyntomodulin is a naturally occurring 37 amino acid peptide hormone found in the colon that has been found to suppress appetite and facilitate weight loss (Wynne K, et al., *Int J Obes (Lond)* 30(12):1729-36(2006)). The sequence of oxyntomodulin, as well as peptide analogs and peptide derivatives thereof, are known in the art (e.g., Bataille D, et al., *Peptides* 2(Suppl 2):41-44 (1981); and U.S. Patent Publication Nos. 2005/0070469 and 2006/0094652).

Gastric Inhibitory Peptide (GIP) is an insulinotrophic peptide hormone (Efendic et al., *Horm Metab Res.* 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotrophic protein. GIP is a 42-amino acid gastrointestinal regulatory peptide that stimulates insulin secretion from pancreatic beta cells in the presence of glucose (Tseng et al., *PNAS* 90:1992-1996 (1993)). The sequence of GIP, as well as peptide analogs and peptide derivatives thereof, are known in the art (e.g., Meier, *Diabetes Metab Res Rev.* 21(2):91-117 (2005) and Efendic, *Horm Metab Res.* 36(11-12):742-6 (2004)).

Glucagon is a peptide hormone, produced by alpha cells of the pancreas, which raises the concentration of glucose in the bloodstream. Its effect is opposite that of insulin, which lowers the glucose concentration. The pancreas releases glucagon when the concentration of glucose in the bloodstream falls too low. Glucagon causes the liver to convert stored glycogen into glucose, which is released into the bloodstream. High blood glucose levels stimulate the release of insulin. Insulin allows glucose to be taken up and used by insulin-dependent tissues. Thus, glucagon and insulin are part of a feedback system that keeps blood glucose levels at a stable level.

Glucagon-like peptide-2 (GLP-2) is a 33 amino acid peptide with the sequence HADGSFSDEMNTILDNLAARDFINWLIQTKITD (SEQ ID NO: 3) in humans. GLP-2 is created by specific post-translational proteolytic cleavage of proglucagon in a process that also liberates the related glucagon-like peptide-1 (GLP-1). GLP-2 is produced by the intestinal endocrine L cell and by various neurons in the central nervous system. Intestinal GLP-2 is co-secreted along with GLP-1 upon nutrient ingestion. When externally administered, GLP-2 produces a number of effects in humans and rodents, including intestinal growth, enhancement of intestinal function, reduction in bone breakdown and neuroprotection. GLP-2 may act in an endocrine fashion to link intestinal growth and metabolism with nutrient intake.

Amylin, as well as analogs and derivatives thereof, are known in the art (e.g., U.S. Pat. Nos. 5,686,411, 5,814,600, 5,998,367, 6,114,304, 6,410,511, 6,608,029, and 6,610,824). For ease of reference, herein, the family of amylin polypeptides, amylin derivatives, variants and analogues are referred to collectively as amylin.

The cDNA sequence encoding the human leptin protein hormone is known (e.g., Masuzaki, H., et al. (Diabetes 44: 855-858, 1995)). Leptin, as well as analogs and derivatives thereof, are known in the art (e.g., U.S. Pat. Nos. 5,521,283, 5,525,705, 5,532,336, 5,552,522, 5,552,523, 5,552,524, 5,554,727, 5,559,208, 5,563,243, 5,563,244, 5,563,245, 5,567,678, 5,567,803, 5,569,743, 5,569,744, 5,574,133, 5,580,954, 5,594,101, 5,594,104, 5,605,886, 5,691,309, and 5,719,266; P.C.T. International Patent Publication Nos. WO96/22308, WO96/31526, WO96/34885, 97/46585, WO97/16550, and WO 97/20933; European Patent Publication No. EP 0 741 187). For ease of reference, herein, the family of leptin polypeptides, leptin derivatives, variants and analogues are referred to collectively as leptin.

Examples of half-lives of some of the peptides are as follows: the exenatide having the amino acid sequence of SEQ ID NO: 1, approximately 2.5 hours; GLP-1, approximately 2 minutes; GIP, approximately 5 minutes; PYY, approximately 8 minutes; glucagon, approximately 6 minutes; oxyntomodulin, approximately 6 minutes; and GLP-2, approximately 6 minutes.

Drug particle formulations for use in the practice of the present invention are exemplified using an exenatide. The examples are not intended to be limiting.

The drugs can also be in various forms including, but not limited to, the following: uncharged molecules; components of molecular complexes; and pharmacologically acceptable salts such as hydrochloride, hydrobromide, sulfate, laurates, palmatates, phosphate, nitrate, borate, acetate, maleate, tartrate, oleates, or salicylates. For acidic drugs, salts of metals, amines or organic cations, for example, quaternary ammonium, can be employed. Furthermore, simple derivatives of the drug such as esters, ethers, amides and the like that have solubility characteristics suitable for the purpose of the invention can also be used herein.

The above drugs and other drugs known to those of skill in the art are useful in methods of treatment for a variety of conditions including but not limited to the following: chronic pain, hemophilia and other blood disorders, endocrine disorders, metabolic disorders, non-alcoholic fatty liver disease (NAFLD), non-alcoholic steatohepatitis (NASH), Alzheimer's disease, cardiovascular diseases (e.g., heart failure, atherosclerosis, and acute coronary syndrome), rheumatologic disorders, diabetes (including type 1, type 2 diabetes mellitus, human immunodeficiency virus treatment-induced, latent autoimmune diabetes in adults, and steroid-induced), hypoglycemia unawareness, restrictive lung disease, chronic obstructive pulmonary disease, lipoatrophy, metabolic syndrome, leukemia, hepatitis, renal failure, infectious diseases (including bacterial infection, viral infection (e.g., infection by human immunodeficiency virus, hepatitis C virus, hepatitis B virus, yellow fever virus, West Nile virus, Dengue virus, Marburg virus, and Ebola virus), and parasitic infection), hereditary diseases (such as cerbrosidase deficiency and adenosine deaminase deficiency), hypertension, septic shock, autoimmune diseases (e.g., Grave's disease, systemic lupus erythematosus, multiple sclerosis, and rheumatoid arthritis), shock and wasting disorders, cystic fibrosis, lactose intolerance, Crohn's diseases, inflammatory bowel disease, gastrointestinal cancers (including colon cancer and rectal cancer), breast cancer, leukemia, lung cancer, bladder cancer, kidney cancer, non-Hodgkin lymphoma, pancreatic cancer, thyroid cancer, endometrial cancer, and other cancers. Further, some of the above agents are useful for the treatment of infectious diseases requiring chronic treatments including, but not limited to, tuberculosis, malaria, leishmaniasis, trypanosomiasis (sleeping sickness and Chagas disease), and parasitic worms.

The amount of drug in drug particle formulations is that amount necessary to deliver a therapeutically effective amount of the agent to achieve the desired therapeutic result in the subject to which the drug is being delivered. In practice, this will vary depending upon such variables, for example, as the particular agent, the severity of the condition, and the desired therapeutic effect. Beneficial agents and their dosage unit amounts are known to the prior art in Goodman & Gilman's The Pharmacological Basis of Therapeutics, llth Ed., (2005), McGraw Hill; Remington's Pharmaceutical Sciences, 18th Ed., (1995), Mack Publishing Co.; and Martin's Physical Pharmacy and Pharmaceutical Sciences, 1.00 edition (2005), Lippincott Williams & Wilkins. Further, highly concentrated drug particles are described in U.S. Patent Publication No. 2010/0092566. Typically, for an osmotic delivery system, the volume of the chamber comprising the drug formulation is between about 100 µl to about 1000 µl, more preferably between about 140 µl and about 200 µl. In one embodiment, the volume of the chamber comprising the drug formulation is about 160 µl.

Drug particle formulations of the invention are preferably chemically and physically stable for at least 1 month, preferably at least 3 months, more preferably at least 6 months, more preferably at least 12 months at delivery temperature, and preferably at least 24 months at delivery temperature. The delivery temperature is typically normal human body temperature, for example, about 37° C., or slightly higher, for example, about 40° C. Further, drug particle formulations of the present invention are preferably chemically and physically stable for at least 3 months, preferably at least 6 months, more preferably at least 12 months, and preferably at least 24 months at storage temperature. Examples of storage temperatures include refrigeration temperature, for example, about 5° C.; or room temperature, for example, about 25° C.

A drug particle formulation may be considered chemically stable if less than about 25%; preferably less than about 20%, preferably less than about 15%, more preferably less than about 10%, and more preferably less than about 5% breakdown products of the drug particles are formed after about 3 months, preferably after about 6 months, preferably after about 12 months at delivery temperature and after about 6 months, after about 12 months, and preferably after about 24 months at storage temperature.

A drug particle formulation may be considered physically stable if less than about 10%, preferably less than about 5%, preferably less than about 3%, more preferably less than about 1% aggregates of the drug are formed after about 3 months, preferably after about 6 months, at delivery temperature and about 6 months, preferably about 12 months, and preferably about 24 months at storage temperature.

When the drug in the drug particle formulation is a protein, the protein solution is kept in a frozen condition and lyophilized or spray dried to a solid state. Tg (glass transition temperature) may be one factor to consider in achieving stable compositions of protein. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., peptide products will not have mobility when stored at room temp or even at 40° C. because the storage temperature is below the Tg. Calculations using molecular information have shown that if a glass transition temperature is above a storage temperature of 50° C. that there is zero mobility for molecules. Zero mobility of molecules correlates with better stability. Tg is also dependent on the moisture concentration in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. In one embodiment of the invention the particles are spray dried. The particles are preferably substantially uniform in shape and size.

The particles are typically sized such that they can be delivered via an implantable osmotic delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, more preferably is less than about 20%, more preferably is less than about than 10%, of the diameter of the delivery orifice. In an embodiment of the particle formulation for use with an osmotic delivery system, wherein the delivery orifice diameter of the implant is about 0.5 mm, particle sizes may be, for example, less than about 150 microns to about 50 microns. In an embodiment of the particle formulation for use with an osmotic delivery system, wherein the delivery orifice diameter of the implant is about 0.1 mm, particle sizes may be, for example, less than about 30 microns to about 10 microns. In one embodiment, the orifice is about 0.25 mm (250 microns) and the particle size is about 2 microns to about 5 microns. Particles of the particle formation may be between 2 microns to less than 50 microns in diameter.

Typically, the particles of the particle formulations, when incorporated in a suspension vehicle, do not settle in less than about 3 months, preferably do not settle in less than about 6 months, more preferably do not settle in less than about 12 months, more preferably do not settle in less than about 24 months at delivery temperature, and most preferably do not settle in less than about 36 months at delivery temperature. The suspension vehicles typically have a viscosity of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise. Generally speaking, smaller particles tend to have a lower settling rate in viscous suspension vehicles than larger particles. Accordingly, micron- to nano-sized particles are typically desirable. In viscous suspension formulation, particles of about 2 microns to about 7 microns of the present invention will not settle for at least 20 years at room temperature based on simulation modeling studies. In an embodiment of the particle formulation of the present invention, for use in an implantable osmotic delivery device, particles have sizes of less than about 50 microns, more preferably less than about 10 microns, more preferably in a range from about 2 microns to about 7 microns.

In one embodiment, a drug particle formulation comprises a drug, as described above, one or more stabilizers, and optionally a buffer. The stabilizers may be, for example, carbohydrate, antioxidant, amino acid, buffer, inorganic compound, or surfactant. The amounts of stabilizers and buffer in the particle formulation can be determined experimentally based on the activities of the stabilizers and buffers and the desired characteristics of the formulation, in view of the teachings of the present specification. Typically, the amount of carbohydrate in the formulation is determined by aggregation concerns. In general, the carbohydrate amount should not be too high so as to avoid promoting crystal growth in the presence of water due to excess carbohydrate unbound to drug. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize drug during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include disaccharides and/or non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate. Further, amino acids that readily oxidize can be used as antioxidants, for example, cysteine, methionine, and tryptophan. A preferred antioxidant is methionine.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, tryptophan, serine, asparagines, cysteine, tyrosine, lysine, and norleucine. Preferred amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

Examples of inorganic compounds that may be included in the particle formulation include, but are not limited to, NaCl, $Na_2SO_4$, $NaHCO_3$, KCl, $KH_2PO_4$, $CaCl_2$, and $MgCl_2$.

In addition, the particle formulation may include other excipients, such as surfactants, and salts. Examples of surfactants include, but are not limited to, Polysorbate 20, Polysorbate 80, PLURONIC® (BASF Corporation, Mount Olive, N.J.) F68, and sodium dodecyl sulfate (SDS). Examples of salts include, but are not limited to, sodium chloride, calcium chloride, and magnesium chloride.

All components included in the particle formulation are typically acceptable for pharmaceutical use in mammals, in particular, in humans.

In summary, a selected drug or combination of drugs is formulated into dried powders in solid state, which preserve maximum chemical and biological stability of the drug. The particle formulation offers long-term storage stability at high temperature, and therefore, allows delivery to a subject of stable and biologically effective drug for extended periods of time.

3.2.0 Vehicle Formulations and Suspension Formulations

In one aspect, the suspension vehicle provides a stable environment in which the drug particle formulation is dispersed. The drug particle formulations are chemically and physically stable (as described above) in the suspension vehicle. The suspension vehicle typically comprises one or more polymer and one or more solvents that form a solution of sufficient viscosity to uniformly suspend the particles comprising the drug. The suspension vehicle may comprise further components, including, but not limited to, surfactants, antioxidants, and/or other compounds soluble in the vehicle.

The viscosity of the suspension vehicle is typically sufficient to prevent the drug particle formulation from settling during storage and use in a method of delivery, for example, in an implantable, osmotic delivery device. The suspension vehicle is biodegradable in that the suspension vehicle disintegrates or breaks down over a period of time in response to a biological environment, while the drug particle is dissolved in the biological environment and the active pharmaceutical ingredient (i.e., the drug) in the particle is absorbed.

The solvent in which the polymer is dissolved may affect characteristics of the suspension formulation, such as the behavior of drug particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than about 10% water.

The solvent may be an acceptable solvent that is not miscible with water. The solvent may also be selected so that the polymer is soluble in the solvent at high concentrations, such as at a polymer concentration of greater than about 30%. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and mixtures thereof.

Examples of polymers for formulation of the suspension vehicles of the present invention include, but are not limited to, a polyester (e.g., polylactic acid and polylactic polyglycolic acid), a polymer comprising pyrrolidones (e.g., polyvinylpyrrolidone having a molecular weight ranging from approximately 2,000 to approximately 1,000,000), ester or ether of an unsaturated alcohol (e.g., vinyl acetate), polyoxyethylene polyoxypropylene block copolymer, or mixtures thereof. Polyvinylpyrrolidone can be characterized by its K-value (e.g., K-17), which is a viscosity index. In one embodiment, the polymer is polyvinylpyrrolidone having a molecular weight of 2,000 to 1,000,000. In a preferred embodiment the polymer is polyvinylpyrrolidone K-17 (typically having an approximate average molecular weight range of 7,900-10,800). The polymer used in the suspension vehicle may include one or more different polymers or may include different grades of a single polymer. The polymer used in the suspension vehicle may also be dry or have low moisture content.

Generally speaking, a suspension vehicle for use in the present invention may vary in composition based on the desired performance characteristics. In one embodiment, the suspension vehicle may comprise about 40 wt % to about 80 wt % polymer(s) and about 20 wt % to about 60 wt % solvent(s). Preferred embodiments of a suspension vehicle include vehicles formed of polymer(s) and solvent(s) combined at the following ratios: about 25 wt % solvent and about 75 wt % polymer; about 50 wt % solvent and about 50 wt % polymer; about 75 wt % solvent and about 25 wt % polymer. Accordingly, in some embodiments the suspension vehicle may comprise selected components and in other embodiments consist essentially of selected components.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the drug contained in the drug particle formulation. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. In preferred embodiments, the suspension vehicles typically have a viscosity, at 33° C., of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise, at 33° C. The viscosity may be measured at 33° C., at a shear rate of $10^{-4}$/sec, using a parallel plate rheometer.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients.

The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The drug particle formulation is added to the suspension vehicle to form a suspension formulation. In some embodiments the suspension formulation may comprise a drug particle formulation and a suspension vehicle and in other embodiments consist essentially of a drug particle formulation and a suspension vehicle.

The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

In preferred embodiments, the suspension formulations of the present invention are substantially homogeneous and flowable to provide delivery of the drug particle formulation from the osmotic delivery device to the subject.

In summary, the components of the suspension vehicle provide biocompatibility. Components of the suspension vehicle offer suitable chemico-physical properties to form stable suspensions of drug particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

4.0.0 Delivery of Suspension Formulations

The suspension formulations described herein may be used in an implantable, osmotic delivery device to provide zero-order, continuous, controlled, and sustained delivery of a compound over an extended period of time, such as over weeks, months, or up to about one year or more. Such an implantable osmotic delivery device is typically capable of delivering the suspension formulation, comprising the drug, at a desired flow rate over a desired period of time. The suspension formulation may be loaded into the implantable, osmotic delivery device by conventional techniques.

A dose and delivery rate can be selected to achieve a desired blood concentration of a drug generally within about 6 half-lives of the drug within the subject after implantation of the device. The blood concentration of the drug is selected to give the optimal therapeutic effects of the drug while avoiding undesirable side effects that may be induced by excess concentration of the drug, while at the same time avoiding peaks and troughs that may induce side effects associated with peak or trough plasma concentrations of the drug.

The implantable, osmotic delivery device typically includes a reservoir having at least one orifice through which the suspension formulation is delivered. The suspension formulation may be stored within the reservoir. In a preferred embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; and 7,163,688; U.S. Pat. Pub. Nos. 2005/0175701, 2007/0281024, 2008/0091176, and 2009/0202608).

The DUROS® delivery device typically consists of a cylindrical reservoir which contains the osmotic engine, piston, and drug formulation. The reservoir is capped at one end by a controlled-rate, semi-permeable membrane and capped at the other end by a diffusion moderator through which suspension formulation, comprising the drug, is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS® device releases a drug at a predetermined rate based on the principle of osmosis. Extracellular fluid enters the DUROS® device through a semi-permeable membrane directly into a salt engine that expands to drive the piston at a slow and even delivery rate. Movement of the piston forces the drug formulation to be released through the orifice or exit port at a predetermined sheer rate. In one embodiment of the present invention, the reservoir of the DUROS® device is load with a suspension formulation wherein the device is capable of delivering the suspension formulation to a subject over an extended period of time (e.g., about 1, about 3, about 6, about 9, about 10, about 12 months, and about 24 months) at a pre-determined, therapeutically effective delivery rate.

The release rate of the drug from the osmotic delivery device typically provides a subject with a predetermined target dose of a drug, for example, a therapeutically effective daily dose delivered over the course of a day; that is, the release rate of the drug from the device, provides substantial steady-state delivery of the drug at a therapeutic concentration to the subject.

Typically, for an osmotic delivery device, the volume of a beneficial agent chamber comprising the beneficial agent formulation is between about 100 µl to about 1000 µl, more preferably between about 120 µl and about 500 µl, more preferably between about 150 µl and about 200 µl. Most preferably the volume is 160 µl.

Typically, the osmotic delivery device is implanted within the subject, for example, subdermally or subcutaneously to provide subcutaneous drug delivery. The device(s) can be implanted subdermally or subcutaneously into either or both arms (e.g., in the inside, outside, or back of the upper arm), into the back, into a buttocks, into a thigh, or into the abdomen. Any body part comprising subcutaneous or subdermal fat is an acceptable site for implantation of an osmotic delivery device. Preferred locations in the abdominal area are under the abdominal skin in the area extending below the ribs and above the belt line. To provide a number of locations for implantation of one or more osmotic delivery device within the abdomen, the abdominal wall can e.g., be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions. Implantation and removal of osmotic delivery devices are generally carried out by medical professionals using local anesthesia (e.g., lidocaine).

Termination of treatment by removal of an osmotic delivery device from a subject is straightforward, and provides the important advantage of immediate cessation of delivery of the drug to the subject.

Preferably, the osmotic delivery device has a fail-safe mechanism to prevent an inadvertent excess or bolus delivery of drug in a theoretical situation like the plugging or clogging of the outlet (diffusion moderator) through which the drug formulation is delivered. To prevent an inadvertent excess or bolus delivery of drug the osmotic delivery device is designed and constructed such that the pressure needed to partially or wholly dislodge or expel the diffusion moderator from the reservoir exceeds the pressure needed to partially or wholly dislodge or expel the semi-permeable membrane to the extent necessary to de-pressurize the reservoir. In such a scenario, pressure would build within the device until it would push the semi-permeable membrane at the other end outward, thereby releasing the osmotic pressure. The osmotic delivery device would then become static and no longer deliver the drug formulation provided that the piston is in a sealing relationship with the reservoir.

The suspension formulations may also be used in infusion pumps, for example, the ALZET® (DURECT Corporation, Cupertino, Calif.) osmotic pumps which are miniature, infusion pumps for the continuous dosing of laboratory animals (e.g., mice and rats).

5.0.0 Exemplary Advantages of Certain Aspects of the Present Invention

In one aspect, the present invention relates to methods of treatment with continuous delivery of insulinotrophic peptides (e.g., an exenatide), for example, by use of an implantable osmotic delivery device. Experiments described herein have demonstrated that continuous delivery of an exenatide using an implantable osmotic delivery device, provided the following benefits for subjects in need of treatment: treating type 2 diabetes mellitus, improving glycemic control (as measured, e.g., by glucose levels, HbA1c, and/or fructosamine), reducing HbA1c, reducing fasting plasma glucose, reducing post-prandial blood glucose levels, reducing adverse gastrointestinal events (e.g., nausea and vomiting) relative to twice-daily injections, weight loss, reducing LDL-C, reducing systolic blood pressure, treating hypertension, reducing fructosamine levels, and improving of quality of life for subjects undergoing treatment.

In addition, the continuous delivery of insulinotrophic peptides (e.g., an exenatide) may be used in the practice of the following methods: treating obesity, controlling appetite, reducing caloric intake, reducing food intake, suppressing appetite, inducing anorexia, treating impaired glucose tolerance, treating post-prandial hyperglycemia, treating post-prandial dumping syndrome, treating hyperglycemic conditions, reducing triglycerides, reducing cholesterol, increasing urine flow, decreasing potassium concentration in the urine, alleviating toxic hypervolemia, inducing rapid diuresis, pre-surgical patient preparation, post-surgical patient treatment, increasing renal plasma flow and glomerular filtration rate, treating pre-eclampsia or eclampsia during pregnancy, increasing cardiac contractility, treating renal failure, treating congestive heart failure, treating nephrotic syndrome, treating pulmonary edema, treating systemic edema, treating cirrhosis, treating impaired glucose tolerance, treating pre-diabetes (blood glucose levels that are higher than normal but not yet high enough to be diagnosed as diabetes), treating type 1 diabetes mellitus (e.g., in combination with insulin), reducing risk of a cardiovascular event due to impaired glucose tolerance, reducing risk of a cerebrovascular event due to impaired glucose tolerance, delaying the progression of diabetes, ameliorating diabetes, delaying diabetes onset, inducing β-cell preservation and restoring β-cell functionality, restoring normoglycemia, providing euglycemic control, treating peripheral vascular disease, treating acute coronary syndrome, treating cardiomyopathy, treating gestational diabetes, treating polycystic ovary syndrome, treating or preventing nephropathy, and treating diabetes induced by a variety of diseases or conditions (for example, steroid induced diabetes, human immunodeficiency virus treatment-induced diabetes, latent autoimmune diabetes in adults, nonalcoholic steatohepatitis, nonalcoholic fatty liver disease, hypoglycemia unawareness, restrictive lung disease, chronic obstructive pulmonary disease, cardiovascular diseases, e.g., heart failure, atherosclerosis, and acute coronary syndrome, lipoatrophy, metabolic syndrome, and treating Alzheimer's disease).

The present invention also provides treatment methods for delivery of an insulinotrophic peptide having the following advantages. The continuous delivery from, for example, an osmotic delivery device, ensures 100% treatment compliance for subjects and avoids the need for twice-daily, daily, weekly, or even monthly injections because the devices described herein can deliver an incretin mimetic for time periods of up to a about year or two years. Avoidance of self-injection is a particular advantage for a subject who is needle phobic. Further, use of implantable devices for continuous delivery provides treatment convenience and avoids scheduling conflicts, for example, with meals, and also eliminates the inconvenience of administration of a drug by injection, as when subjects are in public or busy with daily activities. Also, frequent self-administration of a drug reminds subjects of their disease state and carries a stigma associated with the disease and/or treatment; whereas continuous delivery of a drug from an implanted osmotic delivery device may offer subjects some respite from such reminders and stigma.

The present invention also provides methods to treat subjects at dosage levels of insulinotrophic peptides previously thought to be higher than tolerable dosage levels. For example, continuous delivery of an exenatide is described herein for dosages tolerated at least up to 80 µg/day.

In another aspect the present invention provides methods of dosage escalation. In one embodiment, multiple devices for continuous delivery of a drug, for example, an insulinotrophic peptide, are provided. Each device is capable of delivering a particular drug dose per day. A low-dose device is initially implanted, followed by removal and implantation of a higher daily dose device. Alternatively, the first device may be kept in place and a second device implanted to increase the daily dose. In another alternative, a subject may be started by dosing with an injectable form of the drug (e.g., twice-daily, once-daily, once-weekly, and once- or twice-monthly injection) and transitioned to an implantable device to provide continuous delivery after an initial period. Such transitioning from injectable to implantable may, for example, allow subjects or physicians to try a drug and perhaps be observed for any immediate adverse effects before implantation of a device. Injectable to implantable transitions may also be useful for treatment of subjects who are particularly nervous about possible drug side effects. Also, providing the drug by injection or by continuous delivery at low dose may permit tolerization of the drug at low dose before changing to higher and more efficacious therapeutic doses.

Optimal time periods are determined for a drug concerning how long an initial device remains in place before replacement with a higher dose delivery device. Similarly optimal time periods are determined for how long an initial phase of treatment by injection goes on before implantation of an osmotic delivery device. For example, treatment is commenced at a low dose with low incidence of side effects (e.g., for about 2 weeks, about 3 months, about 6 months, about 9 months, and about a year). The subject adjusts to that dose and subsequently a higher dose delivery device is implanted providing dose escalation. Alternatively, a subject who has been treated with an injectable form dose escalates to an implantable osmotic delivery device. Such dose escalations were shown from the data presented herein to achieve additional benefits in glucose regulation and weight loss through at least 39 weeks. Examples of initial dosages include, but are not limited to, delivery of about 1 µg/day to about 20 µg/day, followed by dose escalation to about 5 µg/day to about 1,000 µg/day. Preferably, escalation of insulinotrophic peptide doses include, but are not limited to, the following: about 10 µg/day followed by about 20 µg/day; about 10 µg/day followed by about 30 µg/day; about 10 µg/day followed by about 40 µg/day; about 10 µg/day followed by about 50 µg/day; about 10 µg/day followed by about 60 µg/day; about 10 µg/day followed by about 70 µg/day; about 10 µg/day followed by about 80 µg/day; about 15 µg/day followed by about 20 µg/day; about 15 µg/day followed by about 30 µg/day; about 15 µg/day followed by about 40 µg/day; about 15 µg/day followed by about 50 µg/day; about 15 µg/day followed by about 60 µg/day; about 15 µg/day followed by about 70 µg/day; about 15 µg/day followed by about 80 µg/day; about 20 µg/day followed by about 30 µg/day; about 20 µg/day followed by about 40 µg/day; about 20 µg/day followed by about 50 µg/day; about 20 µg/day followed by about 60 µg/day; about 20 µg/day followed by about 70 µg/day; about 20 µg/day followed by about 80 µg/day; about 40 µg/day followed by about 50 µg/day; about 40 µg/day followed by about 60 µg/day; about 40 µg/day followed by about 70 µg/day; about 40 µg/day followed by about 80 µg/day; about 50 µg/day followed by about 60 µg/day; about 50 µg/day followed by about 60 µg/day; about 50 µg/day followed by about 70 µg/day; about 50 µg/day followed by about 80 µg/day; about 60 µg/day followed by about 70 µg/day or about 60 µg/day followed by about 80 µg/day. In one embodiment, the present invention includes kits and methods for manufacturing kits comprising one or more lower dose osmotic delivery devices and one or more higher dose osmotic delivery devices (the lower and higher dosages being relative to the other devices in the kit). Such kits may optionally include an implanter, lidocaine, and sterile field/supplies.

Generally, dose escalation is from a low dose of insulinotrophic peptide, for example, about 1 µg/day to about 30 µg/day, to a high dose of greater than the low dose to at least about 80 µg/day.

In another aspect, the present invention provides a method of treating diabetes without a substantial increase in insulin secretion using an insulinotrophic peptide. In a preferred embodiment of this aspect of the present invention the insulinotrophic peptide is an exenatide. Data obtained in the course of the studies described herein demonstrated that, at higher doses of continuous delivery of the exenatide (e.g., 20 µg/day, 40 µg/day, and 80 µg/day), effective treatment of diabetes was achieved in the absence of an increase in insulin production. Insulin levels were measured by an RIA, a chromatographic method, an ECL assay, an ELISA, or an IEMA.

In another aspect, the methods of the present invention allow for the administration of a drug, e.g., an insulinotrophic peptide, without a substantial initial drug burst that typically occurs with depot injections (e.g., initial drug burst of from about 5% of total drug in depot formulation to about 1% of total drug in depot formulation) that provide sustained delivery over a period of time (e.g., depot injections formulated using poly(lactides), poly(glycolides), poly(lactide-co-glycolides), poly(lactic acid)s, poly(glycolic acid)s, poly(lactic acid-co-glycolic acid)s and blends and copolymers thereof).

In a further aspect the present invention is directed to methods of providing greater reduction in plasma blood glucose in a shorter time period (e.g., within the first day and to day 5) than can be achieved using twice-daily daily injections, comprising providing continuous delivery of an insulinotrophic peptide, for example, an exenatide. In one embodiment, continuous delivery is achieved by use of an implantable osmotic delivery device.

Another advantage of the present invention is the ability to remove the delivery device providing continuous delivery of the drug and provide rapid termination of drug delivery for any reason, for example, in the case of myocardial infarction, pregnancy, pancreatitis or suspected pancreatitis, emergency medical care (e.g., termination of drug therapies), or adverse drug reactions.

The present invention uniquely addresses unmet needs relative to injectable incretin mimetics. For example, one shortcoming of a twice-daily injectable exenatide is that greater than 65% of subjects are not treated to or maintained at HbA1c treatment goals. Another disadvantage of a twice-daily injectable exenatide is that greater than 65% of these subjects become noncompliant between 6-12 months when attempting to adhere to the injection treatment schedule. Also, 65% of subjects treated with a twice-daily injectable exenatide are overweight and need sustained weight loss.

Experiments described previously demonstrated that the methods of and osmotic delivery devices comprising an exenatide for use in methods of treating type 2 diabetes mellitus by continuous delivery as set forth by the present invention provide sustained treatment of subjects at target doses, complete subject compliance with the treatment, and sustained weight loss. A target dose typically provides substantial steady-state delivery of the exenatide at a therapeutic concentration to the subject.

The data presented in the Experimental section herein demonstrate that the present invention provides methods of and osmotic delivery devices comprising exenatides for use in methods of treating type 2 diabetes mellitus by continuous delivery, wherein substantial steady-state delivery of the exenatide at therapeutic concentrations is achieved within a time period of about 7 days or less, about 6 days or less, about 5 days or less, about 4 days or less, about 3 days or less, preferably about 2 days or less, more preferably about 1 day or less, and preferably within the first day after implantation of the osmotic delivery device in the subject.

The data also demonstrate that the present invention provides methods of and osmotic delivery devices comprising exenatides for use in methods of treating type 2 diabetes mellitus by continuous delivery, wherein a significant decrease in fasting plasma glucose concentration, relative to the fasting plasma glucose concentration before implantation, is achieved after implantation of the osmotic delivery device in the subject within a time period of between within the first day to about 7 days or less, about 6 days or less, about 5 days or less, about 4 days or less, about 3 days or less, preferably about 2 days or less, more preferably about 1 day or less, and more preferably within the first day after implantation of the osmotic delivery device in the subject.

The data also demonstrate that the present invention provides the capability to terminate the continuous delivery such that the concentration of an exenatide is substantially undetectable in a blood sample from the subject, after termination of continuous delivery, within about 6 half-lives of the drug after termination of continuous delivery, within about 5 half-lives of the drug after termination of continuous delivery, within about 4 half-lives of the drug after termination of continuous delivery, or within about 3 half-lives of the drug after termination of continuous delivery.

Further, the data show that treatment by continuous delivery of an exenatide provided better decreases in HbA1c than treatment by injection. In particular, subjects experienced a decrease in HbA1c % over the administration period of at least about 0.5%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, or at least about 6.0% from baseline over the administration period or a reduction in the amount of HbA1c in the subject's serum of at least about 35 percent, at least about 40 percent, at least about 45 percent, at least about 50 percent, or at least about 55 percent at the end of an administration period relative to the beginning of the administration period.

Also, the data illustrate that the methods of and osmotic delivery devices comprising an exenatide for use in methods of treating type 2 diabetes mellitus by continuous delivery as described herein provide improved tolerization to dose escalation of the exenatide relative to injection of the exenatide.

In addition, these data presented herein demonstrate a significant advantage of the implanted osmotic delivery device of the present invention over an exenatide's administration via injection in terms of reported quality of life for treated subjects.

The comparative data described below demonstrate the superior treatment outcomes using the methods of and osmotic delivery devices comprising an exenatide for use in methods of treating type 2 diabetes mellitus by continuous delivery of the present invention, in combination with metformin therapy, relative to other treatment methods. Such other treatment methods include twice-daily injection of an exenatide, once-weekly injection of an exenatide, once-daily injection of liraglutide, once-weekly injection of taspoglutide, once-daily orally administered sitagliptin, and once-daily orally administered pioglitazone.

In summary, the methods of and osmotic delivery devices comprising an insulinotrophic peptide, for example, an exenatide, for use in methods of treating type 2 diabetes mellitus by continuous delivery as described herein provide a new standard of effective treatment. The present invention provides superior HbA1c reduction, improved weight loss through at least 39 weeks, and complete compliance, as well as long-term glycemic control relative to the use of dipeptidyl peptidase-4 (DPP-4) inhibitors (e.g., sitagliptin), thiazolidinediones (TZDs) (e.g., pioglitazone), other injectable incretin mimetics (e.g., liraglutide and taspoglutide), and twice-daily or once-weekly injection of an exenatide. Further, the present invention provides better insulinotrophic peptide treatment tolerability because no self-injections are required and the methods of and osmotic delivery devices comprising an insulinotrophic peptide for use in methods of treating type 2 diabetes mellitus by continuous delivery provide improved gastrointestinal tolerance.

The present invention relates to use of the ITCA 650 (a once- or twice-yearly continuous subcutaneous delivery of exenatide) for the treatment of type 2 diabetes. The ITCA 650 is a matchstick-size, miniature osmotic pump that is placed sub-dermally to provide continuous and consistent drug therapy via a proprietary formulation technology, which maintains stability of therapeutic proteins and peptides at human body temperatures for extended periods of time. Exenatide, the active agent in ITCA 650, is a glucagon-like peptide-1 (GLP-1) receptor agonist currently marketed globally as twice-daily and once-weekly self-injection therapies for type 2 diabetes. ITCA 650 represents the first injection-free GLP-1 therapy that can deliver a full year of treatment from a single placement of a 6 month or 12 month subcutaneous mini-pump.

ITCA 650 has been the focus of four global phase 3 clinical trial programs called FREEDOM. The FREEDOM clinical program is designed to evaluate the safety and efficacy of ITCA 650 (continuous subcutaneous delivery of exenatide) for the treatment of type 2 diabetes. Over the four phase 3 clinical trials, it is expected that 5,000 patients at more than 500 clinical trial sites in more than 30 countries will be enrolled. The clinical studies will cover a broad range of patients whose diabetes is not controlled by oral anti-diabetes medications including metformin and metformin-based combinations.

The FREEDOM-1 Clinical Trial

The FREEDOM-1 study is a placebo-controlled, double-blind phase 3 trial that tested the efficacy and safety against placebo of ITCA 650 in patients with type 2 diabetes patients whose HbA1c is not controlled on diet and exercise alone, or in many cases, up two or three oral anti-diabetes drugs. Subjects enrolled in the trial had HbA1c measures between 7.5% and 10.0%. 460 patients were randomized into three groups in a 1:1:1 ratio, evaluating ITCA 650 40 mcg/day and 60 mcg/day versus placebo. Subjects in the active arms were treated for the first 13 weeks with 3-month devices that deliver an initial dose of 20 mcg/day, and then treated with 6-month ITCA 650 at doses of 40 mcg/day or 60 mcg/day.

The Primary Endpoint was HbA1c reduction over 39 weeks. Secondary endpoints included changes in weight, and the percent of subjects reaching an HbA1c goal of <7%.

The now completed FREEDOM-1 study showed that ITCA 650 demonstrated positive results when added to standard oral diabetes medications. All endpoints were met regarding HbA1c and weight reductions, as well as the percent of patients treated to goal. Pre-specified sub-group analyses on HbA1c reductions over time also showed clinically and statistically significant impact, including substantial improvement in hyperglycemia, across a wide spectrum of patients and background medications. Significant HbA1c reductions were observed over the 39 weeks ranging from a mean of 1.4% to 1.7% across the majority of patients, with the highest reductions in patients on background metformin. Subjects with a starting baseline HbA1c above 8.5% had mean reductions up to 2.1%. Both the 40 mcg/day and 60 mcg/day mini-pumps demonstrated statistically significant results vs. control and were well tolerated. The FREEDOM-1 study demonstrated ITCA 650 to be significantly superior to placebo for both 40 mcg/day and 60 mcg/day doses, and met all its clinical endpoints.

The FREEDOM-1 High Baseline (HBL) Clinical Trial

Concurrent with FREEDOM-1, a second open-label phase 3 study called FREEDOM-1 HBL (high baseline) was conducted for patients who met all eligibility criteria for FREEDOM-1, but whose baseline HbA1c was greater than 10% (>10%) but less or equal than 12% (≤12%). All patients in this study were treated with ITCA 650 20 mcg/day for the first 3 months and with ITCA 650 60 mcg/day for the next 6 months. Pre-study oral anti-diabetic agents (OADs) were maintained unchanged for the 39 weeks (9 months) of treatment. Subjects in the FREEDOM-1 HBL had high baseline HbA1c levels despite many being on multi-drug therapy when screened into the study.

The now completed FREEDOM-1 HBL trial showed a sustained reduction of 3.4% in HbA1c (from a mean starting baseline of 10.8%) among these treatment-refractory and poorly controlled patients. The HBL study also showed the ability of a 39-week therapy with ITCA 650 to bring 25% of these patients, many uncontrolled on multi-drug therapy, to their HbA1c goal of <7%.

Both studies also showed a G.I. tolerability profile with nausea rates over time in the low single digits and a low single digit discontinuation rate for nausea.

Overall, both studies demonstrated that ITCA 650 provides sustained blood sugar control for many type 2 diabetes patients who are not achieving their goals—and without the need for regular self-injections. The data clearly indicated that the ITCA 650 method of delivery (i.e., a continuous, zero-order kinetic administration of exenatide) results in clinical and statistical significant changes in HbA1c and improvement in glycemic control. The ITCA 650 will help physicians to better manage this serious disease; it represents a new and transformational way of delivering important medicines in treatment of this devastating and growing worldwide epidemic.

EXAMPLES

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, and percent changes) but some experimental errors and deviations should be accounted for. Unless indicated otherwise, temperature is in degrees Centigrade and pressure is at or near atmospheric.

The compositions used to practice the methods of the present invention meet the specifications for content and purity required of pharmaceutical products. Further examples of suspension formulations comprising insulinotrophic peptide can be found in U.S. Patent Publication Nos. 2006/0193918, 2008/0260840, and 2010/0092566.

Example 1

A Phase 3, Randomized, Double-Blind, Placebo-Controlled, Multi-Center Study to Evaluate the Efficacy, Safety and Tolerability of ITCA 650 in Patients with Type 2 Diabetes A Phase 3 clinical trial was designed as a double-blind, placebo-controlled multi-center study to determine whether ITCA 650 60 μg/day or 40 μg/day is superior to ITCA placebo reducing HbA1c in patients with type 2 diabetes following 39 weeks of treatment.

Figure 1:
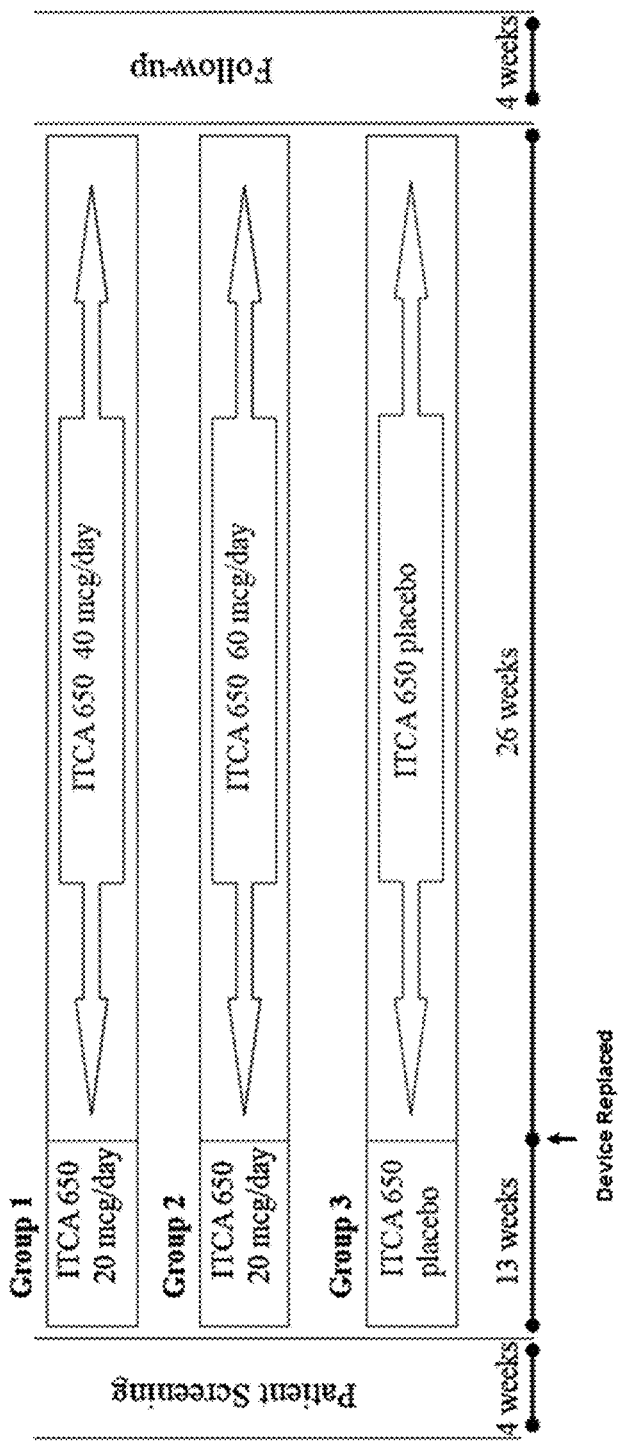
FIG. 1 presents an overview of the 39-week phase 3, randomized, double-blind, placebo-controlled, multi-center study to evaluate the efficacy, safety and tolerability of ITCA 650 in patients with type 2 diabetes described in Example 1.

Efficacy and safety of ITCA 650 versus ITCA placebo was studied during a 39-week treatment period. The study device (ITCA 650 or ITCA placebo) was placed on day 0, replaced at week 13 and removed at week 39. Group 1 was initially treated with an ITCA 650 20 μg/day device for 13 weeks. After 13 weeks, the ITCA 650 20 μg/day device was replaced with an ITCA 650 40 μg/day device for 26 weeks. At week 39 the ITCA 650 40 μg/day device was removed. This dosage scheme and members of this group are hereinafter in this Example referred to as ITCA 650 20/40 μg/day. Group 2 was initially treated with an ITCA 650 20 μg/day device for 13 weeks. After 13 weeks the ITCA 650 20 μg/day device was replaced with an ITCA 650 60 μg/day device for 26 weeks. At week 39 the ITCA 650 60 μg/day device was removed. This dosage scheme and members of this group are hereinafter in this Example referred to as ITCA 650 20/60 μg/day. Group 3 had an ITCA placebo in place for 13 weeks. At week 13 the ITCA placebo device was replaced with a new ITCA placebo device for 26 weeks. At week 39 the ITCA placebo device was removed. The Modified Intent-to-Treat (mITT) population includes all patients from the safety population who had a valid baseline and at least one post-baseline HbA1c value. The Last Observation Carried Forward (LOCF) endpoint is defined as the last non-missing, on-treatment observation that is measured after baseline. Subjects who received rescue therapy were included in the mITT population. The 39 week study is represented graphically in FIG. 1.

A. Demographics of Study Group

Inclusion criteria were as follows. Subjects were 18-80 years of age and diagnosed as having type 2 diabetes mellitus for at least three months prior to screening. Subjects had been on a stable treatment regimen of diet and exercise alone or in combination with a stable and optimal or near-optimal dose of metformin, sulfonylurea, TZD, or combination of these drugs for at least three months. Subjects had a stable body weight (not varying by >10% for at least three months. Calcitonin levels of <50 ng/L (50 pg/mL) and a body mass index (BMI) of ≥2.5 kg/m$^2$ and 45 kg/m$^2$ at time of screening. Women of childbearing potential must have had a negative pregnancy test at Screening. HbA1c levels were greater than or equal to 7.5% and less than or equal to 10%. However, certain subjects who had baseline HbA1c levels outside that range were included as subjects.

Figure 2:
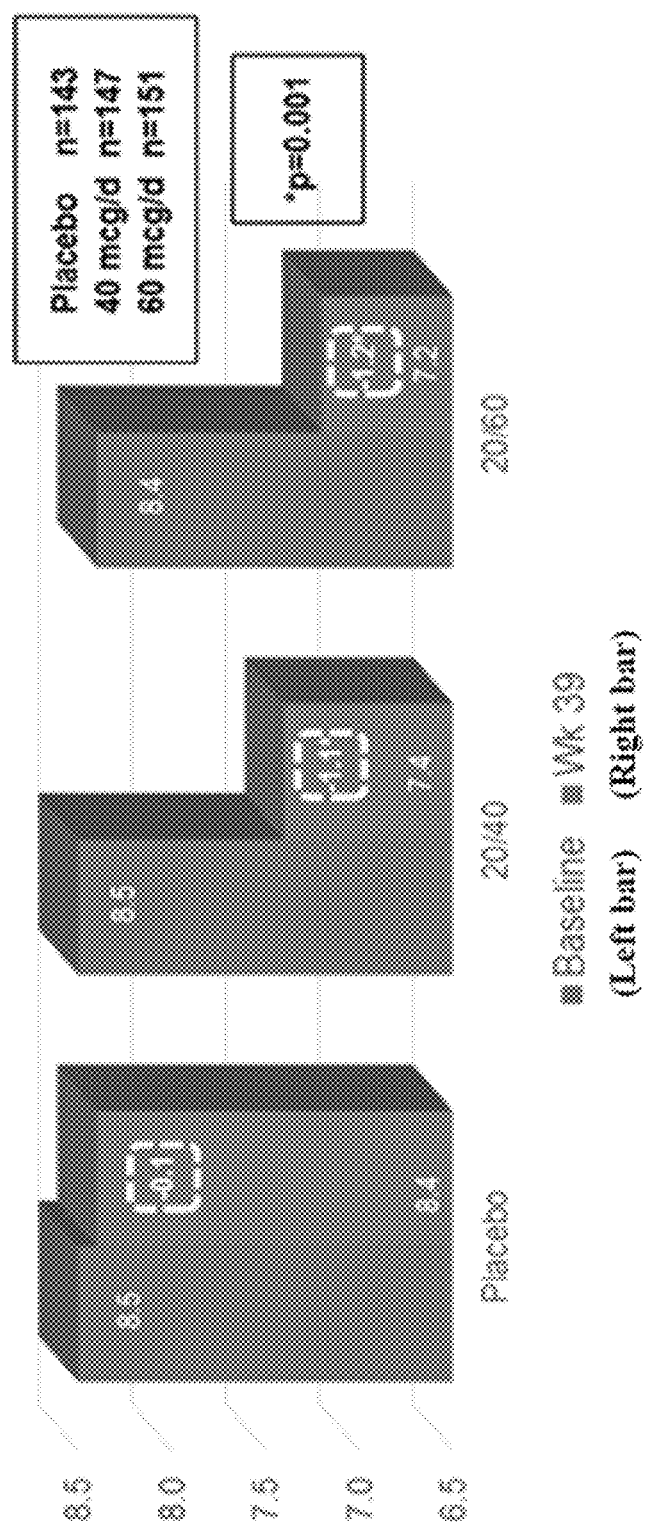
FIG. 2 is a graph showing decreases in HbA1c % relative to baseline at Last Observation Carried Forward (LOCF) endpoint for subjects in the mITT population in the phase 3 clinical trial described in Example 1 for subjects with type 2 diabetes and a baseline HbA1c % pursuant to the study protocol inclusion criterion. The average decreases for the two treatments groups relative to placebo were statistically significant. Baseline values are represented by the left bars and values at LOCF endpoint are represented by the right bars. "20/40" indicates that subjects were treated with ITCA 650 20 µg/day for 13 weeks followed by ITCA 650 40 µg/day at week 39; "20/60" indicates that subjects were treated with ITCA 650 20 µg/day for 13 weeks followed by ITCA 650 60 µg/day at week 39 ("20/60"). Baseline is defined as the last assessment on or before the day of the initial placement of an ITCA 650 osmotic delivery device (containing drug or placebo).

460 subjects were randomized into three groups: ITCA 650 20/40 µg/day, ITCA 650 20/60 µg/day, and ITCA Placebo. Baseline demographics of the initial study phase subjects are presented in Table 1. Subjects' demographics (safety population) were matched across all treatment groups. This data is presented in Table 1. It is noteworthy that the time from diagnosis of Type 2 Diabetes (~9 years) was higher compared to subjects in the phase 2 study described elsewhere (i.e., in Henry et al 2014); thus, they had been exposed to anti-diabetes treatment drugs for longer periods time. Additionally, in the phase 3 study of this Example there were more subjects from minority groups, e.g., African American, the subjects had higher body weight, and the subjects were older. Overall, the subjects in the phase 3 study were less healthy and less likely to respond to a diabetes trial than subjects in the phase 2 study; that is to say, the subjects in the phase 3 trial described in this Example were harder to treat than those in the prior phase 2 study.

subjects in the ITCA 20/60 µg/day group (n=151) had an average Hb1A1c % decrease of 1.2%, whereas subjects in the placebo group (n=143) had an average Hb1A1c % decrease of 0.13%. The average decreases in the two treatments groups relative to placebo were statistically significant. See, FIG. 2. The observed decreases in Hb1A1c % was slightly less than that observed in the phase 2 study described elsewhere (i.e., in Henry et al 2014). However, as mentioned above, the subjects enrolled in the phase 3 study of this Example were less healthy and less likely to respond to a diabetes trial ("harder to treat") than subjects in the phase 2 trial. Yet, reductions in HbA1c were clinically and statistically significant versus placebo at each scheduled time point for the mITT population over 39 weeks.

Over time, subjects who received ITCA 650 20/40 µg/day or 20/60 µg/day demonstrated impressive and sustained reductions in weight relative to placebo. There was a steady drop in body weight between baseline and week 39. Data for

TABLE 1

| Characteristic (unit) | Statistic | ITCA 650 20/40 µg/day (N = 153) | ITCA 650 20/60 µg/day (N = 153) | Placebo (N = 154) | Total (N = 460) |
| --- | --- | --- | --- | --- | --- |
| Age (years) | Mean (SD) | 55.5 (10.26) | 54.7 (9.55) | 54.7 (9.14) | 55.0 (9.65) |
| <50 years | n (%) | 42 (27.5%) | 46 (30.1%) | 41 (26.6%) | 129 (28.0%) |
| 50-64 years | n (%) | 84 (54.9%) | 79 (51.6%) | 93 (60.4%) | 256 (55.7%) |
| 65-74 years | n (%) | 22 (14.4%) | 28 (18.3%) | 18 (11.7%) | 68 (14.8%) |
| ≥75 years | n (%) | 5 (3.3%) | 0 | 2 (1.3%) | 7 (1.5%) |
| Gender | | | | | |
| Male | n (%) | 89 (58.2%) | 91 (59.5%) | 92 (59.7%) | 272 (59.1%) |
| Female | n (%) | 64 (41.8%) | 62 (40.5%) | 62 (40.3%) | 188 (40.9%) |
| Race | | | | | |
| White | n (%) | 129 (84.3%) | 125 (81.7%) | 126 (81.8%) | 380 (82.6%) |
| Black or African American | n (%) | 20 (13.1%) | 21 (13.7%) | 23 (14.9%) | 64 (13.9%) |
| Asian | n (%) | 1 (0.7%) | 2 (1.3%) | 2 (1.3%) | 5 (1.1%) |
| Asian Indian (Indian Subcontinent) | n (%) | 2 (1.3%) | 0 | 0 | 2 (0.4%) |
| American Indian or Alaska Native | n (%) | 0 | 4 (2.6%) | 2 (1.3%) | 6 (1.3%) |
| Native Hawaiian or Other Pacific Islander | n (%) | 1 (0.7%) | 0 | 0 | 1 (0.2%) |
| Other | n (%) | 0 | 0 | 0 | 0 |
| Multiple | n (%) | 0 | 1 (0.7%) | 1 (0.6%) | 2 (0.4%) |
| Ethnicity | | | | | |
| Hispanic or Latino | n (%) | 56 (36.6%) | 47 (30.7%) | 59 (38.3%) | 162 (35.2%) |
| Not Hispanic or Latino | n (%) | 96 (62.7%) | 105 (68.6%) | 95 (61.7%) | 296 (64.3%) |
| Not Reported | n (%) | 1 (0.7%) | 1 (0.7%) | 0 | 2 (0.4%) |

B. Pharmacodynamic Data

Figure 3:
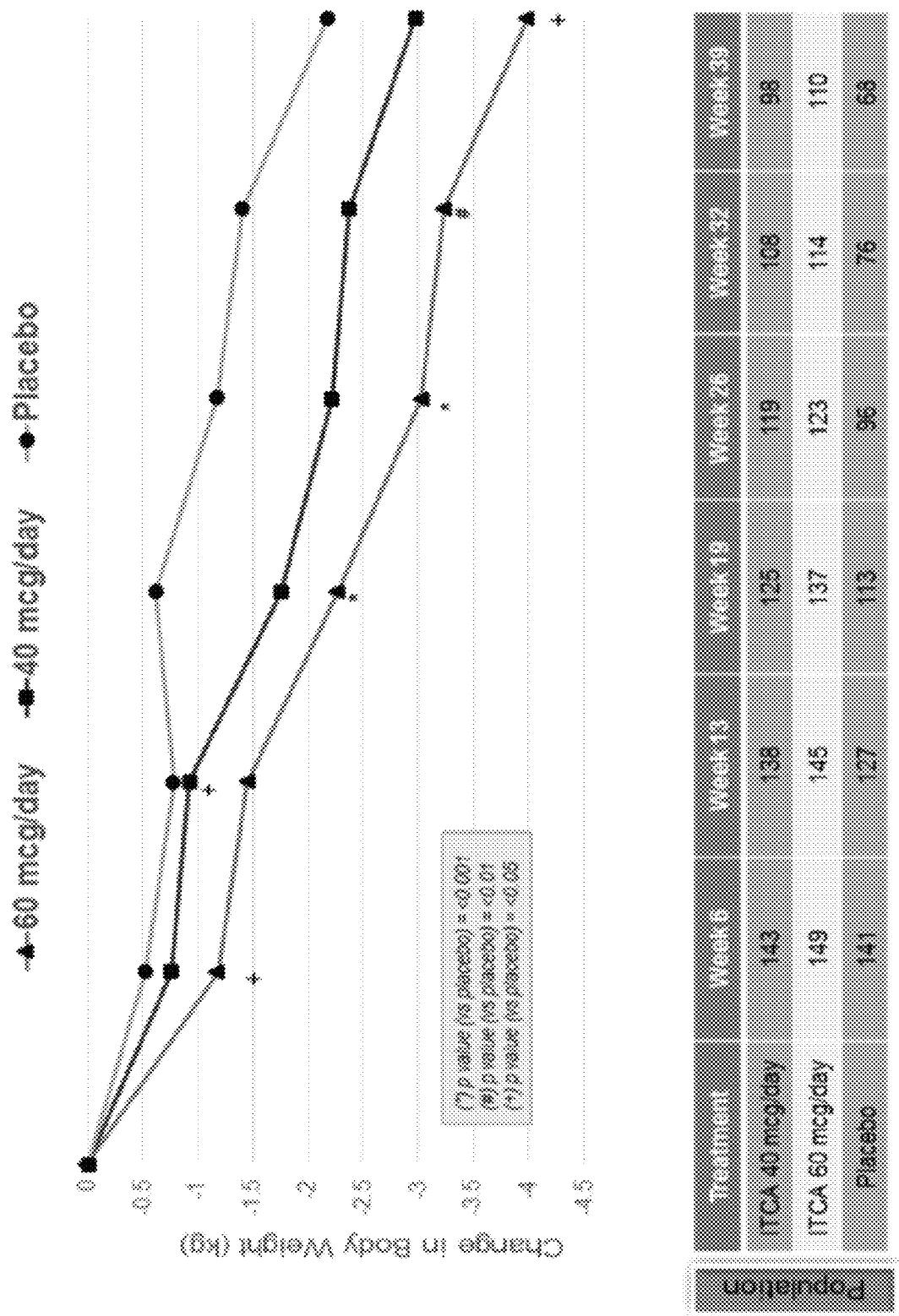
FIG. 3 is a graph showing progressive decreases in bodyweight from baseline by visit for subjects in the mITT population described in Example 1. Subjects were treated with ITCA 650 20 µg/day for the first 13 weeks followed by either ITCA 650 40 µg/day for the following 26 weeks ("ITCA 40 mcg/day" or "40 mcg/day"; data are identified with closed squares) or ITCA 650 60 µg/day for the following 26 weeks ("ITCA 60 mcg/day" or "60 mcg/day"; data are identified with closed triangles). Data for placebo subjects are identified with closed circles.
Figure 4:
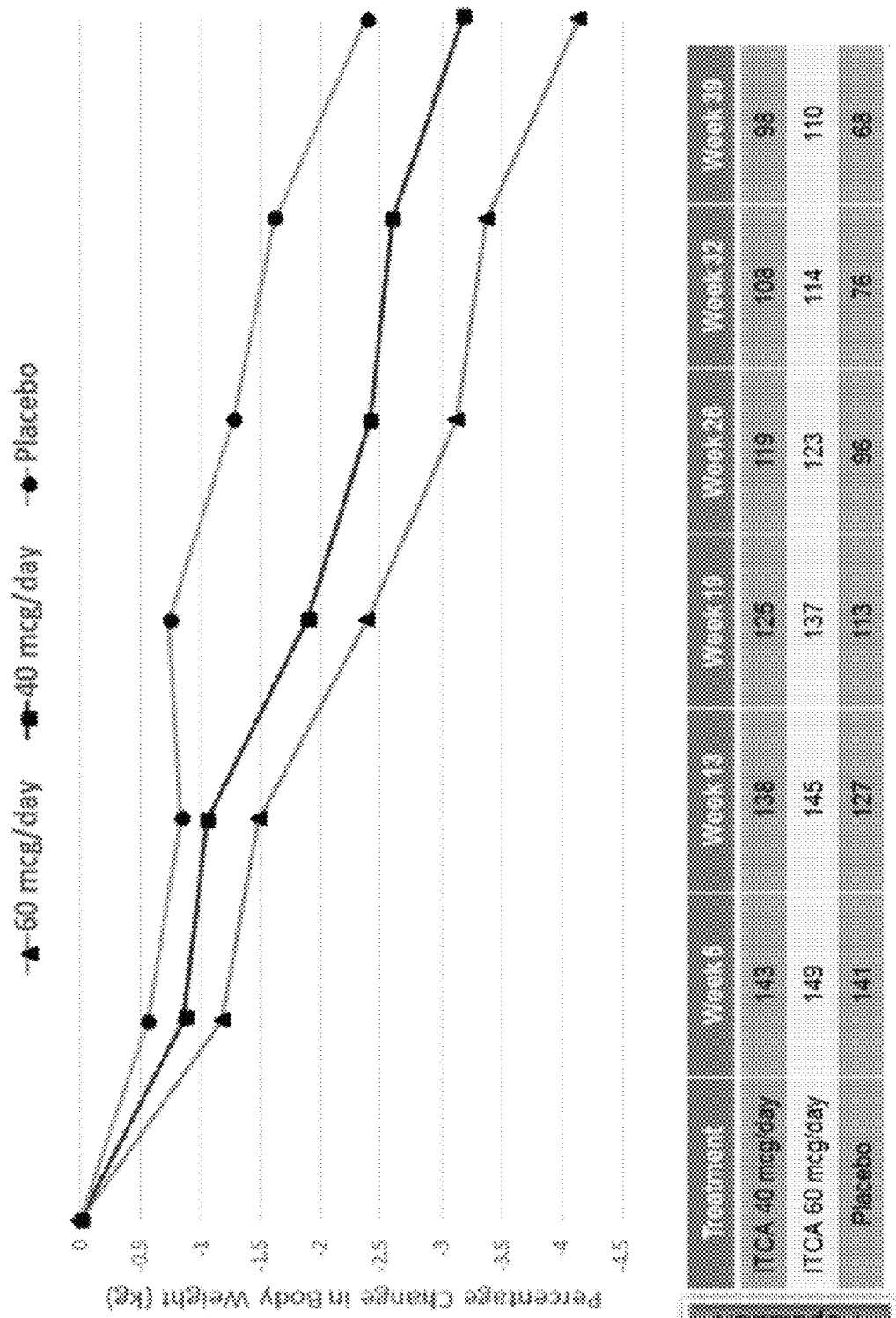
FIG. 4 is a graph showing percentage decreases in bodyweight from baseline by visit for the mITT population described in Example 1. Subjects were treated with ITCA 650 20 µg/day for the first 13 weeks followed by either ITCA 650 40 µg/day for the following 26 weeks ("ITCA 40 mcg/day" or "40 mcg/day"; data identified with closed squares) or ITCA 650 60 µg/day for the following 26 weeks ("ITCA 60 mcg/day" or "60 mcg/day"; data identified with closed triangles). Data for placebo subjects are identified with closed circles.
Figure 5:
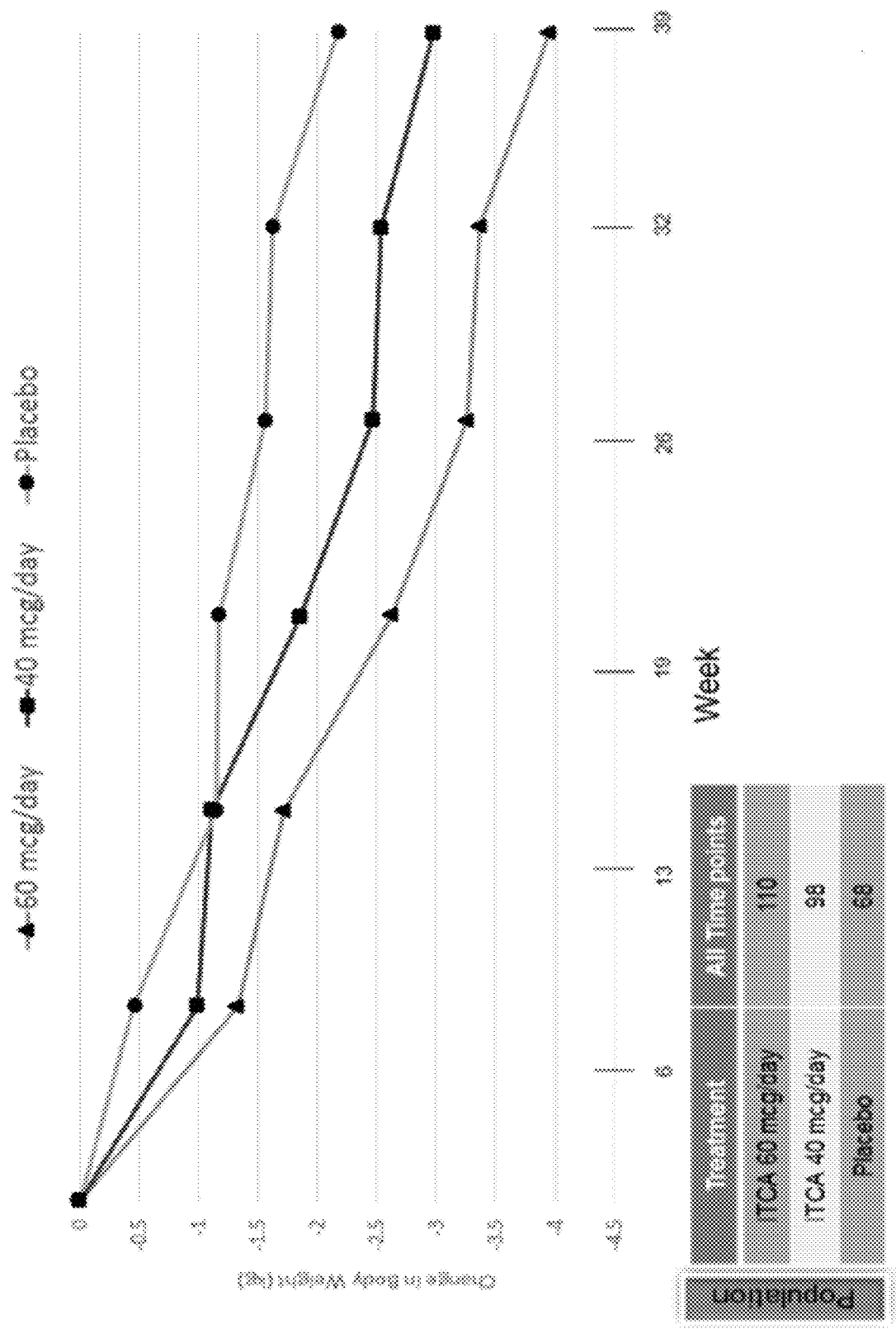
FIG. 5 is a graph showing changes in body weight (kg) from baseline by visit to week 39 for subjects in the mITT population described in Example 1. Subjects were treated with ITCA 650 20 µg/day for the first 13 weeks followed by either ITCA 650 40 µg/day for the following 26 weeks ("ITCA 40 mcg/day" or "40 mcg/day"; data identified with closed squares) or ITCA 650 60 µg/day for the following 26 weeks ("ITCA 60 mcg/day" or "60 mcg/day"; data identified with closed triangles). Data for placebo subjects are identified with closed circles. Data is presented for subjects who received the entire 39 week treatment.

At week 39, subjects in the ITCA 20/40 µg/day group (n=147) had an average Hb1A1c % decrease of 1.12% and the mITT population are shown in Table 2 and illustrated in FIGS. 3 to 5. FIG. 5 shows data for only those subjects who completed the 39 weeks.

TABLE 2

Change from Baseline Body Weight by Visit Modified Intention-to-Treat (mITT) Population

| Visit | Statistic | ITCA 650 20/40 mcg/day (N = 147) | ITCA 650 20/60 mcg/day (N = 151) | Placebo (N = 143) |
| --- | --- | --- | --- | --- |
| Baseline Body Weight (kg) | n | 147 | 151 | 143 |
| | Mean (SD) | 96.68 (18.503) | 97.70 (18.268) | 97.25 (21.626) |
| Week 1 Body Weight (kg) | n | 147 | 149 | 142 |
| | Mean (SD) | 96.05 (18.529) | 96.78 (18.248) | 97.23 (21.683) |

TABLE 2-continued

Change from Baseline Body Weight by Visit Modified Intention-to-Treat (mITT) Population

| Visit | Statistic | ITCA 650 20/40 mcg/day (N = 147) | ITCA 650 20/60 mcg/day (N = 151) | Placebo (N = 143) |
|---|---|---|---|---|
| Change from Baseline to Week 1 | Mean (SD) | −0.63 (1.361) | −0.73 (1.720) | −0.19 (1.761) |
|  | p-value (vs. Placebo) | 0.024 | 0.005 |  |
| Percent Change from Baseline to Week 1 | Mean (SD) | −0.67 (1.418) | −0.76 (1.799) | −0.21 (1.624) |
| Week 6 Body Weight (kg) | n | 143 | 149 | 141 |
|  | Mean (SD) | 95.94 (18.851) | 96.56 (17.951) | 96.79 (21.826) |
| Change from Baseline to Week 6 | Mean (SD) | −0.76 (2.077) | −1.18 (2.548) | −0.52 (1.813) |
|  | p-value (vs. Placebo) | 0.345 | 0.010 |  |
| Percent Change from Baseline to Week 6 | Mean (SD) | −0.86 (2.180) | −1.17 (2.495) | −0.56 (1.884) |
| Week 13 Body Weight (kg) | n | 138 | 145 | 127 |
|  | Mean (SD) | 95.66 (18.787) | 96.30 (18.249) | 96.68 (22.253) |
| Change from Baseline to Week 13 | Mean (SD) | −0.92 (2.526) | −1.45 (3.007) | −0.78 (2.779) |
|  | p-value (vs. Placebo) | 0.705 | 0.055 |  |
| Percent Change from Baseline to Week 13 | Mean (SD) | −1.05 (2.529) | −1.48 (2.936) | −0.83 (2.871) |
| Week 19 Body Weight (kg) | n | 125 | 137 | 113 |
|  | Mean (SD) | 94.06 (18.017) | 94.90 (18.302) | 95.96 (22.631) |
| Change from Baseline to Week 19 | Mean (SD) | −1.75 (3.408) | −2.27 (3.572) | −0.61 (3.611) |
|  | p-value (vs. Placebo) | 0.014 | <0.001 |  |
| Percent Change from Baseline to Week 19 | Mean (SD) | −1.88 (3.322) | −2.39 (3.423) | −0.73 (3.636) |
| Week 26 Body Weight (kg) | n | 119 | 123 | 96 |
|  | Mean (SD) | 93.56 (18.687) | 94.04 (18.253) | 94.01 (22.183) |
| Change from Baseline to Week 26 | Mean (SD) | −2.21 (3.626) | −3.03 (4.176) | −1.17 (3.777) |
|  | p-value (vs. Placebo) | 0.060 | <0.001 |  |
| Percent Change from Baseline to Week 26 | Mean (SD) | −2.41 (3.743) | −3.12 (3.951) | −1.27 (4.019) |
| Week 32 Body Weight (kg) | n | 108 | 114 | 76 |
|  | Mean (SD) | 93.25 (19.087) | 94.49 (18.695) | 94.91 (22.832) |
| Change from Baseline to Week 32 | Mean (SD) | −2.38 (4.150) | −3.23 (4.582) | −1.41 (4.591) |
|  | p-value (vs. Placebo) | 0.150 | 0.007 |  |
| Percent Change from Baseline to Week 32 | Mean (SD) | −2.59 (4.389) | −3.37 (4.290) | −1.62 (4.946) |
| Week 39 Body Weight (kg) | n | 98 | 110 | 68 |
|  | Mean (SD) | 91.67 (17.972) | 93.75 (18.163) | 94.34 (23.331) |
| Change from Baseline to Week 39 | Mean (SD) | −2.97 (4.318) | −3.99 (4.679) | −2.17 (5.134) |
|  | p-value (vs. Placebo) | 0.254 | 0.014 |  |
| Percent Change from Baseline to Week 39 | Mean (SD) | −3.17 (4.607) | −4.14 (4.564) | −2.38 (5.387) |

Figure 6:
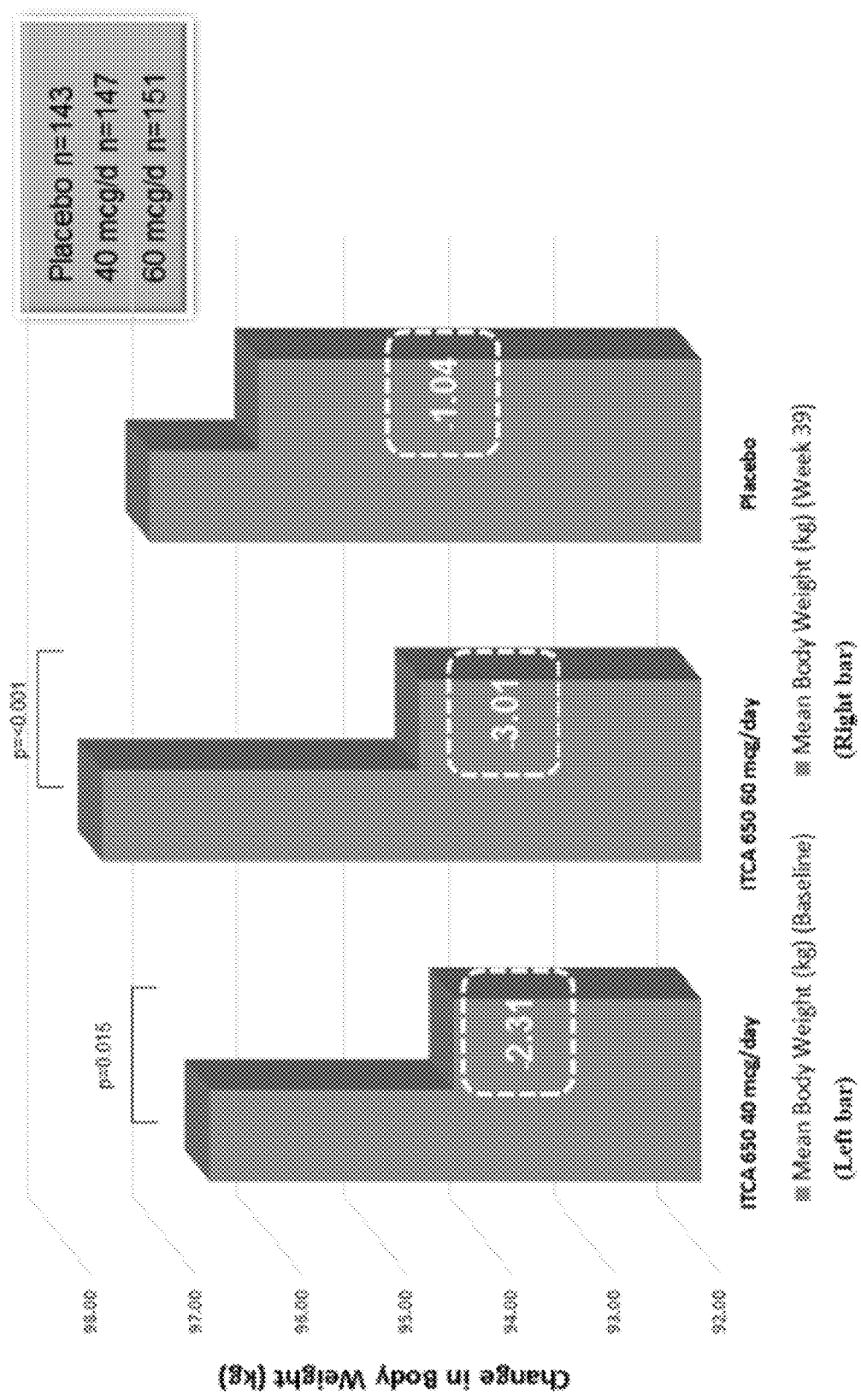
FIG. 6 is a graph showing decreases in body weight relative to baseline at Last Observation Carried Forward (LOCF) endpoint for subjects in the mITT population in the phase 3 clinical trial described in Example 1 for subjects with type 2 diabetes and a baseline HbA1c % pursuant to the study protocol inclusion criterion. The average decreases for the two treatments groups relative to placebo was statistically significant. Baseline values are represented by the left bars and values at 39 weeks are represented by the right bars.

Subjects in the both treatment groups experienced significant weight loss relative to subjects in the placebo group. Last Observation Carried Forward (LOCF) endpoint data are shown in Table 3 and illustrated in FIG. 6.

TABLE 3

|  | Statistic | ITCA 650 20/4 µg/day (N = 147) | ITCA 650 20/60 µg/day (N = 151) | Placebo (N = 143) |
|---|---|---|---|---|
| Baseline Body Weight (kg) | Mean (SD) | 96.68 (18.503) | 97.70 (18.268) | 97.25 (21.626) |
| LOCF Endpoint Body Weight (kg) | Mean (SD) | 94.37 (18.966) | 94.70 (18.672) | 96.21 (22.469) |
| Change from Baseline at LOCF Endpoint | Mean (SD) | −2.31 (4.058) | −3.00 (4.746) | −1.04 (4.421) |
|  | p-value (vs. Placebo) | 0.015 | <0.001 |  |

At week 39, 37.4% of the subjects in the ITCA 20/40 µg/day group had their LOCF endpoint Hb1A1c % reduce to below 7% and 43.7% of the subjects in the ITCA 20/60 µg/day group had their LOCF endpoint Hb1A1c % reduce to below 7%, whereas only 9.1% of subjects in placebo group experienced this reduction. These data are shown in Table 4.

TABLE 4

| Statistic | ITCA 650 20/40 µg/day (N = 147) | ITCA 650 20/60 µg/day (N = 151) | Placebo (N = 143) |
|---|---|---|---|
| n (%) | 55 (37.4%) | 66 (43.7%) | 13 (9.1%) |
| Odds Ratio | 6.446 | 8.146 |  |

TABLE 4-continued

| Statistic | ITCA 650 20/40 μg/day (N = 147) | ITCA 650 20/60 μg/day (N = 151) | Placebo (N = 143) |
|---|---|---|---|
| 97.5% CI of Odds Ratio | (2.985, 13.921) | (3.799, 17.469) | |
| p-value (vs. Placebo) | <0.001 | <0.001 | |

Note:
Odds ratio is the odds of the treatment group attaining the endpoint over the odds in the placebo group.

Data was analyzed for subjects who fit into one of the following two co-treatment groups: subjects who were co-treated with metformin monotherapy and subjects who were co-treated with metformin and sulfonylurea combination therapy. In FIGS. 7 and 8, HbA1c % data is shown for the mITT population from members of each group at LOCF endpoint. Subjects in the 20/40 μg/day group had an average Hb1A1c % decrease of 1.0% and 1.11% respectively for the two co-treated groups and subjects in the 20/60 μg/day group had an average Hb1A1c % decrease of 1.35% and 0.97% respectively for the two co-treated groups. All decreases were statistically significant relative to their respective baseline values.

Data was analyzed for subjects administered sulfonylurea (SU) over the study period or not administered SU. Hb1Ac % decreases at week 13, week 26, and week 39 for various treatment group is shown in Table 5.

TABLE 5

| | Population | Baseline | Week 6 | Week 13 | Week 19 | Week 26 | Week 32 | Week 39 |
|---|---|---|---|---|---|---|---|---|
| ITCA 650 20/60 | mITT | 8.4% | −1.0% | −1.2% | −1.5% | −1.5% | −1.5% | −1.4% |
| | p-value vs Placebo | | 0.001 | 0.001 | 0.001 | 0.001 | 0.001 | 0.001 |
| | Without SU (n = 78) | 8.4% | −1.0% | −1.3% | −1.6% | −1.6% | −1.6% | −1.7% |
| | With SU (n = 73) | 8.4% | −1.0% | −1.1% | −1.4% | −1.5% | −1.4% | −1.2% |
| ITCA 650 20/40 | mITT | 8.5% | −1.0% | −1.2% | −1.5% | −1.4% | −1.4% | −1.3% |
| | p-value vs Placebo | | 0.001 | 0.001 | 0.001 | 0.001 | 0.001 | 0.001 |
| | Without SU (n = 75) | 8.6% | −1.0 | −1.2% | −1.5 | −1.6% | −1.6 | −1.5% |
| | With SU (n = 72) | 8.4% | −1.0 | −1.3% | −1.4 | −1.3% | −1.2 | −1.1% |
| Placebo | Without SU | 8.5% | −0.3% | −0.4% | −0.4% | −0.3% | −0.5% | −0.4% |
| | With SU | 8.6% | −0.3% | −0.4% | −0.4% | −0.5% | −0.5% | −0.5% |

Reductions in HbA1c were clinically and statistically significant versus placebo at 39 weeks for subjects who were treated with ITCA 650 20/40 μg/day or ITCA 650 20/60 μg/day along with diet and exercise but no co-treatment with an oral antidiabetic medication. At week 39, subjects in the 20/40 μg/day group had average Hb1A1c % decrease of 1.1% and subjects in the 20/60 μg/day group had average Hb1A1c % decrease of 1.2%. See, FIG. 9.

Reductions in HbA1c for each treatment group were clinically and statistically significant versus placebo beginning at six weeks and thereafter at each scheduled time point for the mITT population over 39 weeks. See, FIG. 10. The week 26 time point is significant for benchmarking of similar competitive trials.

Subjects with baseline Hb1A1c % of ≤8.5% experienced a clinically meaningful decrease in HbA1c % by week 6 in both ITCA 650 treated groups: −0.84 and −0.79% respectively. The largest reduction in HbA1c was observed at weeks 26 and 39 for the ITCA 650 treated groups. Reductions in HbA1c were clinically significant at each scheduled time point for the mITT population over 39 weeks. See, FIG. 11.

The number of subjects in the mITT population with baseline Hb1A1c % of ≤8.5% at each time point is shown in Table 6.

TABLE 6

| Treatment | Week 6 | Week 13 | Week 26 | Week 39 |
|---|---|---|---|---|
| ITCA 20/40 mcg/day | 79 | 81 | 67 | 56 |
| ITCA 20/60 mcg/day | 87 | 85 | 70 | 63 |
| Placebo | 73 | 69 | 55 | 45 |

Subjects with baseline Hb1A1c % of >8.5% (but ≤10%) also experienced a clinically meaningful decrease in HbA1c % by week 6 in both ITCA 650 treated groups: −1.20 and −1.30% respectively. The largest reduction in HbA1c in the placebo treated group was observed at week 26. See, FIG. 12. The overall placebo effect was less for subjects with baseline Hb1A1c % of ≤8.5% than for subjects with an HbA1%>8.5%.

The number of subjects in the mITT population with baseline Hb1A1c % of >8.5% (but ≤10%) at each time point is shown in Table 7.

TABLE 7

| Treatment | Week 6 | Week 13 | Week 26 | Week 39 |
|---|---|---|---|---|
| ITCA 20/40 mcg/day | 61 | 58 | 54 | 41 |
| ITCA 20/60 mcg/day | 62 | 59 | 55 | 47 |
| Placebo | 66 | 56 | 48 | 23 |

A total of 60.8% in the placebo treated group were considered non-responders with an HbA1c reduction of <0.5% compared to 25.9% for subjects in the ITCA 20/40 μg/day group and 25.8% subjects in the ITCA 20/60 μg/day group. An HbA1c reduction of ≥1% was achieved by 55.8% of patients who completed 39 weeks (ITCA 20/40 μg/day group), 58.3% (20/60 μg/day group) and 21.0% in the placebo treated group. An HbA1c reduction of ≥2% was achieved by 23.1% of patients who completed 39 weeks of ITCA 650 20/40 mcg/day, 24.5% in the ITCA 650 20/60 mcg/day group and only 5.6% in the placebo treated group. Relevant data is displayed below in Table 8.

TABLE 8

| Statistic | | ITCA 650 20/40 mcg/day (N = 147) | ITCA 650 20/60 mcg/day (N = 151) | Placebo (N = 143) |
|---|---|---|---|---|
| Decrease from Baseline at LOCF Endpoint | n | 125 | 131 | 79 |
| <0.5% | n (%) | 38 (25.9%) | 39 (25.8%) | 87 (60.8%) |
| ≥1% | n (%) | 82 (55.8%) | 88 (58.3%) | 30 (21.0%) |
| ≥2% | n (%) | 34 (23.1%) | 37 (24.5%) | 8 (5.6%) |
| ≥3% | n (%) | 7 (4.8%) | 8 (5.3%) | 2 (1.4%) |
| ≥4% | n (%) | 1 (0.7%) | 2 (1.3%) | 0 |
| ≥5% | n (%) | 0 | 0 | 0 |

Note:
Patients with an increase or no change from Baseline at LOCF endpoint are counted in the "<0.5%" row. Patients are counted in all the "Decrease from Baseline" categories that apply.

For subjects who received ITCA 650 20/60 µg/day, subjects who were co-treated with sulfonylurea (SU) experienced smaller decreases in HbA1c % over time when compared to subjects who were not co-treated with sulfonylurea (SU). Decreases in HbA1c % for those treated with ITCA 650 20/60 µg/day was significantly greater than corresponding placebo subjects. See, FIG. 13. Similarly, for subjects who received ITCA 650 20/40 µg/day and were co-treated with sulfonylurea (SU) experienced smaller decreases in HbA1c % over time when compared to subjects who received ITCA 650 20/40 µg/day and were not co-treated with sulfonylurea (SU). Placebo subjects treated with SU or not treated with SU experienced equivalent decreases in HbA1c % until week 19; after week 32, placebo subjects taking SU had a greater decrease in HbA1c % than placebo subjects not taking SU. However, decreases in HbA1c % for those treated with ITCA 650 20/40 µg/day was significantly greater than corresponding placebo subjects. See, FIG. 14.

By the 39$^{th}$ week, subjects who received ITCA 650 20/40 µg/day and were co-treated with SU experienced an average 1.21% decrease in HbA1c % whereas subjects who were not co-treated with SU experienced an average 1.68% decreases in HbA1c %. Similarly, subjects who received ITCA 650 20/60 µg/day and were co-treated with SU experienced an average 1.19% decrease in HbA1c % whereas subjects who were not co-treated with SU experienced an average 1.66% decreases in HbA1c %. The opposite phenomenon was observed for placebo subjects: those treated with SU experienced a 0.54% decrease in HbA1c % whereas subjects who were not treated with SU experienced an average 0.23% decreases in HbA1c %. See, FIG. 15.

For subjects who received ITCA 650 20/60 µg/day, subjects who had a baseline HbA1c % of greater than 8.5% (and less than or equal to 10.0%) experienced greater decreases in HbA1c % over time when compared to subjects who had a baseline HbA1c % of less than 8.5%. Similarly, for subjects who received ITCA 650 20/40 µg/day and had a baseline HbA1c % of greater than 8.5% (and less than or equal to 10.0%) experienced greater decreases in HbA1c % over time when compared to subjects who had a baseline HbA1c % of less than 8.5%. See, FIG. 16. These data were comparable to data obtained in the phase 2 trial (described in Henry et al 2014).

By the 48$^{th}$ week endpoint of the phase 2 trial (described in Henry et al 2014), subjects receiving metformin and implanted with an ITCA 650 20/60 µg/day device had their Hb1A1c % decrease 1.39%. Similarly, by the 39$^{th}$ week endpoint in the presently-described phase 3 trial, subjects receiving metformin and implanted with an ITCA 650 20/60 µg/day device had their Hb1A1c % decrease 1.40%.

C. Safety and Tolerability

Treatment was very-well tolerated. The subjects' disposition for the randomized population was matched across all three treatment groups. This data is presented in Table 9.

TABLE 9

| Disposition Status Primary Reason | Statistic | ITCA 650 20/40 µg/day | ITCA 650 20/60 µg/day | Placebo | Total |
|---|---|---|---|---|---|
| Number of Patients Randomized | n | 153 | 153 | 154 | 460 |
| Number of Patients Treated (Safety Population) | n (%) | 153 (100.0%) | 153 (100.0%) | 154 (100.0%) | 460 (100.0%) |
| Number of Patients Treated with a Post-Baseline HbA1c Result (mITT Population) | n (%) | 147 (96.1%) | 151 (98.7%) | 143 (92.9%) | 441 (95.9%) |
| Number of Patients Who Received Rescue Therapy | n (%) | 26 (17.0%) | 18 (11.8%) | 65 (42.2%) | 109 (23.7%) |
| Number of Patients Who Completed the Treatment | n (%) | 120 (78.4%) | 123 (80.4%) | 123 (79.9%) | 366 (79.6%) |
| Number of Patients Who Prematurely Discontinued Treatment | n (%) | 33 (21.6%) | 30 (19.6%) | 31 (20.1%) | 94 (20.4%) |
| Total Number of Patients Who Completed the 4-Week Follow-up | n (%) | 140 (91.5%) | 141 (92.2%) | 139 (90.3%) | 420 (91.3%) |

Incidence of Treatment-Emergent Adverse Events (TEAE) leading to permanent discontinuation of study medication safety population was as expected. Relevant data is presented in Table 10. Incidence of GI related TEAE that resulted in discontinuation in study medication were similar between the two ITCA 650 treatment groups.

TABLE 10

| System Organ Class/ Preferred Term | Statistic | ITCA 650 20/40 µg/day (N = 153) | ITCA 650 20/60 µg/day (N = 153) | Placebo (N = 154) |
|---|---|---|---|---|
| Any Treatment-Emergent Adverse Event Leading to Permanent Discontinuation of Study Medication | n (%) | 18 (11.8%) | 13 (8.5%) | 6 (3.9%) |
| Gastrointestinal disorders | n (%) | 11 (7.2%) | 11 (7.2%) | 2 (1.3%) |
| Vomiting | n (%) | 4 (2.6%) | 5 (3.3%) | 1 (0.6%) |

TABLE 10-continued

| System Organ Class/ Preferred Term | Statistic | ITCA 650 20/40 μg/day (N = 153) | ITCA 650 20/60 μg/day (N = 153) | Placebo (N = 154) |
| --- | --- | --- | --- | --- |
| Nausea | n (%) | 3 (2.0%) | 5 (3.3%) | 1 (0.6%) |
| Diarrhea | n (%) | 2 (1.3%) | 0 | 0 |
| Abdominal pain | n (%) | 0 | 1 (0.7%) | 0 |
| Abdominal pain upper | n (%) | 1 (0.7%) | 0 | 0 |
| Gastritis | n (%) | 1 (0.7%) | 0 | 0 |
| Metabolism and nutrition disorders | n (%) | 0 | 1 (0.7%) | 1 (0.6%) |
| Hyperglycemia | n (%) | 0 | 1 (0.7%) | 1 (0.6%) |

Note:
A treatment-emergent adverse event is defined as an adverse event starting on or after the initial placement procedure and on or before the date of final removal. Patients with multiple occurrences of an event coded to the same System Organ Class/Preferred term are counted only once for that System Organ Class/Preferred term.

Note: A treatment-emergent adverse event is defined as an adverse event starting on or after the initial placement procedure and on or before the date of final removal. Patients with multiple occurrences of an event coded to the same System Organ Class/Preferred term are counted only once for that System Organ Class/Preferred term.

Incidence of Treatment-Emergent Adverse Events (TEAE) Safety Population was as expected. Relevant data is presented in Table 11.

TABLE 11

| System Organ Class/Preferred Term | Statistic | ITCA 650 20/40 μg/day (N = 153) | ITCA 650 20/60 μg/day (N = 153) | Placebo (N = 154) |
| --- | --- | --- | --- | --- |
| Any Treatment-Emergent Adverse Event | n (%) | 126 (82.4%) | 130 (85.0%) | 110 (71.4%) |
| Gastrointestinal disorders | n (%) | 71 (46.4%) | 74 (48.4%) | 30 (19.5%) |
| Nausea | n (%) | 47 (30.7%) | 48 (31.4%) | 15 (9.7%) |
| Vomiting | n (%) | 29 (19.0%) | 37 (24.2%) | 3 (1.9%) |
| Diarrhea | n (%) | 22 (14.4%) | 19 (12.4%) | 15 (9.7%) |
| Metabolism and nutrition disorders | n (%) | 26 (17.0%) | 34 (22.2%) | 20 (13.0%) |
| Hypoglycemia | n (%) | 14 (9.2%) | 10 (6.5%) | 4 (2.6%) |
| Decreased appetite | n (%) | 5 (3.3%) | 16 (10.5%) | 2 (1.3%) |
| Hyperglycemia | n (%) | 4 (2.6%) | 8 (5.2%) | 11 (7.1%) |

The incidence of nausea within the first week following placement of ITCA 650 20 μg/day was 15-18% compared to 3% in the placebo treated group. Following week 1, the incidence of nausea diminished to 4-6% in the ITCA 650 treatment groups. A transient increase to 15% was observed in the ITCA650 20/60 μg/day treatment group at time of exchange of 20 μg/day device for an ITCA 60 μg/day device (at week 13) but returned to 4% at week 19. From week 19 through week 39, the incidence rate was low and about 3% or less and with ITCA 650 20/60 μg/day treatment group comparable to placebo. Similar patterns were observed for the ITCA 20/40 μg/day treatment group. See, FIG. 17. It is noteworthy that incidence of nausea diminishes quickly over time and soon after the device replacement at week 13, nausea incidence stabilizes to a level comparable to the incidence experienced by placebo subjects.

The incidence of nausea for the phase 3 trial was improved relative to the phase 2 trial. As mentioned above, for both doses in the phase 3 trial (ITCA 650 20/40 mcg/day and ITCA 650 20/60 mcg/day), there was a slight increase in nausea upon replacement of the 20 mcg/day device for the higher dose (40 mcg/day or 60 mcg/day) device; however, incidence of nausea diminished quickly over time. See, FIG. 18.

Overall, treatment with study medication was well tolerated in this completed phase 3 study (ITCA 650 CLP-103). No new safety findings were observed in this study compared to what was observed during the phase 2 trial and related studies (as described above). No pancreatic events or cases of thyroid cancer were observed. All Serious Adverse Events (SAEs) were considered not related to study drug. GI related Adverse Events (AEs) were most common, diminished over time with treatment and were not dose-dependent. Events local to administration site were evenly distributed across the treatment groups. There were no major hypoglycemic events reported. The incidence of minor hypoglycemic events ranged between 2.7-9.2% across the treatment groups. Two patients had drug hypersensitivity (one patient in each dose group) and no patients had an allergic or anaphylactic reaction.

This Phase 3 trial showed efficacy and safety of ITCA 650 in treating type 2 diabetes for up to 39 weeks. Treatment with ITCA 650 20/40 μg/day or ITCA 650 20/60 μg/day for 39 weeks resulted in clinically and statistically significant reductions from baseline and vs. placebo in HbA1c and weight loss, the latter being dose-dependent. A significant proportion of subjects, for either dose, achieved an HbA1c of <7%. FIG. 19 lists certain endpoint data for the trial.

D. Comparison of Present Phase 3 Study and Prior Studies

The positive results obtained in the above-described phase 3 study are surprising in view of previously-described type 2 diabetes studies, e.g., the Duration 6 Trial. A comparison of the subject demographics for the above-described phase 3 study and Duration 6 Trial are shown in FIG. 20.

In the Duration 6 Trial, subjects received once-daily liraglutide (1.8 mg; VICTOZA® High Dose) injections or once-weekly exenatide (2 mg; Bydurenon) injections. In the Duration 6 Trial, liraglutide was "uptitrated" from 0.6 mg per day to 1.2 mg per day and then to 1.8 mg per day, with each titration being completed after at least 1 week. This uptitration is atypical since patients, according to the label for brand name liraglutide (VICTOZA®), should have their dose increased more gradually. An endpoint was a change in HbA1c % from baseline to week 26. As shown in FIG. 21, decreases in HbA1c % over first 26 weeks of the Duration 6 Trial and the above-described phase 3 trial were similar. At 26 weeks, subjects treated with liraglutide had a nearly identical average HbA1c % decrease as subjects in the above-described phase 3 trial. A second endpoint was a decrease in bodyweight. Data for the above-described phase 3 trial is only shown for week 39. See, FIG. 22. Finally, emergent adverse events were comparable between the above-described phase 3 trial and the Duration 6 Trial. See, FIG. 23.

However, the ITCA 650 requires a single (or few) implantations per year whereas the treatment methods of the Duration 6 trial require daily or weekly injections of a drug. Such ease of use enhances patient comfort and thus, long-term, adherence which translates into superior real-world outcome in the treatment of type 2 diabetes.

Example 2

A Phase 3 Clinical Trial Data for Continuous Delivery of Exenatide for Subjects with Type 2 Diabetes Having High Baseline HbA1c A Phase 3 clinical trial was designed as an open-label, multi-center sub-study to evaluate the efficacy, safety, and tolerability of continuous delivery of a synthetic exenatide via a subcutaneously implanted osmotic delivery device in type 2 diabetes subjects with high baseline HbA1c (i.e., serum HbA1c levels >10.0% and ≤12.0%).

Initially, subjects are treated for 39-weeks. Subjects were subcutaneously implanted with a three month ITCA 650 osmotic delivery device delivering an exenatide dose of 20 µg/day, which was replaced after thirteen weeks with a six month ITCA 650 osmotic delivery device delivering an exenatide dose of 60 µg/day; the initial phase of the study includes 39 weeks of treatment. After 39 weeks of treatment, the ITCA 650 60 µg/day device was removed. This dosage scheme and members of this group are hereinafter in this Example referred to as ITCA 650 20/60 µg/day. All subjects return 4 weeks after their end of treatment (ET) visit for a post-treatment follow-up assessment regardless of the reason for treatment discontinuation. The Modified Intent-to-Treat (mITT) population includes all patients from the safety population who had a valid baseline and at least one post-baseline HbA1c value. The Last Observation Carried Forward (LOCF) endpoint is defined as the last non-missing, on-treatment observation that is measured after baseline. Subjects who received rescue therapy were included in the mITT population. The 39 week study is represented graphically in FIG. 24.

Subjects were provided an opportunity to participate in extension phase 1 in which continued efficacy with the ITCA 650 60 µg/day dose regimen was studied for an additional 26 weeks of treatment. Subjects who agreed to continue in extension phase 1 had their ITCA 650 60 µg/day device removed at week 39 and replaced with another ITCA 650 60 µg/day device. Subjects in extension phase 1 had a 4-week post-treatment follow-up visit occurring four weeks after the end of treatment period, i.e., after week 65 or after premature treatment discontinuation. Subjects in the extension phase 1 (until week 65) and their related data are disclosed below in this Example. The 65 week study is represented graphically in FIG. 34.

Subjects completing the first extension phase were provided an opportunity to further be included in a second extension phase in which continued efficacy with the ITCA 650 60 µg/day dose regimen is studied for a further 26 weeks of treatment. Here, subjects who agreed to continue in the second extension phase had their ITCA 650 60 µg/day device removed at week 65 and replaced with another ITCA 650 60 µg/day device. Subjects in the second extension phase will have a 4-week post-treatment follow-up visit occurring four weeks after the end of treatment period, i.e., after week 91 or after premature treatment discontinuation. Subjects who participated in the second extension phase did not have a follow-up visit four weeks after the end of the initial 39 week treatment period.

Subjects are maintained on their pre-study oral antidiabetic medication regimen throughout the entire treatment period for all phases of the study. The 20/60 µg/day dose was selected based on the overall reduction in HbA1c in previous studies, the percent of patients reaching goal, and the robust reduction seen across the spectrum of HbA1c (see, e.g., Example 1). In addition, the tolerability profile was excellent for 60 µg/day and is only modestly less effective than the 80 µg/day dose.

The present study/studies allow evaluation of the safety and efficacy of treatment using continuous delivery of exenatide in type 2 diabetes mellitus over a 39 to 91 week treatment period for subjects having high baseline (HBL) HbA1c % (i.e., greater than 10%).

A. Demographics of Study Group

Inclusion criteria were as follows. Subjects were 18-80 years of age and diagnosed as having type 2 diabetes mellitus for at least three months prior to screening. Subjects had been on a stable treatment regimen of diet and exercise alone or in combination with a stable and optimal or near-optimal dose of metformin, sulfonylurea, TZD, or combination of these drugs for at least three months. Subjects had a stable body weight (not varying by >10% for at least three months. They had calcitonin levels of <50 ng/L (50 pg/mL) and a body mass index (BMI) of ≥2.5 kg/m$^2$ and 45 kg/m$^2$ at time of screening. Women of childbearing potential must have had a negative pregnancy test at Screening. HbA1c levels were greater than 10% and less than or equal to 12%. However, certain subjects who had baseline HbA1c levels outside that range were included as subjects.

Baseline demographics of the initial study phase subjects are presented in Table 12. Sixty (60) patients were randomized of which 59 (98.3%) were (i.e., the mITT population) and 52 patients completed 39-weeks of treatment.

TABLE 12

| | |
|---|---|
| Total number of patients | 60 |
| Years since type 2 diabetes diagnosis | 8.9 years |
| Men | 33 (57%) |
| Women | 25 (43%) |
| Age (mean) | 52.1 years |
| HbA1c baseline % (mean) | 10.7% |
| Weight (mean) | 93.4 kg |
| Body mass index | 32.1 kg/m$^2$ |
| Background therapy | |
| Diet and exercise | 31% |
| Diet and exercise plus oral T2D medications | 69% |

The demographics of the safety population are shown in Table 13.

TABLE 13

| Characteristic (unit) | Statistic | ITCA 650 20/60 mcg/day (N = 60) |
|---|---|---|
| Age (years) | Mean (SD) | 51.9 (10.18) |
| <65 years | n (%) | 51 (85.0%) |
| ≥65 years | n (%) | 9 (15.0%) |
| Male | n (%) | 34 (56.7%) |
| Female | n (%) | 26 (43.3%) |
| Race | | |
| White | n (%) | 48 (80.0%) |
| Black or African American | n (%) | 8 (13.3%) |
| Asian | n (%) | 1 (1.7%) |
| Asian Indian (Indian Subcontinent) | n (%) | 0 |
| American Indian or Alaska Native | n (%) | 0 |
| Native Hawaiian or Other Pacific Islander | n (%) | 1 (1.7%) |
| Other | n (%) | 1 (1.7%) |
| Multiple | n (%) | 1 (1.7%) |

TABLE 13-continued

| Characteristic (unit) | Statistic | ITCA 650 20/60 mcg/day (N = 60) |
|---|---|---|
| Ethnicity | | |
| Hispanic or Latino | n (%) | 23 (38.3%) |
| Not Hispanic or Latino | n (%) | 36 (60.0%) |
| Not Reported | n (%) | 1 (1.7%) |

Baseline Characteristics for the Safety Population are shown in Table 14.

TABLE 14

| Characteristic (unit) | Statistic | ITCA 650 20/60 mcg/day (N = 60) |
|---|---|---|
| Weight (kg) | Mean (SD) | 92.88 (18.836) |
| Height (cm) | Mean (SD) | 169.8 (10.40) |
| BMI (kg/m$^2$) | Mean (SD) | 32.04 (4.898) |
| BMI Category (kg/m$^2$) | | |
| <30 | n (%) | 22 (36.7%) |
| >=30 | n (%) | 38 (63.3%) |
| Missing | n (%) | 0 |
| HbA1C (%) | Mean (SD) | 10.81 (0.654) |
| Fasting Plasma Glucose (mmol/L) | Mean (SD) | 13.70 (3.010) |

Baseline characteristics for the safety population of the first extension phase are presented in Table 15. Thirty-eight patients elected to continue treatment for an additional 26 weeks, up to week 65.

TABLE 15

| Characteristic (unit) | ITCA 650 60 mcg/day (n = 38) mean; # in parentheses is Standard Deviation |
|---|---|
| Weight (kg) | 93.38 (18.328) |
| Height (cm) | 169.4 (9.76) |
| BMI (kg/m$^2$) | 32.40 (5.028) |
| BMI Category (kg/m$^2$) | |
| <30 | 12 (31.6%) |
| >=30 | 26 (68.4%) |
| HbA1C (%) | 10.76 (0.565) |
| Fasting Plasma Glucose (mmol/L) | 13.61 (3.036) |

The demographics of the safety population are shown in Table 16.

TABLE 16

| Characteristic (unit) | ITCA 650 60 mcg/day (n = 38) (n; % refers to percent of n) Mean age 51.1 (SD: 10.30) |
|---|---|
| Age (years) | |
| <65 years | 33 (86.8%) |
| >=65 years | 5 (13.2%) |
| Gender | |
| Male | 20 (52.6%) |
| Female | 18 (47.4%) |

TABLE 16-continued

| Characteristic (unit) | ITCA 650 60 mcg/day (n = 38) (n; % refers to percent of n) Mean age 51.1 (SD: 10.30) |
|---|---|
| Race | |
| White | 28 (73.7%) |
| Black or African American | 7 (18.4%) |
| Asian | 0 |
| Asian Indian (Indian Subcontinent) | 0 |
| American Indian or Alaska Native | 0 |
| Native Hawaiian or Other Pacific Islander | 1 (2.6%) |
| Other | 1 (2.6%) |
| Multiple | 1 (2.6%) |
| Ethnicity | |
| Hispanic or Latino | 13 (34.2%) |
| Not Hispanic or Latino | 24 (63.2%) |
| Not Reported | 1 (2.6%) |

B. Pharmacodynamic Data
(i) Interim Data, Data up to Week 26,
The following pharmacodynamic measurement data were obtained from the initial phase study subjects.

HbA1c levels were measured at 13, 19, and 26 weeks, the results of which are shown in Table 17. At the week 13 time point, subjects had received the exenatide at 20 μg/day for 13 weeks via a three month osmotic delivery device. At the week 19 time point, subjects had received the exenatide at 20 μg/day for 13 weeks and had received the exenatide at 60 μg/day for 6 weeks via a six month osmotic delivery device. At the week 26 time point, subjects had received the exenatide at 20 μg/day for 13 weeks and had received the exenatide at 60 μg/day for 13 weeks. Subjects were enrolled in the study on a rolling basis, so the reduced sample size for later time points does not reflect subject drop out.

TABLE 17

| Time Point (Week) | Sample Size | Baseline | HbA1c % (mean) at Time Point | Change from Baseline |
|---|---|---|---|---|
| 13 | n = 50 | 10.8 | 8.3 | −2.5 |
| 19 | n = 39 | 10.7 | 7.8 | −2.9 |
| 26 | n = 25 | 10.9 | 7.7 | −3.2 |

Patients surprisingly showed excellent HbA1c % decrease at low dose (20 μg/day) after at least a 13 week administration period. 22% of patients had an HbA1c % decrease of at least 4.0. See, Table 18. Of the subjects showing an HbA1c % decrease of at least 4.0 at 13 weeks, seven of those subjects showed a decrease greater than 4.5; four of those subjects showed a decrease greater than 5.0; three of those subjects showed a decrease greater than 5.5; and one subject showed a decrease greater than 6.0. See, Table 18.

TABLE 18

Proportion of subjects who received at least 13 weeks of therapy and had already achieved a 2% or greater reduction in HbA1c

| HbA1c % Reduction | # Patients | % Patients |
|---|---|---|
| ≥2.0 | 39 of 50 | 78% |
| ≥3.0 | 25 of 50 | 50% |
| ≥4.0 | 11 of 50 | 22% |
| ≥5.0 | 4 of 50 | 8% |
| ≥6.0 | 1 of 50 | 2% |

These decreases represent surprising and unprecedented reductions in the total amount of serum HbA1c of at least 35.1%, and as much as 51.7%. After at least 13 weeks of low dose of the exenatide treatment of 20 mcg/day, eleven patients had an HbA1c % decrease of at least 4.0%.

Data for eleven subjects who had an HbA1c % decrease of at least 4.0 at week 13 of the initial study is shown in Table 19. Ten of the eleven subjects decreased their HbA1c level to below the target of 7.0% and nine of the eleven decreased their HbA1c level to 6.5% or below.

TABLE 19

| # Patients | HbA1c % Baseline | HbA1c % at Treatment Point | HbA1c % decrease from Baseline | Overall HbA1c reduction |
|---|---|---|---|---|
| 1 | 12.0 | 5.8 | −6.2 | 51.7% |
| 2 | 10.9 | 5.3 | −5.6 | 51.4% |
| 3 | 11.8 | 5.9 | −5.9 | 50.0% |
| 4 | 11.4 | 6.4 | −5.0 | 43.9% |
| 5 | 11.1 | 6.4 | −4.7 | 42.3% |
| 6 | 11.2 | 6.5 | −4.7 | 42.0% |
| 7 | 11.0 | 6.4 | −4.6 | 41.8% |
| 8 | 10.4 | 6.3 | −4.1 | 39.4% |
| 9 | 10.4 | 6.3 | −4.1 | 39.4% |
| 10 | 11.3 | 6.9 | −4.4 | 38.9% |
| 11 | 11.4 | 7.4 | −4.0 | 35.1% |

At 26 weeks, subjects lost an average of 1.1 kg of body weight. This is less weight loss than is experienced at 24 weeks for non-high baseline subjects (≤10% HbA1c) treated with ITCA 650 20/60 µg/day (i.e., 3.1 kg). It is known that high baseline subjects suffer from Glycosuria (excretion of sugar/calories in urine); this loss of calories in urine helps the high baseline subject keep his/her weight down. However, once the Glycosuria is lessened, the subject ceases losing excess calories in urine. Indeed, it has been reported that high baseline subjects treated with vildagliptin/metformin or liraglutide/metformin resulted in weight increases of 1.29 kg and 1.3 kg, respectively, due to lessening of Glycosuria. Since treating Glycosuria in high baseline subjects is known to cause weight gain in these subjects, the observed lessened weight loss data for high baseline relative to non-high baseline subjects was not unexpected. However, it is noteworthy that the high baseline subjects in this phase 3 study actually lost weight, i.e., −1.1 kg, whereas high baseline subjects in the benchmarking vildagliptin/metformin or liraglutide/metformin studies gained weight (i.e., +1.29 kg and +1.3 kg, respectively). Accordingly, high baseline subjects in this phase 3 trial lost about 2.4 kg of weight relative to high baseline subjects in the vildagliptin/metformin or liraglutide/metformin studies; this relative weight loss was unexpected.

(ii) Data from the Original and Completed 39 Week Study Phase

The following pharmacodynamic measurement data were analyzed at the completion of the 39th week of the phase 3 trial.

As mentioned above, this phase 3 study included a 13 week initial phase in which all treatment subjects (i.e., those not in the placebo group) received an ITCA 650 20 µg/day device. At the end of the initial phase the ITCA 650 20 µg/day device was replaced with an ITCA 650 60 µg/day device. Thus, at the week 39 time point, subjects had received the exenatide at 20 µg/day for 13 weeks and had received the exenatide at 60 µg/day for 26 weeks.

Over time, subjects with high baseline HbA1c % who received ITCA 650 20/60 µg/day demonstrated impressive and sustained reductions in their HbA1c %. There was a steady drop in HbA1c % between baseline and weeks 19; with the most rapid drop being in the first 6 weeks of the study. Subjects' HbA1c % levels remained relatively constant for the rest of the study period. See, FIG. 25.

Tables 20, 21, and 22 show data obtained from subjects with high baseline HbA1c % who received ITCA 650 20/60 µg/day.

TABLE 20

Change from Baseline HbA1c (%) by Visit
Modified Intention-to-Treat Population

| Visit | Statistic | ITCA 650 20/60 mcg/day |
|---|---|---|
| | n | 59 |
| Baseline HbA1c (%) | Mean (SD) | 10.78 (0.593) |
| | n | 59 |
| Week 6 HbA1c (%) | Mean (SD) | 8.96 (0.907) |
| Change from Baseline to Week 6 | Mean (SD) | −1.82 (0.802) |
| | n | 56 |
| Week 13 HbA1c (%) | Mean (SD) | 8.22 (1.187) |
| Change from Baseline to Week 13 | Mean (SD) | −2.53 (1.276) |
| | n | 51 |
| Week 19 HbA1c (%) | Mean (SD) | 7.65 (1.128) |
| Change from Baseline to Week 19 | Mean (SD) | −3.07 (1.284) |
| | n | 45 |
| Week 26 HbA1c (%) | Mean (SD) | 7.61 (1.265) |
| Change from Baseline to Week 26 | Mean (SD) | −3.16 (1.321) |
| | n | 37 |
| Week 32 HbA1c (%) | Mean (SD) | 7.42 (1.274) |
| Change from Baseline to Week 32 | Mean (SD) | −3.35 (1.310) |
| | n | 33 |
| Week 39 HbA1c (%) | Mean (SD) | 7.32 (1.139) |
| Change from Baseline to Week 39 | Mean (SD) | −3.40 (1.325) |

TABLE 21

Change from Baseline HbA1c (%) at Last Observation Carried Forward
(LOCF) endpoint for Modified Intention-to-Treat Population

| | Statistic | ITCA 650 20/60 mcg/day (N = 59) |
|---|---|---|
| Baseline HbA1c (%) | Mean (SD) | 10.78 (0.591) |
| LOCF Endpoint HbA1c (%) | Mean (SD) | 8.00 (1.377) |
| Change from Baseline at LOCF Endpoint | Mean (SD) | −2.78 (1.416) |
| | p-value | <0.001 |

TABLE 22

Proportion of Patients with Decrease in HbA1c
<0.5%, ≥1%, ≥2%, ≥3%, ≥4%, and
≥5% at LOCF Endpoint Modified Intention-to-Treat Population

| | Statistic | ITCA 650 20/60 mcg/day (N = 59) |
|---|---|---|
| Decrease from Baseline at LOCF Endpoint | n | 57 |
| <0.5% | n (%) | 2 (3.4%) |
| ≥1% | n (%) | 53 (89.8%) |
| ≥2% | n (%) | 43 (72.9%) |
| ≥3% | n (%) | 27 (45.8%) |
| ≥4% | n (%) | 13 (22.0%) |
| ≥5% | n (%) | 3 (5.1%) |

Note:
Patients with an increase or no change from Baseline at LOCF endpoint are counted in the "<0.5%" row. Patients are counted in all the "Decrease from Baseline" categories that apply.

Overall, fifteen subjects (24.4%) achieved a LOCF endpoint HbA1c of less than 7%.

Subjects receiving ITCA 60 mcg/day experienced significant weight loss relative to subjects in the placebo group. The LOCF endpoint data are shown in Table 23 and illustrated in FIG. 26.

TABLE 23

Change from Baseline Body Weight at LOCF Endpoint for the Modified Intention-to-Treat Population

|  | Statistic | ITCA 650 60 mcg/day (N = 59) |
|---|---|---|
| Baseline Body Weight (kg) | Mean (SD) | 93.05 (18.948) |
| LOCF Endpoint Body Weight (kg) | Mean (SD) | 91.82 (18.818) |
| Change from Baseline at LOCF Endpoint | Mean (SD) | −1.23 (5.746) |
|  | p-value | <0.05 |

Reduction in body weight was observed from week 6 and continued during the course of the study (39 weeks). The weight loss had not plateaued (reached steady state) at week 39. In comparison, patients treated with other GLP-1 RA's may experience a plateau or rebound of body following 24 or 26 weeks of dosing.

Overall, the 39 week treatment with 20/60 mcg/day of ITCA 650 proved effective. At week 39, HbA1c was reduced by −2.78%. This reduction in HbA1c is clinically and statistically significant. Weight loss of −1.23 kg was observed. 25.4% of patients achieved an HbA1c of <7%. Reduction of HbA1c of ≥1% was achieved by 89.8% of patients who completed 39 weeks of ITCA 650 60 mcg/day. HbA1c reduction of ≥2% was achieved by 72.9% of patients and 45.8% of patients achieved a HbA1c reduction of ≥3% and 22.% had a HbA1c reduction of ≥3% at week 39.

(iii) Data for Up to Week 65, First Extension Phase

The following pharmacodynamic measurement data were analyzed at the completion of extension phase 1 of the phase 3 trial for subjects with high baseline HbA1c.

As mentioned above, the phase 3 study included a 13 week initial phase in which all treatment subjects (i.e., those not in the placebo group) received an ITCA 650 20 μg/day device. At the end of the initial phase, the ITCA 650 20 μg/day device was replaced with an ITCA 650 60 μg/day device. At the first extension phase, subjects who agreed to continue in the first extension phase had their ITCA 650 60 μg/day device removed at week 39 and replaced with another ITCA 650 60 μg/day device and treated for an additional 26 weeks (to week 65). Subjects in the first extension phase had a 4-week post-treatment follow-up visit occurring four weeks after the end of treatment period, i.e., after week 65 or after premature treatment discontinuation, unless they opted to continue directly into the second extension phase (to week 91) with a new 6 month 60 mcg/day ITCA 650 osmotic delivery device.

Thus, at the week 65 time point, subjects who completed the entire treatment period had received the exenatide at 20 μg/day for 13 weeks and had received the exenatide at 60 μg/day for 52 weeks.

Over the first extension phase, subjects demonstrated sustained reductions in their HbA1c %. Clinically and statistically significant reduction in HbA1c of −3.08% relative to baseline was observed at week 65; this was a greater reduction than was observed at 39 weeks for the LOCF endpoint for the mITT populations (i.e., −2.78%). See, FIG. 35.

As shown in FIG. 25, there was a steady and significant reduction in HbA1c % between baseline and every study visit until weeks 19, with the most rapid drop being in the first 6 weeks of the study. Subjects' HbA1c % levels further declined for the rest of the study period including the first extension phase. See, FIG. 36.

Table 24 shows data obtained from subjects with high baseline HbA1c % who received ITCA 650 60 mcg/day into the first extension phase.

TABLE 24

Proportion of patients with a decrease in $HbA_{1c}$ of ≥1%, ≥2%, ≥3%, ≥4%, or ≥5% at LOCF endpoint for mITT population for subjects participating in the first extension phase

|  | ITCA 650 60 mcg/day N = 38 n; % refers to percent of n |
|---|---|
| Decrease from Baseline at LOCF Endpoint | 37 |
| ≥1% | 36 (97.3%) |
| ≥2% | 30 (81.1%) |
| ≥3% | 22 (59.5%) |
| ≥4% | 11 (29.7%) |
| ≥5% | 2 (5.4%) |

Note:
Patients are counted in all the "Decrease from Baseline" categories that apply.

Twelve subjects (31.6%) achieved a LOCF endpoint HbA1c of less than 7%.

A comparison of efficacy of the initial 39 week phase and the first extension phase is shown in Table 25.

TABLE 25

| Efficacy Summary | Week 39 | Week 65 |
|---|---|---|
| mITT Population (n) | 59 | 38 |
| % Change in HbA1c (LOCF Endpoint) | −2.78 | −3.08 |
| p-value | <0.001 | <0.001 |
| % Treated To Goal (Week 39) of HbA1c <7% | 25.4 | 31.9 |
| % of percent with HbA1c reduction of 1% or more | 89.8 | 97.3 |
| % of percent with HbA1c reduction of 2% or more | 72.9 | 81.1 |
| % of percent with HbA1c reduction of 3% or more | 45.8 | 59.5 |

Overall, the first extension phase of the trial demonstrated that an additional 26 weeks treatment with ITCA 650 60 mcg/day was effective. HbA1c was reduced at week 65 by −3.08%. This reduction in HbA1c is clinically and statistically significant. 31.9% of patients achieved an HbA1c of <7%. HbA1c reduction of ≥1% was achieved by 97.3% of patients, HbA1c reduction of ≥2% was achieved by 81.1% of patients, HbA1c reduction of ≥3% was achieved by 59.5% of patients, HbA1c reduction of ≥4% was achieved by 11% of subjects, and HbA1c reduction of ≥5% was achieved by 5.4% of patients. The durability of treatment effect was confirmed following more than one year of treatment in these originally poorly controlled diabetic patients.

C. Safety and Tolerability (i) Data Up to Week 39

Treatment was well tolerated. There was low incidence and severity of gastrointestinal side effects: 28% of subjects experienced mid- to moderate nausea, 18% experienced vomiting and 18% experienced diarrhea. Three minor cases of hypoglycemia were reported. No cases of major hypoglycemia were reported.

In the Safety Population, the incidence of nausea within the first week following placement of ITCA 650 60 μg/day was 16%. Following week 1, the incidence of nausea progressively diminished to about 3-7% by week 13. A transient increase to 16% was observed at week 13 when the 20 mcg/day device was replaced with ITCA650 60 mcg/day but returned to about 4% at week 19. From week 19 through week 39, the incidence rate was low, about 1% or less with ITCA 650 20/60 mcg/day treatment group comparable to placebo. See, FIG. 27.

The incidence of Treatment-Emergent Events (TEAE) in the Safety Population is shown in Table 26.

TABLE 26

| System Organ Class/Preferred Term | Statistic | ITCA 650 20/60 mcg/day (N = 60) |
| --- | --- | --- |
| Any Treatment-Emergent Adverse Event | n (%) | 52 (86.7%) |
| Gastrointestinal disorders | n (%) | 35 (58.3%) |
| Nausea | n (%) | 21 (35.0%) |
| Vomiting | n (%) | 16 (26.7%) |
| Diarrhea | n (%) | 14 (23.3%) |
| Constipation | n (%) | 4 (6.7%) |
| Dyspepsia | n (%) | 4 (6.7%) |
| Abdominal distension | n (%) | 3 (5.0%) |
| Flatulence | n (%) | 3 (5.0%) |
| Gastro esophageal reflux disease | n (%) | 3 (5.0%) |
| Metabolism and nutrition disorders | n (%) | 12 (20.0%) |
| Hypoglycemia | n (%) | 4 (6.7%) |

Only six patients discontinued treatment, of which only three were due to adverse events attributable to treatment; see Table 27. One subject was lost to follow-up.

TABLE 27

| System Organ Class/Preferred Term | Statistic | ITCA 650 60 mcg/day (N = 60) |
| --- | --- | --- |
| Any Treatment-Emergent Adverse Event Leading to Permanent Discontinuation of Study Medication | n (%) | 6 (10.0%) |
| Gastrointestinal disorders | n (%) | 4 (6.7%) |
| Vomiting | n (%) | 3 (5.0%) |
| Diarrhea | n (%) | 1 (1.7%) |
| Nausea | n (%) | 1 (1.7%) |
| Metabolism and nutrition disorders | n (%) | 1 (1.7%) |
| Hyperglycemia | n (%) | 1 (1.7%) |

Note:
A treatment-emergent adverse event is defined as an adverse event starting on or after the initial placement procedure and on or before the date of final removal for the Sub-Study Phase. Patients with multiple occurrences of an event coded to the same System Organ Class/Preferred Term were counted only once for that System Organ Class/Preferred Term.

Twenty patients (33.3%) received rescue therapy. The criteria for rescue therapy are as follows: (1) Between day 0 and week 13, two or more fasting self-monitoring of blood glucose (SMBG) values >240 mg/dL during any 7-day period and confirmed by a fasting plasma glucose (FPG) determination at the site. When a patient reported two or more fasting SMBG values >240 mg/dL during any 7-day period after day 0 every effort was to be made to have the patient return to the clinic for an FPG measurement as soon as possible but within 7 days. (2) Following week 13, two or more fasting SMBG values >200 mg/dL during any 7-day period and confirmed by an FPG determination at the site. (3) Two consecutive FPG values >240 mg/dL (day 0 through week 13) or >200 mg/dL (after week 13) at the site. When two or more FPG values >240 mg/dL (day 0 through week 13) or >200 mg/dL (after week 13) were reported for a patient the patient was to be contacted and requested to return to the clinic for a second FPG measurement as soon as possible but within 7 days. (4) Increase in HbA1c: HbA1c elevations of +1.5% from day 0 or HbA1c>8.5% at week 26 and onwards. One re-test was permitted.

For the initial 39 week phase, the ITCA650 60 mcg/day dose was well tolerated and the incidences of Treat-Emergent Adverse Events (TEAE) were low. The most common system organ classes affected were Gastrointestinal, General Disorder and Administration Site Conditions, Infections and Infestation and Musculoskeletal. The most common adverse events were nausea, vomiting and diarrhea. GI related AEs were most common (23.3-35%) and diminished over time with treatment. Events local to administration site were similar to observations from the trial described above in Example 1. No new safety signals were observed in this study compared to what was observed during Phase 2 and for this class. There were a total of six Serious Adverse Events (10.0%) were reported. The Serious Adverse Events all coded as causality not related. ITCA 650 20/60 mcg/day was overall well tolerated with a discontinuation rate of 13.3%.

(ii) Data Up to Week 65, Extension Phase 1

Treatment with 60 mcg/day for an additional 26 weeks, up to week 65, was very well tolerated. Thirty eight subjects elected to continue treatment into the first extension phase. Thirty five subjects (92.1%) completed the first extension phase and three (7.9%) subjects prematurely discontinued treatment. One subject (2.6%) received rescue therapy during the first extension phase. Thirty two subjects agreed to continue into a second extension phase.

The incidence during the first extension phase of Newly Emergent Adverse Events for the safety population is shown in Table 28.

TABLE 28

| AESI Category | Statistic | ITCA 650 60 mcg/day (n = 38) |
| --- | --- | --- |
| Any Adverse Events of Special Interest Occurring During the First Extension Phase | n (%) Events | 10 (26.3%) 16 |
| Hypoglycemia | n (%) | 1 (2.6%) |
|  | Events (%) | 1 (6.3%) |
| Nausea | n (%) | 6 (15.8%) |
|  | Events (%) | 6 (37.5%) |
| Vomiting | n (%) | 3 (7.9%) |
|  | Events (%) | 3 (18.8%) |
| Diarrhea | n (%) | 1 (2.6%) |
|  | Events (%) | 2 (12.5%) |

Note:
n (%) = number of patients in the specified category and the percentage is based on the total number of patient in the analysis population; Events (%) = number of events in the specified category and the percentage is based on the total number of events.

The incidence during the first extension phase of Treatment-Emergent Events (TEAE) in the safety population is shown in Table 29.

TABLE 29

| System Organ Class/Preferred Term | ITCA 650 60 mcg/day N = 38 (% refers to percent of n) |
| --- | --- |
| Any Treatment-Emergent Adverse Event Occurring During the Sub-study 1st Extension Phase | 24 (63.2%) |
| Gastrointestinal disorders | 9 (23.7%) |
| Nausea | 6 (15.8%) |

TABLE 29-continued

| System Organ Class/Preferred Term | ITCA 650 60 mcg/day<br>N = 38 (% refers<br>to percent of n) |
|---|---|
| Vomiting | 3 (7.9%) |
| Diarrhea | 1 (2.6%) |

Note:
A treatment-emergent adverse event is defined as an adverse event starting on or after the initial placement procedure and on or before the date of final removal for the Sub-study 1st Extension Phase.

The incidence of Treatment-Emergent Adverse Events, during the first extension phase, leading to permanent discontinuation of study medication for safety population subjects is shown in Table 30.

TABLE 30

| System Organ Class/Preferred Term | ITCA 650 60 mcg/day<br>N = 38 (% refers<br>to percent of n) |
|---|---|
| Any Treatment-Emergent Adverse Event Leading to Permanent Discontinuation of Study Medication Occurring During the Sub-study 1st Extension Phase | 1 (2.6%) |
| Gastrointestinal disorders | 1 (2.6%) |
| Dyspepsia | 1 (2.6%) |
| Nausea | 1 (2.6%) |

Note:
A treatment-emergent adverse event is defined as an adverse event starting on or after the initial placement procedure and on or before the date of final removal for the Sub-study 1st Extension Phase. Patients with multiple occurrences of an event coded to the same system organ class/preferred term are counted only once for that system organ class/preferred term.

Treatment with 60 mcg/day for an additional 26 weeks was very well tolerated. No new safety signals were observed in first extension phase when compared to what was observed during initial 39 weeks of the phase three study of Example 2. No Adverse Events of Special Interest, i.e., no pancreatic events, thyroid nodules or neoplasms, CV/MACE events or major hypoglycemic events, were reported. There were no Serious Adverse Events (SAEs) reported during the first extension phase. Incidence of new treatment-emergent adverse events (nausea, vomiting, and diarrhea) was very low with an incidence of 10.5% within the first week of placement, followed by an incidence of 0-4.5% throughout the study. Only one patient discontinued due to GI side effects. There were no major hypoglycemic events reported and the incidence of minor hypoglycemia was 6.3%.

Overall, no new safety signals emerged. The ITCA 650 was well tolerated and incidences of treatment emergent Adverse Events and Adverse Events of Special Interest were very low.

Other Embodiments

From the foregoing description, it will be apparent that variations and modifications may be made to the invention described herein to adopt it to various usages and conditions. Such embodiments are also within the scope of the following claims.

All citations to sequences, patents and publications in this specification are herein incorporated by reference to the same extent as if each independent patent and publication was specifically and individually indicated to be incorporated by reference.

What is claimed is:

1. A method of treating type 2 diabetes mellitus in a subject having a baseline hemoglobin A1c (HbA1c) % of greater than 10.0% comprising measuring a subject's baseline body weight and providing the subject a substantial steady-state delivery of a dose of at least 20 mcg/day of an exenatide from an osmotic delivery device, wherein the substantial steady-state delivery of the exenatide from the osmotic delivery device is continuous over an administration period of at least about 1 month, the method produces a decrease in the body weight of the subject of at least 3% relative to the subject's baseline body weight, and the decrease in the subject's body weight is achieved within 39 weeks after implantation of the osmotic delivery device.

2. The method of claim 1, wherein the substantial steady-state delivery of the exenatide at a therapeutic concentration is achieved within a time period of about 7 days after implantation of the osmotic delivery device in the subject.

3. The method of claim 1, wherein the substantial steady-state delivery of the exenatide from the osmotic delivery device is continuous over an administration period of at least about 2 months.

4. The method of claim 1, wherein the osmotic delivery device comprises
    an impermeable reservoir comprising interior and exterior surfaces and first and second open ends,
    a semi-permeable membrane in sealing relationship with the first open end of the reservoir,
    an osmotic engine within the reservoir and adjacent the semi-permeable membrane,
    a piston adjacent the osmotic engine, wherein the piston forms a movable seal with the interior surface of the reservoir, the piston divides the reservoir into a first chamber and a second chamber, the first chamber comprising the osmotic engine,
    a suspension formulation, wherein the second chamber comprises the suspension formulation and the suspension formulation is flowable and comprises the exenatide, and
    a diffusion moderator inserted in the second open end of the reservoir, the diffusion moderator adjacent the suspension formulation.

5. The method of claim 4, wherein the suspension formulation comprises:
    a particle formulation comprising the exenatide and
    a vehicle formulation.

6. The method of claim 5, wherein the vehicle formulation comprises a solvent and a polymer.

7. The method of claim 6, wherein the vehicle formulation has a viscosity of between about 10,000 poise and about 20,000 poise at 37° C.

8. The method of claim 6, wherein the solvent is selected from the group consisting of benzyl benzoate, lauryl lactate, and lauryl alcohol.

9. The method of claim 6, wherein the polymer is a polyvinylpyrrolidone.

10. The method of claim 1, wherein the mcg/day dose of the exenatide is about 20 mcg/day.

11. The method of claim 1, wherein the mcg/day dose of the exenatide is about 40 mcg/day.

12. The method of claim 1, wherein the mcg/day dose of the exenatide is about 60 mcg/day.

13. The method of claim 1, wherein the subject has a baseline HbA1c % of less than or equal to 12.0%.

14. The method of claim 1, wherein the subject is a human.

15. The method of claim 1, wherein the subject has not previously received a drug for treating type 2 diabetes mellitus.

16. The method of claim 1, wherein the subject is further provided one or more other drugs for treating type 2 diabetes mellitus.

17. The method of claim 16, wherein the one or more other drugs is insulin or an anti-diabetic drug selected from the group consisting of a DPP4 inhibitor, a SGLT2 inhibitor, metformin, a sulfonylurea, and a thiazolidinedione (TZD).

18. The method of claim 1, wherein the subject is in a Modified Intention-to-Treat (mITT) Population.

19. The method of claim 1, wherein the method produces a decrease in the body weight of the subject of at least 4% relative to the subject's baseline body weight.

20. A method of treating type 2 diabetes mellitus in a subject having a baseline hemoglobin A1c (HbA1c) % of greater than 10.0% comprising providing the subject a substantial steady-state delivery of a dose of at least 20 mcg/day of an exenatide from an osmotic delivery device, wherein the substantial steady-state delivery of the exenatide from the osmotic delivery device is continuous over an administration period of at least about 1 month, the method produces a decrease in the body weight of the subject of at least 3% relative to the subject's baseline body weight upon implantation of the osmotic delivery device, and the decrease in the subject's body weight is achieved within 39 weeks after implantation of the osmotic delivery device.

21. The method of claim 20, wherein the method produces a decrease in the body weight of the subject of at least 4% relative to the subject's baseline body weight upon implantation of the osmotic delivery device.

22. A method of treating type 2 diabetes mellitus in a population having a mean baseline hemoglobin A1c (HbA1c) % of greater than 10.0% comprising measuring a population's mean baseline body weight and providing the population a substantial steady-state delivery of a dose of at least 20 mcg/day of an exenatide from an osmotic delivery device, wherein the substantial steady-state delivery of the exenatide from the osmotic delivery device is continuous over an administration period of at least about 1 month, the method produces a decrease in the mean body weight of the population of at least 3% relative to the population's mean baseline body weight, and the decrease in the population's body weight is achieved within 39 weeks after implantation of the osmotic delivery device.

23. The method of claim 22, wherein the mcg/day dose of the exenatide is about 20 mcg/day.

24. The method of claim 22, wherein the mcg/day dose of the exenatide is about 40 mcg/day.

25. The method of claim 22, wherein the mcg/day dose of the exenatide is about 60 mcg/day.

26. The method of claim 22, wherein the population is a Modified Intention-to-Treat (mITT) Population.

27. The method of claim 22, wherein the method produces a decrease in the mean body weight of the population of at least 4% relative to the population's mean baseline body weight.

* * * * *

SEQUENCE LISTING

```
<160> NUMBER OF SEQ ID NOS: 3

<210> SEQ ID NO 1
<211> LENGTH: 39
<212> TYPE: PRT
<213> ORGANISM: Heloderma suspectum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 28
<212> TYPE: PRT
<213> ORGANISM: Homo sapiens

<400> SEQUENCE: 2

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 3
```

```
<211> LENGTH: 33
<212> TYPE: PRT
<213> ORGANISM: Homo sapiens

<400> SEQUENCE: 3

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```